US011866495B2

(12) United States Patent
Willuda et al.

(10) Patent No.: US 11,866,495 B2
(45) **Date of Patent: *Jan. 9, 2024**

(54) ANTI-CEACAM6 ANTIBODIES AND USES THEREOF

(71) Applicant: Deutsches Krebsforschungszentrum Stiftung des öffentlichen Rechts, Heidelberg (DE)

(72) Inventors: Jörg Willuda, Glienicke/Nordbahn (DE); Mark Trautwein, Whippany, NJ (US); Uwe Gritzan, Cologne (DE); Christoph Freiberg, Wuppertal (DE); Frank Dittmer, Düsseldorf (DE); Dorian Schönfeld, Cologne (DE); Julian Marius Glück, Meerbusch (DE); Jessica Pinkert, Wuppertal (DE); Eva-Maria Gutierrez, Illertissen (DE); Sven Golfier, Berlin (DE); Simon Holton, Berlin (DE); Philip Beckhove, Heidelberg (DE); Yingzi Ge, Wiesloch (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 647 days.

This patent is subject to a terminal disclaimer.

(21) Appl. No.: 16/776,329

(22) Filed: Jan. 29, 2020

(65) Prior Publication Data

US 2020/0157214 A1 May 21, 2020

Related U.S. Application Data

(63) Continuation of application No. 15/561,013, filed as application No. PCT/EP2016/056104 on Mar. 21, 2016, now Pat. No. 10,584,167.

(30) Foreign Application Priority Data

Mar. 23, 2015 (EP) .................................... 15160292

(51) Int. Cl.

*A61K 39/00* (2006.01)
*C07K 16/28* (2006.01)
*A61P 35/00* (2006.01)

(52) U.S. Cl.

CPC .......... *C07K 16/2803* (2013.01); *A61P 35/00* (2018.01); *A61K 39/001182* (2018.08); *C07K 2317/21* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01); *C07K 2317/94* (2013.01)

(58) Field of Classification Search

CPC .............................................. A61K 39/001182

See application file for complete search history.

(56) References Cited

U.S. PATENT DOCUMENTS

| | | | | |
|---|---|---|---|---|
| 7,943,743 | B2 | 5/2011 | Korman | |
| 8,008,449 | B2 | 8/2011 | Korman | |
| 8,217,149 | B2 | 7/2012 | Irving | |
| 8,609,089 | B2 | 12/2013 | Langermann | |
| 8,779,108 | B2 | 7/2014 | Queva | |
| 8,900,587 | B2 | 12/2014 | Carven | |
| 10,584,167 | B2 * | 3/2020 | Willuda | C07K 16/2803 |
| 2014/0341917 | A1 | 11/2014 | Nastri | |
| 2014/0356353 | A1 | 12/2014 | Queva | |
| 2015/0079109 | A1 | 3/2015 | Li | |
| 2017/0275375 | A1 | 9/2017 | Rossi | |
| 2019/0263905 | A1 | 8/2019 | Yoon | |

FOREIGN PATENT DOCUMENTS

| | | | |
|---|---|---|---|
| CN | 102482701 | A | 5/2012 |
| EP | 3560957 | A2 | 10/2019 |
| WO | 2011/034660 | A1 | 3/2011 |
| WO | 2013173223 | A1 | 11/2013 |
| WO | 2015117002 | A1 | 8/2015 |

(Continued)

OTHER PUBLICATIONS

Paul, Fundamental Immunology, 3rd Edition, 1993, pp. 292-295 (Year: 1993).*
Almagro & Fransson, Frontiers in Bioscience 2008; 13:1619-33 (Year: 2008).*
Rudikoff et al(Proc. Natl. Acad. Sci. USA 1982 vol. 79: p. 1979) (Year: 1982).*
Pascalis et al (The Journal of Immunology (2002) 169, 3076-3084) (Year: 2002).*
Casset et al. (2003) BBRC 307, 198-205 (Year: 2003).*

(Continued)

*Primary Examiner* — Sheela J. Huff
(74) *Attorney, Agent, or Firm* — Taft Stettinius & Hollister LLP

(57) ABSTRACT

The present invention provides recombinant antigen-binding regions and antibodies and functional fragments containing such antigen-binding regions that are specific for human and *Macaca fascicularis* CEACAM6 (Carcinoembryonic antigen-related cell adhesion molecule 6, CD66c, Non-specific crossreacting antigen, NCA, NCA-50/90), and which do not significantly cross-react with the closely related human CEACAM1, human CEACAM3, and human CEACAM5. The invention further provides methods to generate this kind of antibodies.
The antibodies, accordingly, can be used to treat cancer and other disorders and conditions associated with expression of the CEACAM6. The invention also provides nucleic acid sequences encoding the foregoing antibodies, vectors containing the same, pharmaceutical compositions and kits with instructions for use.

20 Claims, 30 Drawing Sheets

Specification includes a Sequence Listing.

(56) References Cited

FOREIGN PATENT DOCUMENTS

| | | | |
|---|---|---|---|
| WO | 2016161270 | A1 | 10/2016 |
| WO | 2016150899 | A3 | 11/2016 |
| WO | 2017178493 | A1 | 10/2017 |
| WO | 2017205721 | A1 | 11/2017 |
| WO | 2018013818 | A3 | 2/2018 |
| WO | 2018039020 | A1 | 3/2018 |
| WO | 2018129553 | A1 | 7/2018 |
| WO | 2018088877 | A9 | 11/2018 |

OTHER PUBLICATIONS

D'Angelo et al., Frontiers in Immunology vol. 9 p. 1 (2018) (Year: 2018).*

Nui et al Journal of Controlled Release vol. 161, p. 18 (2012). (Year: 2012).*

Du et al, Cancer Research vol. 71, Supplement 1 Abstract 4582 (2011). (Year: 2011).*

Strome et al., The Oncologist, 2007; 12:1084-95 (Year: 2007).*

Brand et al., Anticancer Res. 2006; 26:463-70 (Year: 2006).*

Anonymous (Jan. 1, 2018) "History of Changes for study NCT03596372: Study of BAY1834942 in Patients With Solid Tumors", retrieved from URL:https://clinicaltrials.gov/ct2/history/NCT03596372?V6=View#StudyPageTop, pp. 1-6.

Burugu, S. et al. (2018) "Emerging targets in cancer immunotherapy," Seminars in Cancer Biology, 52:39-52.

Butt, S. et al. (2018) "Role of immunotherapy in bladder cancer: past, present and future," Cancer Chemotherapy and Pharmacology, 18:629-645.

International Search Report and Written Opinion dated Feb. 25, 2020 for International Application No. PCT/EP2019/084849, filed Dec. 12, 2019, 18 pages.

International Search Report and Written Opinion dated Jan. 28, 2020 for International Application No. PCT/EP2019/080520, filed Nov. 7, 2019, 15 pages.

Marin-Acevedo, J. et al. (2018) "Next generation of immune checkpointtherapy in cancer: new developments and challenges," Journal of Hematology & Oncology, 11(39):1-20.

Pardoll, D. (Apr. 2012) "The blockade of immune checkpoints in cancer immunotherapy," Nature Review, Cancer, 12:252-264.

Shen, X. et al. (2018) "Efficacy of PD-1 or PD-L1 inhibitors and PD-L1 expression status in cancer: meta-analysis," the BMJ, 9 pages.

Wen, A. et al. (Dec. 1, 2010) "The Role of the Transcription Factor CREB in Immune Function," J Immunol., 185(11):6413-6419.

Willuda, J. et al. (Jul. 1, 2019) "Abstract LB-075: Increased T cell-activation resulting from the combination of the anti-CEACAM6 function-blocking antibody BAY 1834942 with checkpoint inhibitors targeting either PD-1/PD-L1 or TIM-3," Cancer Res. 79(13, suppl.):1-4.

Willuda, J. et al. (Jul. 2018) "Abstract 1771: BAY 1834942 is an immunotherapeutic antibody blocking the novel immune checkpoint regulator CEACAM6 (CD66c)," Cancer Res. 78(13, suppl.):1-4.

Wittemer-Rump, S. et al. (Jul. 1, 2018) "Abstract 2791: Physiologically based pharmacokinetic modeling and simulations to estimate the efficacious dose of the CEACAM6 function-blocking antibody BAY 1834942," Cancer Res. 78(13, suppl.):2791.

Wolchok, J. et al. (Jul. 11, 2013) "Safety and clinical activity of combined PD-1 (nivolumab) and CTLA-4 (ipilimumab) blockade in advanced melanoma patients," N Engl J Med., 369(2): 122-133.

Lee, O-J. et al. (2015). "CEACAM6 as detected by the AP11 antibody is a marker notable for mucin-producing adenocarcinomas," Virchows Arch, 466:151-159.

Riley, C.J. et al. (2009). "Design and Activity of a Murine and Humanized anti-CEACAM6 scFv in the Treatment of Pancreatic Cancer," Cancer Res. 69(5):1933-1940.

* cited by examiner

Fig. 2

>TPP-2971_VL

DIVMTQSQKFMSTSVGDRVSITC*KASQNVGTAVA*WYQQKPGQSPKLLIY*SASNRYT*
GVPDRFTGSGSGTDFTLTISNMQSEDLADYFC*QQYSSYPLT*FGAGTKLELK

>TPP-2971_VH

QVTLKESGPGILQPSQTLSLTCSFSGFSLS*TYGIGVG*WIRQPSGKDLEWLA*HIWWND*
*NKY**YNTALKS*RLTISKDTSNNQVFLKIASVDTADTATYYCAR*ISLPYFDY*WGQGTTLTV
SS

>TPP-3187_VL

DIVMTQSQKFMSTSVGDRVSITC*KASQNVGTAVA*WYQQKPGQSPKLLIY*SASNRYT*
GVPDRFTGSGSGTDFTLTISNMQSEDLADYFC*QQYNNYPLT*FGAGTKLELK

>TPP-3187_VH

QVTLKESGPGILQPSQTLSLTCSFSGFSLT*TYGIGVG*WIRQPSGKGLEWLA*HIWWND*
*NKY**YNTALKS*RLTISKDTSNNQVFLKIASVDTADTATYYCAR*ISLPYFDY*WGQGTTLTV
SS

Fig. 3

>TPP-3310_VL

DIQLTQSPSFLSASVGDRVTITC*KASQNVGTAVA*WYQQKPGKAPKLLIY*SASNRYT*G
VPSRFSGSGSGTEFTLTISSLQPEDFATYYC*QQYSSYPLT*FGGGTKVEIK

>TPP-3310_VH

QVTLRESGPALVKPTQTLTLTCTFSGFSLS*TYGIGVG*WIRQPPGKALEWLA*HIWWND*
*NKY**YSTSLKT*RLTISKDTSKNQVVLTMTNMDPVDTATYYCAR*ISLPYFDY*WGQGTTLT
VSS

>TPP-3714_VL

DIQLTQSPSFLSASVGDRVTITC*KASQNVGTAVA*WYQQKPGKAPKLLIY*SASNRYT*G
VPSRFSGSGSGTEFTLTISSLQPEDFATYYC*QQYSSYPLT*FGGGTKVEIK

>TPP-3714_VH

QVTLRESGPALVKPTQTLTLTCTFSGFSLS*TYGIGVG*WIRQPPGKALEWLA*HIWWND*
*NKY**YSTSLKT*RLTISKDTSKNQVVLTMTNMDPVDTATYYCAR*ISLPYFDY*WGQGTLVT
VSS

Fig. 4

>TPP-3820_VL

DIQLTQSPSFLSASVGDRVTITC*KASQNVGTAVA*WYQQKPGKAPKLLIY*SASNRYT*G
VPSRFSGSGSGTEFTLTISSLQPEDFATYYC*QQYNNYPLT*FGGGTKVEIK

>TPP-3820_VH

QVTLRESGPALVKPTQTLTLTCTFSGFSLT*TYGIGVG*WIRQPPGKGLEWLA*HIWWND*
*NKY**YSTSLKT*RLTISKDTSKNQVVLTMTNMDPVDTATYYCAR*ISLPYFDY*WGQGTLVT
VSS

>TPP-3821_VL

DIQLTQSPSFLSASVGDRVTITC*KASQNVGTAVA*WYQQKPGKAPKLLIY*SASNRYT*G
VPSRFSGSGSGTEFTLTISSLQPEDFATYYC*QQYNNYPLT*FGGGTKVEIK

>TPP-3821_VH

QVTLRESGPALVKPTQTLTLTCTFSGFSLS*TYGIGVG*WIRQPPGKALEWLA*HIWWND*
*NKY**YSTSLKT*RLTISKDTSKNQVVLTMTNMDPVDTATYYCAR*ISLPYFDY*WGQGTLVT
VSS

FIG. 8A

>TPP-2971 VH (PRT)
```
QVTLKESGPGILQPSQTLSLTCSFSGFSLSTYGIGVGWIRQPSGKDLEWLAHIWWNDNKYYNTALKSRLTISKDTSNNQV
                              |-----|              |----HCDR2-----|
                              HCDR1

FLKIASVDTADTATYYCARISLPYFDYWGQGTTLTVSS
                   |------|
                   HCDR3
```

>TPP-2971 VL (PRT)
```
DIVMTQSQKFMSTSVGDRVSITCKASQNVGTAVAWYQQKPGQSPKLLIYSASNRYTGVPDRFTGSGSGTDFTLTISNMQS
                       |--LCDR1--|               |-----|
                                                 LCDR2

EDLADYFCQQYSSYPLTFGAGTKLELK
        |-LCDR3-|
```

>TPP-3186 VH (PRT)
```
QVTLKESGPGILQPSQTLSLTCSFSGFSLSTYGIGVGCIRQPSGKGLEWLAHIWWNDNKYYNTALKSRLTISKDTSNNQV
                              |-----|              |----HCDR2-----|
                              HCDR1

FLKIASVDTADTATYYCARISLPYFDYWGQGTTLTVSS
                   |------|
                   HCDR3
```

>TPP-3186 VL (PRT)
```
DIVMTQSQKFMSTSVGDRVSITCKASQNVGTAVAWYQQKPGQSPKLLIYSASNRYTGVPDRFTGSGSGTDFTFTISNMQS
                       |--LCDR1--|               |-----|
                                                 LCDR2

EDLADYFCQQYSSYPLTFGAGTKLELK
        |-LCDR3-|
```

>TPP-3187 VH (PRT)
```
QVTLKESGPGILQPSQTLSLTCSFSGFSLTTYGIGVGWIRQPSGKGLEWLAHIWWNDNKYYNTALKSRLTISKDTSNNQV
                              |-----|              |----HCDR2-----|
                              HCDR1

FLKIASVDTADTATYYCARISLPYFDYWGQGTTLTVSS
                   |------|
                   HCDR3
```

>TPP-3187 VL (PRT)
```
DIVMTQSQKFMSTSVGDRVSITCKASQNVGTAVAWYQQKPGQSPKLLIYSASNRYTGVPDRFTGSGSGTDFTLTISNMQS
                       |--LCDR1--|               |-----|
                                                 LCDR2

EDLADYFCQQYNNYPLTFGAGTKLELK
        |-LCDR3-|
```

>TPP-3308 VH (PRT)
```
QVTLKESGPGILQPSQTLSLTCSFSGFSLSTYGIGVGWIRQPSGKDLEWLAHIWWNDNKYYNTALKSRLTISKDTSNNQV
                              |-----|              |----HCDR2-----|
                              HCDR1

FLKIASVDTADTATYYCARISLPYFDYWGQGTTLTVSS
                   |------|
                   HCDR3
```

>TPP-3308 VL (PRT)
```
DIVMTQSQKFMSTSVGDRVSITCKASQNVGTAVAWYQQKPGQSPKLLIYSASNRYTGVPDRFTGSGSGTDFTLTISNMQS
```

FIG. 8B

```
                          |--LCDR1--|                   |-----|
                                                        LCDR2

EDLADYFCQQYSSYPLTFGAGTKLELK
        |-LCDR3-|
```

>TPP-3308 Heavy Chain (PRT)

```
QVTLKESGPGILQPSQTLSLTCSFSGFSLSTYGIGVGWIRQPSGKDLEWLAHIWWNDNKYYNTALKSRLTISKDTSNNQV
|----------------------------------------------------------VH---------------------
                                   |-----|                 |----HCDR2-----|
                                   HCDR1

FLKIASVDTADTATYYCARISLPYFDYWGQGTTLTVSSASTKGPSVFPLAPCSRSTSESTAALGCLVKDYFPEPVTVSWN
-------------------------------------|
                    |------|
                    HCDR3

SGALTSGVHTFPAVLQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVVHQDWLNGKEYKCKV

SNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG
```

>TPP-3308 Light Chain (PRT)

```
DIVMTQSQKFMSTSVGDRVSITCKASQNVGTAVAWYQQKPGQSPKLLIYSASNRYTGVPDRFTGSGSGTDFTLTISNMQS
|------------------------------------------------------VL-------------------------
                          |--LCDR1--|                   |-----|
                                                        LCDR2

EDLADYFCQQYSSYPLTFGAGTKLELKRTVAAPSVFIFPPSDEQLKSGTASVVCLLNNFYPREAKVQWKVDNALQSGNSQ
---------------------------|
        |-LCDR3-|

ESVTEQDSKDSTYSLSSTLTLSKADYEKHKVYACEVTHQGLSSPVTKSFNRGEC
```

>TPP-3308 Heavy Chain (DNA)

```
CAGGTCACACTGAAAGAGAGCGGCCCTGGCATCCTGCAGCCCAGCCAGACCCTGAGCCTGACCTGCAGCTTCAGCGGCTT
|---------------------------------------------------------------------------------

CAGCCTGAGCACCTACGGCATCGGCGTGGGCTGGATCAGACAGCCCAGCGGCAAGGACCTGGAATGGCTGGCCCACATCT
----------------------------------------------------------------------------------

GGTGGAACGACAACAAGTACTACAACACCGCCCTGAAGTCCCGGCTGACCATCAGCAAGGACACCAGCAACAACCAGGTG
----------------VH----------------------------------------------------------------

TTCCTGAAGATCGCCAGCGTGGACACCGCCGATACCGCCACCTACTACTGCGCCCGGATCAGCCTGCCCTACTTCGACTA
----------------------------------------------------------------------------------

CTGGGGCCAGGGCACCACCCTGACCGTGTCCTCAGCCAGCACCAAGGGCCCCAGCGTGTTCCCTCTGGCCCCTTGTAGCA
-----------------------------------|

GAAGCACCAGCGAGTCTACAGCCGCCCTGGGCTGCCTCGTGAAGGACTACTTTCCCGAGCCCGTGACCGTGTCCTGGAAC

TCTGGCGCTCTGACAAGCGGCGTGCACACCTTTCCAGCCGTGCTGCAGAGCAGCGGCCTGTACTCTCTGAGCAGCGTCGT
```

FIG. 8C

```
GACAGTGCCCAGCAGCAACTTCGGCACCCAGACCTACACCTGTAACGTGGACCACAAGCCCAGCAACACCAAGGTGGACA

AGACCGTGGAACGGAAGTGCTGCGTGGAATGCCCCCCTTGTCCTGCCCCTCCAGTGGCTGGCCCTTCCGTGTTCCTGTTC

CCCCCAAAGCCCAAGGACACCCTGATGATCAGCCGGACCCCCGAAGTGACCTGCGTGGTGGTGGATGTGTCCCACGAGGA

CCCCGAGGTGCAGTTCAATTGGTACGTGGACGGCGTGGAAGTGCACAACGCCAAGACCAAGCCCAGAGAGGAACAGTTCA

ACAGCACCTTCCGGGTGGTGTCCGTGCTGACCGTGGTGCATCAGGACTGGCTGAACGGCAAAGAGTACAAGTGCAAGGTG

TCCAACAAGGGCCTGCCTGCCCCCATCGAGAAAACCATCAGCAAGACCAAAGGCCAGCCCCGCGAGCCCCAGGTGTACAC

ACTGCCTCCAAGCCGGGAAGAGATGACCAAGAACCAGGTGTCCCTGACCTGTCTCGTGAAAGGCTTCTACCCCTCCGATA

TCGCCGTGGAATGGGAGAGCAACGGCCAGCCCGAGAACAACTACAAGACCACCCCCCCCATGCTGGACAGCGACGGCTCA

TTCTTCCTGTACAGCAAGCTGACAGTGGACAAGTCCCGGTGGCAGCAGGGCAACGTGTTCAGCTGCAGCGTGATGCACGA

GGCCCTGCACAACCACTACACCCAGAAGTCCCTGAGCCTGAGCCCTGGC
```

>TPP-3308 Light Chain (DNA)

```
GACATCGTGATGACCCAGAGCCAGAAATTCATGAGCACCAGCGTGGGCGACCGGGTGTCCATCACATGCAAGGCCAGCCA
|-------------------------------------------------------------------------------

GAACGTGGGCACCGCCGTGGCCTGGTATCAGCAGAAGCCCGGCCAGAGCCCCAAGCTGCTGATCTACAGCGCCAGCAACC
-------------------------------------------------------------------------------V

GGTACACCGGCGTGCCCGACAGATTCACAGGCAGCGGCAGCGGCACCGACTTCACCCTGACCATCAGCAACATGCAGAGC
L-------------------------------------------------------------------------------

GAGGACCTGGCCGACTACTTCTGCCAGCAGTACAGCAGCTACCCCCTGACCTTCGGAGCCGGCACCAAGCTGGAACTGAA
--------------------------------------------------------------------------------

ACGAACCGTGGCCGCTCCCAGCGTGTTCATCTTCCCACCTAGCGACGAGCAGCTGAAGTCCGGCACAGCCTCTGTCGTGT
|

GCCTGCTGAACAACTTCTACCCCCGCGAGGCCAAGGTGCAGTGGAAGGTGGACAATGCCCTGCAGAGCGGCAACAGCCAG

GAAAGCGTGACCGAGCAGGACAGCAAGGACTCCACCTACAGCCTGAGCAGCACCCTGACCCTGAGCAAGGCCGACTACGA

GAAGCACAAGGTGTACGCCTGCGAAGTGACCCACCAGGGCCTGTCTAGCCCCGTGACCAAGAGCTTCAACCGGGGCGAGT

GT
```

>TPP-3310 VH (PRT)

```
QVTLRESGPALVKPTQTLTLTCTFSGFSLSTYGIGVGWIRQPPGKALEWLAHIWWNDNKYYSTSLKTRLTISKDTSKNQV
                              |-----|                  |----HCDR2-----|
                              HCDR1

VLTMTNMDPVDTATYYCARISLPYFDYWGQGTTLTVSS
                   |------|
                   HCDR3
```

>TPP-3310 VL (PRT)

```
DIQLTQSPSFLSASVGDRVTITCKASQNVGTAVAWYQQKPGKAPKLLIYSASNRYTGVPSRFSGSGSGTEFTLTISSLQP
                         |--LCDR1--|                     |-----|
                                                         LCDR2
```

FIG. 8D

```
EDFATYYCQQYSSYPLTFGGGTKVEIK
         |-LCDR3-|
```

>TPP-3310 Heavy Chain (PRT)

```
QVTLRESGPALVKPTQTLTLTCTFSGFSLSTYGIGVGWIRQPPGKALEWLAHIWWNDNKYYSTSLKTRLTISKDTSKNQV
|--------------------------------------------------------------VH-----------------
                                 |-----|                  |----HCDR2-----|
                                 HCDR1

VLTMTNMDPVDTATYYCARISLPYFDYWGQGTTLTVSSASTKGPSVFPLAPCSRSTSESTAALGCLVKDYFPEPVTVSWN
--------------------------------------|
                       |------|
                       HCDR3

SGALTSGVHTFPAVLQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVVHQDWLNGKEYKCKV

SNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG
```

>TPP-3310 Light Chain (PRT)

```
DIQLTQSPSFLSASVGDRVTITCKASQNVGTAVAWYQQKPGKAPKLLIYSASNRYTGVPSRFSGSGSGTEFTLTISSLQP
|-----------------------------------------------------VL--------------------------
                         |--LCDR1--|                    |-----|
                                                        LCDR2

EDFATYYCQQYSSYPLTFGGGTKVEIKRTVAAPSVFIFPPSDEQLKSGTASVVCLLNNFYPREAKVQWKVDNALQSGNSQ
---------------------------|
         |-LCDR3-|

ESVTEQDSKDSTYSLSSTLTLSKADYEKHKVYACEVTHQGLSSPVTKSFNRGEC
```

>TPP-3310 Heavy Chain (DNA)

```
CAAGTGACCCTGAGAGAGTCCGGCCCTGCCCTCGTGAAGCCTACCCAGACCCTGACACTGACCTGCACCTTCTCCGGCTT
|---------------------------------------------------------------------------------

CTCCCTGTCCACCTACGGCATCGGCGTGGGCTGGATCAGACAGCCTCCTGGCAAGGCCCTGGAATGGCTGGCTCACATCT
----------------------------------------------------------------------------------

GGTGGAACGACAACAAGTACTACTCCACCTCCCTGAAAACCCGGCTGACCATCTCCAAGGACACCTCCAAGAACCAGGTG
----------------VH----------------------------------------------------------------

GTGCTGACCATGACCAACATGGACCCCGTGGACACCGCCACCTACTACTGCGCCAGAATCTCCCTGCCCTACTTCGACTA
----------------------------------------------------------------------------------

CTGGGGCCAGGGCACCACACTGACCGTCAGCTCAGCTTCCACCAAGGGCCCCTCCGTGTTCCCTCTGGCCCCTTGCTCCC
------------------------------------|

GGTCCACCTCTGAGTCTACCGCCGCTCTGGGCTGCCTGGTGAAAGACTACTTCCCCGAGCCCGTGACCGTGTCCTGGAAC

TCTGGCGCCCTGACCTCCGGCGTGCACACCTTTCCAGCCGTGCTGCAGTCCTCCGGCCTGTACTCCCTGTCCTCCGTGGT

GACAGTGCCCTCCTCCAACTTCGGCACCCAGACCTACACCTGTAACGTGGACCACAAGCCCTCCAACACCAAGGTGGACA
```

FIG. 8E

```
AGACCGTGGAACGGAAGTGCTGCGTGGAATGCCCACCCTGTCCTGCTCCACCTGTGGCTGGCCCCAGCGTGTTCCTGTTC

CCCCCAAAGCCCAAGGACACCCTGATGATCTCCCGGACCCCCGAAGTGACCTGCGTGGTGGTGGACGTGTCCCACGAGGA

CCCCGAGGTGCAGTTCAATTGGTACGTGGACGGCGTGGAAGTGCACAACGCCAAGACCAAGCCCAGAGAGGAACAGTTCA

ACTCCACCTTCCGGGTGGTGTCCGTGCTGACCGTGGTGCATCAGGACTGGCTGAACGGCAAAGAGTACAAGTGCAAGGTC

TCCAACAAGGGCCTGCCTGCCCCCATCGAAAAGACCATCAGCAAGACCAAGGGCCAGCCCCGCGAGCCCCAGGTGTACAC

ACTGCCCCCCAGCCGGGAAGAGATGACCAAGAACCAGGTGTCCCTGACCTGTCTGGTGAAAGGCTTCTACCCCTCCGACA

TTGCCGTGGAATGGGAGTCCAACGGACAGCCTGAGAACAACTACAAGACCACCCCCCCCATGCTGGACTCCGACGGCTCA

TTCTTCCTGTACTCCAAGCTGACAGTGGACAAGTCCCGGTGGCAGCAGGGCAACGTGTTCTCCTGCTCCGTGATGCACGA

GGCCCTGCACAACCACTACACCCAGAAGTCCCTGTCCCTGAGCCCCGGC

>TPP-3310 Light Chain (DNA)
GATATCCAGCTGACCCAGTCCCCCAGCTTCCTGTCTGCCTCTGTGGGCGACAGAGTGACCATCACATGCAAGGCCTCCCA
|---------------------------------------------------------------------------------

GAACGTGGGCACCGCCGTGGCTTGGTATCAGCAGAAGCCTGGCAAGGCCCCCAAGCTGCTGATCTACTCCGCCTCCAACC
---------------------------------------------------------------------------------V

GGTACACCGGCGTGCCCTCTAGATTCTCCGGCTCTGGCTCTGGCACCGAGTTTACCCTGACCATCTCCAGCCTGCAGCCC
L---------------------------------------------------------------------------------

GAGGACTTCGCCACCTACTACTGCCAGCAGTACTCCTCCTACCCCCTGACCTTTGGCGGAGGCACCAAGGTGGAAATCAA
----------------------------------------------------------------------------------

GCGGACCGTGGCCGCTCCCTCCGTGTTTATCTTCCCACCCTCCGACGAGCAGCTGAAGTCCGGCACAGCTTCCGTCGTGT
|

GCCTGCTGAACAACTTCTACCCCCGCGAGGCCAAGGTGCAGTGGAAGGTGGACAACGCCCTGCAGTCCGGCAACTCCCAG

GAATCCGTGACCGAGCAGGACTCCAAGGACAGCACCTACTCCCTGTCCTCCACCCTGACCCTGTCCAAGGCCGACTACGA

GAAGCACAAGGTGTACGCCTGCGAAGTGACCCACCAGGGCCTGTCTAGCCCCGTGACCAAGTCTTTCAACCGGGGCGAGT

GT


>TPP-3322 VH (PRT)
QVTLKESGPGILQPSQTLSLTCSFSGFSLSTYGIGVGCIRQPSGKGLEWLAHIWWNDNKYYNTALKSRLTISKDTSNNQV
                                  |-----|                |----HCDR2-----|
                                  HCDR1

FLKIASVDTADTATYYCARISLFYFDYWGQGTTLTVSS
                      |------|
                     HCDR3

>TPP-3322 VL (PRT)
DIVMTQSQKFMSTSVGDRVSITCKASQNVGTAVAWYQQKPGQSPKLLIYSASNRYTGVPDRFTGSGSGTDFTFTISNMQS
                          |--LCDR1--|                    |-----|
                                                         LCDR2

EDLADYFCQQYSSYPLTFGAGTKLELK
         |-LCDR3-|
```

FIG. 8F

>TPP-3322 Heavy Chain (PRT)

```
QVTLKESGPGILQPSQTLSLTCSFSGFSLSTYGIGVGCIRQPSGKGLEWLAHIWWNDNKYYNTALKSRLTISKDTSNNQV
|---------------------------------------------------------------VH---------------------
                                   |-----|                 |----HCDR2-----|
                                   HCDR1

FLKIASVDTADTATYYCARISLPYFDYWGQGTTLTVSSASTKGPSVFPLAPCSRSTSESTAALGCLVKDYFPEPVTVSWN
--------------------------------------|
                       |-------|
                       HCDR3

SGALTSGVHTFPAVLQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVVHQDWLNGKEYKCKV

SNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG
```

>TPP-3322 Light Chain (PRT)

```
DIVMTQSQKFMSTSVGDRVSITCKASQNVGTAVAWYQQKPGQSPKLLIYSASNRYTGVPDRFTGSGSGTDFTFTISNMQS
|----------------------------------------------------------VL---------------------------
                         |--LCDR1--|                  |-----|
                                                      LCDR2

EDLADYFCQQYSSYPLTFGAGTKLELKRTVAAPSVFIFPPSDEQLKSGTASVVCLLNNFYPREAKVQWKVDNALQSGNSQ
---------------------------|
        |-LCDR3-|

ESVTEQDSKDSTYSLSSTLTLSKADYEKHKVYACEVTHQGLSSPVTKSFNRGEC
```

>TPP-3322 Heavy Chain (DNA)

```
CAGGTCACACTGAAAGAGAGCGGCCCTGGCATCCTGCAGCCCAGCCAGACCCTGAGCCTGACCTGCAGCTTCAGCGGCTT
|-------------------------------------------------------------------------------

CAGCCTGAGCACCTACGGCATCGGCGTGGGCTGCATCAGACAGCCCAGCGGCAAGGGCCTGGAATGGCTGGCCCACATCT
--------------------------------------------------------------------------------

GGTGGAACGACAACAAGTACTACAACACCGCCCTGAAGTCCCGGCTGACCATCAGCAAGGACACCAGCAACAACCAGGTG
-------------------VH-----------------------------------------------------------

TTCCTGAAGATCGCCAGCGTGGACACCGCCGATACCGCCACCTACTACTGCGCCCGGATCAGCCTGCCCTACTTCGACTA
--------------------------------------------------------------------------------

CTGGGGCCAGGGCACCACCCTGACCGTGTCCTCAGCCAGCACCAAGGGCCCCAGCGTGTTCCCTCTGGCCCCTTGTAGCA
-----------------------------------|

GAAGCACCAGCGAGTCTACAGCCGCCCTGGGCTGCCTCGTGAAGGACTACTTTCCCGAGCCCGTGACCGTGTCCTGGAAC

TCTGGCGCTCTGACAAGCGGCGTGCACACCTTTCCAGCCGTGCTGCAGAGCAGCGGCCTGTACTCTCTGAGCAGCGTCGT

GACAGTGCCCAGCAGCAACTTCGGCACCCAGACCTACACCTGTAACGTGGACCACAAGCCCAGCAACACCAAGGTGGACA

AGACCGTGGAACGGAAGTGCTGCGTGGAATGCCCCCCTTGTCCTGCCCCTCCAGTGGCTGGCCCTTCCGTGTTCCTGTTC
```

FIG. 8G

```
CCCCCAAAGCCCAAGGACACCCTGATGATCAGCCGGACCCCCGAAGTGACCTGCGTGGTGGTGGATGTGTCCCACGAGGA

CCCCGAGGTGCAGTTCAATTGGTACGTGGACGGCGTGGAAGTGCACAACGCCAAGACCAAGCCCAGAGAGGAACAGTTCA

ACAGCACCTTCCGGGTGGTGTCCGTGCTGACCGTGGTGCATCAGGACTGGCTGAACGGCAAAGAGTACAAGTGCAAGGTG

TCCAACAAGGGCCTGCCTGCCCCCATCGAGAAAACCATCAGCAAGACCAAAGGCCAGCCCCGCGAGCCCCAGGTGTACAC

ACTGCCTCCAAGCCGGGAAGAGATGACCAAGAACCAGGTGTCCCTGACCTGTCTCGTGAAAGGCTTCTACCCCTCCGATA

TCGCCGTGGAATGGGAGAGCAACGGCCAGCCCGAGAACAACTACAAGACCACCCCCCCCATGCTGGACAGCGACGGCTCA

TTCTTCCTGTACAGCAAGCTGACAGTGGACAAGTCCCGGTGGCAGCAGGGCAACGTGTTCAGCTGCAGCGTGATGCACGA

GGCCCTGCACAACCACTACACCCAGAAGTCCCTGAGCCTGAGCCCTGGC
```

>TPP-3322 Light Chain (DNA)

```
GACATCGTGATGACCCAGAGCCAGAAATTCATGAGCACCAGCGTGGGCGACCGGGTGTCCATCACATGCAAGGCCAGCCA
|~~~~~~~~~~~~~~~~~~~~~~~~~~~~~~~~~~~~~~~~~~~~~~~~~~~~~~~~~~~~~~~~~~~~~~~~~~~~~~~

GAACGTGGGCACCGCCGTGGCCTGGTATCAGCAGAAGCCCGGCCAGAGCCCCAAGCTGCTGATCTACAGCGCCAGCAACC
-------------------------------------------------------------------------------V

GGTACACCGGCGTGCCCGACAGATTCACAGGCAGCGGCAGCGGCACCGACTTCACCTTCACCATCAGCAACATGCAGAGC
L-------------------------------------------------------------------------------

GAGGACCTGGCCGACTACTTCTGCCAGCAGTACAGCAGCTACCCCCTGACCTTCGGAGCCGGCACCAAGCTGGAACTGAA
--------------------------------------------------------------------------------

ACGAACCGTGGCCGCTCCCAGCGTGTTCATCTTCCCACCTAGCGACGAGCAGCTGAAGTCCGGCACAGCCTCTGTCGTGT
|

GCCTGCTGAACAACTTCTACCCCCGCGAGGCCAAGGTGCAGTGGAAGGTGGACAATGCCCTGCAGAGCGGCAACAGCCAG

GAAAGCGTGACCGAGCAGGACAGCAAGGACTCCACCTACAGCCTGAGCAGCACCCTGACCCTGAGCAAGGCCGACTACGA

GAAGCACAAGGTGTACGCCTGCGAAGTGACCCACCAGGGCCTGTCTAGCCCCGTGACCAAGAGCTTCAACCGGGGCGAGT

GT
```

>TPP-3323 VH (PRT)

```
QVTLKESGPGILQPSQTLSLTCSFSGFSLTTYGIGVGWIRQPSGKGLEWLAHIWWNDNKYYNTALKSRLTISKDTSNNQV
                                 |-----|                      |----HCDR2------|
                                 HCDR1

FLKIASVDTADTATYYCARISLPYFDYWGQGTTLTVSS
                   |------|
                   HCDR3
```

>TPP-3323 VL (PRT)

```
DIVMTQSQKFMSTSVGDRVSITCKASQNVGTAVAWYQQKPGQSPKLLIYSASNRYTGVPDRFTGSGSGTDFTLTISNMQS
                           |--LCDR1--|                         |-----|
                                                               LCDR2

EDLADYFCQQYNNYPLTFGAGTKLELK
        |-LCDR3-|
```

>TPP-3323 Heavy Chain (PRT)

```
QVTLKESGPGILQPSQTLSLTCSFSGFSLTTYGIGVGWIRQPSGKGLEWLAHIWWNDNKYYNTALKSRLTISKDTSNNQV
```

FIG. 8H

```
|-----------------------------------------------------------VH--------------------
                                  |-----|                  |----HCDR2-----|
                                  HCDR1

FLKIASVDTADTATYYCARISLPYFDYWGQGTTLTVSSASTKGPSVFPLAPCSRSTSESTAALGCLVKDYFPEPVTVSWN
--------------------------------------|
                      |------|
                      HCDR3

SGALTSGVHTFPAVLQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVVHQDWLNGKEYKCKV

SNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG
```

>TPP-3323 Light Chain (PRT)

```
DIVMTQSQKFMSTSVGDRVSITCKASQNVGTAVAWYQQKPGQSPKLLIYSASNRYTGVPDRFTGSGSGTDFTLTISNMQS
|----------------------------------------------------VL---------------------------
                        |--LCDR1--|                  |-----|
                                                     LCDR2

EDLADYFCQQYNNYPLTFGAGTKLELKRTVAAPSVFIFPPSDEQLKSGTASVVCLLNNFYPREAKVQWKVDNALQSGNSQ
---------------------------|
        |-LCDR3-|

ESVTEQDSKDSTYSLSSTLTLSKADYEKHKVYACEVTHQGLSSPVTKSFNRGEC
```

>TPP-3323 Heavy Chain (DNA)

```
CAAGTGACCCTGAAAGAGTCCGGCCCTGGCATCCTGCAGCCTTCCCAGACCCTGTCCCTGACCTGCTCCTTCTCCGGCTT
|---------------------------------------------------------------------------------

CTCCCTGACCACCTACGGCATCGGCGTGGGCTGGATCAGACAGCCTTCTGGCAAGGGCCTGGAATGGCTGGCCCACATCT
----------------------------------------------------------------------------------

GGTGGAACGACAACAAGTACTACAACACCGCCCTGAAGTCCCGGCTGACCATCTCCAAGGACACCTCCAACAACCAGGTG
----------------VH----------------------------------------------------------------

TTCCTGAAGATCGCCTCCGTGGACACCGCCGATACCGCCACCTACTACTGCGCCCGGATCTCCCTGCCCTACTTCGACTA
----------------------------------------------------------------------------------

TTGGGGCCAGGGCACCACCCTGACCGTCAGCTCAGCTTCCACCAAGGGCCCCTCCGTGTTCCCTCTGGCCCCTTGCTCCC
------------------------------------|

GGTCCACCTCTGAGTCTACCGCCGCTCTGGGCTGCCTGGTGAAAGACTACTTCCCCGAGCCCGTGACCGTGTCCTGGAAC

TCTGGCGCCCTGACCTCCGGCGTGCACACCTTTCCAGCCGTGCTGCAGTCCTCCGGCCTGTACTCCCTGTCCTCCGTGGT

GACAGTGCCCTCCTCCAACTTCGGCACCCAGACCTACACCTGTAACGTGGACCACAAGCCCTCCAACACCAAGGTGGACA

AGACCGTGGAACGGAAGTGCTGCGTGGAATGCCCACCCTGTCCTGCTCCACCTGTGGCTGGCCCCAGCGTGTTCCTGTTC

CCCCCAAAGCCCAAGGACACCCTGATGATCTCCCGGACCCCCGAAGTGACCTGCGTGGTGGTGGACGTGTCCCACGAGGA
```

FIG. 8I

```
CCCCGAGGTGCAGTTCAATTGGTACGTGGACGGCGTGGAAGTGCACAACGCCAAGACCAAGCCCAGAGAGGAACAGTTCA

ACTCCACCTTCCGGGTGGTGTCCGTGCTGACCGTGGTGCATCAGGACTGGCTGAACGGCAAAGAGTACAAGTGCAAGGTC

TCCAACAAGGCCCTGCCTGCCCCCATCGAAAAGACCATCAGCAAGACCAAGGGCCAGCCCCGCGAGCCCCAGGTGTACAC

ACTGCCCCCCAGCCGGGAAGAGATGACCAAGAACCAGGTGTCCCTGACCTGTCTGGTGAAAGGCTTCTACCCCTCCGACA

TTGCCGTGGAATGGGAGTCCAACGGACAGCCTGAGAACAACTACAAGACCACCCCCCCCATGCTGGACTCCGACGGCTCA

TTCTTCCTGTACTCCAAGCTGACAGTGGACAAGTCCCGGTGGCAGCAGGGCAACGTGTTCTCCTGCTCCGTGATGCACGA

GGCCCTGCACAACCACTACACCCAGAAGTCCCTGTCCCTGAGCCCCGGC
```

>TPP-3323 Light Chain (DNA)

```
GACATCGTGATGACCCAGTCCCAGAAATTCATGTCCACCTCCGTGGGCGACCGGGTGTCCATCACATGCAAGGCCTCTCA
|-------------------------------------------------------------------------------

GAACGTGGGCACCGCCGTGGCCTGGTATCAGCAGAAGCCTGGCCAGTCCCCCAAGCTGCTGATCTACTCCGCCTCCAACC
-------------------------------------------------------------------------------V

GGTACACCGGCGTGCCCGATAGATTCACCGGCTCTGGCTCTGGCACCGACTTCACCCTGACCATCTCCAACATGCAGTCC
L-------------------------------------------------------------------------------

GAGGACCTGGCCGACTACTTCTGCCAGCAGTACAACAACTACCCCCTGACCTTCGGCGCTGGCACCAAGCTGGAACTGAA
--------------------------------------------------------------------------------

GAGAACCGTGGCCGCTCCCTCCGTGTTTATCTTCCCACCCTCCGACGAGCAGCTGAAGTCCGGCACAGCTTCCGTCGTGT
|

GCCTGCTGAACAACTTCTACCCCCGCGAGGCCAAGGTGCAGTGGAAGGTGGACAACGCCCTGCAGTCCGGCAACTCCCAG

GAATCCGTGACCGAGCAGGACTCCAAGGACAGCACCTACTCCCTGTCCTCTACCCTGACCCTGTCCAAGGCCGATTACGA

GAAGCACAAGGTGTACGCCTGCGAAGTGACCCACCAGGGCCTGTCTAGCCCCGTGACCAAGTCTTTCAACCGGGGCGAGT

GT
```

>TPP-3705 VH (PRT)

```
EVQLVESGGGLVQPGGSLRLSCAASGFTFSLYQMHWVRQAPGKGLEWVSWISFSGGNTGYADSVKGRFTISRDNSKNTLY
                                 |---|                  |-----HCDR2------|
                                 HCDR1

LQMNSLRAEDTAVYYCARATGYSSPWYLDFWGQGTLVTVSS
                    |--HCDR3---|
```

>TPP-3705 VL (PRT)

```
DIQMTQSPSSLSASVGDRVTITCQASHEIDNYLNWYQQKPGKAPKLLIYDAYWLKTGVPSRFSGSGSGTDFTLTISSLQP
                         |--LCDR1--|                    |-----|
                                                        LCDR2

EDIATYYCQGYDDLSVTFGGGTKVDIK
         |-LCDR3-|
```

>TPP-3705 Heavy Chain (PRT)

```
EVQLVESGGGLVQPGGSLRLSCAASGFTFSLYQMHWVRQAPGKGLEWVSWISFSGGNTGYADSVKGRFTISRDNSKNTLY
|----------------------------------------------------------VH-------------------
                                 |---|                  |-----HCDR2------|
                                 HCDR1
```

FIG. 8J

```
LQMNSLRAEDTAVYYCARATGYSSPWYLDPWGQGTLVTVSSASTKGPSVFPLAPCSRSTSESTAALGCLVKDYFPEPVTV
----------------------------------------¦
                  ¦--HCDR3---¦

SWNSGALTSGVHTFPAVLQSSGLYSLSSVVTVPSSNFGTQTYTCNVDHKPSNTKVDKTVERKCCVECPPCPAPPVAGPSV

FLFPPKPKDTLMISRTPEVTCVVVDVSHEDPEVQFNWYVDGVEVHNAKTKPREEQFNSTFRVVSVLTVVHQDWLNGKEYK

CKVSNKGLPAPIEKTISKTKGQPREPQVYTLPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPG
```

>TPP-3705 Light Chain (PRT)

```
DIQMTQSPSSLSASVGDRVTITCQASHEIDNYLNWYQQKPGKAPKLLIYDAYWLKTGVPSRFSGSGSGTDFTLTISSLQP
|-----------------------------------------------------VL---------------------------
                       |--LCDR1--|                       |------|
                                                          LCDR2

EDIATYYCQGYDDLSVTFGGGTKVDIKRTVAAPSVFIFPPSDEQLKSGTASVVCLLNNFYPREAKVQWKVDNALQSGNSQ
---------------------------|
          |-LCDR3-|

ESVTEQDSKDSTYSLSSTLTLSKADYEKHKVYACEVTHQGLSSPVTKSFNRGEC
```

>TPP-3705 Heavy Chain (DNA)

```
GAAGTGCAGCTGGTGGAATCCGGCGGAGGCCTGGTGCAGCCTGGCGGATCTCTGAGACTGTCTTGTGCCGCCTCCGGCTT
|---------------------------------------------------------------------------------

CACCTTCAGCCTGTACCAGATGCACTGGGTGCGACAGGCCCCTGGCAAGGGACTGGAATGGGTGTCCTGGATCTCCTTCT
----------------------------------------------------------------------------------

CCGGCGGCAATACCGGCTACGCCGACTCCGTGAAGGGCCGGTTCACCATCTCCCGGGACAACTCCAAGAACACCCTGTAC
----------------------VH----------------------------------------------------------

CTGCAGATGAACTCCCTGCGGGCCGAGGACACCGCCGTGTACTACTGTGCTAGAGCCACCGGCTACTCCTCCCCCTGGTA
----------------------------------------------------------------------------------

TCTGGATCCTTGGGGCCAGGGCACACTCGTGACCGTCAGCTCAGCTTCCACCAAGGGCCCCTCCGTGTTCCCTCTGGCCC
----------------------------------------------¦

CTTGCTCCCGGTCCACCTCTGAGTCTACCGCCGCTCTGGGCTGCCTGGTGAAAGACTACTTCCCCGAGCCCGTGACCGTG

TCCTGGAACTCTGGCGCCCTGACCTCCGGCGTGCACACCTTTCCAGCCGTGCTGCAGTCCTCCGGCCTGTACTCCCTGTC

CTCCGTGGTGACAGTGCCCTCCTCCAACTTCGGCACCCAGACCTACACCTGTAACGTGGACCACAAGCCCTCCAACACCA

AGGTGGACAAGACCGTGGAACGGAAGTGCTGCGTGGAATGCCCACCCTGTCCTGCTCCACCTGTGGCTGGCCCCAGCGTG

TTCCTGTTCCCCCCAAAGCCCAAGGACACCCTGATGATCTCCCGGACCCCCGAAGTGACCTGCGTGGTGGTGGACGTGTC

CCACGAGGACCCCGAGGTGCAGTTCAATTGGTACGTGGACGGCGTGGAAGTGCACAACGCCAAGACCAAGCCCAGAGAGG
```

FIG. 8K

```
AACAGTTCAACTCCACCTTCCGGGTGGTGTCCGTGCTGACCGTGGTGCATCAGGACTGGCTGAACGGCAAAGAGTACAAG

TGCAAGGTCTCCAACAAGGGCCTGCCTGCCCCCATCGAAAAGACCATCAGCAAGACCAAGGGCCAGCCCCGCGAGCCCCA

GGTGTACACACTGCCCCCCAGCCGGGAAGAGATGACCAAGAACCAGGTGTCCCTGACCTGTCTGGTGAAAGGCTTCTACC

CCTCCGACATTGCCGTGGAATGGGAGTCCAACGGACAGCCTGAGAACAACTACAAGACCACCCCCCCCATGCTGGACTCC

GACGGCTCATTCTTCCTGTACTCCAAGCTGACAGTGGACAAGTCCCGGTGGCAGCAGGGCAACGTGTTCTCCTGCTCCGT

GATGCACGAGGCCCTGCACAACCACTACACCCAGAAGTCCCTGTCCCTGAGCCCCGGC
```

>TPP-3705 Light Chain (DNA)

```
GACATCCAGATGACCCAGAGCCCTTCCAGCCTGTCCGCCTCTGTGGGCGACAGAGTGACCATCACCTGTCAGGCCTCCCA
|-------------------------------------------------------------------------------

CGAGATCGACAACTACCTGAACTGGTATCAGCAGAAGCCCGGCAAGGCCCCCAAGCTGCTGATCTACGATGCCTACTGGC
------------------------------------------------------------------------------V

TGAAAACCGGCGTGCCCTCCAGATTCTCCGGCTCTGGCTCTGGCACCGACTTTACCCTGACCATCTCCAGCCTGCAGCCC
L-------------------------------------------------------------------------------

GAGGATATCGCCACCTACTATTGTCAGGGCTACGACGACCTGTCCGTGACCTTTGGCGGAGGCACCAAGGTGGACATCAA
--------------------------------------------------------------------------------

GCGGACAGTGGCCGCTCCCTCCGTGTTTATCTTCCCACCCTCCGACGAGCAGCTGAAGTCCGGCACAGCTTCCGTCGTGT
|

GCCTGCTGAACAACTTCTACCCCCGCGAGGCCAAGGTGCAGTGGAAAGTGGATAACGCCCTGCAGTCCGGCAACTCCCAG

GAATCCGTGACCGAGCAGGACTCCAAGGACAGCACCTACTCCCTGTCCTCCACCCTGACCCTGTCCAAGGCCGACTACGA

GAAGCACAAGGTGTACGCCTGCGAAGTGACCCACCAGGGCCTGTCTAGCCCCGTGACCAAGTCTTTCAACCGGGGCGAGT

GT
```

>TPP-3707 VH (PRT)

```
EVQLVESGGGLVQPGGSLRLSCAASGFTFSLYQMHWVRQAPGKGLEWVSWISPSGGNTGYADSVKGRFTISRDNSKNTLY
                              |---|              |-----HCDR2------|
                              HCDR1

LQMNSLRAEDTAVYYCARATGYSSPWYLDPWGQGTLVTVSS
                 |--HCDR3---|
```

>TPP-3707 VL (PRT)

```
DIQMTQSPSSLSASVGDRVTITCQASHEIDNYLNWYQQKPGKAPKLLIYDAYWSKTGVPSRFSGSGSGTDFTLTISSLQP
                      |--LCDR1--|              |-----|
                                               LCDR2

EDIATYYCQGYDDLSVTFGGGTKVDIK
        |-LCDR3-|
```

>TPP-3707 Heavy Chain (PRT)

```
EVQLVESGGGLVQPGGSLRLSCAASGFTFSLYQMHWVRQAPGKGLEWVSWISPSGGNTGYADSVKGRFTISRDNSKNTLY
|----------------------------------------------------------VH--------------------
                              |---|              |-----HCDR2-----|
                              HCDR1

LQMNSLRAEDTAVYYCARATGYSSPWYLDPWGQGTLVTVSSASTKGPSVFPLAPCSRSTSESTAALGCLVKDYFPEPVTV
----------------------------------------|
```

FIG. 8L

```
                          |--HCDR3---|

SWNSGALTSGVHTFPAVLQSSGLYSLSSVVTVPSSNFGTQTYTCNVDHKPSNTKVDKTVERKCCVECPPCPAPPVAGPSV

FLFPPKPKDTLMISRTPEVTCVVVDVSHEDPEVQFNWYVDGVEVHNAKTKPREEQFNSTFRVVSVLTVVHQDWLNGKEYK

CKVSNKGLPAPIEKTISKTKGQPREPQVYTLPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPG
```

>TPP-3707 Light Chain (PRT)

```
DIQMTQSPSSLSASVGDRVTITCQASHEIDNYLNWYQQKPGKAPKLLIYDAYWSKTGVPSRFSGSGSGTDFTLTISSLQP
|-----------------------------------------------------VL-------------------------
                           |--LCDR1--|                     |-----|
                                                           LCDR2

EDIATYYCQGYDDLSVTFGGGTKVDIKRTVAAPSVFIFPPSDEQLKSGTASVVCLLNNFYPREAKVQWKVDNALQSGNSQ
---------------------------|
         |-LCDR3-|

ESVTEQDSKDSTYSLSSTLTLSKADYEKHKVYACEVTHQGLSSPVTKSFNRGEC
```

>TPP-3707 Heavy Chain (DNA)

```
GAAGTGCAGCTGGTGGAATCCGGCGGAGGCCTGGTGCAGCCTGGCGGATCTCTGAGACTGTCTTGTGCCGCCTCCGGCTT
|--------------------------------------------------------------------------------

CACCTTCAGCCTGTACCAGATGCACTGGGTGCGACAGGCCCCTGGCAAGGGACTGGAATGGGTGTCCTGGATCTCCTTCT
---------------------------------------------------------------------------------

CCGGCGGCAATACCGGCTACGCCGACTCCGTGAAGGGCCGGTTCACCATCTCCCGGGACAACTCCAAGAACACCCTGTAC
----------------------VH---------------------------------------------------------

CTGCAGATGAACTCCCTGCGGGCCGAGGACACCGCCGTGTACTACTGTGCTAGAGCCACCGGCTACTCCTCCCCCTGGTA
---------------------------------------------------------------------------------

TCTGGATCCTTGGGGCCAGGGCACACTCGTGACCGTCAGCTCAGCTTCCACCAAGGGCCCCTCCGTGTTCCCTCTGGCCC
---------------------------------------------|

CTTGCTCCCGGTCCACCTCTGAGTCTACCGCCGCTCTGGGCTGCCTGGTGAAAGACTACTTCCCCGAGCCCGTGACCGTG

TCCTGGAACTCTGGCGCCCTGACCTCCGGCGTGCACACCTTTCCAGCCGTGCTGCAGTCCTCCGGCCTGTACTCCCTGTC

CTCCGTGGTGACAGTGCCCTCCTCCAACTTCGGCACCCAGACCTACACCTGTAACGTGGACCACAAGCCCTCCAACACCA

AGGTGGACAAGACCGTGGAACGGAAGTGCTGCGTGGAATGCCCACCCTGTCCTGCTCCACCTGTGGCTGGCCCCAGCGTG

TTCCTGTTCCCCCCAAAGCCCAAGGACACCCTGATGATCTCCCGGACCCCCGAAGTGACCTGCGTGGTGGTGGACGTGTC

CCACGAGGACCCCGAGGTGCAGTTCAATTGGTACGTGGACGGCGTGGAAGTGCACAACGCCAAGACCAAGCCCAGAGAGG

AACAGTTCAACTCCACCTTCCGGGTGGTGTCCGTGCTGACCGTGGTGCATCAGGACTGGCTGAACGGCAAAGAGTACAAG
```

FIG. 8M

```
TGCAAGGTCTCCAACAAGGGCCTGCCTGCCCCCATCGAAAAGACCATCAGCAAGACCAAGGGCCAGCCCCGCGAGCCCCA

GGTGTACACACTGCCCCCCAGCCGGGAAGAGATGACCAAGAACCAGGTGTCCCTGACCTGTCTGGTGAAAGGCTTCTACC

CCTCCGACATTGCCGTGGAATGGGAGTCCAACGGACAGCCTGAGAACAACTACAAGACCACCCCCCCCATGCTGGACTCC

GACGGCTCATTCTTCCTGTACTCCAAGCTGACAGTGGACAAGTCCCGGTGGCAGCAGGGCAACGTGTTCTCCTGCTCCGT

GATGCACGAGGCCCTGCACAACCACTACACCCAGAAGTCCCTGTCCCTGAGCCCCGGC
```

>TPP-3707 Light Chain (DNA)

```
GACATCCAGATGACCCAGAGCCCTTCCAGCCTGTCCGCCTCTGTGGGCGACAGAGTGACCATCACCTGTCAGGCCTCCCA
|-------------------------------------------------------------------------------

CGAGATCGACAACTACCTGAACTGGTATCAGCAGAAGCCCGGCAAGGCCCCCAAGCTGCTGATCTACGACGCCTACTGGT
-------------------------------------------------------------------------------V

CCAAGACCGGCGTGCCCTCCAGATTCTCCGGCTCTGGCTCTGGCACCGACTTTACCCTGACCATCTCCAGCCTGCAGCCC
L-------------------------------------------------------------------------------

GAGGATATCGCCACCTACTATTGTCAGGGCTACGACGACCTGTCCGTGACCTTTGGCGGAGGCACCAAGGTGGACATCAA
--------------------------------------------------------------------------------

GCGGACAGTGGCCGCTCCCTCCGTGTTTATCTTCCCACCCTCCGACGAGCAGCTGAAGTCCGGCACAGCTTCCGTCGTGT
|

GCCTGCTGAACAACTTCTACCCCCGCGAGGCCAAGGTGCAGTGGAAAGTGGATAACGCCCTGCAGTCCGGCAACTCCCAG

GAATCCGTGACCGAGCAGGACTCCAAGGACAGCACCTACTCCCTGTCCTCCACCCTGACCCTGTCCAAGGCCGACTACGA

GAAGCACAAGGTGTACGCCTGCGAAGTGACCCACCAGGGCCTGTCTAGCCCCGTGACCAAGTCTTTCAACCGGGGCGAGT

GT
```

>TPP-3714 VH (PRT)

```
QVTLRESGPALVKPTQTLTLTCTFSGFSLSTYGIGVGWIRQPPGKALEWLAHIWWNDNKYYSTSLKTRLTISKDTSKNQV
                              |------|                    |-----HCDR2------|
                              HCDR1

VLTMTNMDPVDTATYYCARISLPYFDYWGQGTLVTVSS
                     |-------|
                     HCDR3
```

>TPP-3714 VL (PRT)

```
DIQLTQSPSFLSASVGDRVTITCKASQNVGTAVAWYQQKPGKAPKLLIYSASNRYTGVPSRFSGSGSGTEFTLTISSLQP
                           |--LCDR1--|                       |------|
                                                             LCDR2

EDFATYYCQQYSSYPLTFGGGTKVEIK
        |-LCDR3-|
```

>TPP-3714 Heavy Chain (PRT)

```
QVTLRESGPALVKPTQTLTLTCTFSGFSLSTYGIGVGWIRQPPGKALEWLAHIWWNDNKYYSTSLKTRLTISKDTSKNQV
|-----------------------------------------------------------VH------------------
                              |------|                    |-----HCDR2------|
                              HCDR1

VLTMTNMDPVDTATYYCARISLPYFDYWGQGTLVTVSSASTKGPSVFPLAPCSRSTSESTAALGCLVKDYFPEPVTVSWN
-------------------------------------|
                     |-------|
                     HCDR3
```

FIG. 8N

```
SGALTSGVHTFPAVLQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVVHQDWLNGKEYKCKV

SNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG

>TPP-3714 Light Chain (PRT)
DIQLTQSPSFLSASVGDRVTITCKASQNVGTAVAWYQQKPGKAPKLLIYSASNRYTGVPSRFSGSGSGTEFTLTISSLQP
|----------------------------------------------------VL---------------------------
                          |--LCDR1--|                 |-----|
                                                      LCDR2

EDFATYYCQQYSSYPLTFGGGTKVEIKRTVAAPSVFIFPPSDEQLKSGTASVVCLLNNFYPREAKVQWKVDNALQSGNSQ
----------------------------|
         |~LCDR3~|

ESVTEQDSKDSTYSLSSTLTLSKADYEKHKVYACEVTHQGLSSPVTKSFNRGEC

>TPP-3714 Heavy Chain (DNA)
CAAGTGACCCTGAGAGAGTCCGGCCCTGCCCTCGTGAAGCCTACCCAGACCCTGACACTGACCTGCACCTTCTCCGGCTT
|---------------------------------------------------------------------------------

CTCCCTGTCCACCTACGGCATCGGCGTGGGCTGGATCAGACAGCCTCCTGGCAAGGCCCTGGAATGGCTGGCTCACATCT
----------------------------------------------------------------------------------

GGTGGAACGACAACAAGTACTACTCCACCTCCCTGAAAACCCGGCTGACCATCTCCAAGGACACCTCCAAGAACCAGGTG
-----------------VH---------------------------------------------------------------

GTGCTGACCATGACCAACATGGACCCCGTGGACACCGCCACCTACTACTGCGCCAGAATCTCCCTGCCCTACTTCGACTA
----------------------------------------------------------------------------------

CTGGGGCCAGGGCACACTCGTGACCGTCAGCTCAGCTTCCACCAAGGGCCCCTCCGTGTTCCCTCTGGCCCCTTGCTCCC
-----------------------------------|

GGTCCACCTCTGAGTCTACCGCCGCTCTGGGCTGCCTGGTGAAAGACTACTTCCCCGAGCCCGTGACCGTGTCCTGGAAC

TCTGGCGCCCTGACCTCCGGCGTGCACACCTTTCCAGCCGTGCTGCAGTCCTCCGGCCTGTACTCCCTGTCCTCCGTGGT

GACAGTGCCCTCCTCCAACTTCGGCACCCAGACCTACACCTGTAACGTGGACCACAAGCCTTCCAACACCAAGGTGGACA

AGACCGTGGAACGGAAGTGCTGCGTGGAATGCCCACCCTGTCCTGCTCCACCTGTGGCTGGCCCCAGCGTGTTCCTGTTC

CCCCCAAAGCCCAAGGACACCCTGATGATCTCCCGGACCCCCGAAGTGACCTGCGTGGTGGTGGACGTGTCCCACGAGGA

CCCCGAGGTGCAGTTCAATTGGTACGTGGACGGCGTGGAAGTGCACAACGCCAAGACCAAGCCCAGAGAGGAACAGTTCA

ACTCCACCTTCCGGGTGGTGTCCGTGCTGACCGTGGTGCATCAGGACTGGCTGAACGGCAAAGAGTACAAGTGCAAGGTC

TCCAACAAGGGCCTGCCTGCCCCCATCGAAAAGACCATCAGCAAGACCAAGGGCCAGCCCCGCGAGCCCCAGGTGTACAC
```

FIG. 8O

```
ACTGCCCCCCAGCCGGGAAGAGATGACCAAGAACCAGGTGTCCCTGACCTGTCTGGTGAAAGGCTTCTACCCCTCCGACA

TTGCCGTGGAATGGGAGTCCAACGGACAGCCTGAGAACAACTACAAGACCACCCCCCCCATGCTGGACTCGGACGGCTCA

TTCTTCCTGTACTCCAAGCTGACAGTGGACAAGTCCCGGTGGCAGCAGGGCAACGTGTTCTCCTGCTCCGTGATGCACGA

GGCCCTGCACAACCACTACACCCAGAAGTCCCTGTCCCTGAGCCCCGGC
```

>TPP-3714 Light Chain (DNA)

```
GATATCCAGCTGACCCAGTCCCCCAGCTTCCTGTCTGCCTCTGTGGGCGACAGAGTGACCATCACATGCAAGGCCTCCCA
|-------------------------------------------------------------------------------

GAACGTGGGCACCGCCGTGGCTTGGTATCAGCAGAAGCCTGGCAAGGCCCCCAAGCTGCTGATCTACTCCGCCTCCAACC
------------------------------------------------------------------------------V

GGTACACCGGCGTGCCCTCTAGATTCTCCGGCTCTGGCTCTGGCACCGAGTTTACCCTGACCATCTCCAGCCTGCAGCCC
L-------------------------------------------------------------------------------

GAGGACTTCGCCACCTACTACTGCCAGCAGTACTCCTCCTACCCGCTGACCTTTGGCGGAGGCACCAAGGTGGAAATCAA
--------------------------------------------------------------------------------

GCGGACCGTGGCCGCTCCCTCCGTGTTTATCTTCCCACCCTCCGACGAGCAGCTGAAGTCCGGCACAGCTTCCGTCGTGT
|

GCCTGCTGAACAACTTCTACCCCCGCGAGGCCAAGGTGCAGTGGAAGGTGGACAACGCCCTGCAGTCCGGCAACTCCCAG

GAATCCGTGACCGAGCAGGACTCCAAGGACAGCACCTACTCCCTGTCCTCCACCCTGACCCTGTCCAAGGCCGACTACGA

GAAGCACAAGGTGTACGCCTGCGAAGTGACCCACCAGGGCCTGTCTAGCCCCGTGACCAAGTCTTTCAACCGGGGCGAGT

GT
```

>TPP-3820 VH (PRT)

```
QVTLRESGPALVKPTQTLTLTCTFSGFSLTTYGIGVGWIRQPPGKGLEWLAHIWWNDNKYYSTSLKTRLTISKDTSKNQV
                                |-----|                |----HCDR2-----|
                                HCDR1

VLTMTNMDPVDTATYYCARISLPYFDYWGQGTLVTVSS
                      |------|
                      HCDR3
```

>TPP-3820 VL (PRT)

```
DIQLTQSPSFLSASVGDRVTITCKASQNVGTAVAWYQQKPGKAPKLLIYSASNRYTGVPSRFSGSGSGTEFTLTISSLQP
                        |--LCDR1--|                   |-----|
                                                       LCDR2

EDFATYYCQQYNNYPLTFGGGTKVEIK
         |-LCDR3-|
```

>TPP-3820 Heavy Chain (PRT)

```
QVTLRESGPALVKPTQTLTLTCTFSGFSLTTYGIGVGWIRQPPGKGLEWLAHIWWNDNKYYSTSLKTRLTISKDTSKNQV
|-----------------------------------------------------------VH------------------
                                |-----|                |----HCDR2-----|
                                HCDR1

VLTMTNMDPVDTATYYCARISLPYFDYWGQGTLVTVSSASTKGPSVFPLAPCSRSTSESTAALGCLVKDYFPEPVTVSWN
--------------------------------------|
                      |------|
                      HCDR3

SGALTSGVHTFPAVLQSSGLYSLSSVVTVPSSNFGTQTYTCNVDHKPSNTKVDKTVERKCCVECPPCPAPPVAGPSVFLF
```

FIG. 8P

```
PPKPKDTLMISRTPEVTCVVVDVSHEDPEVQFNWYVDGVEVHNAKTKPREEQFNSTFRVVSVLTVVHQDWLNGKEYKCKV

SNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG


>TPP-3820 Light Chain (PRT)
DIQLTQSPSFLSASVGDRVTITCKASQNVGTAVAWYQQKPGKAPKLLIYSASNRYTGVPSRFSGSGSGTEFTLTISSLQP
|------------------------------------------------------VL---------------------------
                           |--LCDR1--|                     |-----|
                                                           LCDR2

EDFATYYCQQYNNYPLTFGGGTKVEIKRTVAAPSVFIFPPSDEQLKSGTASVVCLLNNFYPREAKVQWKVDNALQSGNSQ
---------------------------|
         |-LCDR3-|

ESVTEQDSKDSTYSLSSTLTLSKADYEKHKVYACEVTHQGLSSPVTKSFNRGEC


>TPP-3820 Heavy Chain (DNA)
CAAGTGACCCTGAGAGAGTCCGGCCCTGCCCTCGTGAAGCCTACCCAGACCCTGACACTGACCTGCACCTTCAGCGGCTT
|-------------------------------------------------------------------------------

CAGCCTGACCACCTACGGCATCGGCGTGGGCTGGATCAGACAGCCTCCTGGCAAGGGCCTGGAATGGCTGGCCCACATCT
--------------------------------------------------------------------------------

GGTGGAACGACAACAAGTACTACAGCACCAGCCTGAAAACCCGGCTGACCATCAGCAAGGACACCAGCAAGAACCAGGTG
----------------VH--------------------------------------------------------------

GTGCTGACCATGACCAACATGGACCCCGTGGACACCGCCACCTACTACTGCGCCAGAATCAGCCTGCCCTACTTCGACTA
--------------------------------------------------------------------------------

CTGGGGCCAGGGCACCCTCGTGACAGTGTCATCAGCCAGCACCAAGGGCCCCAGCGTGTTCCCTCTGGCCCCTTGTAGCA
----------------------------------|

GAAGCACCAGCGAGTCTACAGCCGCCCTGGGCTGCCTCGTGAAGGACTACTTTCCCGAGCCCGTGACCGTGTCCTGGAAC

TCTGGCGCTCTGACAAGCGGCGTGCACACCTTTCCAGCCGTGCTGCAGAGCAGCGGCCTGTACTCTCTGAGCAGCGTCGT

GACAGTGCCCAGCAGCAACTTCGGCACCCAGACCTACACCTGTAACGTGGACCACAAGCCCAGCAACACCAAGGTGGACA

AGACCGTGGAACGGAAGTGCTGCGTGGAATGCCCCCCTTGTCCTGCCCCTCCAGTGGCTGGCCCTTCCGTGTTCCTGTTC

CCCCCAAAGCCCAAGGACACCCTGATGATCAGCCGGACCCCCGAAGTGACCTGCGTGGTGGTGGATGTGTCCCACGAGGA

CCCCGAGGTGCAGTTCAATTGGTACGTGGACGGCGTGGAAGTGCACAACGCCAAGACCAAGCCCAGAGAGGAACAGTTCA

ACAGCACCTTCCGGGTGGTGTCCGTGCTGACCGTGGTGCATCAGGACTGGCTGAACGGCAAAGAGTACAAGTGCAAGGTG

TCCAACAAGGGCCTGCCTGCCCCCATCGAGAAAACCATCAGCAAGACCAAAGGCCAGCCCCGCGAGCCCCAGGTGTACAC

ACTGCCTCCAAGCCGGGAAGAGATGACCAAGAACCAGGTGTCCCTGACCTGTCTCGTGAAAGGCTTCTACCCCTCCGATA
```

FIG. 8Q

```
TCGCCGTGGAATGGGAGAGCAACGGCCAGCCCGAGAACAACTACAAGACCACCCCCCCATGCTGGACAGCGACGGCTCA

TTCTTCCTGTACAGCAAGCTGACAGTGGACAAGTCCCGGTGGCAGCAGGGCAACGTGTTCAGCTGCAGCGTGATGCACGA

GGCCCTGCACAACCACTACACCCAGAAGTCCCTGAGCCTGAGCCCTGGC
```

>TPP-3820 Light Chain (DNA)

```
GATATCCAGCTGACCCAGAGCCCCAGCTTTCTGAGCGCCAGCGTGGGCGACAGAGTGACCATCACATGCAAGGCCAGCCA
|-------------------------------------------------------------------------------

GAACGTGGGCACAGCCGTGGCCTGGTATCAGCAGAAGCCTGGCAAGGCCCCCAAGCTGCTGATCTACAGCGCCAGCAACC
------------------------------------------------------------------------------V

GGTACACCGGCGTGCCCAGCAGATTTTCTGGCAGCGGCTCCGGCACCGAGTTCACCCTGACAATCAGCAGCCTGCAGCCC
L-------------------------------------------------------------------------------

GAGGACTTCGCCACCTACTACTGCCAGCAGTACAACAACTACCCCCTGACCTTCGGCGGAGGCACCAAGGTGGAAATTAA
--------------------------------------------------------------------------------

ACGAACCGTGGCCGCTCCCAGCGTGTTCATCTTCCCACCTAGCGACGAGCAGCTGAAGTCCGGCACAGCCTCTGTCGTGT
|

GCCTGCTGAACAACTTCTACCCCCGCGAGGCCAAGGTGCAGTGGAAGGTGGACAATGCCCTGCAGAGCGGCAACAGCCAG

GAAAGCGTGACCGAGCAGGACAGCAAGGACTCCACCTACAGCCTGAGCAGCACCCTGACCCTGAGCAAGGCCGACTACGA

GAAGCACAAGGTGTACGCCTGCGAAGTGACCCACCAGGGCCTGTCTAGCCCCGTGACCAAGAGCTTCAACCGGGGCGAGT

GT
```

>TPP-3821 VH (PRT)

```
QVTLRESGPALVKPTQTLTLTCTFSGFSLSTYGIGVGWIRQPPGKALEWLAHIWWNDNKYYSTSLKTRLTISKDTSKNQV
                                        |------|                    |----HCDR2------|
                                        HCDR1

VLTMTNMDPVDTATYYCARISLPYFDYWGQGTLVTVSS
                          |-------|
                          HCDR3
```

>TPP-3821 VL (PRT)

```
DIQLTQSPSFLSASVGDRVTITCKASQNVGTAVAWYQQKPGKAPKLLIYSAGNRYTGVPSRFSGSGSGTEFTLTISSLQP
                                |--LCDR1--|                 |------|
                                                            LCDR2

EDFATYYCQQYNNYPLTFGGGTKVEIK
          |-LCDR3-|
```

>TPP-3821 Heavy Chain (PRT)

```
QVTLRESGPALVKPTQTLTLTCTFSGFSLSTYGIGVGWIRQPPGKALEWLAHIWWNDNKYYSTSLKTRLTISKDTSKNQV
|-----------------------------------------------------------------VH------------------------
                                        |-----|                     |----HCDR2------|
                                        HCDR1

VLTMTNMDPVDTATYYCARISLPYFDYWGQGTLVTVSSASTKGPSVFPLAPCSRSTSESTAALGCLVKDYFPEPVTVSWN
-----------------------------------------|
                          |-------|
                          HCDR3

SGALTSGVHTFPAVLQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVVHQDWLNGKEYKCKV
```

FIG. 8R

```
SNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG


>TPP-3821 Light Chain (PRT)
DIQLTQSPSFLSASVGDRVTITCKASQNVGTAVAWYQQKPGKAPKLLIYSASNRYTGVPSRFSGSGSGTEFTLTISSLQP
|-----------------------------------------------------VL----------------------------
                         |--LCDR1--|                  |-----|
                                                      LCDR2

EDFATYYCQQYNNYPLTFGGGTKVEIKRTVAAPSVFIFPPSDEQLKSGTASVVCLLNNFYPREAKVQWKVDNALQSGNSQ
---------------------------|
          |-LCDR3-|

ESVTEQDSKDSTYSLSSTLTLSKADYEKHKVYACEVTHQGLSSPVTKSFNRGEC


>TPP-3821 Heavy Chain (DNA)
CAGGTCACACTGAGAGAGTCCGGCCCTGCCCTGGTGAAACCCACCCAGACCCTGACCCTGACATGCACCTTCAGCGGCTT
|-------------------------------------------------------------------------------

CAGCCTGAGCACCTACGGCATCGGCGTGGGCTGGATCAGACAGCCCCCTGGCAAGGCCCTGGAATGGCTGGCCCACATCT
--------------------------------------------------------------------------------

GGTGGAACGACAACAAGTACTACAGCACCAGCCTGAAAACCCGGCTGACCATCAGCAAGGACACCAGCAAGAACCAGGTG
-----------------VH-------------------------------------------------------------

GTGCTGACCATGACCAACATGGACCCCGTGGACACCGCCACCTACTACTGCGCCCGGATCAGCCTGCCCTACTTCGACTA
--------------------------------------------------------------------------------

CTGGGGCCAGGGCACCCTGGTGACCGTGTCCTCAGCCAGCACCAAGGGCCCCAGCGTGTTCCCTCTGGCCCCTTGTAGCA
-----------------------------------|

GAAGCACCAGCGAGTCTACAGCCGCCCTGGGCTGCCTCGTGAAGGACTACTTTCCCGAGCCCGTGACCGTGTCCTGGAAC

TCTGGCGCTCTGACAAGCGGCGTGCACACCTTTCCAGCCGTGCTGCAGAGCAGCGGCCTGTACTCTCTGAGCAGCGTCGT

GACAGTGCCCAGCAGCAACTTCGGCACCCAGACCTACACCTGTAACGTGGACCACAAGCCCAGCAACACCAAGGTGGACA

AGACCGTGGAACGGAAGTGCTGCGTGGAATGCCCCCCTTGTCCTGCCCCTCCAGTGGCTGGCCCTTCCGTGTTCCTGTTC

CCCCCAAAGCCCAAGGACACCCTGATGATCAGCCGGACCCCCGAAGTGACCTGCGTGGTGGTGGATGTGTCCCACGAGGA

CCCCGAGGTGCAGTTCAATTGGTACGTGGACGGCGTGGAAGTGCACAACGCCAAGACCAAGCCCAGAGAGGAACAGTTCA

ACAGCACCTTCCGGGTGGTGTCCGTGCTGACCGTGGTGCATCAGGACTGGCTGAACGGCAAAGAGTACAAGTGCAAGGTG

TCCAACAAGGGCCTGCCTGCCCCCATCGAGAAAACCATCAGCAAGACCAAAGGCCAGCCCCGCGAGCCCCAGGTGTACAC

ACTGCCTCCAAGCCGGGAAGAGATGACCAAGAACCAGGTGTCCCTGACCTGTCTCGTGAAAGGCTTCTACCCCTCCGATA

TCGCCGTGGAATGGGAGAGCAACGGCCAGCCCGAGAACAACTACAAGACCACCCCCCCCATGCTGGACAGCGACGGCTCA
```

FIG. 8S

```
TTCTTCCTGTACAGCAAGCTGACAGTGGACAAGTCCCGGTGGCAGCAGGGCAACGTGTTCAGCTGCAGCGTGATGCACGA

GGCCCTGCACAACCACTACACCCAGAAGTCCCTGAGCCTGAGCCCTGGC

>TPP-3821 Light Chain (DNA)
GATATCCAGCTGACCCAGAGCCCCAGCTTTCTGAGCGCCAGCGTGGGCGACAGAGTGACCATCACATGCAAGGCCAGCCA
|-------------------------------------------------------------------------------

GAACGTGGGCACAGCCGTGGCCTGGTATCAGCAGAAGCCTGGCAAGGCCCCCAAGCTGCTGATCTACAGCGCCAGCAACC
-------------------------------------------------------------------------------V

GGTACACCGGCGTGCCCAGCAGATTTTCTGGCAGCGGCTCCGGCACCGAGTTCACCCTGACAATCAGCAGCCTGCAGCCC
L-------------------------------------------------------------------------------

GAGGACTTCGCCACCTACTACTGCCAGCAGTACAACAACTACCCCCTGACCTTCGGCGGAGGCACCAAGGTGGAAATTAA
--------------------------------------------------------------------------------

ACGAACCGTGGCCGCTCCCAGCGTGTTCATCTTCCCACCTAGCGACGAGCAGCTGAAGTCCGGCACAGCCTCTGTCGTGT
|

GCCTGCTGAACAACTTCTACCCCCGCGAGGCCAAGGTGCAGTGGAAGGTGGACAATGCCCTGCAGAGCGGCAACAGCCAG

GAAAGCGTGACCGAGCAGGACAGCAAGGACTCCACCTACAGCCTGAGCAGCACCCTGACCCTGAGCAAGGCCGACTACGA

GAAGCACAAGGTGTACGCCTGCGAAGTGACCCACCAGGGCCTGTCTAGCCCCGTGACCAAGAGCTTCAACCGGGGCGAGT

GT
```

ANTI-CEACAM6 ANTIBODIES AND USES THEREOF

CROSS REFERENCE TO RELATED APPLICATIONS

This application is a continuation application of U.S. patent application Ser. No. 15/561,013, filed Sep. 22, 2017, which is a National Phase application under 35 U.S.C. § 371 of International Application No. PCT/EP2016/056104, filed Mar. 21, 2016, which claims priority benefit of European Application No. 15160292.7, filed Mar. 23, 2015, the disclosures of each of which are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052017801 seqlist.txt, date recorded: Jan. 29, 2020, size: 233 KB).

FIELD OF THE INVENTION

The present invention provides recombinant antigen-binding regions and antibodies and functional fragments containing such antigen-binding regions that are specific for human and *Macaca fascicularis* CEACAM6 (Carcinoembryonic antigen-related cell adhesion molecule 6, CD66c, Non-specific crossreacting antigen, NCA, NCA-50/90), and which therefore do not significantly cross-react with the closely related human CEACAM1, human CEACAM3, and human CEACAM5. The invention further provides methods to generate this kind of antibodies.

The antibodies, accordingly, can be used to treat cancer and other disorders and conditions associated with the expression of the CEACAM6. The invention also provides nucleic acid sequences encoding the foregoing antibodies, vectors containing the same, pharmaceutical compositions and kits with instructions for use.

BACKGROUND OF THE INVENTION

Antibody-based therapy is an effective and clinically established treatment of various cancers, including solid tumors. For example, HERCEPTIN® has been used successfully to treat breast cancer and RITUXAN® is effective in B-cell related cancer types. Central to the development of a novel successful antibody-based therapy is the isolation of antibodies against cell-surface proteins found to be preferentially expressed on target cells (e.g. cancer cells, immune cells etc) that are able to functionally modify the activity of the corresponding receptor.

Antibody blockade of immune checkpoint molecules for immune cell activation and thus for immunotherapy of cancer is a clinically validated approach. In 2011 the CTLA-4 blocking antibody Ipilimumab has been approved by the FDA for the $2^{nd}$ line therapy of metastatic melanoma (Yervoy). Another example is the blockade of the PD-1/PD-L1 axis for which several drugs are either approved or currently under clinical development and for which impressive clinical responses have been reported in melanoma, RCC and lung cancer (Henick et al., Expert Opin Ther Targets. 2014 December; 18(12):1407-20)).

Proteins of the Carcinoembryonic antigen-related cell adhesion molecule (CEACAM) family belong to the immunoglobulin (Ig) supergene family and generally exhibit a variable (V)-like domain identified as the N domain. The N domain is followed by either none or up to six constant C2-like Ig domains (termed A or B). These extracellular domains are required for CEACAM functionality as homo- and heterophilic intercellular adhesion molecules (Obrinck, Curr Opin Cell Biol. 1997 October; 9(5):616-26) or as human and rodent pathogen receptors (Kuespert et al., Curr Opin Cell Biol. 2006 October; 18(5):565-71; Voges et al., PLoS One. 2012; 7(6):e39908). CEACAM receptors associate as dimers or oligomers and multiple associations with other partners at the membrane and consequently modulate important functions. In addition to their expression in human tissues, the CEACAM gene family is highly conserved in 27 other mammalian species and is best described in mouse, rat, cattle, dog, platypus and opossum (Kammerer and Zimmermann, BMC Biol. 2010 Feb. 4; 8:12). The best characterized biological function of CEACAMs is the support of cell-cell adhesion through their homo- and heterophilic interactions, including a role in the differentiation and formation of a three-dimensional tissue structure, angiogenesis, apoptosis, tumor suppression, and metastasis. (Kuespert et al., Curr Opin Cell Biol. 2006 October; 18(5):565-71). More details on the family members are described in other reviews (Horst and Wagener, Handb Exp Pharmacol. 2004; (165): 283-341; Gray-Owen and Blumberg, Nat Rev Immunol. 2006 June; 6(6):433-46).

CEACAM6 (Carcinoembryonic antigen-related cell adhesion molecule 6, CD66c, Non-specific crossreacting antigen, NCA, NCA-50/90) is a glycosylphosphatidylinositol (GPI)-linked cell surface protein with one N-domain and 2 C2-like domains which mediate a number of possible cis or trans directed interactions of CEACAM proteins through their extracellular domains with a variety of membrane receptors, a few of which have been identified. (Beauchemin and Arabzadeh, Cancer Metastasis Rev. 2013 December; 32(3-4):643-71).

CEACAM6 is expressed in a variety of epithelia of normal human tissue such as colon (Blumenthal et al., BMC Cancer, 2007 Jan. 3; 7:2.), lung (Kolla et al., Am J Physiol Lung Cell Mol Physiol 296: L1019-L1030) and granulocytes (Kuroki et al., Biochem Biophys Res Commun. 1992 Jan. 31; 182(2):501-6). In the granulocytic lineage CEACAM6 was expressed at all stages of granulocytic maturation except for the early lineage-committed precursor cell (Strickland et al., J Pathol. 2009 July; 218(3):380-90); Scholzel et al., American Journal of Pathology, 156 (2), 595-605). CEACAM6 is not expressed in rodents. (Beauchemin et al., Exp Cell Res. 1999 Nov. 1; 252(2):243-9).

CEACAM6 expression has been described for several cancers. In colon cancer CEACAM6 is upregulated in 55% of the cases and an independent prognostic factor allowing subdivision of patients into low and high-risk groups (Jantscheff et al., J Clin Oncol. 2003 Oct. 1; 21(19):3638-46). In pancreatic adenocarcinoma 92% (n=82) of analyzed specimens were found to be positive while CEACAM6 expression was more prevalent in high-grade than in low grade PanlN lesions (Duxbury et al., Ann Surg. 2005 March; 241(3):491-6). This was confirmed in another study where >90% of invasive pancreatic adenocarcinomas (110 of 115 tested) showed a robust (over-) expression of CEACAM6 (Strickland et al., J Pathol. 2009 July; 218(3):380-90). In addition, Blumenthal et al. reported CEACAM6 expression in breast tumors, in pancreatic tumors, ovarian adenocarcinomas, lung adenocarcinoma, lymph node metastases and metastases from breast, colon and lung tumors. (Blumenthal et al., BMC Cancer. 2007 Jan. 3; 7:2).

CEACAM6 expression in breast cancer was also reported by others (Maraqa et al., Clin Cancer Res. 2008 Jan. 15; 14(2):405-11; Poola et al., Clin Cancer Res. 2006 Aug. 1; 12(15):4773-83; Balk-Moller et al., Am J Pathol. 2014 April; 184(4):1198-208); Tsang et al., Breast Cancer Res Treat. 2013 November; 142(2):311-22). In addition CEACAM6 expression has been reported in multiple myeloma (Witzens-Harig et al., Blood 2013 May 30; 121 (22):4493-503), gastric cancer (Deng et al., Genet Mol Res. 2014 Sep. 26; 13(3):7686-97) and head and neck cancer (Cameron et al., Mol Cancer. 2012 Sep. 28; 11:74).

Experimental evidence supports a role for CEACAM6 as important regulator of metastasis. Kim et al. have shown that attenuating CEACAM6 expression in LoVo cells using a CEACAM6-specific siRNA or increasing its expression in HCT116 cells, respectively, impeded or augmented invasion through the extracellular matrix (Kim et al., Clin Chim Acta. 2013 Jan. 16; 415:12-9). Suppression of CEACAM6 expression leads to elevated E-cadherin promoter activity. Blumenthal et al. showed that CEACAM5 and CEACAM6 contributed to CRC metastatic dissemination which could be blocked by monoclonal antibodies in vivo. (Blumenthal et al., BMC Cancer. 2007 Jan. 3; 7:2). Also it has been shown that CEACAM6 is expressed in CD133-positive cells in colon cancer samples able to form stem cell-enriched colon spheres for which proliferation, clonogenic potential, as well as in vivo tumorigenic potential were significantly hampered upon its silencing (Gemei et al., Cancer. 2013 Feb. 15; 119(4):729-38). In breast cancer it was shown that tamoxifen resistant samples are CEACAM6 overexpressing and CEACAM6 was a significant predictor of recurrence of the disease (Maraqa et al., Clin Cancer Res. 2008 Jan. 15; 14(2):405-11). siRNA mediated CEACAM6 silencing in a MMU1-tamoxifen-resistant MCF7 cell derivative reversed endocrine resistance, anchorage independence of these cells and invasive properties (Lewis-Wambi et al., Eur J Cancer. 2008 August; 44(12):1770-9). In lung adenocarcinoma CEACAM6 expression was significantly associated with adverse clinical outcome (Kobayashi et al., Br J Cancer. 2012 Nov. 6; 107(10):1745-53). In pancreatic cancer CEACAM6 silencing with siRNA reversed the acquired anoikis resistance of Mia(AR) pancreatic tumor cells. Overexpression of CEACAM6 in Capan2 pancreatic cancer cells augmented gemcitabine resistance whereas siRNA-mediated suppression of CEACAM6 expression in BxPC3 cells chemosensitized them to the drug by modulating AKT activity in an Src dependent manner (Duxbury et al., Cancer Res. 2004 Jun. 1; 64(11):3987-93). These effects corresponded to increased invasiveness of high CEACAM6 expressing cells exhibiting c-src activity and matrix metalloproteinase (MMP9) expression (Duxbury et al., Br J Cancer. 2004 Oct. 4; 91(7):1384-90).

T-cell responses against tumor-associated antigens have been described in many tumors (Beckhove et al., J Clin Invest. 2004 July; 114(1):67-76; Choi et al., Blood. 2005 Mar. 1; 105(5):2132-4; Sommerfeldt et al., Cancer Res. 2006 Aug. 15; 66(16):8258-65; Schmitz-Winnenthal et al., Cancer Res. 2005 Nov. 1; 65(21):10079-87.; Jager et al., Proc Natl Acad Sci USA. 2000 Apr. 25; 97(9):4760-5; Romero et al., Adv Immunol. 2006; 92:187-224) and often cause an accumulation of tumor specific memory T cells in lymphoid organs or in the blood (Choi et al., Blood. 2005 Mar. 1; 105(5):2132-4; Feuerer et al., Nat Med. 2001 April; 7(4):452-8; Letsch et al., Cancer Res. 2003 Sep. 1; 63(17): 5582-6). However, the capacity of T cells to react against autologous tumor cells is generally low (Horna and Sotomayor, Curr Cancer Drug Targets. 2007 February; 7(1):41-53); Yang and Carbone, Adv Cancer Res. 2004; 92:13-27). Many tumors have the capacity to block effector functions of T cells which contributes to the limited activity of tumor immunotherapy. T-cell unresponsiveness against tumor cells has been demonstrated for a broad variety of cancers (Pardoll, Nat Immunol. 2012 December; 13(12):1129-32).

CEACAM6 also contributes to the regulation of CD8+ T cell response. Recently, Witzens-Harig et al. demonstrated in multiple myeloma expressing several CEACAM family members that treatment with anti-CEACAM6 mAbs or siRNA silencing CEACAM6 reinstated T cell reactivity against malignant plasma cells indicating a role for CEACAM6 in CD8+ T cell response regulation (Witzens-Harig et al., Blood 2013 May 30; 121(22):4493-503). So far, a receptor for CEACAM6 on T cells has not been identified. However, co-culture of CEACAM6 positive myeloma cells with T cells resulted in the modulation of T cell signaling events including an activation of SHP phosphatases by CEACAM6 ligation (Lin and Weiss, J Cell Sci. 2001 January; 114(Pt 2):243-4; Latour et al., Mol Cell Biol. 1997 August; 17(8):4434-41; Wen et al., J Immunol. 2010 Dec. 1; 185(11):6413-9). CEACAM6 has no intrinsic signaling capacity, and its inhibitory capacity is presumably mediated by binding to receptors on the T cell surface. Such a receptor can be for example CEACAM1 for which mechanism for the modulation of innate and adaptive immune responses have been described. CEACAM1 (CD66a) possesses a cytoplasmic tail containing an immunoreceptor tyrosine-based inhibitory (ITIM) motif. CEACAM1 is stored in intracellular vesicles and upon T cell activation is rapidly (24 h to 72 h) externalized and expressed on the T cell surfacewhere it mediates the blockade of T-cell effector functions after homo- or heterophilic binding to ligands expressed on target cells (Gray-Owen and Blumberg, Nat Rev Immunol. 2006 June; 6(6):433-46). The nature of this binding is unknown and could be either homo- or heterophilic binding to other CEACAMs or binding to other components of the extracellular matrix, growth factor receptors, integrins, or cadherins. Homophilic interactions have been reported between CEACAM1 and CEACAM1 (Ortenberg et al., Mol Cancer Ther. 2012 June; 11(6):1300-10). Heterophilic CEACAM interactions have been described for example between CEACAM1 and CEACAM5, and CEACAM6 and CEACAM8 (Cavallaro and Christofori, Nat Rev Cancer. 2004 February; 4(2):118-32).

As described above CEACAM6 is a very attractive target for therapeutic intervention in cancer immunotherapy. As noted, CEACAM6 is a member of a family of highly homologous proteins. An antibody suitable for human therapy, which is relieving immunosuppression of CEACAM6, must therefore be able to distinguish between CEACAM6 and other paralogous proteins like CEACAM1, CEACAM3, CEACAM5, which each display different functions and tissue distributions, to restrict its mode of action and localization to CEACAM6 and to avoid unwanted adverse side effects.

As CEACAM6 is not only expressed on tumor cells but also on normal tissues (especially granulocytes but also epithelial cells of e.g. lung and gastrointestinal cells—Chan and Stanners, Mol Ther. 2004 June; 9(6):775-85; Strickland et al., J Pathol. 2009 July; 218(3):380-90), it is absolutely crucial to be able to predict the adverse side effect profile of the therapeutic antibody. This is all the more important, since the anticipated mode of action will be inhibition of immunosuppression, i.e. an immunoactivation, which can result in serious hazards (incident of CD28 superagonist TGN1412 trial; Suntharalingam et al., N Engl J Med. 2006 Sep. 7; 355(10):1018-28). So indirect effects on the immune system on top of direct effects on granulocytes need to be carefully assessed. To enable the development of a human therapeutic antibody and a predictive pre-clinical tolerability testing, it is mandatory for the antibody to exhibit relevant cross-reactivity to a toxicology relevant species, in case of CEACAM6 to non-human primates, preferentially *Macaca fascicularis* (cynomolgus).

As a prerequisite, a therapeutic antibody needs to bind with high affinity to human CEACAM6 on cells, to bind selectively to CEACAM6 (without binding to any paralogs), to be cross-reactive to monkey CEACAM6 within one order of magnitude of monovalent $K_D$ (to safely reflect binding on normal tissues in the toxicology monkey model even at low surface densities under non-avidity based binding conditions), to bind to a similar epitope as on human CEACAM6, to be able to relieve CEACAM6-mediated immunosuppression, to be non-immunogenic in human therapy (i.e. a human or humanized antibody), and to be stable enough to allow for clinical development, formulation and storage over extended periods of time as a pharmaceutical. The latter is important as it has been noted earlier that physical degradation (especially aggregation) may enhance immune response to a therapeutic protein (Hermeling et al., Pharm Res. 2004 June; 21(6):897-903) and aggregation is closely connected to unfolding of IgG and its thermal stability (Vermeer and Norde, Biophys J. 2000 January; 78(1):394-404).

Several anti-CEACAM6 antibodies exist. Most of them are non-human reagent antibodies, many of them are polyclonal. The specificity and selectivity to human CEACAM6 as well as cross-reactivity to monkey CEACAM6 is in most of the cases not disclosed or known.

Therapeutic antibodies directed against CEACAM6 are also known in the art. Some are not selective to human CEACAM6 (e.g. MN-3 from Immunomedics, Neo201/h16C3 from Neogenix; both binding in addition to human CEACAM5). A single domain antibody 2A3 and its fusion variants (WO2012040824 and Niu et al., J Control Release. 2012 Jul. 10; 161(1):18-24) are not characterized with respect to selectivity and cross-reactivity to monkey CEACAM6.

Selective anti-CEACAM6 antibodies apparently cross-reactive to monkey CEACAM6 are not disclosed (Strickland et al., J Pathol. 2009 July; 218(3):380-90).

The murine antibody 9A6 (Genovac/Aldevron) is the only antibody described to be able to modulate the immunosuppressive activity of CEACAM6 (Witzens-Harig et al., Blood 2013 May 30; 121(22):4493-503). 9A6 inhibits the immunosuppressive activity of CEACAM6, leading to enhanced cytokine secretion by T cells in vitro and anti-tumor efficacy in vivo (Khandelwal et al., Poster Abstract 61, Meeting Abstract from 22nd Annual International Cancer Immunotherapy Symposium Oct. 6-8, 2014, New York City, USA). Although its selectivity appears appropriate, it was previously not characterized with regards to its cross-reactivity to monkey CEACAM6. In addition, its murine nature precludes a direct therapeutic application in humans.

As shown in the examples, the antibody 9A6 binds to recombinant human CEACAM6 but no binding to recombinant *Macaca mulatta* or *Macaca fascicularis* CEACAM6 was detected. For comparison, Neo201-hIgG1 was also tested. This antibody displayed high affinity binding to both human and monkey CEACAM6. But Neo201 binds to human CEACAM5 and CEACAM6 and is therefore not specific for CEACAM6.

In conclusion there is high need for a therapeutic monoclonal antibody that comprises the following features:

i. The antibody is a high affinity binder of human CEACAM6.
ii. The antibody is selective to CEACAM6, not binding to any paralogs, especially CEACAM1, CEACAM3, and CEACAM5.
iii. The antibody is cross-reactive to monkey CEACAM6 within one order of magnitude of monovalent $K_D$.
iv. The antibody is non-immunogenic in human therapy, i.e. it is a human or humanized antibody.
v. The antibody is able to relieve CEACAM6-mediated immunosuppression.

Such an antibody does not exist in the prior art. 9A6 binding to N-terminal domain 1 of human CEACAM6 is the only known anti-CEACAM6 antibody that is able to relieve CEACAM6-mediated immunosuppression, yet lacks cross-reactivity to monkey CEACAM6 apart from being a mouse antibody. Neo201 binds to a different domain outside of N-terminal domain 1 of CEACAM6. Therapeutic efficacy of Neo201-hIgG1 has been published to be based on ADCC (Proceedings of the 102nd Annual Meeting of the American Association for Cancer Research; 2011 Apr. 2-6; Orlando, FL Philadelphia (Pa.): AACR: Du et al., Cancer Res Apr. 15, 2011; 71(8 Supplement): 4582).

The inventors assumed that relief of CEACAM6-mediated immunosuppression is connected to binding to N-terminal domain 1. But generation of antibodies binding to N-terminal domain 1 of CEACAM6 results in a challenging selectivity problem.

The sequence alignment in FIG. 1 shows a very high degree of similarity of protein sequences of human CEACAM6 and human CEACAM3, human CEACAM5 and human CEACAM1 throughout the entire extracellular region. The target region (domain 1 of human CEACAM6) is especially similar to other CEACAMs, which is also reflected in Table 7. The paralogs of human CEACAM6 (e.g. CEACAM1, CEACAM3, and CEACAM5) are much more similar to human CEACAM6 than the cynomolgus ortholog. In fact, there are only 2 positions in the N-terminal region in the primary sequence that are identical in human and cynomolgus CEACAM6 but different from amino acids in the other human paralogs (marked in FIG. 1 with asterisks).

Unexpectedly the inventors were able to find a method to generate antibodies comprising all of the desired selectivity and functional features.

SUMMARY OF THE INVENTION

This invention is related to antibodies, or antigen-binding antibody fragments thereof, or variants thereof which display high affinity for human and *Macaca fascicularis* CEACAM6 protein, and which do not significantly cross-react with the closely related human CEACAM1, human CEACAM3, and human CEACAM5. This means the antibodies, or antigen-binding antibody fragments thereof, or variants thereof are selective for CEACAM6. The antibodies provided bind to the N-terminal domain 1 which is highly conserved among these proteins.

The anti-CEACAM6 antibodies of this invention are able to change in vitro the cytokine profile of tumor specific T cells towards a more cytotoxic and/or activated phenotype characterized by increased IFN-gamma, and/or IL-2 and/or TNF-alpha secretion. Therefore the antibodies of this invention are able to relieve CEACAM6-mediated immunosuppression, and induce an immunoactivation, which finally results in an anti-tumor efficacy in vivo.

The antibodies of this invention, or antigen-binding antibody fragments thereof, or variants thereof interfere with CEACAM6 and CEACAM1 interaction which might be a mechanism for the modulation of innate and adaptive immune responses.

The antibodies of the invention are thus suitable for the treatment of cancer as well as metastases thereof, in particular CEACAM6 expressing tumors, such as colorectal cancer, non-small-cell lung cancer (NSCLC), small cell lung cancer (SCLC), pancreatic cancer, gastric cancer, breast cancer and multiple myeloma.

The invention describes antibodies that are distinguished from existing anti-CEACAM6 antibodies, in that they are able to bind to human and *Macaca fascicularis* CEACAM6 within one order of magnitude of monovalent $K_D$ (to safely reflect binding on normal tissues in toxicology monkey model even at low surface densities under non-avidity based binding conditions) and do not significantly cross-react with the closely related paralogs CEACAM1, CEACAM3, and CEACAM5. So these antibodies are suitable for preclinical toxicological studies in cynomolgus monkeys to evaluate their safety profiles. As CEACAM6 is not only expressed on tumor cells but also on normal tissues (especially granulocytes but also epithelial cells of e.g. lung and gastrointestinal cells—Chan and Stanners, Mol Ther. 2004 June; 9(6):775-85; Strickland et al., J Pathol. 2009 July; 218(3):380-90), it is absolutely crucial to be able to predict the adverse side effect profile of the therapeutic antibody. This is all the more important, since the anticipated mode of action will be inhibition of immunosuppression, i.e. an immunoactivation, which can result in serious hazards (incident of CD28 superagonist TGN1412 trial), so indirect effects on immune system on top of direct effects on granulocytes need to be carefully assessed.

Highly preferred anti-CEACAM6 antibodies of the invention are depicted in Table 1 characterized by their structural features.

In some embodiments, the anti-CEACAM6 antibody of the invention binds to an epitope of human CEACAM6, wherein said epitope comprises one or more amino acid residues selected from the group consisting of Gln60, Asn61, Arg62, Ile63, Va183, Ile84, Gly85, Thr90, Ser127, Asp128 and Leu129 of SEQ ID NO: 179.

In certain embodiments, the anti-CEACAM6 antibody of the invention binds to an epitope of human CEACAM6, wherein said epitope comprises the amino acid residues Gln60, Asn61, Arg62, Ile63, Va183, Ile84, Gly85, Thr90, Ser127, Asp128 and Leu129 of SEQ ID NO: 179.

In some embodiments, the anti-CEACAM6 antibody of the invention interacts with, e.g. binds to, an epitope of human CEACAM6, wherein said epitope comprises one, two, three four, five, eight, ten, fifteen or more amino acid residues selected from the group consisting of Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179.

In certain embodiments, the anti-CEACAM6 antibody of the invention interacts with, e.g. binds to, an epitope of human CEACAM6, wherein said epitope comprises the amino acid residues Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179.

An anti-CEACAM6 antibody of the invention might be co-administered with known medicaments, and in some instances the antibody might itself be modified. For example, an antibody could be conjugated to a cytotoxic agent, immunotoxin, toxophore or radioisotope to potentially further increase efficacy.

The invention further provides antibodies which constitute a tool for diagnosis of malignant or dysplastic conditions in which CEACAM6 expression is elevated compared to normal tissue. Provided are anti-CEACAM6 antibodies conjugated to a detectable marker. Preferred markers are a radiolabel, an enzyme, a chromophore or a fluorophore.

The invention is also related to polynucleotides encoding the antibodies of the invention, or antigen-binding fragments thereof, cells expressing the antibodies of the invention, or antigen-binding fragments thereof, methods for producing the antibodies of the invention, or antigen-binding fragments thereof, methods for inhibiting the growth of dysplastic cells using the antibodies of the invention, or antigen-binding fragments thereof, and methods for treating and detecting cancer using the antibodies of the invention, or antigen-binding fragments thereof.

The invention is also related to isolated nucleic acid sequences, each of which can encode an aforementioned antibody or antigen-binding fragment thereof that is specific for an epitope of CEACAM6. Nucleic acids of the invention are suitable for recombinant production of antibodies or antigen-binding antibody fragments. Thus, the invention also relates to vectors and host cells containing a nucleic acid sequence of the invention.

Compositions of the invention may be used for therapeutic or prophylactic applications. The invention, therefore, includes a pharmaceutical composition comprising an inventive antibody or antigen-binding fragment thereof and a pharmaceutically acceptable carrier or excipient therefore. In a related aspect, the invention provides a method for treating a disorder or condition associated with the undesired presence of CEACAM6 expressing cells. In a preferred embodiment the aforementioned disorder is cancer. Such method contains the steps of administering to a subject in need thereof an effective amount of the pharmaceutical composition that contains an inventive antibody as described or contemplated herein.

Further this invention is related to methods to generate this kind of antibodies. The invention provides instructions for using an antibody library to isolate one or more members of such library that binds specifically to CEACAM6. In addition, the invention provides instruction for immunizing mice to produce hybridoma cell lines that secrete antibodies that bind specifically to CEACAM6 and which are cross-reactive to *Macaca fascicularis* (cynomolgus monkey) CEACAM6. Instructions for humanization of murine antibodies that bind specifically to CEACAM6 are also provided by the invention.

DESCRIPTION OF THE FIGURES

FIG. 2: Amino acid sequences of the variable domains VL and VH of TPP-2971. Sequences grafted into human frameworks are highlighted as underlined bold letters. CDRs according to Kabat definition are written as italic letters. Grey shaded letters represent differences of the sequences from TPP-3187 in comparison to TPP-2971. TPP-2971, 792.15H12C9, VL (SEQ ID NO:7); TPP-2971, 792.15H12C9, VH (SEQ ID NO:3); TPP-3187, 792.15C4F4, VL (SEQ ID NO:27); TPP-3187, 792.15C4F4, VH (SEQ ID NO:23).

FIG. 3: Amino acid sequences of the variable domains VL and VH of TPP-3310 and TPP-3714. Sequences derived from the murine CDRs of TPP-2971 are highlighted as underlined bold letters. CDRs according to Kabat definition are written as italic letters. The antibodies TPP-3310 and TPP-3714 differ in two amino acids within the VH framework highlighted as underlined non-bold letters. TPP-3310, TPP-2971HU1-hIgG2Kappa, VL (SEQ ID NO:51); TPP-3310, TPP-2971HU1-hIgG2Kappa, VH (SEQ ID NO:47); TPP-3714, TPP-2971 HU2-hIgG2Kappa, VL (SEQ ID NO:123); TPP-3714, TPP-2971HU2-hIgG2Kappa, VH (SEQ ID NO:119).

FIG. 4: Amino acid sequences of the variable domains VL and VH of TPP-3820 and TPP-3821. Sequences derived from the murine CDRs of TPP-3187 are highlighted as underlined bold letters. CDRs according to Kabat definition are written as italic letters. The antibodies TPP-3820 and TPP-3821 differ in two amino acids within the VH framework highlighted as underlined non-bold letters. TPP-3820, 3187HU1-hIgG2Kappa, VL (SEQ ID NO:137); TPP-3820, 3187HU1-hIgG2Kappa, VH (SEQ ID NO:133); TPP-3821, 3187HU2-hIgG2Kappa, VL (SEQ ID NO:151); TPP-3821, 3187HU2-hIgG2Kappa, VH (SEQ ID NO:147).

FIG. 5A+FIG. 5B. IFN-gamma ELISpot assay of survivin-peptide specific T cells and KS tumor cells. 10,000 KS tumor cells were co-cultivated together with 2,500 Survivin TC for 20 h. The antibody concentration in the co-culture was 30 μg/ml. FIG. 5C. IFN-gamma ELISA assay of survivin-peptide specific TC and KS tumor cells. 10,000 KS tumor cells were co-cultivated together with 20,000 Survivin TC for 20 h. The antibody concentration in the coculture was 30 μg/ml. X-axis shows the different conditions tested: in FIG. 5A: 1=10,000 KS cells; 2=2,500 T cells; 3=no antibody treatment; 4=isotype-matched antibody control; 5=TPP-3470 (9A6-hIgG2) 6=TPP-3323; in FIG. 5B: 1=10,000 KS cells; 2=2,500 T cells; 3=no antibody treatment; 4=isotype-matched antibody control; 5=TPP-3470 (9A6-hIgG2) 6=TPP-3310; 7=TPP-3707; in C: 1=10,000 KS cells; 2=20,000 T cells; 3=no antibody treatment; 4=isotype-matched antibody control; 5=TPP-3470 (9A6-hIgG2) 6=TPP-3310; 7=TPP-3707; the Y-axis corresponds to the IFN-gamma spot-counts per well (in A and B) or IFN-gamma concentration in pg/ml (in C). Asterisks indicate statistically significant results according to Student's t test, unpaired, two-tailed. Error bars represent SEM.

FIG. 6A. IFN-gamma Luminex analysis. FIG. 6B. IL-2 Luminex analysis. FIG. 6C. TNFa Luminex analsysis. Luminex cytokine analysis of survivin-peptide specific TC and KS tumor cells. 10,000 KS tumor cells were co-cultivated together with 20,000 Survivin TC for 20 h. The antibody concentration in the coculture was 30 μg/ml. X-axis depicts the different conditions tested: 1=10,000 KS cells; 2=20,000 T cells; 3=no antibody treatment; 4=isotype-matched antibody control; 5=TPP-3470 (9A6-hIgG2) 6=TPP-3310; 7=TPP-3707; the Y-axis corresponds to the cytokine concentration in pg/ml.

FIGS. 8A-S: Annotated sequences of preferred anti-CEACAM6 antibodies of this invention. Provided are protein and DNA sequences for heavy and light chains of IgGs as well as for VH and VL regions of selected antibodies. Below the sequences important regions are annotated (VH and VL regions in full length IgGs, and the CDR regions (H-CDR1, H-CDR2, H-CDR3, L-CDR1, L-CDR2, L-CDR3)). FIG. 8A shows TPP-2971, 792.15H12C9, VH (SEQ ID NO:3); TPP-2971, 792.15H12C9, VL (SEQ ID NO:7); TPP-3186, 792.11G2D10, VH (SEQ ID NO:13); TPP-3186, 792.11G2D10, VL (SEQ ID NO:17); TPP-3187, 792.15C4F4, VH (SEQ ID NO:23); TPP-3187, 792.15C4F4, VL (SEQ ID NO:27); TPP-3308, TPP-2971X1-hIgG2Kappa, VH (SEQ ID NO:33); and N-terminus of TPP-3308, TPP-2971X1-hIgG2Kappa, VL (SEQ ID NO:37). FIG. 8B shows C-terminus of TPP-3308, TPP-2971X1-hIgG2Kappa, VL (SEQ ID NO:37), TPP-3308, TPP-2971X1-hIgG2Kappa, Heavy Chain (SEQ ID NO:43); TPP-3308, TPP-2971X1-hIgG2Kappa, Light Chain (SEQ ID NO:44); and 5' end of TPP-3308, TPP-2971X1-hIgG2Kappa, Heavy Chain (SEQ ID NO:45). FIG. 8C shows 3' end of TPP-3308, TPP-2971X1-hIgG2Kappa, Heavy Chain (SEQ ID NO:45); TPP-3308, TPP-2971X1-hIgG2Kappa, Light Chain (SEQ ID NO:46); TPP-3310, TPP-2971HU1-hIgG2Kappa, VH (SEQ ID NO:47); and N-terminus of TPP-3310, TPP-2971HU1-hIgG2Kappa, VL (SEQ ID NO:51). FIG. 8D shows C-terminus of TPP-3310, TPP-2971HU1-hIgG2Kappa, VL (SEQ ID NO:51); TPP-3310, TPP-2971HU1-hIgG2Kappa, Heavy Chain (SEQ ID NO:57); TPP-3310, TPP-2971HU1-hIgG2Kappa, Light Chain (SEQ ID NO:58); and 5' end of TPP-3310, TPP-2971HU1-hIgG2Kappa, Heavy Chain (SEQ ID NO:59). FIG. 8E shows 3' end of TPP-3310, TPP-2971HU1-hIgG2Kappa, Heavy Chain (SEQ ID NO:59); TPP-3310, TPP-2971HU1-hIgG2Kappa, Light Chain (SEQ ID NO:60); TPP-3322, TPP-3186X1-hIgG2, VH (SEQ ID NO:61); and TPP-3322, TPP-3186X1-hIgG2, VL (SEQ ID NO:65). FIG. 8F shows TPP-3322, TPP-3186X1-hIgG2, Heavy Chain (SEQ ID NO:71); TPP-3322, TPP-3186X1-hIgG2, Light Chain (SEQ ID NO:72); and 5' end of TPP-3322, TPP-3186X1-hIgG2, Heavy Chain (SEQ ID NO:73). FIG. 8G shows 3' end of TPP-3322, TPP-3186X1-hIgG2, Heavy Chain (SEQ ID NO:73); TPP-3322, TPP-3186X1-hIgG2, Light Chain (SEQ ID NO:74); TPP-3323, TPP-3187X1-hIgG2, VH (SEQ ID NO:75); TPP-3323, TPP-3187X1-hIgG2, VL (SEQ ID NO:79); and N-terminus of TPP-3323, TPP-3187X1-hIgG2, Heavy Chain (SEQ ID NO:85). FIG. 8H shows C-terminus of TPP-3323, TPP-3187X1-hIgG2, Heavy Chain (SEQ ID NO:85); TPP-3323, TPP-3187X1- hIgG2, Light Chain (SEQ ID NO:86); and 5' end of TPP-3323, TPP-3187X1-hIgG2, Heavy Chain (SEQ ID NO:87). FIG. 8I shows 3' end of TPP-3323, TPP-3187X1-hIgG2, Heavy Chain (SEQ ID NO:87); TPP-3323, TPP-3187X1-hIgG2, Light Chain (SEQ ID NO:88); TPP-3705, 090E-M007-A09-Mat1-hIgG2-hIgG2Kappa, VH (SEQ ID NO:91); TPP-3705, 090E-M007-A09-Mat1-hIgG2-hIgG2Kappa, VL (SEQ ID NO:95); and N-terminus of TPP-3705, 090E-M007-A09-Mat1-hIgG2-hIgG2Kappa, Heavy Chain (SEQ ID NO:101). FIG. 8J shows C-terminus of TPP-3705, 090E-M007-A09-Mat1-hIgG2-hIgG2Kappa, Heavy Chain (SEQ ID NO:101); TPP-3705, 090E-M007-A09-Mat1-hIgG2-hIgG2Kappa, Light Chain (SEQ ID NO:102); and 5' end of TPP-3705, 090E-M007-A09-Mat1-hIgG2-hIgG2Kappa, Heavy Chain (SEQ ID NO:103). FIG. 8K shows 3' end of TPP-3705, 090E-M007-A09-Mat1-hIgG2-hIgG2Kappa, Heavy Chain (SEQ ID NO:103); TPP-3705, 090E-M007-A09-Mat1-hIgG2-hIgG2Kappa, Light Chain (SEQ ID NO:104); TPP-3707, 090E-M007-A09-Mat2-hIgG2-hIgG2Kappa, VH (SEQ ID NO:105); TPP-3707, 090E-M007-A09-Mat2-hIgG2-hIgG2Kappa, VL (SEQ ID NO:109); and N-terminus of TPP-3707, 090E-M007-A09-Mat2-hIgG2-hIgG2Kappa, Heavy Chain (SEQ ID NO:115). FIG. 8L shows C-terminus of TPP-3707, 090E-M007-A09-Mat2-hIgG2-hIgG2Kappa, Heavy Chain (SEQ ID NO:115); TPP-3707, 090E-M007-A09-Mat2-hIgG2-hIgG2Kappa, Light Chain (SEQ ID NO:116); and 5' end of TPP-3707, 090E-M007-A09-Mat2-hIgG2-hIgG2Kappa, Heavy Chain (SEQ ID NO:117). FIG. 8M shows 3' end of TPP-3707, 090E-M007-A09-Mat2-hIgG2-hIgG2Kappa, Heavy Chain (SEQ ID NO:117); TPP-3707, 090E-M007-A09-Mat2-hIgG2-hIgG2Kappa, Light Chain (SEQ ID NO:118); TPP-3714, TPP-2971HU2-hIgG2Kappa, VH (SEQ ID NO:119); TPP-3714, TPP-2971HU2-hIgG2Kappa, VL (SEQ ID NO:123); and N-terminus of TPP-3714, TPP-2971HU2-hIgG2Kappa, Heavy Chain (SEQ ID NO:129). FIG. 8N shows C-terminus of TPP-3714, TPP-2971HU2-hIgG2Kappa, Heavy Chain (SEQ ID NO:129); TPP-3714, TPP-2971HU2-hIgG2Kappa, Light Chain (SEQ ID NO:130); and 5' end of TPP-3714, TPP-2971HU2-hIgG2Kappa, Heavy Chain (SEQ ID NO:131). FIG. 8O shows 3' end of TPP-3714, TPP-2971HU2-hIgG2Kappa, Heavy Chain (SEQ ID NO:131); TPP-3714, TPP-2971HU2-hIgG2Kappa, Light Chain (SEQ ID NO:132); TPP-3820, 3187HU1-hIgG2Kappa, VH (SEQ ID NO:133); TPP-3820, 3187HU1-hIgG2Kappa, VL (SEQ ID NO:137); and N-terminus of TPP-3820, 3187HU1-hIgG2Kappa, Heavy Chain (SEQ ID NO:143). FIG. 8P shows C-terminus of TPP-3820, 3187HU1-hIgG2Kappa, Heavy Chain (SEQ ID NO:143); TPP-3820, 3187HU1-hIgG2Kappa, Light Chain (SEQ ID NO:144); and 5' end of TPP-3820, 3187HU1-hIgG2Kappa, Heavy Chain (SEQ ID NO:145). FIG. 8Q shows 3' end of TPP-3820, 3187HU1-hIgG2Kappa, Heavy Chain (SEQ ID NO:145); TPP-3820, 3187HU1-hIgG2Kappa, Light Chain (SEQ ID NO:146); TPP-3821, 3187HU2-hIgG2Kappa, VH (SEQ ID NO:147); TPP-3821, 3187HU2-hIgG2Kappa, VL (SEQ ID NO:151); and N-terminus of TPP-3821, 3187HU2-hIgG2Kappa, Heavy Chain (SEQ ID NO:157). FIG. 8R shows C-terminus of TPP-3821, 3187HU2-hIgG2Kappa, Heavy Chain (SEQ ID NO:157); TPP-3821, 3187HU2-hIgG2Kappa, Light Chain (SEQ ID NO:158); and 5' end of TPP-3821, 3187HU2-hIgG2Kappa, Heavy Chain (SEQ ID NO:159). FIG. 8S shows 3' end of TPP-3821, 3187HU2-hIgG2Kappa, Heavy Chain (SEQ ID NO:159); and TPP-3821, 3187HU2-hIgG2Kappa, Light Chain (SEQ ID NO:160).

FIG. 11A. 20,000 KS breast cancer tumor cells in co-culture with 20,000 survivin specific T cells FIG. 11B. 40,000 HCT-116-hC6 tumor cells in co-culture with 20,000 survivin specific T cells. Cytotoxicity was monitored for ~100 h. Antibodies were used at 30 μg/ml final concentration: #1, time point of T cell addition; #2, tumor cells only; #3, no antibody; #4, isotype-matched antibody control; #5, anti-PD-L1 Ab as human IgG2; #6, TPP-3470 9A6 Ab as human IgG2; #7 TPP-3310 hIgG2. Asterisks indicate statistically significant results according to Student's t test, unpaired, two-tailed. X, x-axis, Time (Hours); Y, Y-Axis, normalized cell index.

FIG. 12A and FIG. 12B: 10,000 HCC2935 tumor cells in co-culture with 50,000 pancreatic cancer infiltrating lymphocyte cells (TIL-12). Cytotoxicity was monitored for ~150 h. An anti-CD3×EpCAM bispecific mAb (0.25 ng/ml) has been added in co-culture to direct T cells against the tumor cells independent of HLA.

FIG. 12A: #1, T cell addition; #2 tumor cells only; #3, no antibody; #4, isotype-matched antibody control; #5, anti-PD-L1 Ab as human IgG2; #6, TPP-3470; #7 TPP-3310; Antibodies were used at 30 μg/ml.

FIG. 12B: Concentration dependency of TPP-3310-mediated effect: #1, T cell addition; #2, tumor cells only; #3, TPP-3310 at 0.07 μg/ml; #4, TPP-3310 at 0.02 μg/ml; #5, isotype-matched antibody control at 50 μg/ml; #6, TPP-3310 at 0.021 μg/ml; #7, TPP-3310 at 0.062 μg/ml; #8, TPP-3310 at 1.85 μg/ml; #9, TPP-3310 at 5.5 μg/ml; #10, TPP-3310 at 16.67 μg/ml; #11, TPP-3310 at 50 μg/ml;

Figure 1:
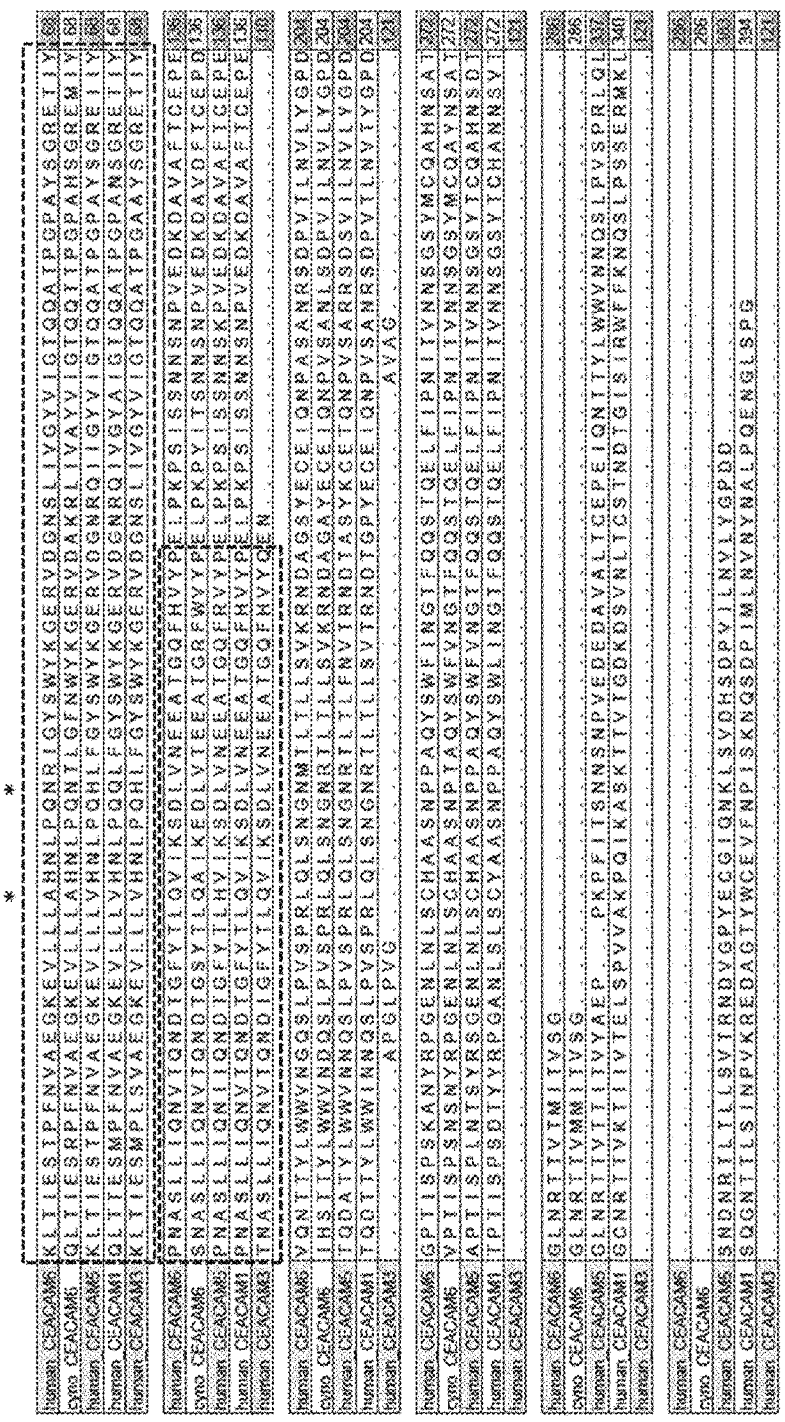
FIG. 1: Protein sequence alignment of extracellular regions of human CEACAM6 paralogs as well as *Macaca fascicularis* (cynomolgus monkey) CEACAM6 ortholog. Numbers indicate amino acid position after removal of signal peptide sequence. Positions in N-terminal region in the primary sequence that are identical in human and cynomolgus CEACAM6 but different from amino acids in this position in the other human paralogs are marked with asterisks. N-terminal domain 1 is boxed. Human_CEACAM6 (SEQ ID NO:179 (full length)); cyno_CEACAM6 (SEQ ID NO:177 (full length)); human_CEACAM5 (SEQ ID NO:176 (full length)); human_CEACAM1 (SEQ ID NO:173 (full length)); human_CEACAM3 (SEQ ID NO:175 (full length)).

X—x-axis, Time (hours); Y, Y-Axis, normalized cell index

DETAILED DESCRIPTION OF THE INVENTION

The present invention is based on the discovery of novel antibodies that have a specific affinity for CEACAM6 and can deliver a therapeutic benefit to a subject. The antibodies of the invention, which may be human, humanized or chimeric, can be used in many contexts, which are more fully described herein.

Definitions

Unless defined otherwise, all technical and scientific terms used herein have the meaning commonly understood by one of ordinary skill in the art to which this invention belongs. The following references, however, can provide one of skill in the art to which this invention pertains with a general definition of many of the terms used in this invention, and can be referenced and used so long as such definitions are consistent with the meaning commonly understood in the art. Such references include, but are not limited to, Singleton et al., Dictionary of Microbiology and Molecular Biology (2nd ed. 1994); The Cambridge Dictionary of Science and Technology (Walker ed., 1988); Hale &

Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2nd Edition, W.B. Saunders Company. Any additional technical resource available to the person of ordinary skill in the art providing definitions of terms used herein having the meaning commonly understood in the art can be consulted. For the purposes of the present invention, the following terms are further defined. Additional terms are defined elsewhere in the description. As used herein and in the appended claims, the singular forms "a," and "the" include plural reference unless the context clearly dictates otherwise. Thus, for example, reference to "a gene" is a reference to one or more genes and includes equivalents thereof known to those skilled in the art, and so forth.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

As used herein "CEACAM6" designates the "carcinoembryonic antigen-related cell adhesion molecule 6", also known as "CD66c" (Cluster of Differentiation 66c), or Non-specific crossreacting antigen, or NCA, or NCA-50/90. CEACAM6 is a glycosylphosphatidylinositol (GPI)-linked cell surface protein involved in cell-cell adhesion. CEACAM6 is highly expressed on the surface of different tumor cells like colon, pancreatic, breast and lung cancer.

A reference sequence for human CEACAM6 is available from UniProtKB/Swiss-Prot data base under accession number P40199.3 (SEQ-ID NO:179=TPP-4639), including signal peptide (positions 1-34) and propetide chain (positions 321-344). A single nucleotide polymorphism has been observed at position 239 (G to V exchange). The mature extracellular domain of human CEACAM6 consists of amino acids at position 35-320 of SEQ-ID No: 179.

```
human CEACAM6
                                    (SEQ-ID NO: 179)
MGPPSAPPCRLHVPWKEVLLTASLLTFWNPPTTAKLTIESTPFNVAEGK

EVLLLAHNLPQNRIGYSWYKGERVDGNSLIVGYVIGTQQATPGPAYSGR

ETIYPNASLLIQNVTQNDTGFYTLQVIKSDLVNEEATGQFHVYPELPKP

SISSNNSNPVEDKDAVAFTCEPEVQNTTYLWWVNGQSLPVSPRLQLSNG

NMTLTLLSVKRNDAGSYECEIQNPASANRSDPVTLNVLYGPDGPTISPS

KANYRPGENLNLSCHAASNPPAQYSWFINGTFQQSTQELFIPNITVNNS

GSYMCQAHNSATGLNRTTVTMITVSGSAPVLSAVATVGITIGVLARVAL

I
```

A *Macaca fascicularis* (cynomolgus monkey) protein sequence of CEACAM6 was deduced by the inventors and is represented by TPP-4189 (SEQ-ID No: 177). The mature extracellular domain of cynomolgus CEACAM6 consists of amino acids at position 35-320 of SEQ-ID No: 177.

```
Macaca fascicularis (cynomolgus monkey) CEACAM6
                                    (SEQ-ID NO: 177)
MGPPSAPPCRICVPWKEVLLTASLLTFWSPPTTAQLTIESRPFNVAEGK

EVLLLAHNLPQNTLGFNWYKGERVDAKRLIVAYVIGTQQTTPGPAHSGR

EMIYSNASLLIQNVTQNDTGSYTLQAIKEDLVTEEATGRFWVYPELPKP

YITSNNSNPVEDKDAVDFTCEPDIHSTTYLWWVNDQSLPVSPRLQLSNG

NRTLTLLSVKRNDAGAYECEIQNPVSANLSDPVILNVLYGPDVPTISPS

NSNYRPGENLNLSCHAASNPTAQYSWFVNGTFQQSTQELFIPNITVNNS

GSYMCQAYNSATGLNRTTVMMITVSGSAPGLSAVATVGIMIGVLARVAL

I
```

Domain organization of human and *Macaca fascicularis* (cynomolgus monkey) CEACAM6 is as follows (based on UniProtKB/Swiss-Prot data base sequence under accession number P40199.3 and SEQ-ID NO:179=TPP-4639 & SEQ-ID No: 177=TPP-4189, respectively):

| Human and cynomolgus CEACAM6 domains | Positions on SEQ-ID NO: 179 = TPP-4639 and SEQ-ID No: 177 = TPP-4189, respectively |
|---|---|
| Domain 1<br>also known as N domain<br>also known as N-terminal domain 1<br>(Ig-like V-type) | 35-142 |
| Domain 2<br>also known as A domain<br>(Ig-like C2-type 1) | 145-232 |
| Domain 3<br>also known as B domain<br>(Ig-like C2-type 2) | 237-314 |

human CEACAM1 full-length protein is available from UniProtKB/Swiss-Prot data base under accession number P13688.2 (SEQ-ID No: 173=TPP-4185). The mature extracellular domain of human CEACAM1 consists of amino acids at position 35-428 of SEQ-ID No: 173.

```
human CEACAM1
                                    (SEQ-ID NO: 173)
MGHLSAPLHRVRVPWQGLLLTASLLTFWNPPTTAQLTTESMPFNVAEGK

EVLLLVHNLPQQLFGYSWYKGERVDGNRQIVGYAIGTQQATPGPANSGR

ETIYPNASLLIQNVTQNDTGFYTLQVIKSDLVNEEATGQFHVYPELPKP

SISSNNSNPVEDKDAVAFTCEPETQDTTYLWWINNQSLPVSPRLQLSNG

NRTLTLLSVTRNDTGPYECEIQNPVSANRSDPVTLNVTYGPDTPTISPS

DTYYRPGANLSLSCYAASNPPAQYSWLINGTFQQSTQELFIPNITVNNS

GSYTCHANNSVTGCNRTTVKTIIVTELSPVVAKPQIKASKTTVTGDKDS

VNLTCSTNDTGISIRWFFKNQSLPSSERMKLSQGNTTLSINPVKREDAG

TYWCEVFNPISKNQSDPIMLNVNYNALPQENGLSPGAIAGIVIGVVALV

ALIAVALACFLHFGKTGRASDQRDLTEHKPSVSNHTQDHSNDPPNKMNE

VTYSTLNFEAQQPTQPTSASPSLTATEIIYSEVKKQ
```

human CEACAM3 full-length protein is available from UniProtKB/Swiss-Prot data base under accession number P40198.2 (SEQ-ID No: 175=TPP-4187). The mature extracellular domain of human CEACAM3 consists of amino acids at position 35-155 of SEQ-ID No: 175.

```
human CEACAM3
                                    (SEQ-ID NO: 175)
MGPPSASPHRECIPWQGLLLTASLLNFWNPPTTAKLTIESMPLSVAEGK

EVLLLVHNLPQHLFGYSWYKGERVDGNSLIVGYVIGTQQATPGAAYSGR

ETIYTNASLLIQNVTQNDIGFYTLQVIKSDLVNEEATGQFHVYQENAPG

LPVGAVAGIVTGVLVGVALVAALVCFLLLAKTGRTSIQRDLKEQQPQAL

APGRGPSHSSAFSMSPLSTAQAPLPNPRTAASIYEELLKHDTNIYCRMD

HKAEVAS
```

human CEACAM5 full-length protein is available from UniProtKB/Swiss-Prot data base under accession number P06731.3 (SEQ-ID No: 176=TPP-4188). The mature extracellular domain of human CEACAM5 consists of amino acids at position 35-685 of SEQ-ID No: 176.

```
human CEACAM5
                                    (SEQ-ID NO: 176)
MESPSAPPHRWCIPWQRLLLTASLLTFWNPPTTAKLTIESTPFNVAEGK

EVLLLVHNLPQHLFGYSWYKGERVDGNRQIIGYVIGTQQATPGPAYSGR

EIIYPNASLLIQNIIQNDTGFYTLHVIKSDLVNEEATGQFRVYPELPKP

SISSNNSKPVEDKDAVAFTCEPETQDATYLWWVNNQSLPVSPRLQLSNG

NRTLTLFNVTRNDTASYKCETQNPVSARRSDSVILNVLYGPDAPTISPL

NTSYRSGENLNLSCHAASNPPAQYSWFVNGTFQQSTQELFIPNITVNNS

GSYTCQAHNSDTGLNRTTVTTITVYAEPPKPFITSNNSNPVEDEDAVAL

TCEPEIQNTTYLWWVNNQSLPVSPRLQLSNDNRTLTLLSVTRNDVGPYE

CGIQNKLSVDHSDPVILNVLYGPDDPTISPSYTYYRPGVNLSLSCHAAS

NPPAQYSWLIDGNIQQHTQELFISNITEKNSGLYTCQANNSASGHSRTT

VKTITVSAELPKPSISSNNSKPVEDKDAVAFTCEPEAQNTTYLWWVNGQ

SLPVSPRLQLSNGNRTLTLFNVTRNDARAYVCGIQNSVSANRSDPVTLD

VLYGPDTPIISPPDSSYLSGANLNLSCHSASNPSPQYSWRINGIPQQHT

QVLFIAKITPNNNGTYACFVSNLATGRNNSIVKSITVSASGTSPGLSAG

ATVGIMIGVLVGVALI
```

The terms "anti-CEACAM6 antibody" and "an antibody that binds to CEACAM6" refer to an antibody that is capable of binding CEACAM6 with sufficient affinity such that the antibody is useful as a diagnostic and/or therapeutic agent in targeting CEACAM6. In one embodiment, the extent of binding of an anti-CEACAM6 antibody to an unrelated, non-CEACAM6 protein is less than about 5%, or preferably less than about 2% of the binding of the antibody to CEACAM6 as measured, e.g., by a surface plasmon resonance (SPR). In certain embodiments, an antibody that binds to CEACAM6 has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CEACAM6 antibody binds to an epitope of CEACAM6 that is conserved among CEACAM6 from different species.

The term "antibody", as used herein, is intended to refer to immunoglobulin molecules, preferably comprised of four polypeptide chains, two heavy (H) chains and two light (L) chains which are typically inter-connected by disulfide bonds. Each heavy chain is comprised of a heavy chain variable region (abbreviated herein as VH) and a heavy chain constant region. The heavy chain constant region can comprise e.g. three domains CH1, CH2 and CH3. Each light chain is comprised of a light chain variable region (abbreviated herein as VL) and a light chain constant region. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and up to four FRs arranged from amino-terminus to carboxy-terminus e.g. in the following order: FR1, CDR1, FR2, CDR2, FR3, CDR3, FR4.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (e.g. about residues 24-34 (L1), 50-56 (L2) and 89-97 (L3) in the light chain variable domain and 31-35 (H1), 50-65 (H2) and 95-102 (H3) in the heavy chain variable domain; (Kabat et al., Sequences of Proteins of Immulological Interest, 5th Ed. Public Health Service, National Institutes of Health, Bethesda, MD (1991)) and/or those residues from a "hypervariable loop" (e.g. about residues 26-32 (L1), 50-52 (L2) and 91-96 (L3) in the light chain variable domain and 26-32 (H1), 53-55 (H2) and 96-101 (H3) in the heavy chain variable domain (Chothia and Lesk; J Mol Biol 196: 901-917 (1987)). In some instances, a complementarity determining region can include amino acids from both a CDR region defined according to Kabat and a hypervariable loop.

Depending on the amino acid sequence of the constant domain of their heavy chains, intact antibodies can be assigned to different "classes". There are five major classes of intact antibodies: IgA, IgD, IgE, IgG, and IgM, and several of these maybe further divided into "subclasses" (isotypes), e.g., IgG1, IgG2, IgG3, IgG4, IgA1, and IgA2. A preferred class of immunoglobulins for use in the present invention is IgG.

The heavy-chain constant domains that correspond to the different classes of antibodies are called [alpha], [delta], [epsilon], [gamma], and [mu], respectively. The subunit structures and three-dimensional configurations of different classes of immunoglobulins are well known. As used herein antibodies are conventionally known antibodies and functional fragments thereof.

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hyper variable region(s) of an antibody, e.g., the CDR1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320).

"Functional fragments", "antigen-binding antibody fragments", or "antibody fragments" of the invention include but are not limited to Fab, Fab', Fab'-SH, $F(ab')_2$, and Fv fragments; diabodies; single domain antibodies (DAbs), linear antibodies; single-chain antibody molecules (scFv); and multispecific, such as bi- and tri-specific, antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "multi-specific" or "multi-functional" antibody is understood to have each of its binding sites identical. The $F(ab')_2$ or Fab may be engineered to minimize or completely remove the intermolecular disulfide interactions that occur between the CH1 and CL domains.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

Variants of the antibodies or antigen-binding antibody fragments contemplated in the invention are molecules in which the binding activity of the antibody or antigen-binding antibody fragment is maintained.

"Binding proteins" contemplated in the invention are for example antibody mimetics, such as Affibodies, Adnectins, Anticalins, DARPins, Avimers, Nanobodies (reviewed by Gebauer M. et al., Curr. Opinion in Chem. Biol. 2009; 13:245-255; Nuttall S. D. et al., Curr. Opinion in Pharmacology 2008; 8:608-617).

A "human" antibody or antigen-binding fragment thereof is hereby defined as one that is not chimeric (e.g., not "humanized") and not from (either in whole or in part) a non-human species. A human antibody or antigen-binding fragment thereof can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained there from. Another example of a human antibody or antigen-binding fragment thereof is one that is encoded by a nucleic acid isolated from a library of antibody sequences of human origin (e.g., such library being based on antibodies taken from a human natural source). Examples of human antibodies include antibodies as described in Soderlind et al., Nature Biotech. 2000, 18:853-856.

A "humanized antibody" or humanized antigen-binding fragment thereof is defined herein as one that is (i) derived from a non-human source (e.g., a transgenic mouse which bears a heterologous immune system), which antibody is based on a human germline sequence; (ii) where amino acids of the framework regions of a non-human antibody are partially exchanged to human amino acid sequences by genetic engineering or (iii) CDR-grafted, wherein the CDRs of the variable domain are from a non-human origin, while one or more frameworks of the variable domain are of human origin and the constant domain (if any) is of human origin.

A "chimeric antibody" or antigen-binding fragment thereof is defined herein as one, wherein the variable domains are derived from a non-human origin and some or all constant domains are derived from a human origin.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. The term monoclonal antibody specifically includes chimeric, humanized and human antibodies.

An "isolated" antibody is one that has been identified and separated from a component of the cell that expressed it. Contaminant components of the cell are materials that would interfere with diagnostic or therapeutic uses of the antibody, and may include enzymes, hormones, and other proteinaceous or nonproteinaceous solutes.

An "isolated" nucleic acid is one that has been identified and separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

As used herein, an antibody "binds specifically to", is "specific to/for" or "specifically recognizes" an antigen of interest, e.g. a tumor-associated polypeptide antigen target, is one that binds the antigen with sufficient affinity such that the antibody is useful as a therapeutic agent in targeting a cell or tissue expressing the antigen, and does not significantly cross-react with other proteins or does not significantly cross-react with proteins other than orthologs and variants (e.g. mutant forms, splice variants, or proteolytically truncated forms) of the aforementioned antigen target. The term "specifically recognizes" or "binds specifically to" or is "specific to/for" a particular polypeptide or an epitope on a particular polypeptide target as used herein can be exhibited, for example, by an antibody, or antigen-binding fragment thereof, having a monovalent $K_D$ for the antigen of less than about $10^{-4}$ M, alternatively less than about $10^{-5}$ M, alternatively less than about $10^{-6}$ M, alternatively less than about $10^{-7}$ M, alternatively less than about $10^{-8}$ M, alternatively less than about $10^{-9}$ M, alternatively less than about $10^{-10}$ M, alternatively less than about $10^{-11}$ M, alternatively less than about $10^{-12}$ M, or less. An antibody "binds specifically to," is "specific to/for" or "specifically recognizes" an antigen if such antibody is able to discriminate between such antigen and one or more reference antigen(s). In its most general form, "specific binding", "binds specifically to", is "specific to/for" or "specifically recognizes" is referring to the ability of the antibody to discriminate between the antigen of interest and an unrelated antigen, as determined, for example, in accordance with one of the following methods. Such methods comprise, but are not limited to surface plasmon resonance (SPR), Western blots, ELISA-, RIA-, ECL-, IRMA-tests and peptide scans. For example, a standard ELISA assay can be carried out. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative is more than 5-fold, 10-fold, 50-fold, and preferably more than 100-fold. Typically, determination of binding specificity is performed by using not a single reference antigen, but a set of about three to five unrelated antigens, such as milk powder, BSA, transferrin or the like.

"Binding affinity" or "affinity" refers to the strength of the total sum of non-covalent interactions between a single binding site of a molecule and its binding partner. Unless indicated otherwise, as used herein, "binding affinity" refers to intrinsic binding affinity which reflects a 1:1 interaction between members of a binding pair (e.g. an antibody and an antigen). The dissociation constant "$K_D$" is commonly used to describe the affinity between a molecule (such as an antibody) and its binding partner (such as an antigen) i.e. how tightly a ligand binds to a particular protein. Ligand-protein affinities are influenced by non-covalent intermolecular interactions between the two molecules. Affinity can be measured by common methods known in the art, including those described herein. In one embodiment, the "$K_D$" or "$K_D$ value" according to this invention is measured by using surface plasmon resonance assays using suitable devices including but not limited to Biacore instruments like Biacore T100, Biacore T200, Biacore 2000, Biacore 4000, a Biacore 3000 (GE Healthcare Biacore, Inc.), or a ProteOn XPR36 instrument (Bio-Rad Laboratories, Inc.).

As used herein, the term "epitope" includes any protein determinant capable of specific binding to an immunoglobulin or T-cell receptor. Epitopic determinants usually consist of chemically active surface groupings of molecules such as amino acids or sugar side chains, or combinations thereof and usually have specific three dimensional structural characteristics, as well as specific charge characteristics.

An "antibody that binds to the same epitope" as a reference antibody or "an antibody which competes for binding" to a reference antibody refers to an antibody that blocks binding of the reference antibody to its antigen in a competition assay by 10%, 20%, 30%, 40%, 50% or more, and conversely, the reference antibody blocks binding of the antibody to its antigen in a competition assay by 10%, 20%, 30%, 40%, 50% or more. An exemplary competition assay is provided herein.

An "antibody which binds to an epitope of a target protein Z wherein said epitope comprises the amino acid residues X1, X2, X3, . . . " is an antibody which comprises atoms within 5 Å, preferentially within 4 Å, to atoms of said amino acid residues X1, X2, X3, . . . of the target protein Z after binding of the antibody to its target protein. Such epitopes can be determined by using an X-ray crystal structure as exemplified in example 16.

"Antibody-dependent cell-mediated cytotoxicity" or "ADCC" refers to a form of cytotoxicity in which secreted Ig bound onto Fc gamma receptors (FcγRs) present on certain cytotoxic cells (e.g. NK cells, neutrophils, and macrophages) enable these cytotoxic effector cells to bind specifically to an antigen-bearing target cell and subsequently kill the target cell e.g. with cytotoxins. To assess ADCC activity of an antibody of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., J. Immunol. Methods 202: 163 (1996), may be performed. Polypeptide variants with altered Fc region amino acid sequences (polypeptides with a variant Fc region) and increased or decreased Clq binding are described, e.g., in U.S. Pat. No. 6,194,551 BI and WO 1999/51642.

As used herein, a "naked antibody" refers to an antibody that is not conjugated to a heterologous moiety (e.g. a cytotoxic moiety) or radiolabel. This naked antibody may be present in a pharmaceutical composition.

The term "immunoconjugate" (interchangeably referred to as "antibody-drug conjugate," or "ADC") refers to an antibody conjugated to one or more cytotoxic or cytostatic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). Immunoconjugates have been used for the local delivery of cytotoxic agents, i.e., drugs that kill or inhibit the growth or proliferation of cells, in the treatment of cancer (e.g. Liu et al., Proc Natl. Acad. Sci. (1996), 93, 8618-8623)). Immunoconjugates allow for the targeted delivery of a drug moiety to a tumor, and intracellular accumulation therein, where systemic administration of unconjugated drugs may result in unacceptable levels of toxicity to normal cells and/or tissues. Toxins used in antibody-toxin conjugates include bacterial toxins such as diphtheria toxin, plant toxins such as ricin, small molecule toxins such as geldanamycin. The toxins may exert their cytotoxic effects by mechanisms including tubulin binding, DNA binding, or topoisomerase inhibition.

"Percent (%) sequence identity" with respect to a reference polynucleotide or polypeptide sequence, respectively, is defined as the percentage of nucleic acid or amino acid residues, respectively, in a candidate sequence that are identical with the nucleic acid or amino acid residues, respectively, in the reference polynucleotide or polypeptide sequence, respectively, after aligning the sequences and introducing gaps, if necessary, to achieve the maximum percent sequence identity. Conservative substitutions are not considered as part of the sequence identity. Preferred are un-gapped alignments. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

"Sequence homology" indicates the percentage of amino acids that either is identical or that represent conservative amino acid substitutions.

The term "maturated antibodies" or "maturated antigen-binding fragments" such as maturated Fab variants includes derivatives of an antibody or antibody fragment exhibiting stronger binding—i. e. binding with increased affinity—to a given antigen such as the extracellular domain of a target protein. Maturation is the process of identifying a small number of mutations e.g. within the six CDRs of an antibody or antibody fragment leading to this affinity increase. The maturation process is the combination of molecular biology methods for introduction of mutations into the antibody and screening for identifying the improved binders.

An "antagonistic" antibody or a "blocking" antibody is one which significantly inhibits (either partially or completely) a biological activity of the antigen it binds.

An "agonistic" antibody or an antibody with "agonistic activity" is one that binds to its target and induces the activation (either partially or completely) of the respective target, that e.g. leads to activation of the signaling pathways or biological effects (either partially or completely) that are mediated by the respective target. An "agonistic" antibody or an antibody with "agonistic activity" as used herein is an antibody which may mimic at least one of the functional activities of a polypeptide of interest.

The term "pharmaceutical formulation"/"pharmaceutical composition" refers to a preparation which is in such form as to permit the biological activity of an active ingredient contained therein to be effective, and which contains no additional components which are unacceptably toxic to a subject to which the formulation would be administered.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell", "host cell line", and "host cell culture" are used interchangeably and refer to cells into which exogenous nucleic acid has been introduced, including the progeny of such cells. Host cells include "transformants", "transformed cells", "transfectants", "transfected cells", and "transduced cells", which include the primary transformed/transfected/transduced cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Antibodies of this Invention

This invention is related to antibodies, or antigen-binding antibody fragments thereof, or variants thereof which bind specifically to human CEACAM6 and *Macaca fascicularis* CEACAM6, and which therefore do not significantly cross-react with the closely related human CEACAM1, human CEACAM3, and human CEACAM5.

Antibodies of this invention, or antigen-binding antibody fragments thereof, or variants thereof bind specifically to the mature extracellular domain of CEACAM6 and the mature extracellular domain of *Macaca fascicularis* CEACAM6, and do not significantly cross-react with the closely related mature extracellular domains of human CEACAM1, of human CEACAM3, and of human CEACAM5. The mature extracellular domains might be part of the full length proteins expressed on the cell surface as well as soluble proteins (naturally occurring or recombinantly expressed).

Antibodies of this invention, or antigen-binding antibody fragments thereof, or variants thereof bind specifically to proteins comprising the mature extracellular domain of human CEACAM6 and/or the mature extracellular domain of *Macaca fascicularis* CEACAM6, and do not significantly cross-react with proteins comprising only the closely related mature extracellular domains of human CEACAM1 and/or of human CEACAM3, and/or of human CEACAM5.

It is an embodiment of this invention to provide antibodies or antigen-binding antibody fragments thereof, or variants thereof which are specific for human and *Macaca fascilularis* CEACAM6, which means, the antibodies are cross-reactive to human and *Macaca fascilularis* CEACAM6.

It is an embodiment of this invention to provide antibodies or antigen-binding antibody fragments thereof, or a variants thereof which are selective for CEACAM6, which means these do not significantly cross-react with the closely related CEACAM1, CEACAM3, and CEACAM5.

It is another embodiment of the invention to provide antibodies, or antigen-binding antibody fragments thereof, or variants thereof, which bind to human CEACAM6 and are cross-reactive to CEACAM6 of another species including, but not limited to, monkey with similar affinity. Preferably, said other species is a non-human primate, such as for example *Macaca fascicularis, Macaca mulatta*, orangutang, gorilla, and chimpanzee. Most preferably, the antibodies, or antigen-binding antibody fragments thereof, or variants thereof bind to human CEACAM6 and are cross-reactive to cynomolgus CEACAM6.

A monoclonal antibody binding to antigen 1 (Ag1) is "cross-reactive" to antigen 2 (Ag2) when the $EC_{50}$ and/or $K_D$ values are in a similar range for both antigens. In the present disclosure, a monoclonal antibody binding to Ag1 is cross-reactive to Ag2 when the ratio of affinity for Ag1 to affinity for Ag2 is equal or less 10 (≤10) and equal or greater than 0.1 (≥0.1), which means that the affinities for Ag1 and Ag2 do not differ more than a factor of 10 (the affinities are within one order of magnitude of monovalent $K_D$), on condition that affinities are measured with the same method in the same experimental setting for both antigens.

Accordingly, the antibody according to the invention has a ratio of affinity for human CEACAM6 to the affinity for *Macaca fascicularis* CEACAM6 which is equal or less 10 (≤10) and equal or greater than 0.1 (≥0.1), which means that the affinities for human and *Macaca fascicularis* CEACAM6 do not differ more than a factor of 10 (the affinities are within one order of magnitude of monovalent $K_D$). Thus, the antibody of this invention, or antigen-binding antibody fragment thereof, or variant thereof according to the invention may be used in toxicological studies performed in monkeys because the toxicity profile observed in monkeys would be relevant to anticipate potential adverse effects in humans.

A monoclonal antibody binding to antigen 1 (Ag1) is "not significantly cross-reactive" to antigen 3 (Ag3) when the affinities are very different for the two antigens. Affinity for Ag3 may not be measurable if the binding response (the measured binding signal in an assay) is too low. In the present application, a monoclonal antibody binding to Ag1 is "not significantly cross-reactive" to Ag3, when the binding response (the measured binding signal in an assay) of the monoclonal antibody to Ag3 is less than 5%, preferably less than 2% of the binding response of the same monoclonal antibody to Ag1 in the same experimental setting and at the same antibody concentration. In practice, the antibody concentration used can be the EC50 or $K_D$ or the concentration required to reach the saturation plateau obtained with Ag1.

According to the invention the antibodies or antigen-binding antibody fragments thereof, or variants thereof do not significantly cross react with human CEACAM1, human CEACAM3, and human CEACAM5.

A preferred embodiment of the invention has an affinity for human CEACAM6 and *Macaca fascicularis* CEACAM6 which is ≤400 nM, preferably ≤200 nM, alternatively preferably ≤100 nM, determined as monovalent affinity to recombinant CEACAM6 (see Example 2) as shown in Table 13, Table 18 and Table 20.

According to the invention the antibodies or antigen-binding antibody fragments thereof, or variants thereof bind to human CEACAM6 domain 1 (represented by amino acids 35-142 of SEQ-ID NO:179) and to *Macaca fascicularis* CEACAM6 domain 1 (represented by amino acids 35-142 of SEQ-ID NO:177) (affinities are within one order of magnitude of monovalent $K_D$). The CEACAM6 domain 1 is also known as N domain.

It is an embodiment of the invention to provide antibodies or antigen-binding antibody fragments thereof, or variants thereof which bind specifically to human CEACAM6 domain 1 (represented by amino acids 35-142 of SEQ-ID NO:179) and specifically to *Macaca fascicularis* CEACAM6 domain 1 (represented by amino acids 35-142 of SEQ-ID NO:177) with affinities (monovalent $K_D$) which are within one order of magnitude. Highly preferred are antibodies or antigen-binding antibody fragments thereof, or variants thereof which have an affinity for both, human CEACAM6 domain 1 and *Macaca fascicularis* CEACAM6 domain 1 of $K_D$≤100 nM.

Antibodies of this invention, or antigen-binding antibody fragments thereof, or variants thereof bind specifically to proteins comprising human CEACAM6 domain 1 (represented by amino acids 35-142 of SEQ-ID NO:179) and/or *Macaca fascicularis* CEACAM6 domain 1 (represented by amino acids 35-142 of SEQ-ID NO:177).

Antibodies of this invention, or antigen-binding antibody fragments thereof, or variants thereof bind specifically to proteins comprising human CEACAM6 domain 1 (represented by amino acids 35-142 of SEQ-ID NO:179) and/or *Macaca fascicularis* CEACAM6 domain 1 (represented by amino acids 35-142 of SEQ-ID NO:177) and do not significantly cross-react with the closely related human CEACAM1, human CEACAM3, and human CEACAM5.

Antibodies of this invention, or antigen-binding antibody fragments thereof, or variants thereof bind specifically to proteins comprising human CEACAM6 domain 1 (represented by amino acids 35-142 of SEQ-ID NO:179) and/or *Macaca fascicularis* CEACAM6 domain 1 (represented by amino acids 35-142 of SEQ-ID NO:177) and do not significantly cross-react with proteins comprising only the closely related mature extracellular domains of human CEACAM1, and/or of human CEACAM3, and/or of human CEACAM5.

It is an embodiment of the invention to provide antibodies, or antigen-binding antibody fragments thereof, or variants thereof which bind specifically to the mature extracellular domain of CEACAM6 and the mature extracellular domain of *Macaca fascicularis* CEACAM6, and compete for binding to the 9A6 antibody (Genovac/Aldevron) on human CEACAM6 and do not significantly cross-react with the closely related mature extracellular domains of human CEACAM1, of human CEACAM3, and of human CEACAM5.

It is an embodiment of the invention to provide antibodies, or antigen-binding antibody fragments thereof, or a variants thereof which bind specifically to human CEACAM6 domain 1 (represented by amino acids 35-142 of SEQ-ID NO:179) and to *Macaca fascicularis* CEACAM6 domain 1 (represented by amino acids 35-142 of SEQ-ID NO:177), and compete for binding to the 9A6 antibody (Genovac/Aldevron) on human CEACAM6.

It is an embodiment of the invention to provide antibodies or antigen-binding antibody fragments thereof, or variants thereof which bind specifically to human CEACAM6 and *Macaca fascicularis* CEACAM6, and which interfere with CEACAM6 and CEACAM1 interaction. An antibody interferes with the CEACAM6 and CEACAM1 interaction, when the binding signal of a preformed antibody-CEACAM6-complex is more than 20%, preferably more than 50% reduced compared to that of the CEACAM6 protein alone in a typical binding assay with CEACAM1 which is provided in the examples. Interference with CEACAM6 and CEACAM1 interaction might be a mechanism for the modulation of innate and adaptive immune responses.

It is an embodiment of the invention to provide antibodies or antigen-binding antibody fragments thereof, or variants thereof which bind specifically to human CEACAM6 and *Macaca fascicularis* CEACAM6, and which have an immunomodulatory activity. "Immunomodulation" is the adjustment of the immune response to a desired level as in immunopotention, immunosuppression or induction of immunologic tolerance. An "immunomodulatory antibody" drug is an immune response-modifying agent that stimulates or suppresses the immune response for the treatment of a disease e.g. cancer or anti-inflammation. The invention provides an anti-CEACAM6 immunomodulatory antibody, as shown in Example 11, which blocks CEACAM6 which is an immune cell suppressive ligand on cancer cells and potentially other cells including components of the immune system which results into a change of the immune marker expression profile and activation status of T cells towards an anti-tumor T cell re-activation and an effective anti-cancer immune response. An antibody binding to CEACAM6 domain 1 is preferred.

Figure 5A:
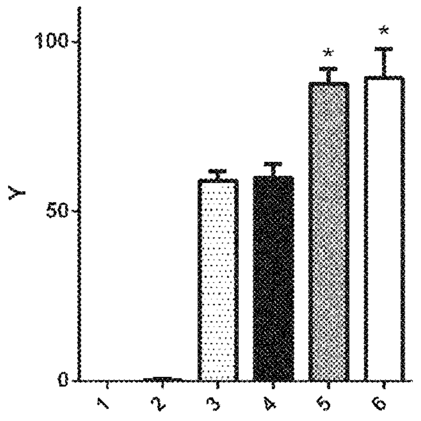
FIGS. 5A-C: In vitro pharmacological effect of anti-CEACAM6 antibodies on IFN-gamma secretion of survivin peptide specific T cells and extent of this secretion.
Figure 5B:
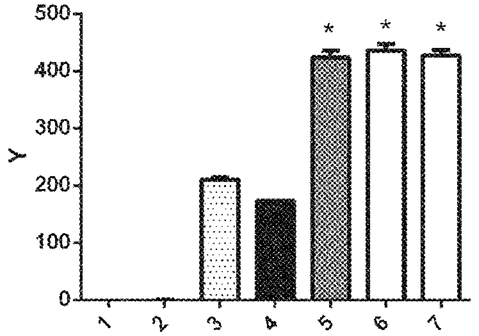
Figure 5C:
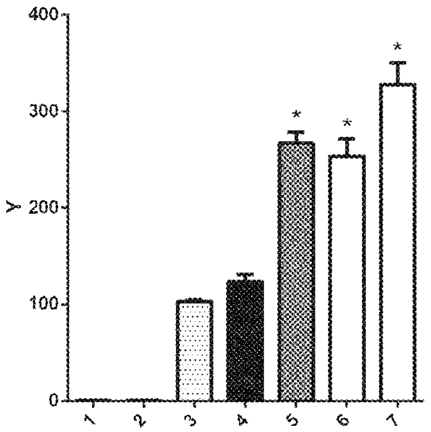
Figure 6A:
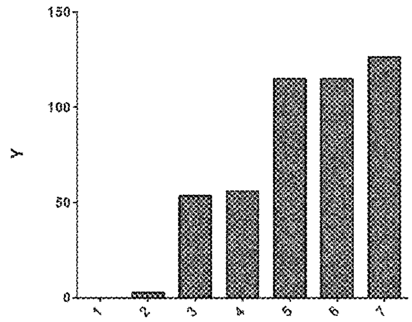
FIGS. 6A-C: In vitro pharmacological effect of anti-CEACAM6 antibodies on cytokine secretion (IFN-gamma, IL-2 and TNF-alpha) of survivin peptide specific T cells.
Figure 6B:
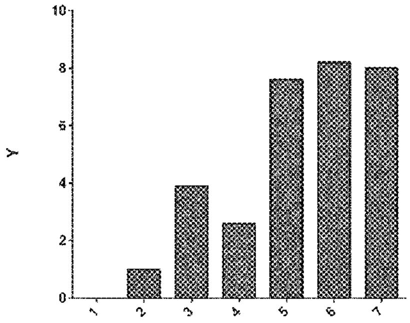
Figure 6C:
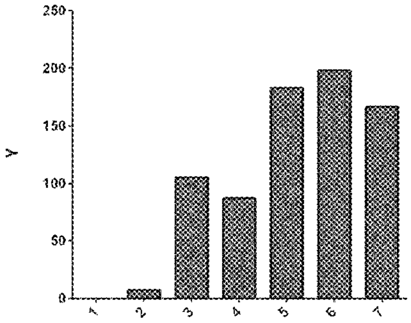

It is an embodiment of the invention to provide antibodies or antigen-binding antibody fragments thereof, or variants thereof which bind specifically to human CEACAM6 and *Macaca fascicularis* CEACAM6, and which are able to relieve CEACAM6 mediated immunosuppression of tumor antigen specific T cells as measured by either IFN-gamma secretion of tumor antigen specific T cells or the number of IFN-gamma secreting activated T cells. An anti-CEACAM6 antibody is able to relieve CEACAM6 mediated immunosuppression of tumor antigen specific T cells if an antibody in the co-culture of tumor specific T cells with tumor cells yields a >1.2, preferably >1.5 times increase in IFN-gamma secretion compared to the control samples. Preferably the tumor antigen specific T cells are $CD8^+$ T cells. Preferred is an antibody which does not significantly cross-react with the closely related CEACAM1, CEACAM3, and CEACAM5 and which binds to CEACAM6 domain 1. This is exemplary shown by blockade of CEACAM6 by antibodies of the invention in the co-culture of survivin-peptide specific $CD8^+$ T cells with KS tumor cells, which yields a >1.5 times increase in IFN-gamma secretion compared to the control samples that were treated with the isotype-matched control (FIG. 5 and FIG. 6).

It is an embodiment of the invention to provide antibodies or antigen-binding antibody fragments thereof, or variants thereof which bind specifically to human CEACAM6 and *Macaca fascicularis* CEACAM6, and which are able to change the cytokine profile of tumor antigen specific T cells towards a more cytotoxic and/or activated phenotype characterized by increased IFN-gamma and/or IL-2 and/or TNF-alpha secretion. Preferably the tumor antigen specific T cells are $CD8^+$ T cells and the phenotype is an increased IFN-gamma and IL-2 and TNF-alpha secretion. An anti-CEACAM6 antibody is able to change the cytokine profile of tumor antigen specific T cells towards a more cytotoxic and/or activated phenotype if the antibody in the co-culture of tumor specific $CD8^+$ T cells with tumor cells yields a >1.2, preferably >1.5 times increase in IFN-gamma and/or IL-2 and/or TNF-alpha secretion compared to the control samples that were treated with the isotype-matched control. Blockade of CEACAM6 by antibodies of the invention in the co-culture of survivin-peptide specific T cells with KS tumor cells yields a >1.5 times increase in IFN-gamma, IL-2 and TNF-alpha secretion compared to the control samples that were treated with the isotype-matched control (FIG. 6).

It is an embodiment of the invention to provide antibodies, or antigen-binding antibody fragments thereof, or variants thereof, which bind to a broad range of different CEACAM6 expressing cell lines including, but not limited to the ones shown in the examples. These examples include human cell lines from many tumor origins (e.g. NSCLC, SCLC, CRC, PancCA, BreastCA, GastricCA, multiple myeloma, cervix, skin cancer which represent cancer indications previously described in the literature to be CEACAM6 positive (see introduction or review Beauchimen and Arabzadeh, Cancer Metastasis Rev. 2013 December; 32(3-4):643-71).

It is an embodiment of the invention to provide antibodies, or antigen-binding antibody fragments thereof, or variants thereof that are safe for human administration. Preferably the antibodies are chimeric, humanized or human. Highly preferred are humanized or human antibodies.

Nevertheless in certain assays an expression of the antibodies of this invention as murine IgG is preferred; immunohistochemistry with human samples for example can be analyzed more easily by using murine antibodies or human-mouse chimeric antibodies.

It is another embodiment of the invention to provide antibodies which constitute a tool for diagnosis of malignant or dysplastic conditions in which CEACAM6 expression is elevated compared to normal tissue or where CEACAM6 is shed from the cell surface and becoming detectable in serum. Provided are anti-CEACAM6 antibodies conjugated to a detectable marker. Preferred markers are a radiolabel, an enzyme, a chromophore or a fluorophore.

Throughout this document, reference is made to the following preferred anti-CEACAM6 antibodies of the invention as depicted in Table 1.

TABLE 1

Protein sequences of preferred antibodies of this invention

| | | SEQ ID NO: VH Protein | SEQ ID NO: H-CDR1 | SEQ ID NO: H-CDR2 | SEQ ID NO: H-CDR3 | SEQ ID NO: VL Protein | SEQ ID NO: L-CDR1 | SEQ ID NO: L-CDR2 | SEQ ID NO: L-CDR3 | SEQ ID NO: IgG Heavy Chain | SEQ ID NO: IgG Light Chain |
|---|---|---|---|---|---|---|---|---|---|---|---|
| TPP-2971 | mIgG1 | 3 | 4 | 5 | 6 | 7 | 8 | 9 | 10 | | |
| TPP-3308 | hIgG2-chim | 33 | 34 | 35 | 36 | 37 | 38 | 39 | 40 | 43 | 44 |
| TPP-3310 | hIgG2 | 47 | 48 | 49 | 50 | 51 | 52 | 53 | 54 | 57 | 58 |
| TPP-3714 | hIgG2 | 119 | 120 | 121 | 122 | 123 | 124 | 125 | 126 | 129 | 130 |
| TPP-3187 | mIgG1 | 23 | 24 | 25 | 26 | 27 | 28 | 29 | 30 | | |
| TPP-3323 | hIgG2-chim | 75 | 76 | 77 | 78 | 79 | 80 | 81 | 82 | 85 | 86 |
| TPP-3820 | hIgG2 | 133 | 134 | 135 | 136 | 137 | 138 | 139 | 140 | 143 | 144 |
| TPP-3821 | hIgG2 | 147 | 148 | 149 | 150 | 151 | 152 | 153 | 154 | 157 | 158 |
| TPP-3186 | mIgG1 | 13 | 14 | 15 | 16 | 17 | 18 | 19 | 20 | | |
| TPP-3322 | hIgG2-chim | 61 | 62 | 63 | 64 | 65 | 66 | 67 | 68 | 71 | 72 |
| TPP-3707 | hIgG2 | 105 | 106 | 107 | 108 | 109 | 110 | 111 | 112 | 115 | 116 |
| TPP-3705 | hIgG2 | 91 | 92 | 93 | 94 | 95 | 96 | 97 | 98 | 101 | 102 |

The sequences of preferred antibodies of this invention or antigen-binding fragments thereof depicted in Table 1 are further provided and explained in FIG. 8.

TPP-3308 represents an antibody comprising a heavy chain region corresponding to SEQ ID NO: 43 and a light chain region corresponding to SEQ ID NO: 44.

TPP-3310 represents an antibody comprising a heavy chain region corresponding to SEQ ID NO: 57 and a light chain region corresponding to SEQ ID NO: 58.

TPP-3714 represents an antibody comprising a heavy chain region corresponding to SEQ ID NO: 129 and a light chain region corresponding to SEQ ID NO: 130.

TPP-3323 represents an antibody comprising a heavy chain region corresponding to SEQ ID NO: 85 and a light chain region corresponding to SEQ ID NO: 86.

TPP-3820 represents an antibody comprising a heavy chain region corresponding to SEQ ID NO: 143 and a light chain region corresponding to SEQ ID NO: 144.

TPP-3821 represents an antibody comprising a heavy chain region corresponding to SEQ ID NO: 157 and a light chain region corresponding to SEQ ID NO: 158.

TPP-3322 represents an antibody comprising a heavy chain region corresponding to SEQ ID NO: 71 and a light chain region corresponding to SEQ ID NO: 72.

TPP-3707 represents an antibody comprising a heavy chain region corresponding to SEQ ID NO: 115 and a light chain region corresponding to SEQ ID NO: 116.

TPP-3705 represents an antibody comprising a heavy chain region corresponding to SEQ ID NO: 101 and a light chain region corresponding to SEQ ID NO: 102.

In a further preferred embodiment the antibodies or antigen-binding fragments comprise heavy or light chain CDR sequences which are at least 50%, 55%, 60% 70%, 80%, 90, or 95% identical to at least one, preferably corresponding, CDR sequence of the antibodies "TPP-2971", "TPP-3186", "TPP-3187", "TPP-3308", "TPP-3310", "TPP-3322", "TPP-3323", "TPP-3705", "TPP-3707", "TPP-3714", "TPP-3820", "TPP-3821" or at least 50%, 60%, 70%, 80%, 90%, 92% or 95% identical to the VH or VL sequence of "TPP-2971", "TPP-3186", "TPP-3187", "TPP-3308", "TPP-3310", "TPP-3322", "TPP-3323", "TPP-3705", "TPP-3707", "TPP-3714", "TPP-3820", "TPP-3821", respectively.

In a further preferred embodiment the antibody of the invention or antigen-binding fragment thereof comprises at least one CDR sequence or at least one variable heavy chain or variable light chain sequence as depicted in Table 1.

In a preferred embodiment the antibody of the invention or antigen-binding fragment thereof comprises a heavy chain antigen-binding region that comprises SEQ ID NO:4 (H-CDR1), SEQ ID NO:5 (H-CDR2) and SEQ ID NO:6 (H-CDR3) and comprises a light chain antigen-binding region that comprises SEQ ID NO:8 (L-CDR1), SEQ ID NO:9 (L-CDR2) and SEQ ID NO:10 (L-CDR3).

In a preferred embodiment the antibody of the invention or antigen-binding fragment thereof comprises a heavy chain antigen-binding region that comprises SEQ ID NO:34 (H-CDR1), SEQ ID NO:35 (H-CDR2) and SEQ ID NO:36 (H-CDR3) and comprises a light chain antigen-binding region that comprises SEQ ID NO:38 (L-CDR1), SEQ ID NO:39 (L-CDR2) and SEQ ID NO:40 (L-CDR3).

In a preferred embodiment the antibody of the invention or antigen-binding fragment thereof comprises a heavy chain antigen-binding region that comprises SEQ ID NO:48 (H-CDR1), SEQ ID NO:49 (H-CDR2) and SEQ ID NO:50 (H-CDR3) and comprises a light chain antigen-binding region that comprises SEQ ID NO:52 (L-CDR1), SEQ ID NO:53 (L-CDR2) and SEQ ID NO:54 (L-CDR3).

In a preferred embodiment the antibody of the invention or antigen-binding fragment thereof comprises a heavy chain antigen-binding region that comprises SEQ ID NO:120 (H-CDR1), SEQ ID NO:121 (H-CDR2) and SEQ ID NO:122 (H-CDR3) and comprises a light chain antigen-binding region that comprises SEQ ID NO:124 (L-CDR1), SEQ ID NO:125 (L-CDR2) and SEQ ID NO:126 (L-CDR3).

In a preferred embodiment the antibody of the invention or antigen-binding fragment thereof comprises a heavy chain antigen-binding region that comprises SEQ ID NO:24 (H-CDR1), SEQ ID NO:25 (H-CDR2) and SEQ ID NO:26 (H-CDR3) and comprises a light chain antigen-binding region that comprises SEQ ID NO:28 (L-CDR1), SEQ ID NO:29 (L-CDR2) and SEQ ID NO:30 (L-CDR3).

In a preferred embodiment the antibody of the invention or antigen-binding fragment thereof comprises a heavy chain antigen-binding region that comprises SEQ ID NO:76 (H-CDR1), SEQ ID NO:77 (H-CDR2) and SEQ ID NO:78 (H-CDR3) and comprises a light chain antigen-binding region that comprises SEQ ID NO:80 (L-CDR1), SEQ ID NO:81 (L-CDR2) and SEQ ID NO:82 (L-CDR3).

In a preferred embodiment the antibody of the invention or antigen-binding fragment thereof comprises a heavy chain antigen-binding region that comprises SEQ ID NO:134 (H-CDR1), SEQ ID NO:135 (H-CDR2) and SEQ ID NO:136 (H-CDR3) and comprises a light chain antigen-binding region that comprises SEQ ID NO:138 (L-CDR1), SEQ ID NO:139 (L-CDR2) and SEQ ID NO:140 (L-CDR3).

In a preferred embodiment the antibody of the invention or antigen-binding fragment thereof comprises a heavy chain antigen-binding region that comprises SEQ ID NO:148 (H-CDR1), SEQ ID NO:149 (H-CDR2) and SEQ ID NO:150 (H-CDR3) and comprises a light chain antigen-binding region that comprises SEQ ID NO:152 (L-CDR1), SEQ ID NO:153 (L-CDR2) and SEQ ID NO:154 (L-CDR3).

In a preferred embodiment the antibody of the invention or antigen-binding fragment thereof comprises a heavy chain antigen-binding region that comprises SEQ ID NO:62 (H-CDR1), SEQ ID NO:63 (H-CDR2) and SEQ ID NO:64 (H-CDR3) and comprises a light chain antigen-binding region that comprises SEQ ID NO:66 (L-CDR1), SEQ ID NO:67 (L-CDR2) and SEQ ID NO:68 (L-CDR3).

In a preferred embodiment the antibody of the invention or antigen-binding fragment thereof comprises a heavy chain antigen-binding region that comprises SEQ ID NO:14 (H-CDR1), SEQ ID NO:15 (H-CDR2) and SEQ ID NO:16 (H-CDR3) and comprises a light chain antigen-binding region that comprises SEQ ID NO:18 (L-CDR1), SEQ ID NO:19 (L-CDR2) and SEQ ID NO:20 (L-CDR3).

In a preferred embodiment the antibody of the invention or antigen-binding fragment thereof comprises a heavy chain antigen-binding region that comprises SEQ ID NO:106 (H-CDR1), SEQ ID NO:107 (H-CDR2) and SEQ ID NO:108 (H-CDR3) and comprises a light chain antigen-binding region that comprises SEQ ID NO:110 (L-CDR1), SEQ ID NO:111 (L-CDR2) and SEQ ID NO:112 (L-CDR3).

In a preferred embodiment the antibody of the invention or antigen-binding fragment thereof comprises a heavy chain antigen-binding region that comprises SEQ ID NO:92 (H-CDR1), SEQ ID NO:93 (H-CDR2) and SEQ ID NO:94 (H-CDR3) and comprises a light chain antigen-binding region that comprises SEQ ID NO:96 (L-CDR1), SEQ ID NO:97 (L-CDR2) and SEQ ID NO:98 (L-CDR3).

Antibodies differ in sequence, not only within their complementarity determining regions (CDRs), but also in the framework (FR). These sequence differences are encoded in the different V-genes. The human antibody germline repertoire has been completely sequenced. There are about 50 functional VH germline genes which can be grouped into six subfamilies according to sequence homology VH1, VH2, VH3, VH4, VH5 and VH6 (Tomlinson et al., 1992, J. Mol. Biol. 227, 776-798; Matsuda & Honjo, 1996, Advan. Immunol. 62, 1-29). About 40 functional VL kappa genes comprising seven subfamilies are known (Cox et al., 1994, Eur. J. Immunol. 24, 827-836; Barbie & Lefranc, 1998, Exp. Clin. Immunogenet. 15, 171-183): Vkappa1, Vkappa2, Vkappa3, Vkappa4, Vkappa5, Vkappa6 and Vkappa7. Disclosed herein are heavy chains of antibodies of this invention that belong to the human VH2 subfamily and the light chains of antibodies of this invention that belong to the human Vkappa1 subfamily, respectively. It is known that framework sequences of antibodies belonging to the same subfamily are closely related, e.g. antibodies comprising a human VH3 subfamily member all share comparable stability (Honegger et al., 2009, Protein Eng Des Sel. 22(3):121-134). It is well known in the art that CDRs from antibodies can be grafted on different frameworks while maintaining special features of the corresponding origin antibody. CDRs have been successfully grafted on frameworks belonging to a different species as well as on frameworks of the same species belonging to a different subfamily. In a further embodiment the antibody or antigen-binding fragment of the invention comprises at least one CDR sequence of antibody of the invention as depicted in Table 1 and a human variable chain framework sequence.

In a preferred embodiment the antibody or antigen-binding fragment of the invention comprises a variable light chain or light chain antigen-binding region comprising the L-CDR1, L-CDR2 and L-CDR3 sequence of the variable light chain and a variable heavy chain or heavy chain antigen-binding region comprising the H-CDR1, H-CDR2 and H-CDR3 sequence of the variable heavy chain antibody of the invention as depicted in Table 1 and a human variable light and human variable heavy chain framework sequence.

In a highly preferred embodiment the antibody of the invention or antigen-binding fragment thereof comprises a variable heavy chain sequence as presented by SEQ ID NO:3 (VH) and a variable light chain sequences as presented by SEQ ID NO:7 (VL).

In a highly preferred embodiment the antibody of the invention or antigen-binding fragment thereof comprises a variable heavy chain sequence as presented by SEQ ID NO:33 (VH) and a variable light chain sequences as presented by SEQ ID NO:37 (VL).

In a highly preferred embodiment the antibody of the invention or antigen-binding fragment thereof comprises a variable heavy chain sequence as presented by SEQ ID NO:47 (VH) and a variable light chain sequences as presented by SEQ ID NO:51 (VL).

In a highly preferred embodiment the antibody of the invention or antigen-binding fragment thereof comprises a variable heavy chain sequence as presented by SEQ ID NO:119 (VH) and a variable light chain sequences as presented by SEQ ID NO:123 (VL).

In a highly preferred embodiment the antibody of the invention or antigen-binding fragment thereof comprises a variable heavy chain sequence as presented by SEQ ID NO:23 (VH) and a variable light chain sequences as presented by SEQ ID NO:27 (VL).

In a highly preferred embodiment the antibody of the invention or antigen-binding fragment thereof comprises a variable heavy chain sequence as presented by SEQ ID NO:75 (VH) and a variable light chain sequences as presented by SEQ ID NO:79 (VL).

In a highly preferred embodiment the antibody of the invention or antigen-binding fragment thereof comprises a variable heavy chain sequence as presented by SEQ ID NO:133 (VH) and a variable light chain sequences as presented by SEQ ID NO:137 (VL).

In a highly preferred embodiment the antibody of the invention or antigen-binding fragment thereof comprises a variable heavy chain sequence as presented by SEQ ID NO:147 (VH) and a variable light chain sequences as presented by SEQ ID NO:151 (VL).

In a highly preferred embodiment the antibody of the invention or antigen-binding fragment thereof comprises a variable heavy chain sequence as presented by SEQ ID NO:13 (VH) and a variable light chain sequences as presented by SEQ ID NO:17 (VL).

In a highly preferred embodiment the antibody of the invention or antigen-binding fragment thereof comprises a variable heavy chain sequence as presented by SEQ ID NO:61 (VH) and a variable light chain sequences as presented by SEQ ID NO:65 (VL).

In a highly preferred embodiment the antibody of the invention or antigen-binding fragment thereof comprises a variable heavy chain sequence as presented by SEQ ID NO:105 (VH) and a variable light chain sequences as presented by SEQ ID NO:109 (VL).

In a highly preferred embodiment the antibody of the invention or antigen-binding fragment thereof comprises a variable heavy chain sequence as presented by SEQ ID NO:91 (VH) and a variable light chain sequences as presented by SEQ ID NO:95 (VL).

In some embodiments, the anti-CEACAM6 antibody of the invention or an antigen-binding antibody fragment thereof, or a variant thereof binds to an epitope of human CEACAM6, wherein said epitope comprises one or more amino acid residues selected from the group consisting of Gln60, Asn61, Arg62, Ile63, Va183, Ile84, Gly85, Thr90, Ser127, Asp128 and Leu129 of SEQ ID NO: 179.

In certain embodiments, the anti-CEACAM6 antibody of the invention or an antigen-binding antibody fragment thereof, or a variant thereof binds to an epitope of human CEACAM6, wherein said epitope comprises the amino acid residues Gln60, Asn61, Arg62, Ile63, Va183, Ile84, Gly85, Thr90, Ser127, Asp128 and Leu129 of SEQ ID NO: 179.

In some embodiments, the anti-CEACAM6 antibody of the invention or an antigen-binding antibody fragment thereof, or a variant thereof interacts with, e.g. binds to, an epitope of human CEACAM6, wherein said epitope comprises one, two, three four, five, eight, ten, fifteen or more amino acid residues selected from the group consisting of Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179.

In certain embodiments, the anti-CEACAM6 antibody of the invention or an antigen-binding antibody fragment thereof, or a variant thereof interacts with, e.g. binds to, an epitope of human CEACAM6, wherein said epitope comprises the amino acid residues Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179.

In some embodiments, the anti-CEACAM6 antibody of the invention or an antigen-binding antibody fragment thereof, or a variant thereof binds to an epitope of human CEACAM6, wherein said epitope comprises one or more amino acid residues selected from the group consisting of Gln60, Asn61, Arg62, Ile63, Va183, Ile84, Gly85, Thr90, Ser127, Asp128 and Leu129 of SEQ ID NO: 179, and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

In certain embodiments, the anti-CEACAM6 antibody of the invention or an antigen-binding antibody fragment thereof, or a variant thereof binds to an epitope of human CEACAM6, wherein said epitope comprises the amino acid residues Gln60, Asn61, Arg62, Ile63, Va183, Ile84, Gly85, Thr90, Ser127, Asp128 and Leu129 of SEQ ID NO: 179, and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

In some embodiments, the anti-CEACAM6 antibody of the invention or an antigen-binding antibody fragment thereof, or a variant thereof interacts with, e.g. binds to, an epitope of human CEACAM6, wherein said epitope comprises one, two, three four, five, eight, ten, fifteen or more amino acid residues selected from the group consisting of Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179, and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

In certain embodiments, the anti-CEACAM6 antibody of the invention or an antigen-binding antibody fragment thereof, or a variant thereof interacts with, e.g. binds to, an epitope of human CEACAM6, wherein said epitope comprises the amino acid residues Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179, and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

In some embodiments, the anti-CEACAM6 antibody of the invention or an antigen-binding antibody fragment thereof, or a variant thereof binds to an epitope of human CEACAM6, wherein said epitope comprises one or more amino acid residues selected from the group consisting of Gln60, Asn61, Arg62, Ile63, Va183, Ile84, Gly85, Thr90, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL).

In certain embodiments, the anti-CEACAM6 antibody of the invention binds to an epitope of human CEACAM6, wherein said epitope comprises the amino acid residues Gln60, Asn61, Arg62, Ile63, Va183, Ile84, Gly85, Thr90, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL).

In some embodiments, the anti-CEACAM6 antibody of the invention interacts with, e.g. binds to, an epitope of human CEACAM6, wherein said epitope comprises one, two, three four, five, eight, ten, fifteen or more amino acid residues selected from the group consisting of Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL).

In certain embodiments, the anti-CEACAM6 antibody of the invention interacts with, e.g. binds to, an epitope of human CEACAM6, wherein said epitope comprises the amino acid residues Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL).

In some embodiments, the anti-CEACAM6 antibody of the invention or an antigen-binding antibody fragment thereof, or a variant thereof binds to an epitope of human CEACAM6, wherein said epitope comprises one or more amino acid residues selected from the group consisting of Gln60, Asn61, Arg62, Ile63, Va183, Ile84, Gly85, Thr90, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL), and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

In certain embodiments, the anti-CEACAM6 antibody of the invention binds to an epitope of human CEACAM6, wherein said epitope comprises the amino acid residues Gln60, Asn61, Arg62, Ile63, Va183, Ile84, Gly85, Thr90, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL) and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

In some embodiments, the anti-CEACAM6 antibody of the invention interacts with, e.g. binds to, an epitope of human CEACAM6, wherein said epitope comprises one, two, three four, five, eight, ten, fifteen or more amino acid residues selected from the group consisting of Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL) and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

In certain embodiments, the anti-CEACAM6 antibody of the invention interacts with, e.g. binds to, an epitope of human CEACAM6, wherein said epitope comprises the amino acid residues Pro59, Gln60, Asn61, Arg62, Ile63, Gly64, Va183, Ile84, Gly85, Thr86, Gln88, Thr90, Pro91, Ile125, Ser127, Asp128 and Leu129 of SEQ ID NO: 179, and wherein said antibody or antigen-binding antibody fragment thereof, or variant thereof competes for binding to CECEAM6 with an antibody comprising a variable heavy chain sequence as presented by SEQ ID NO:47 (VH) and a variable light chain sequences as presented by SEQ ID NO:51 (VL) and wherein said antibody or antigen-binding antibody fragment thereof, or variant thereof binds to a human CEACAM6 protein comprising an Ile63Leu mutation and does not bind to a human CEACAM6 protein comprising an Ile63Phe mutation (numbering according to SEQ-ID:179).

An antibody of the invention may be an IgG (immunoglobulin G e.g. IgG1 IgG2, IgG3, IgG4) or IgA, IgD, IgE, IgM, while an antibody fragment may be a Fab, Fab', $F(ab')_2$, Fab'-SH or scFv, for example. An inventive antibody fragment, accordingly, may be, or may contain, an antigen-binding region that behaves in one or more ways as described herein.

In a preferred embodiment the antibodies or antigen-binding antibody fragments of the invention are monoclonal.

In some embodiments antibodies of the invention or antigen-binding fragments thereof, or nucleic acids encoding the same are isolated. An isolated biological component (such as a nucleic acid molecule or protein such as an antibody) is one that has been substantially separated or purified away from other biological components in the cell of the organism in which the component naturally occurs, e.g., other chromosomal and extra-chromosomal DNA and RNA, proteins and organelles. The term also embraces nucleic acids and proteins prepared by recombinant expression in a host cell as well as chemically synthesized nucleic acids.

Antibody Generation

An antibody of the invention may be derived from a recombinant antibody library that is based on amino acid sequences that have been isolated from the antibodies of a large number of healthy volunteers e.g. using the n-CoDeR® technology the fully human CDRs are recombined into new antibody molecules (Carlson & Soderlind, Expert Rev Mol Diagn. 2001 May; 1(1):102-8). Or alternatively for example antibody libraries as the fully human antibody phage display library described in Hoet R M et al., Nat Biotechnol 2005; 23(3):344-8) can be used to isolate CEACAM6-specific antibodies. Antibodies or antibody fragments isolated from human antibody libraries are considered human antibodies or human antibody fragments herein.

Human antibodies may be further prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. For example immunization of genetically engineered mice inter alia immunization of hMAb mice (e.g. VelocImmune Mouse® or XENOMOUSE®) may be performed.

Further antibodies may be generated using the hybridoma technology (for example see Köhler and Milstein Nature. 1975 Aug. 7; 256(5517):495-7), resulting in for example murine, rat, or rabbit antibodies which can be converted into chimeric or humanized antibodies. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Natl Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall' Acqua et al., Methods 36:43-60 (2005) (describing "FR shuffling"); and Osboum et al., Methods 36:61-68 (2005) and Klimka et al., Br. J. Cancer, 83:252-260 (2000) (describing the "guided selection" approach to FR shuffling).

Examples are provided for the generation of antibodies using a recombinant antibody library and immunization of mice combined with subsequent humanization.

It is a further aspect of the invention to provide a method to generate antibodies specifically binding to human CEACAM6 and to *Macaca fascicularis* CEACAM6, which do not significantly cross-react with human CEACAM1, human CEACAM3, and human CEACAM5. It is an embodiment of the invention to provide a method for generation of anti-CEACAM6 antibodies characterized by comprising the steps of immunization of an animal, preferentially a mouse, with cynomolgus CECAM6 domain 1 (represented by amino acids 35-142 of SEQ-ID NO:177), determining the amino acid sequence of antibodies specifically binding to human CEACAM6 and to cynomolgus CEACAM6, followed optionally by humanization or generation of a chimeric antibody, and expression of said antibodies. The expression system can be a recombinant or a cell free expression system. Suitable host cells for recombinant expression are prokaryotic and eukaryotic cells. Preferred are mammalian expression systems.

Peptide Variants

Antibodies or antigen-binding fragments of the invention are not limited to the specific peptide sequences provided herein. Rather, the invention also embodies variants of these polypeptides. With reference to the instant disclosure and conventionally available technologies and references, the skilled worker will be able to prepare, test and utilize functional variants of the antibodies disclosed herein, while appreciating these variants having the ability to bind to CEACAM6 fall within the scope of the present invention.

A variant can include, for example, an antibody that has at least one altered complementary determining region (CDR) (hyper-variable) and/or framework (FR) (variable) domain/position, vis-à-vis a peptide sequence disclosed herein.

By altering one or more amino acid residues in a CDR or FR region, the skilled worker routinely can generate mutated or diversified antibody sequences, which can be screened against the antigen, for new or improved properties, for example.

A further preferred embodiment of the invention is an antibody or antigen-binding fragment in which the VH and VL sequences are selected as shown in Table 1. The skilled worker can use the data in Table 1 to design peptide variants that are within the scope of the present invention. It is preferred that variants are constructed by changing amino acids within one or more CDR regions; a variant might also have one or more altered framework regions. Alterations also may be made in the framework regions. For example, a peptide FR domain might be altered where there is a deviation in a residue compared to a germline sequence.

Alternatively, the skilled worker could make the same analysis by comparing the amino acid sequences disclosed herein to known sequences of the same class of such antibodies, using, for example, the procedure described by Knappik A., et al., JMB 2000, 296:57-86.

Furthermore, variants may be obtained by using one antibody as starting point for further optimization by diversifying one or more amino acid residues in the antibody, preferably amino acid residues in one or more CDRs, and by screening the resulting collection of antibody variants for variants with improved properties. Particularly preferred is diversification of one or more amino acid residues in CDR3 of VL and/or VH. Diversification can be done e.g. by synthesizing a collection of DNA molecules using trinucleotide mutagenesis (TRIM) technology (Virnekas B. et al., Nucl. Acids Res. 1994, 22: 5600.). Antibodies or antigen-binding fragments thereof include molecules with modifications/variations including but not limited to e.g. modifications leading to altered half-life (e.g. modification of the Fc part or attachment of further molecules such as PEG), altered binding affinity or altered ADCC or CDC activity.

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophane, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in 1-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Glycosylation Variants

Where the antibody comprises an Fc region, the carbohydrate attached thereto may be altered. Native antibodies produced by mammalian cells typically comprise a branched, biantennary oligosaccharide that is generally attached by an N-linkage to Asn297 using Kabat EU numbering of the CH2 domain of the Fc region; see, e.g., Wright et al. Trends Biotechnol. 15: 26-32 (1997).

In certain embodiments, an antibody provided herein is altered to increase or decrease the extent to which the antibody is glycosylated. Addition or deletion of glycosylation sites to an antibody may be conveniently accomplished by altering the expression system (e.g. host cell) and/or by altering the amino acid sequence such that one or more glycosylation sites is created or removed.

In one embodiment of this invention, aglycosyl antibodies having decreased effector function or antibody derivatives are prepared by expression in a prokaryotic host. Suitable prokaryotic hosts for include but are not limited to *E. coli, Bacillus subtilis, Salmonella typhimurium* and various species within the genera *Pseudomonas, Streptomyces*, and *Staphylococcus.*

In one embodiment, antibody variants are provided having decreased effector function, which are characterized by a modification at the conserved N-linked site in the CH2 domains of the Fc portion of said antibody. In one embodiment of present invention, the modification comprises a mutation at the heavy chain glycosylation site to prevent glycosylation at the site. Thus, in one preferred embodiment of this invention, the aglycosyl antibodies or antibody derivatives are prepared by mutation of the heavy chain glycosylation site,—i.e., mutation of N297 using Kabat EU numbering and expressed in an appropriate host cell.

In another embodiment of the present invention, aglycosyl antibodies or antibody derivatives have decreased effector function, wherein the modification at the conserved N-linked site in the CH2 domains of the Fc portion of said antibody or antibody derivative comprises the removal of the CH2 domain glycans,—i.e., deglycosylation. These aglycosyl antibodies may be generated by conventional methods and then deglycosylated enzymatically. Methods for enzymatic deglycosylation of antibodies are well known in the art (e.g. Winkelhake & Nicolson (1976), J Biol Chem. 251(4):1074-80).

In another embodiment of this invention, deglycosylation may be achieved using the glycosylation inhibitor tunicamycin (Nose & Wigzell (1983), Proc Natl Acad Sci USA, 80(21):6632-6). That is, the modification is the prevention of glycosylation at the conserved N-linked site in the CH2 domains of the Fc portion of said antibody.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function.

Examples of publications related to "defucosylated" or "fucose-deficient" antibody variants include: Okazaki et al. J Mol. Biol. 336: 1239-1249 (2004); Yamane-Ohnuki et al. Biotech. Bioeng. 87: 614 (2004).

Examples of cell lines capable of producing defucosylated antibodies include Lec13 CHO cells deficient in protein fucosylation (Ripka et al. Arch. Biochem. Biophys. 249: 533-545 (1986); and WO 2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006)).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546.

Antibody variants with at least one galactose residue in the oligosaccharide attached to the Fc region are also provided. Such antibody variants may have improved CDC function. Such antibody variants are described, e.g., in WO1997/30087; WO1998/58964; and WO1999/22764.

Fc Region Variants

In certain embodiments, one or more amino acid modifications (e.g. a substitution) may be introduced into the Fc region of an antibody (e.g., a human IgG1, IgG2, IgG3 or IgG4 Fc region) provided herein, thereby generating an Fc region variant.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. In some embodiments, alterations are made in the Fc region that result in altered (i.e., either improved or diminished) Clq binding and/or Complement Dependent Cytotoxicity (CDC).

In certain embodiments, the invention contemplates an antibody variant that possesses an increased or decreased half-live. Antibodies with increased half-lives and improved binding to the neonatal Fc receptor (FcRn), which is responsible for the transfer of maternal IgGs to the fetus (Guyer et al., J Immunol. 117:587 (1976) and Kim et al., J Immunol. 24:249 (1994)), are described in US2005/0014934 (Hinton et al.). Those antibodies comprise an Fc region with one or more substitutions therein which improve binding of the Fc region to FcRn.

Antibody-Drug Conjugates (ADC)

The invention also provides antibody-drug conjugates (ADC, immunoconjugates) comprising an anti-CEACAM6 antibody conjugated to one or more cytotoxic agents, such as chemotherapeutic agents or drugs, growth inhibitory agents, toxins (e.g., protein toxins, enzymatically active toxins of bacterial, fungal, plant, human or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP0425235); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof; an anthracycline such as daunomycin or doxorubicin; methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alphasarcin, *Aleurites fordii* proteins, dianthin proteins, *Phytolaca americana* proteins (P API, P APII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{227}Th$, $^{225}Ac$, $^{211}At$, $^{131}I$, $^{125}I$, $^{90}Y$, $^{186}Re$, $^{188}Re$, $^{153}Sm$, $^{212}Bi$, $^{32}P$, $^{212}Pb$ and radioactive isotopes of Lu. When the radioconjugate is used for detection, it may comprise a radioactive atom for scintigraphic studies, for example Tc99m, or a spin label for nuclear magnetic resonance (NMR) imaging, such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52: 12 7-131 (1992).

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

DNA Molecules of the Invention

The present invention also relates to the DNA molecules that encode an antibody of the invention or antigen-binding fragment thereof. The DNA sequences used for the antibodies expressed are given in Table 32. These sequences are optimized in certain cases for mammalian expression. DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 supra and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

Functionally Equivalent DNA Variants

Yet another class of DNA variants within the scope of the invention may be described with reference to the product they encode. These functionally equivalent polynucleotides are characterized by the fact that they encode the same peptide sequences due to the degeneracy of the genetic code.

It is recognized that variants of DNA molecules provided herein can be constructed in several different ways. For example, they may be constructed as completely synthetic DNAs. Methods of efficiently synthesizing oligonucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences of the present invention (see Table 32). The recombinant constructs of the present invention can be used in connection with a vector, such as a plasmid, phagemid, phage or viral vector, into which a DNA molecule encoding an antibody of the invention or antigen-binding fragment thereof or variant thereof is inserted.

An antibody, antigen binding portion, or variant thereof provided herein can be prepared by recombinant expression of nucleic acid sequences encoding light and heavy chains or portions thereof in a host cell. To express an antibody, antigen binding portion, or variant thereof recombinantly a host cell can be transfected with one or more recombinant expression vectors carrying DNA fragments encoding the light and/or heavy chains or portions thereof such that the light and heavy chains are expressed in the host cell. Standard recombinant DNA methodologies are used to prepare and/or obtain nucleic acids encoding the heavy and light chains, incorporate these nucleic acids into recombinant expression vectors and introduce the vectors into host cells, such as those described in Sambrook, Fritsch and Maniatis (eds.), Molecular Cloning; A Laboratory Manual, Second Edition, Cold Spring Harbor, NY, (1989), Ausubel, F. M. et al. (eds.) Current Protocols in Molecular Biology, Greene Publishing Associates, (1989) and in U.S. Pat. No. 4,816,397 by Boss et al..

In addition, the nucleic acid sequences encoding variable regions of the heavy and/or light chains can be converted, for example, to nucleic acid sequences encoding full-length antibody chains, Fab fragments, or to scFv. The VL- or VH-encoding DNA fragment can be operatively linked, (such that the amino acid sequences encoded by the two DNA fragments are in-frame) to another DNA fragment encoding, for example, an antibody constant region or a flexible linker. The sequences of human heavy chain and light chain constant regions are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

To create a polynucleotide sequence that encodes a scFv, the VH- and VL-encoding nucleic acids can be operatively linked to another fragment encoding a flexible linker such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554).

To express the antibodies, antigen binding fragments thereof or variants thereof standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. Suitable host cells are prokaryotic and eukaryotic cells. Examples for prokaryotic host cells are e.g. bacteria, examples for eukaryotic hosts cells are yeasts, insects and insect cells, plants and plant cells, transgenic animals, or mammalian cells. In some embodiments, the DNAs encoding the heavy and light chains are inserted into separate vectors. In other embodiments, the DNA encoding the heavy and light chains is inserted into the same vector. It is understood that the design of the expression vector, including the selection of regulatory sequences is affected by factors such as the choice of the host cell, the level of expression of protein desired and whether expression is constitutive or inducible.

Therefore, an embodiment of the present invention are also host cells comprising the vector or a nucleic acid molecule, whereby the host cell can be a higher eukaryotic host cell, such as a mammalian cell, a lower eukaryotic host cell, such as a yeast cell, and may be a prokaryotic cell, such as a bacterial cell.

Another embodiment of the present invention is a method of using the host cell to produce an antibody and antigen binding fragments, comprising culturing the host cell under suitable conditions and recovering said antibody.

Therefore another embodiment of the present invention is the production of the antibodies according to this invention with the host cells of the present invention and purification of these antibodies to at least 95% homogeneity by weight.

Bacterial Expression

Useful expression vectors for bacterial use are constructed by inserting a DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include but are not limited to *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and a bacterial origin of replication derived from commercially available plasmids typically containing elements of the well-known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore, an embodiment of the present invention is an expression vector comprising a nucleic acid sequence encoding for the novel antibodies of the present invention.

Antibodies of the present invention or antigen-binding fragments thereof or variants thereof include naturally purified products, products of chemical synthetic procedures, and products produced by recombinant techniques from a prokaryotic host, including, for example, *E. coli, Bacillus subtilis, Salmonella typhimurium* and various species within the genera *Pseudomonas, Streptomyces*, and *Staphylococcus*, preferably, from *E. coli* cells.

Mammalian Expression

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Expression of the antibodies may be constitutive or regulated (e.g. inducible by addition or removal of small molecule inductors such as Tetracyclin in conjunction with Tet system). For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.. The recombinant expression vectors can also include origins of replication and selectable markers (see e.g., U.S. Pat. Nos. 4,399,216, 4,634,665 and 5,179,017). Suitable selectable markers include genes that confer resistance to drugs such as G418, puromycin, hygromycin, blasticidin, zeocin/bleomycin or methotrexate or selectable marker that exploit auxotrophies such as Glutamine Synthetase (Bebbington et al., Biotechnology (N Y). 1992 February; 10(2):169-75), on a host cell into which the vector has been introduced. For example, the dihydrofolate reductase (DHFR) gene confers resistance to methotrexate, neo gene confers resistance to G418, the bsd gene from *Aspergillus terreus* confers resistance to blasticidin, puromycin N-acetyl-transferase confers resistance to puromycin, the Sh ble gene product confers resitance to zeocin, and resistance to hygromycin is conferred by the *E. coli* hygromycin resistance gene (hyg or hph). Selectable markers like DHFR or Glutamine Synthetase are also useful for amplification techniques in conjunction with MTX and MSX.

Transfection of the expression vector into a host cell can be carried out using standard techniques such as electroporation, nucleofection, calcium-phosphate precipitation, lipofection, polycation-based transfection such as polyethlylenimine (PEI)-based transfection and DEAE-dextran transfection.

Suitable mammalian host cells for expressing the antibodies, antigen binding fragments thereof or variants thereof provided herein include Chinese Hamster Ovary (CHO cells) such as CHO-K1, CHO-S, CHO-K1SV [including dhfr− CHO cells, described in Urlaub and Chasin, (1980) Proc. Natl. Acad. Sci. USA 77:4216-4220 and Urlaub et al., Cell. 1983 June; 33(2):405-12, used with a DHFR selectable marker, e.g., as described in R. J. Kaufman and P. A. Sharp (1982) Mol. Biol. 159:601-621; and other knockout cells exemplified in Fan et al., Biotechnol Bioeng. 2012 April; 109(4):1007-15], NSO myeloma cells, COS cells, HEK293 cells, HKB11 cells, BHK21 cells, CAP cells, EB66 cells, and SP2 cells.

Expression might also be transient or semi-stable in expression systems such as HEK293, HEK293T, HEK293-EBNA, HEK293E, HEK293-6E, HEK293-Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for instance Durocher et al., Nucleic Acids Res. 2002 Jan. 15; 30(2):E9).

In some embodiments, the expression vector is designed such that the expressed protein is secreted into the culture medium in which the host cells are grown. The antibodies, antigen binding fragments thereof or variants thereof can be recovered from the culture medium using standard protein purification methods.

Purification

Antibodies of the invention or antigen-binding fragments thereof or variants thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention or antigen-binding fragments thereof or variants thereof include naturally purified products, products of chemical synthetic procedures, and products produced by recombinant techniques from an eukaryotic host, including, for example, yeast, higher plant, insect and mammalian cells. Depending upon the host employed in a recombinant production procedure, the antibody of the present invention can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

In preferred embodiments, the antibody is purified (1) to greater than 95% by weight of antibody as determined e.g. by the Lowry method, UV-Vis spectroscopy or by by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or non-reducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

Therapeutic Methods

Therapeutic methods involve administering to a subject in need of treatment a therapeutically effective amount of an antibody or an antigen-binding fragment thereof or a variant thereof contemplated by the invention. A "therapeutically effective" amount hereby is defined as the amount of an antibody or antigen-binding fragment that is of sufficient quantity to reduce proliferation of CEACAM6 positive cell or to reduce size of a CEACAM6 expressing tumor in a treated area of a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, dog, monkey or other lower-order primate).

It is an embodiment of the invention to provide an antibody or antigen-binding fragment thereof for use as medicament.

It is an embodiment of the invention to provide an antibody or antigen-binding fragment thereof for use as a medicament for the treatment of cancer. In a preferred embodiment the cancer is a tumor and in a highly preferred embodiment the cancer is a solid tumor.

It is an embodiment of the invention to use the antibody or antigen-binding fragment thereof in the manufacture of a medicament for the treatment of a disease.

It is an embodiment of the invention to use the antibody or antigen-binding fragment thereof in the manufacture of a medicament for the treatment of cancer. In a preferred embodiment the cancer is a tumor and in a highly preferred embodiment the cancer is a solid tumor.

The inventive antibodies or antigen-binding fragments thereof can be used as a therapeutic or a diagnostic tool in a variety of situations with aberrant CEACAM6-signaling, e.g. cell proliferative disorders such as cancer or fibrotic diseases. Disorders and conditions particularly suitable for treatment with an antibody of the inventions are solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Tumors of the digestive tract include, but are not limited to anal, colon, colorectal, esophageal, gallbladder, gastric, pancreatic, rectal, small-intestine, and salivary gland cancers.

Examples of esophageal cancer include, but are not limited to esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumors.

Examples of breast cancer include, but are not limited to triple negative breast cancer, invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Examples of ovarian cancer include, but are not limited to serous tumour, endometrioid tumor, mucinous cystadenocarcinoma, granulosa cell tumor, Sertoli-Leydig cell tumor and arrhenoblastoma Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumors of the urinary tract include, but are not limited to bladder, penile, kidney, renal pelvis, ureter, urethral, and hereditary and sporadic papillary renal cancers.

Examples of kidney cancer include, but are not limited to renal cell carcinoma, urothelial cell carcinoma, juxtaglomerular cell tumor (reninoma), angiomyolipoma, renal oncocytoma, Bellini duct carcinoma, clear-cell sarcoma of the kidney, mesoblastic nephroma and Wilms' tumor.

Examples of bladder cancer include, but are not limited to transitional cell carcinoma, squamous cell carcinoma, adenocarcinoma, sarcoma and small cell carcinoma.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to squamous cell cancer of the head and neck, laryngeal, hypopharyngeal, nasopharyngeal, oropharyngeal cancer, salivary gland cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

In a preferred embodiment, the antibodies of the invention or antigen-binding fragments thereof are suitable for a therapeutic or diagnostic method for the treatment or diagnosis of a cancer disease comprised in a group consisting of colorectal cancer, non-small-cell lung cancer (NSCLC), small cell lung cancer (SCLC), pancreatic cancer, gastric cancer, breast cancer and multiple myeloma.

In addition, the inventive antibodies or antigen-binding fragments thereof can also be used as a therapeutic or a diagnostic tool in a variety of other disorders wherein CEACAM6 is involved such as, but not limited to lung infection e.g. influenza, Crohns disease, inflammatory bowel disease, psoriasis, lung cystic fibrosis, prevention of bacterial docking to GI-intract, trauma, bleeding burn, surgery, stroke, myocardial infarction, sepsis, pneumonia, vaccination for infection & cancer, chronic virus infection.

The disorders mentioned above have been well characterized in humans, but also exist with a similar etiology in other animals, including mammals, and can be treated by administering pharmaceutical compositions of the present invention.

An antibody of the invention or an antigen-binding fragment thereof or a variant thereof might be co-administered with known medicaments, and in some instances the antibody might itself be modified. For example, an antibody or an antigen-binding fragment thereof or a variant thereof could be conjugated to a cytotoxic agent or radioisotope to potentially further increase efficacy.

Antibodies of the present invention or antigen-binding fragments thereof or variants thereof may be administered as the sole pharmaceutical agent or in combination with one or more additional therapeutic agents where the combination causes no unacceptable adverse effects. This combination therapy includes administration of a single pharmaceutical dosage formulation which contains an antibody of the invention or an antigen-binding fragment thereof or a variants thereof and one or more additional therapeutic agents, as well as administration of an antibody of the invention and each additional therapeutic agent in its own separate pharmaceutical dosage formulation. For example, an antibody of the invention or an antigen-binding fragment thereof or a variant thereof and a therapeutic agent may be administered to the patient together in a single liquid composition, or each agent may be administered in separate dosage formulation.

Where separate dosage formulations are used, an antibody of the invention or an antigen-binding fragment thereof or a variants thereof and one or more additional therapeutic agents may be administered at essentially the same time (e.g., concurrently) or at separately staggered times (e.g., sequentially).

In particular, antibodies of the present invention or antigen-binding fragments thereof or variants thereof may be used in fixed or separate combination with other anti-tumor agents such as alkylating agents, anti-metabolites, plant-derived anti-tumor agents, hormonal therapy agents, topoisomerase inhibitors, immunologicals, antibodies, antibody drugs, biological response modifiers, anti-angiogenic compounds, cell therapies, and other anti-tumor drugs including but not limited to camptothecin derivatives, kinase inhibitors, targeted drugs.

In this regard, the following is a non-limiting list of examples of secondary agents that may be used in combination with the antibodies of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and Paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, Irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-ni, GM-CSF and other immune enhancing agents such as L19-1L2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; ALNX6000, Urelumab, PF-005082566, Galunisertib, AZ10606120, NF340, BMS-777607;

Immunologicals also include drugs directed towards immune checkpoint modulators or co-inhibitory receptors including but not limited to CTLA-4, PD1, PD-L1, B7-H3 receptor, B7-H4 receptor, BTLA, TIM3, LAG3, KIRDL, 2B4, VISTA, CD244, CD160, TIGIT, CEACAM1, CEACAM5, HHLA2. Specifically some of these drugs are Ipilimumab, Tremelimumab, Nivolumab, Pembrolizumab, Pidilizumab, AMP-224, AMP-514, PDR001, MDX1105, BMS-936,559, Atezolizumab, Medi4736, Avelumab, MSB0010718C, MGA271, IMP321, BMS-986,016, Bavituximab, MNRP1685A, Celecoxib, PF-04418948, RQ-15986;

Immunologicals also include activators of co-stimulatory receptors including drugs directed towards but not limited to CD28, ICOS, 4-1BB, OX40, CD27, KIRDS, GITR, HVEM, TNFRSF25, CD40L. TMIGD2, TIM-1, CEACAM1, CEACAM5. Among those drugs are CP-870893, Lucatumumab, Dacetuzumab, Anti-OX40, MED10562, MED16469, MED16383, CDX-1127, TRX518, Varlilumab;

Immunologicals also include agents that modulate Treg activity including those directed but not limited to FOXP3, CD25, CCR4. Among those agents is daclizumab;

Immunologicals also include agents that modulate the activity of myeloid derived suppressor cells including those directed but not limited to CSF1R. An example is emactuzumab, Taladafil;

Immunologicals also include agents which modulate the innate immune cell response including agents directed to Toll-like receptors including but not limited to TLR3, TLR4, TLR7, TLR8, TLR9, NGK2A, NKG2D. These drugs are for example Imiquimod, CPG7909 (PF-3512676, CPG2006); MGN1703, SD-101, hiltonol (Poly ICLC), Anti-NGK2A (IPH2201), OM-174, 852A, VTX-2337, IMO-2055;

Immunologicals also include drugs which modulate the innate immune cell response including drugs directed but not limited to CSF-1, CSF1R, KIR, ILTs, LIRs, MICA, MICB, CD244, CCL2, CD47. Specifically some of these drugs are Anti-KIR (IHP2101; IPH2101; 1-7F9); Lirilumab (IPH2012; BMS-986,015); Carlumab (CNT0888), IMC-CS4, FPA008, PLX3397, ARRY-382, CC-90002, Anti-CD47 (Hu5F9-G4), BLZ945;

Immunologicals also include agents for immune cell retargeting including but not limited to bispecific antibodies, Darts e.g. against B7-H3, Bites e.g CD19×CD3; e.g. Removab anti-EPCAM×CD3×FC, NK cell targeting agents;

Immunologicals also include agents which modulate the tumor microenvironment and improve immune cell infiltration and response including Vaccines and Adjuvants and which are not limited to GVAX, FVAX;

In this regard Vaccines comprise dendritic cell-based vaccines, viral vaccines, mRNA based vaxxines, multipeptide based vaccines;

Immunologicals also include agents for improved immune cell infiltration including but not limited to IFN-g, IL15, IL21, IL2, CXCR4, CXCI12, Some of these drugs are Denenicokin (BMS982, 470), ALT-803, hetlL15, Ulocuplumab, BKT140, CXCR2-specific mab, AD3100, Maravirox, PF-4136309;

Immunologicals also include agents or modalities which improve the priming and activation of APCs and T cells including drugs directed to but not limited to m-TOR GSK3beta inhibitors, loaded DCs (e.g. Provenge), Radiation therapy, external beam radiation;

Immunologicals also include Kynurenine pathway modulators including drugs directed to but not limited to IDO1, IDO2, TDO. Among those drugs are INCB024360, Indoximod (NLG8189; 1-methyl-D-tryptophan, D-1MT), GDC-0919, NLG919, LM10;

Immunologicals also include Adenosine Pathway modulators including drugs directed to but not limited to CD39, CD73, A2A receptor, A2B receptor. Such drugs include Compound9, NCX-4016, AT38, SCH58261, SCH420814, PSB1115, ARL67176, AMPCP;

Immunologicals also include TGFbeta/ALK5 pathway modulator. Such drugs include OY2157299, EW-7187;

Immunologicals also include Sting activators;

Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, bevacizumab, brivanib alaninat, cilengtide, combretastatin, endostatin, fenretinide, halofuginone, pazopanib, ranibizumab, rebima-stat, recentin, regorafenib, removab, revlimid, sorafenib, squalamine, sunitinib, telatinib, thalidomide, ukrain, vatalanib, and vitaxin;

Antiangiogenic agents also include VEGF inhibitors including but not limited to sorafenib, regorafenib, bevacizumab, sunitinib, recentin, axitinib, aflibercept, telatinib, brivanib alaninate, vatalanib, pazopanib, and ranibizumab;

Antibody drugs include, but are not limited to, trastuzumab, cetuximab, bevacizumab, rituximab, ticilimumab, ipilimumab, tremelimumab, pembrolizumab, nivolumab, Pidilizumab, RG-7446/MPDL3280A, BMS-936559 (MDX1105), Durvalumab (Medi-4736), MSB-0010718C, lumiliximab, catumaxomab, atacicept, oregovomab, panitumumab and alemtuzumab;

Antibody drugs also include antibody drug conjugates including but not limited to those targeting Mesothelin, C4.4A, FGFR2, HER2, PSMA;

Antibody drugs also include Thorium targeted conjugates but not limited to those targeting Mesothelin, C4.4A, FGFR2, HER2, PSMA, CEACAM6;

Antibody drugs also include bispecific (or multispecific) antibody formats including but not limited to bispecific (or multispecific) IgGs and bispecific (or multispecific) antibody fragments as well as protein fusions and conjugates thereof (e.g. CrossMab, DAF(2in1), DAF(4in1), DutaMab, DT-IgG, KiHassembled IgG, charge pair assembled IgG, KiH-commonLC, Fab-arm exchange, SEEDbody, Triomab, LUZ-Y, Fcab, κλ-mAb, orthogonal Fab, DVD-IgG, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH-IgG-scFab, 2scFv-IgG, IgG-2scFv, scFv4-Ig, Zybody, DVI-IgG (4in1), di-nanobody, BiTE, Diabody, DART, DART-Fc, TandAb, scDiabody, scDlabody-CH3, Diabody-CH3, Triple Body, Miniantibody, Minibody, TriBi minibody, scFv-CH3 KIH, Fab-scFv, scFv-CH-CL-scFv, F(ab')2, F(ab')2-scFv2, scFv-KIH, Fab-scFv-Fc, Tetravalent HCAb, scDiabody-Fc, Diabody-Fc, Tandem scFv-Fc, Intrabody, Dock and Lock fusion, ImmTAC, HSAbody, scDiabody-HAS, Tandem scFv-toxin, IgG-IgG, Cov-X-Body, scFv1-PEG-scFv2 and others);

Antibody drugs also include recombinant proteins generated by recombinant technologies with antibody-like binding properties such as but not limited to DARPIN molecules;

Cell therapies include, but are not limited to tumor infiltrating lymphocyte isolated from cancer patients such as Ex vivo stimulated T cells e.g. Sipuleucel-T;

Cell therapies include, but are not limited to tumor infiltrating lymphocyte isolated from cancer patients such as Sipuleucel-T and genetically engineered T cells bearing chimeric antigen receptors (CARs) such as e.g. CD19-CAR-T cells; CAR-Her2-T-cells;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin, PI3065, TG100-115;

EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K inhibitors such as PI3K inhibitor 1 (2-amino-N-[7-methoxy-8-(3-morpholin-4-ylpropoxy)-2,3-dihydroimidazo

[1,2-c]quinazolin-5-yl]pyrimidine-5-carboxamide dihydrochloride (see compound of Examples 1 and 2 WO 2012/136553)

and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

BRAFV600E inhibitors such as Vemurafenib, Dabrafenib;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors and Raf inhibitors such as sorafenib;

Farnesyl transferase inhibitors such as, e.g., tipifarnib;

Tyrosine kinase inhibitors including, e.g., dasatinib, nilotibib, regorafenib, bosutinib, sorafenib, bevacizumab, sunitinib, cediranib, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors;

Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis factor related apoptosis inducing ligand receptor 1 agonists such as, e.g., mapatumumab;

Tumor necrosis factor related apoptosis inducing ligand receptor 2 agonists such as e.g., lexatumumab, conatumumab, CS-1008, PR095780;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

In addition, the antibodies of the invention can be combined with modalities which cause immunogenic cell death including but not limited to ultraviolet light, oxidizing treatments, heat shock, targeted and untargeted radiotherapy, shikonin, high-hydrostatic pressure, oncolytic viruses, and photodynamic therapy;

In addition, the antibodies of the invention can be combined with agents which cause immunogenic cell death including but not limited to sunitinib, JAK2 inhibitors, anthracyclincs, doxorubicin, mitoxantrone, oxaliplatin, and cyclophosphamide, targeted and untargeted microtubule-destabilizing drugs (like e.g. auristatins and maytansinoids);

The compounds of the present invention may also be employed in cancer treatment in conjunction with radiation therapy and/or surgical intervention;

Furthermore, the antibodies of the invention may be utilized, as such or in compositions, in research and diagnostics, or as analytical reference standards, and the like, which are well known in the art;

Diagnostic Methods

Anti-CEACAM6 antibodies or antigen-binding fragments thereof can be used for detecting the presence of CEACAM6-expressing tumors. The presence of CEACAM6-containing cells or shed CEACAM6 within various biological samples, including serum, and tissue biopsy specimens, may be detected with anti-CEACAM6 antibodies. In addition, anti-CEACAM6 antibodies may be used in various imaging methodologies such as immunoscintigraphy with a $^{99}$Tc (or other isotope) conjugated antibody. For example, an imaging protocol similar to the one described using a $^{111}$In conjugated anti-PSMA antibody may be used to detect pancreatic or ovarian carcinomas (Sodee et al., Clin. Nuc. Med. 21: 759-766, 1997). Another method of detection that can be used is positron emitting tomography by conjugating the antibodies of the invention with a suitable isotope (see Herzog et al., J. Nucl. Med. 34:2222-2226, 1993).

Pharmaceutical Compositions and Administration

To treat any of the foregoing disorders, pharmaceutical compositions for use in accordance with the present invention may be formulated in a conventional manner using one or more physiologically acceptable carriers or excipients. An antibody of the invention or antigen-binding fragment thereof can be administered by any suitable means, which can vary, depending on the type of disorder being treated. Possible administration routes include parenteral (e.g., intramuscular, intravenous, intra-arterial, intraperitoneal, or subcutaneous), intrapulmonary and intranasal, and, if desired for local immunosuppressive treatment, intralesional administration. In addition, an antibody of the invention or an antigen-binding fragment thereof or a variant thereof might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

An embodiment of the present invention are pharmaceutical compositions which comprise anti-CEACAM6 antibodies or antigen-binding fragments thereof or variants thereof, alone or in combination with at least one other agent, such as a stabilizing compound, which may be administered in any sterile, biocompatible pharmaceutical carrier, including, but not limited to, saline, buffered saline, dextrose, and water. A further embodiment are pharmaceutical compositions comprising a CEACAM6 binding antibody or antigen-binding fragment thereof and a further pharmaceutically active compound that is suitable to treat CEACAM6 related diseases such as cancer. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methylcellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores can be provided with suitable coatings such as concentrated sugar solutions, which may also contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine or phosphate or Tris, 0.1%-2% sucrose and/or 2%-7% mannitol at a pH range of 4.5 to 7.5 optionally comprising additional substances like polysorbate that is combined with buffer prior to use.

After pharmaceutical compositions comprising a compound of the invention formulated in an acceptable carrier have been prepared, they can be placed in an appropriate container and labeled for treatment of an indicated condition. For administration of anti-CEACAM6 antibodies or antigen-binding fragment thereof, such labeling would include amount, frequency and method of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Therapeutically Effective Dose

Pharmaceutical compositions suitable for use in the present invention include compositions wherein the active ingredients are contained in an effective amount to achieve the intended purpose, i.e. treatment of a particular disease state characterized by CEACAM6 expression.

The determination of an effective dose is well within the capability of those skilled in the art.

Determining a therapeutically effective amount of the novel antibody of this invention or an antigen-binding fragment thereof or a variant thereof, largely will depend on particular patient characteristics, route of administration, and the nature of the disorder being treated. General guidance can be found, for example, in the publications of the International Conference on Harmonization and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

For any compound, the therapeutically effective dose can be estimated initially either in cell culture assays, e.g., neoplastic cells, or in animal models, usually mice, rabbits, dogs, pigs or monkeys. The animal model is also used to achieve a desirable concentration range and route of administration. Such information can then be used to determine useful doses and routes for administration in humans.

A therapeutically effective dose refers to that amount of antibody or antigen-binding fragment thereof, that ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, e.g., tumor size and location; age, weight and gender of the patient; diet, time and frequency of administration, drug combination(s), reaction sensitivities, and tolerance/response to therapy. Long acting pharmaceutical compositions might be administered for example every 3 to 4 days, every week, once every two weeks, or once every three weeks, depending on half-life and clearance rate of the particular formulation.

Normal dosage amounts may vary from 0.1 to 100,000 micrograms, up to a total dose of about 10 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc. Preferred specific activities for a radiolabelled antibody may range from 0.1 to 10 mCi/mg of protein (Riva et al., Clin. Cancer Res. 5:3275-3280, 1999; Ulaner et al., 2008 Radiology 246(3):895-902)

A further preferred embodiment of the invention is:

1. An isolated antibody or antigen-binding fragment thereof specifically binding to human CEACAM6 and to *Macaca fascicularis* CEACAM6.
2. An isolated antibody or antigen-binding fragment thereof specifically binding to the mature extracellular domain of human CEACAM6 (represented by amino acids at position 35-320 of SEQ-ID No: 179) and to the mature extracellular domain of *Macaca fascicularis* CEACAM6 (represented by amino acids at position 35-320 of SEQ-ID No: 177).
3. An isolated antibody or antigen-binding fragment thereof specifically binding to human CEACAM6 domain 1 (represented by amino acids 35-142 of SEQ-ID NO:179) and to *Macaca fascicularis* CEACAM6 domain 1 (represented by amino acids 35-142 of SEQ-ID NO:177).
4. An isolated antibody or antigen-binding fragment thereof specifically binding to a protein comprising human CEACAM6 domain 1 (represented by amino acids 35-142 of SEQ-ID NO:179) and to a protein comprising *Macaca fascicularis* CEACAM6 domain 1 (represented by amino acids 35-142 of SEQ-ID NO:177).
5. The antibody or antigen-binding fragment thereof according to any one of embodiments 1 to 4, which does not significantly cross-react with human CEACAM1, human CEACAM3, and human CEACAM5.
6. The antibody or antigen-binding fragment thereof according to any one of embodiments 1 to 5 able to bind to human and *Macaca fascicularis* CEACAM6, or the mature extracellular domain thereof, or the domain 1 thereof and the affinities are within one order of magnitude of monovalent $K_D$.
7. The antibody or antigen-binding fragment thereof according to any one of the preceding embodiments which competes for binding to the 9A6 antibody (Genovac/Aldevron) on human CEACAM6.
8. The antibody or antigen-binding fragment thereof according to any one of the preceding embodiments which interferes with the CEACAM6 and CEACAM1 interaction.
9. The antibody or antigen-binding fragment thereof according to any one of the preceding embodiments which is able to change the cytokine profile of tumor antigen specific T cells towards a more activated phenotype characterized by an IFN-gamma secretion increase, preferably by a ≥1.5 times (1.5 times or higher) increase compared to control samples.
10. The antibody or antigen-binding fragment thereof according to any one of the preceding embodiments which is able to induce immunomodulation.
11. The antibody or antigen-binding fragment thereof according to any one of the preceding embodiments which is able to relieve CEACAM6 mediated immunosuppression of tumor antigen specific T cells as measured by either IFN-gamma secretion of tumor antigen specific T cells or the number of IFN-gamma secreting activated T cells.
12. The antibody or antigen-binding fragment thereof according to any one of the preceding embodiments which is able to change the cytokine profile of tumor antigen specific T cells towards a more cytotoxic and/or activated phenotype characterized by an IFN-gamma and/or IL-2 and/or TNF-alpha secretion increase, preferably by a ≥1.5 times (1.5 times or higher) increase of IFN-gamma and/or IL-2 and/or TNF-alpha secretion compared to control samples.
13. The antibody or antigen-binding fragment thereof according to any one of the preceding embodiments which binds to an epitope of human CEACAM6, wherein said epitope comprises one or more amino acid residues selected from the group consisting of Gln60, Asn61, Arg62, Ile63, Va183, Ile84, Gly85, Thr90, Ser127, Asp128 and Leu129 of SEQ ID NO: 179.
14. The antibody or antigen-binding fragment thereof according to embodiment 13 which binds to an epitope of human CEACAM6, wherein said epitope comprises the amino acid residues Gln60, Asn61, Arg62, Ile63, Va183, Ile84, Gly85, Thr90, Ser127, Asp128 and Leu129 of SEQ ID NO: 179.
15. The antibody or antigen-binding fragment thereof according to embodiment 13 or 14 which binds to a human CEACAM6 protein comprising an Ile63Leu mutation and which does not bind to a human CEACAM6 protein comprising an Ile63Phe mutation according to SEQ ID NO: 179 numbering.

16. The antibody or antigen-binding fragment thereof according to any one of the preceding embodiments comprising:

i. a heavy chain antigen-binding region that comprises an H-CDR1 comprising SEQ ID NO:48, an H-CDR2 comprising SEQ ID NO:49, and an H-CDR3 comprising SEQ ID NO:50 and a light chain antigen-binding region that comprises a L-CDR1 comprising SEQ ID NO:52, a L-CDR2 comprising SEQ ID NO:53, and a L-CDR3 comprising SEQ ID NO:54, or ii. a heavy chain antigen-binding region that comprises an H-CDR1 comprising SEQ ID NO:106, an H-CDR2 comprising SEQ ID NO:107, and an H-CDR3 comprising SEQ ID NO:108 and a light chain antigen-binding region that comprises a L-CDR1 comprising SEQ ID NO:110, a L-CDR2 comprising SEQ ID NO:111, and a L-CDR3 comprising SEQ ID NO:112, or iii. a heavy chain antigen-binding region that comprises an H-CDR1 comprising SEQ ID NO:4, an H-CDR2 comprising SEQ ID NO:5, and an H-CDR3 comprising SEQ ID NO:6 and a light chain antigen-binding region that comprises a L-CDR1 comprising SEQ ID NO:8, a L-CDR2 comprising SEQ ID NO:9, and a L-CDR3 comprising SEQ ID NO:10, or iv. a heavy chain antigen-binding region that comprises an H-CDR1 comprising SEQ ID NO:34, an H-CDR2 comprising SEQ ID NO:35, and an H-CDR3 comprising SEQ ID NO:36 and a light chain antigen-binding region that comprises a L-CDR1 comprising SEQ ID NO:38, a L-CDR2 comprising SEQ ID NO:39, and a L-CDR3 comprising SEQ ID NO:40, or v. a heavy chain antigen-binding region that comprises an H-CDR1 comprising SEQ ID NO:120, an H-CDR2 comprising SEQ ID NO:121, and an H-CDR3 comprising SEQ ID NO:122 and a light chain antigen-binding region that comprises a L-CDR1 comprising SEQ ID NO:124, a L-CDR2 comprising SEQ ID NO:125, and a L-CDR3 comprising SEQ ID NO:126, or vi. a heavy chain antigen-binding region that comprises an H-CDR1 comprising SEQ ID NO:24, an H-CDR2 comprising SEQ ID NO:25, and an H-CDR3 comprising SEQ ID NO:26 and a light chain antigen-binding region that comprises a L-CDR1 comprising SEQ ID NO:28, a L-CDR2 comprising SEQ ID NO:29, and a L-CDR3 comprising SEQ ID NO:30, or vii. a heavy chain antigen-binding region that comprises an H-CDR1 comprising SEQ ID NO:76, an H-CDR2 comprising SEQ ID NO:77, and an H-CDR3 comprising SEQ ID NO:78 and a light chain antigen-binding region that comprises a L-CDR1 comprising SEQ ID NO:80, a L-CDR2 comprising SEQ ID NO:81, and a L-CDR3 comprising SEQ ID NO:82, or viii. a heavy chain antigen-binding region that comprises an H-CDR1 comprising SEQ ID NO:134, an H-CDR2 comprising SEQ ID NO:135, and an H-CDR3 comprising SEQ ID NO:136 and a light chain antigen-binding region that comprises a L-CDR1 comprising SEQ ID NO:138, a L-CDR2 comprising SEQ ID NO:139, and a L-CDR3 comprising SEQ ID NO:140, or ix. a heavy chain antigen-binding region that comprises an H-CDR1 comprising SEQ ID NO:148, an H-CDR2 comprising SEQ ID NO:149, and an H-CDR3 comprising SEQ ID NO:150 and a light chain antigen-binding region that comprises a L-CDR1 comprising SEQ ID NO:152, a L-CDR2 comprising SEQ ID NO:153, and a L-CDR3 comprising SEQ ID NO:154, or x. a heavy chain antigen-binding region that comprises an H-CDR1 comprising SEQ ID NO:14, an H-CDR2 comprising SEQ ID NO:15, and an H-CDR3 comprising SEQ ID NO:16 and a light chain antigen-binding region that comprises a L-CDR1 comprising SEQ ID NO:18, a L-CDR2 comprising SEQ ID NO:19, and a L-CDR3 comprising SEQ ID NO:20, or xi. a heavy chain antigen-binding region that comprises an H-CDR1 comprising SEQ ID NO:62, an H-CDR2 comprising SEQ ID NO:63, and an H-CDR3 comprising SEQ ID NO:64 and a light chain antigen-binding region that comprises a L-CDR1 comprising SEQ ID NO:66, a L-CDR2 comprising SEQ ID NO:67, and a L-CDR3 comprising SEQ ID NO:68, or xii. a heavy chain antigen-binding region that comprises an H-CDR1 comprising SEQ ID NO:92, an H-CDR2 comprising SEQ ID NO:93, and an H-CDR3 comprising SEQ ID NO:94 and a light chain antigen-binding region that comprises a L-CDR1 comprising SEQ ID NO:96, a L-CDR2 comprising SEQ ID NO:97, and a L-CDR3 comprising SEQ ID NO:98.

17. The antibody or antigen-binding fragment thereof according to any one of the preceding embodiments comprising:

i. a variable heavy chain sequence as presented by SEQ ID NO: 47 and a variable light chain sequence as presented by SEQ ID NO: 51, or ii. a variable heavy chain sequence as presented by SEQ ID NO: 105 and a variable light chain sequence as presented by SEQ ID NO: 109, or iii. a variable heavy chain sequence as presented by SEQ ID NO: 3 and a variable light chain sequence as presented by SEQ ID NO: 7, or iv. a variable heavy chain sequence as presented by SEQ ID NO: 33 and a variable light chain sequence as presented by SEQ ID NO: 37, or v. a variable heavy chain sequence as presented by SEQ ID NO: 119 and a variable light chain sequence as presented by SEQ ID NO: 123, or vi. a variable heavy chain sequence as presented by SEQ ID NO: 23 and a variable light chain sequence as presented by SEQ ID NO: 27, or vii. a variable heavy chain sequence as presented by SEQ ID NO: 75 and a variable light chain sequence as presented by SEQ ID NO: 79, or viii. a variable heavy chain sequence as presented by SEQ ID NO: 133 and a variable light chain sequence as presented by SEQ ID NO: 137, or ix. a variable heavy chain sequence as presented by SEQ ID NO: 147 and a variable light chain sequence as presented by SEQ ID NO: 151, or x. a variable heavy chain sequence as presented by SEQ ID NO: 13 and a variable light chain sequence as presented by SEQ ID NO: 17, or xi. a variable heavy chain sequence as presented by SEQ ID NO: 61 and a variable light chain sequence as presented by SEQ ID NO: 65, or xii. a variable heavy chain sequence as presented by SEQ ID NO: 91 and a variable light chain sequence as presented by SEQ ID NO: 95.

18. The antibody according to any one of the preceding embodiments, which is an IgG antibody.

19. The antibody according to embodiment 18 comprising:

i. a heavy chain region corresponding to SEQ ID NO: 57 and a light chain region corresponding to SEQ ID NO: 58, or ii. a heavy chain region corresponding to SEQ ID NO: 115 and a light chain region corresponding to SEQ ID NO: 116, or iii. a heavy chain region corresponding to SEQ ID NO: 43 and a light chain region corresponding to SEQ ID NO: 44, or iv. a heavy chain region corresponding to SEQ ID NO: 129 and a light chain region corresponding to SEQ ID NO: 130, or v. a heavy chain region corresponding to SEQ ID NO: 85 and a light chain region corresponding to SEQ ID NO: 86, or vi. a heavy chain region corresponding to SEQ ID NO: 143 and a light chain region corresponding to SEQ ID NO: 144, or vii. a heavy chain region corresponding to SEQ ID NO: 157 and a light chain region corresponding to SEQ ID NO: 158, or viii. a heavy chain region corresponding to SEQ ID NO: 71 and a light chain region corresponding to SEQ ID NO: 72, or ix. a heavy chain region corresponding to SEQ ID NO: 101 and a light chain region corresponding to SEQ ID NO: 102.

20. The antigen-binding fragment according to embodiments 1 to 17, which is an scFv, Fab, Fab' fragment or a $F(ab')_2$ fragment.

21. The antibody or antigen-binding fragment according to any one of the preceding embodiments, which is a monoclonal antibody or antigen-binding fragment.

22. The antibody or antigen-binding fragment according to any one of the preceding embodiments, which is human, humanized or chimeric antibody or antigen-binding fragment.

23. An antibody-drug conjugate, comprising an antibody or antigen binding fragment thereof according to any one of the embodiments 1 to 22.

24. An isolated nucleic acid sequence that encodes the antibody or antigen-binding fragment according to any one of the embodiments 1 to 22.

25. A vector comprising a nucleic acid sequence according to embodiment 24.

26. An isolated cell expressing an antibody or antigen-binding fragment according to any one of the embodiments 1 to 22 and/or comprising a nucleic acid according to embodiment 24 or a vector according to embodiment 25.

27. An isolated cell according to embodiment 26, wherein said cell is a prokaryotic or an eukaryotic cell.

28. A method of producing an antibody or antigen-binding fragment according to any one of the embodiments 1 to 22 comprising culturing of a cell according to embodiment 27 and purification of the antibody or antigen-binding fragment.

29. An antibody or antigen-binding fragment according to any one of the embodiments 1 to 22 or an antibody-drug conjugate according to embodiment 23 for use as a medicament.

30. An antibody or antigen-binding fragment according to any one of the embodiments 1 to 22 or an antibody-drug conjugate according to embodiment 23 for use as a diagnostic agent.

31. An antibody or antigen-binding fragment according to any one of the embodiments 1 to 22 or an antibody-drug conjugate according to embodiment 23 for use as a medicament for the treatment of cancer.

32. An antibody or antigen-binding fragment according to any one of the embodiments 1 to 22 or an antibody-drug conjugate according to embodiment 23 in the manufacture of a medicament for the treatment of a disease.

33. An antibody or antigen-binding fragment according to any one of the embodiments 1 to 22 or an antibody-drug conjugate according to embodiment 23 in the manufacture of a medicament for the treatment of cancer.

34. A pharmaceutical composition comprising an antibody or antigen-binding fragment according to any one of the embodiments 1 to 22 or an antibody-drug conjugate according to embodiment 23.

35. A combination of a pharmaceutical composition according to embodiment 34 and one or more therapeutically active compounds.

36. A method for treating a disorder or condition associated with the undesired presence of CEACAM6, comprising administering to a subject in need thereof an effective amount of the pharmaceutical composition according to embodiment 34 or a combination according to embodiment 35.

37. A process for the preparation of anti-CEACAM6 antibodies specifically binding to human CEACAM6 and *Macaca fascicularis* CEACAM6, which process comprises immunization of an animal, preferentially a mouse, with a protein comprising cynomolgus CECAM6 domain 1 represented by amino acids 35-142 of SEQ-ID NO:177, determining the amino acid sequence of antibodies specifically binding to human CEACAM6 and to cynomolgus CEACAM6, followed optionally by humanization or generation of a chimeric antibody, and recombinant expression of said antibodies.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., Molecular Cloning: A Laboratory Manual, 2nd Ed.; Cold Spring Harbor Laboratory Press, Cold Spring Harbor, N.Y., 1989.

Example 1: Monkey CEACAM6 Sequences & Tool Generation

An overview of protein sequences of antigens and reference compounds used is provided in Table 2:

TABLE 2

Name, Protein-IDs and SEQ-IDs used in this study

| Name | Protein-ID | Description | SEQ-ID |
|---|---|---|---|
| human CEACAM6 | TPP-4639 | full-length | SEQ-ID NO: 179 |
| *Macaca fascicularis* CEACAM6 | TPP-4189 | full-length | SEQ-ID NO: 177 |
| human CEACAM1 | TPP-4185 | full-length | SEQ-ID NO: 173 |
| human CEACAM3 | TPP-4187 | full-length | SEQ-ID NO: 175 |
| human CEACAM5 | TPP-4188 | full-length | SEQ-ID NO: 176 |
| human CEACAM8 | TPP-4190 | full-length | SEQ-ID NO: 178 |
| human CEACAM19 | TPP-4186 | full-length | SEQ-ID NO: 174 |
| human CEACAM6 | TPP-1436 | extracellular (mature form) (R&D Systems 3934-CM) | SEQ-ID NO: 162 |
| human CEACAM1 | TPP-1437 | extracellular (mature form) (R&D Systems 2244-CM) | SEQ-ID NO: 163 |
| human CEACAM3 | TPP-2755 | extracellular (mature form) (Sino Biological Inc. 11933-H08H) | SEQ-ID NO: 172 |
| human CEACAM5 | TPP-1438 | extracellular (mature form) (R&D Systems 4128-CM) | SEQ-ID NO: 164 |
| *Macaca mulatta* CEACAM6-Xa-Fc-His | TPP-1306 | extracellular (mature form), fusion to Xa-Fc-His | SEQ-ID NO: 161 |
| Human CEACAM6-Xa-Fc-His | TPP-1790 | extracellular (mature form), fusion to Xa-Fc-His | SEQ-ID NO: 165 |
| Human CEACAM6-Dom1-*MacMul*-Xa-Fc-His | TPP-1791 | extracellular (mature form), fusion to Xa-Fc-His, Domain 1 replaced by corresponding *Macaca mulatta* domain | SEQ-ID NO: 166 |
| Human CEACAM6-Dom2-*MacMul*-Xa-Fc-His | TPP-1792 | extracellular (mature form), fusion to Xa-Fc-His, Domain 2 replaced by corresponding *Macaca mulatta* domain | SEQ-ID NO: 167 |
| Human CEACAM6-Dom3-*MacMul*-Xa-Fc-His | TPP-1793 | extracellular (mature form), fusion to Xa-Fc-His, Domain 3 replaced by corresponding *Macaca mulatta* domain | SEQ-ID NO: 168 |
| Human CEACAM6 | APP-320 | Extracellular (mature form), obtained by cleavage with Factor Xa of TPP-1790 | |
| Human CEACAM6-Domain 1-His | TPP-1794 | Domain 1, fusion to His (expressed in *E. coli*) | SEQ-ID NO: 169 |
| *Macaca fascicularis* CEACAM6-Xa-Fc-His | TPP-2443 | extracellular (mature form), fusion to Xa-Fc-His | SEQ-ID NO: 170 |
| *Macaca fascicularis* CEACAM6 | APP-319 | extracellular (mature form), obtained by Factor Xa cleavage of TPP-2443 | |
| *Macaca fascicularis* CEACAM6-Domain 1-Xa-Fc-His | TPP-2452 | Domain 1, fusion to Xa-Fc-His | SEQ-ID NO: 171 |
| *Macaca fascicularis* CEACAM6-Domain 1 | APP-325 | Domain 1, obtained by Factor Xa cleavage of TPP-2452 | |
| Neo201 (human IgG1) | TPP-1173 | based on US20130189268 | SEQ-ID NO: 1 & SEQ-ID NO: 2 |
| Neo201 (human IgG2) | TPP-3688 | based on US20130189268 | SEQ-ID NO: 89 & SEQ-ID: 90 |
| 9A6 (mouse IgG1) | TPP-1744 | Based on Genovac/Aldevron (GM-0509) | |

TABLE 2-continued

| Name, Protein-IDs and SEQ-IDs used in this study | | | |
|---|---|---|---|
| Name | Protein-ID | Description | SEQ-ID |
| 9A6 (chimeric hIgG1) | TPP-1745 | Based on Genovac/Aldevron (GM-0509) | |
| 9A6 (chimeric hIgG2) | TPP-3470 | Based on Genovac/Aldevron (GM-0509) | |

Protein sequences for human CEACAMs were obtained from UniProtKB/TrEMBL database: human CEACAM6 (P40199), human CEACAM1 (P13688), human CEACAM3 (P40198), human CEACAM5 (P06731), human CEACAM8 (P31997), human CEACAM19 (Q7Z692). The *Macaca mulatta* (rhesus monkey) protein sequence of CEACAM6 was also available (F6YVW1). The *Macaca fascicularis* (cynomolgus monkey) protein sequence of CEACAM6 was deduced from publicly available nucleotide sequences by a) applying common intron/exon splicing rules b) comparison to different monkey/primate protein sequences and c) conservation of genomic structure between human/primate/monkey. Cynomolgus CEACAM6 is represented by TPP-4189.

Recombinant extracellular domains of CEACAMs were obtained from commercial sources or produced in-house. To this end, the extracellular domains were C-terminally appended with a Factor Xa cleavage site, a human IgG1 Fc fragment as well as a His Tag and expressed in HEK293 cells using standard transient transfection procedures. Proteins were purified from the cell culture supernatant via Protein-A and size exclusion chromatography. In cases, in which the Fc-part needed to be removed, proteins were cleaved with Factor Xa according to the manufacturer's recommendations (e.g. Factor Xa Protease from Hematologic Technologies Inc. HTI No. HCXA-0060) and subsequently purified by Protein-A and size exclusion chromatography. In cases in which biotinylated proteins were needed, commercial biotinylation kits were used (e.g. EZ-Link Amine-PEG3-Biotin from Pierce #21347) and degree of biotinylation was characterized by commercial kits (e.g. Biotin Quantitation Kit from Pierce #28005).

The single N-terminal domain 1 of human CEACAM6 was produced as 6× His fused protein construct in *E. coli* BL21 DE3 using pET28a vector (Novagen). After overnight induction with IPTG at 37° C., recombinant protein was isolated and refolded from inclusion bodies. Prior to refolding, inclusion bodies were washed in Tris buffer pH 8.5 containing 150 mM NaCl, 1 mM EDTA, 0.1% Tween20 and solubilized in the same buffer containing 8 M urea and no detergent. The solution was diluted (1:10) slowly into 50 mM CHES pH 9.2 containing 500 mM arginine and incubated at 4° C. for 16 h. Purification was achieved performing standard Nickel-NTA chromatography and size exclusion chromatography in 30 mM Tris buffer pH 8.5, 150 mM NaCl on Superdex 75.

The 9A6 murine IgG1 antibody (GM-0509) was obtained from Genovac and chimerized to human IgG1 and human IgG2. The basis of Neo201 protein sequence as either human IgG1 or human IgG2 was US20130189268. All antibodies were expressed in HEK293 cells using standard transient transfection procedures and purified from the cell culture supernatant via Protein-A and size exclusion chromatography.

Stable HeLa cell lines expressing different full-length human CEACAM-receptors were generated. Therefore sequences of the following receptors were transfected: human CEACAM1 (TPP-4185), human CEACAM3 (TPP-4187), human CEACAM5 (TPP-4188), human CEACAM6 (TPP-4639), human CEACAM8 (TPP-4190), human CEACEAM19 (TPP-4186) or cynomolgus CEACAM6 (TPP-4189). The HeLa cell line does not endogenously express any of these receptors on the surface as was confirmed by FACS analysis, and surface expression could only be detected after transfection of the respective CEACAM-receptor. Briefly, expression constructs were cloned into UCOE-based vectors (EMD Millipore Corporation) and transfected in HeLa cells. After selection with hygromycin, suitable stable clones were screened by Western blotting of total cell lysate as well as FACS staining of cellular surface using suitable antibodies (human CEACAM1: #MAB22441 from R&D Systems; human CEACAM5: #MAB41281 from R&D Systems; human CEACAM6: #MAB3934 from R&D Systems; human CEACAM8: ab90294 from abcam; human CEACAM19: #NBP1-70494 from Novus; human CEACAM3: AF4166 from R&D Systems; cynomolgus CEACAM6: Neo201-hIgG1).

Example 2: Characterization of Immunomodulating 9A6-mIgG1 Antibody

9A6 antibody has been described in the literature as being immunomodulatory (Witzens-Harig et al., Blood 2013 May 30; 121(22):4493-503). This antibody was characterized with regards to its affinity, its selectivity towards other human CEACAMs, its cross-reactivity to monkey CEACAM6, its specific binding to a certain domain on CEACAM6, and its selectivity towards other human CEACAMs.

Affinity Measurements Using Surface Plasmon Resonance (SPR)

Surface plasmon resonance (SPR) experiments for quantitative binding analyses were performed either using a Biacore T100, Biacore T200 or a Biacore 4000 instrument (GE Healthcare Biacore, Inc.) equipped with Series S Sensor Chips CM5 (GE Healthcare Biacore, Inc.). Binding assays were carried out at 25° C. with assay buffer HBS-EP+(10 mM HEPES pH 7.4, 150 mM NaCl, 3 mM EDTA, 0.05% Surfactant P20). Antibodies were captured with an anti-hIgG capture antibody covalently immobilized to the chip surface via amine coupling chemistry. Reagents for amine coupling (1-ethyl-3-(3-dimethylaminopropyl) carbodiimide hydrochloride (EDC), N-hydroxysuccinimide (NHS), ethanolamine-HCl pH 8.5) were used from the Amine Coupling Kit (GE Healthcare, product code BR-1000-50). Anti-hIgG, anti-mIgG capture antibodies and immobilization buffer (10 mM sodium acetate pH 5.0) were used from the Human Antibody Capture Kit (GE Healthcare, BR-1008-39) and the Mouse Antibody Capture Kit (GE Healthcare, BR-1008-38), respectively. The sensor chip surface was activated with a freshly prepared solution of 0.2 M EDC and 0.05 M NHS passed over the chip surface for 420 s at a flow rate of 10 μl/min, followed by an injection of anti-hIgG or anti-mIgG capture antibody (dissolved to 25 μg/ml in immobilization buffer) for 180 s at a flow rate of 5 al/min. Excess of activated groups were blocked with a 1 molar solution of ethanolamine injected at a flow rate of 10 μl/min for 420 s.

CEACAM antigens were used as analyte to determine $K_D$ values. Antibodies were captured for 20 s at a flow rate of 10 μl/min prior to each analyte injection. For kinetic affinity determination various concentrations between 1.56 and 200 nM of human CEACAM1, human CEACAM3, human CEACAM5, human CEACAM6, cynomolgus CEACAM6, cynomolgus CEACAM6-domain 1 protein in assay buffer (see above) were injected over the captured antibodies at a flow rate of 60 μl/min for 3 minutes and the dissociation was monitored for 10 minutes.

Obtained sensorgrams were double-referenced, i.e. in-line reference cell correction followed by buffer sample subtraction. $K_D$ values were calculated based on the ratio of dissociation ($k_d$) and association ($k_a$) rate constants which were obtained by globally fitting sensorgrams with a first order 1:1 Langmuir binding model, implemented in the Biacore Evaluation Software Package (Biacore T100/T200/4000 Evaluation Software, GE Healthcare Biacore, Inc.).

Sandwich Competition Experiments by SPR

Sandwich competition experiments by SPR were performed in a similar manner as outlined above with minor modifications. First, each antibody to be analyzed was covalently immobilized on the sensor surface via amine coupling (for details see above). To check whether a different antibody competes for binding to a certain CEACAM antigen, the respective antigen was captured by injection over the immobilized antibody and the second antibody to be tested for competition was immediately injected subsequently. If the second antibody binds to the antigen bound by the first antibody (+), both antibodies do not show competition and vice versa, if no binding is observed by injection of the second antibody (−), both antibodies compete for a similar epitope.

Domain Mapping Studies Using ELISA

To elucidate specific epitope information, several chimeric domain constructs were designed, expressed and purified. Briefly, the wild type human CEACAM6 sequence was C-terminally fused with a human IgG1 Fc fragment, expressed in HEK293 cells and purified from the supernatant via Protein-A and size exclusion chromatography (TPP-1790). In order to create different domain chimeras, the human sequence of one single domain was consequently replaced by the corresponding *Macaca mulatta* sequence (F6YVW1) in the Fc-fused human CEACAM6. This created three different domain chimeras hDom1-hDom2-mDom3 (TPP-1793), hDom1-mDom2-hDom3 (TPP-1792), and mDom1-hDom2-hDom3 (TPP-1791), together with the wild-type *Macaca mulatta* Fc fusion construct as control (TPP-1306). In addition to the chimeras, the single domain 1 of human CEACAM6 was produced as described above from *E. coli* (TPP-1794).

Mapping of the domain specificity of the antibodies was carried out using an ELISA assay:

For ELISA analysis, the Fc-fused domain chimeras and the single domain 1 were coated on Nunc MaxiSorb plates and blocked with SmartBlock solution. After incubation with an IgG-concentration series (1 nM-1000 nM) for 1 h, plates were washed with PBS/T. Analysis of the bound IgGs to the CEACAM6 domain constructs was achieved over detection via Anti-Human IgG (Fab specific)-Peroxidase antibody (A0293, Sigma). Fluorescence detection was performed with AmplexRed (A12222, Invitrogen) following standard protocols.

ELISA-Based Binding Analysis

ELISAs were used to characterize the binding of antibodies to various CEACAM paralogs and orthologs. Black 384-well plates were coated with 25 al/well of various CEACAM protein preparations at 2 μg/ml in coating buffer (Candor) for 1 h at 37° C. After one wash with PBS/0.05% Tween-20, wells were blocked with 100% Smart Block (Candor) for one hour at 37° C. After three washes with PBS/0.05% Tween-20, dilution series of the antibodies in PBS/0.05% Tween-20/10% Smart Block ranging from 2 ag/ml to 2 ng/ml were added and the plates were incubated for 1 h at room temperature. After three washes with PBS/0.05% Tween-20, an appropriate secondary antibody was added. For detection of proteins with a human Fc such as TPP-1173, an anti-human IgG HRP (Sigma A0170) was used at 1:10.000 dilution. For detection of proteins with a mouse Fc such as TPP-1744 an anti-mouse IgG HRP (ThermoScientific 31432) was used at 1:10.000 dilution. PBS/0.05% Tween-20/10% Smart Block was used as dilution buffer. The plates were incubated for 1 hour at room temperature. After three washes, the plates were developed with Amplex Red (Life Technologies) and fluorescence was read at an emission wavelength of 590 nm. GraphPad Prism 6.0 software was used to calculate $EC_{50}$ values using four-parameter non-linear curve fit.

Results

To measure the monovalent affinity of 9A6 to human CEACAM6 and to assess its cross-reactivity towards monkey CEACAM6, SPR experiments were conducted as outlined above. Results are shown in Table 3:

TABLE 3

SPR analysis: monovalent $K_D$ (in nM)

| | Alias | Recombinant human CEACAM6 (R&D Systems; TPP-1436) | Recombinant *macaca mulatta* CEACAM6 (TPP-1306) |
|---|---|---|---|
| 9A6-mIgG1 | TPP-1744 | 22 | – |
| Neo201-hIgG1 | TPP-1173 | 10 | 23 |

"–": no binding detected

As shown, 9A6-mIgG1 can bind with high affinity (22 nM) to recombinant human CEACAM6. However, no binding to *Macaca mulatta* CEACAM6 was detected. For comparison, Neo201-hIgG1 was also tested. This antibody displayed high affinity binding to both human and monkey CEACAM6. In summary, 9A6 displays high affinity binding to human CEACAM6 but it is not cross-reactive to monkey CEACAM6.

To map the binding domain of 9A6 on CEACAM6, binding on different human/monkey chimera was assessed by ELISA as outlined above. To be able to compare to Neo201-hIgG1 (TPP-1173), 9A6 was chimerized to a human IgG1 (TPP-1745). Results are shown in Table 4:

TABLE 4

| Domain mapping analysis by ELISA binding assay | | | | | | |
|---|---|---|---|---|---|---|
| | TPP-# | Origin of domain 1 | Origin of domain 2 | Origin of domain 3 | 9A6-hIgG1 (TPP-1745) | Neo201-hIgG1 (TPP-1173) |
| hWT | 1790 | human | human | human | + | + |
| DOM1 MM | 1791 | M. mulatta | human | human | – | + |
| DOM2 MM | 1792 | human | M. mulatta | human | + | + |
| DOM3 MM | 1793 | human | human | M. mulatta | + | + |
| hDOM1 | 1794 | human | – | – | + | – |
| MM WT | 1306 | M. mulatta | M. mulatta | M. mulatta | – | + |

"+" denotes binding detected;
"–" denotes no binding detected

9A6 is able to bind to wildytpe human CEACAM6, and to chimeras employing Domain 2 or 3 of *Macaca mulatta* CEACAM6. However, it fails to bind to a chimera employing Domain 1 of *Macaca mulatta* CEACAM6 or to wildtype *Macaca mulatta* CEACAM6. Consistent with this, it is able to bind to the single domain 1 of human CEACAM6. In contrast, Neo201-hIgG1 binds to all forms tested except for single domain 1 of human CEACAM6. In conclusion, 9A6 binds to the N-terminal Domain 1 of human CEACAM6.

To substantiate the results, a competition experiment was performed as outlined above. Results are shown in Table 5.

TABLE 5

| Sandwich competition experiments by SPR on recombinant human CEACAM6 (R&D Systems, TPP-1436) | | |
|---|---|---|
| | 9A6-mIgG1 (TPP-1744) | Neo201-hIgG1 (TPP-1173) |
| 9A6-mIgG1 (TPP-1744) | – | + |
| Neo201-hIgG1 (TPP-1173) | + | – |

If the second antibody binds to the antigen bound by the first antibody (+), both antibodies do not show competition and vice versa, if no binding is observed by injection of the second antibody (–), both antibodies compete for a similar epitope As evident from Table 5, 9A6-mIgG1 and Neo201-hIgG1 do not compete with each other for binding to human CEACAM6. This is consistent with the published epitope of Neo201 residing outside domain 1.

To analyze the selectivity of 9A6 towards different CEACAM6 orthologs and to allow comparison to Neo201-hIgG1, 9A6 was chimerized to hIgG1 (TPP-1745). In ELISA binding experiment conducted as outlined above, the $EC_{50}$ values listed in Table 6 have been obtained:

TABLE 6

| Selectivity/cross-reactivity analysis by binding ELISA - $EC_{50}$ values in nM | | | | | |
|---|---|---|---|---|---|
| | TPP- | Human CEACAM6 (TPP-1436) | Human CEACAM3 (TPP-2755) | Human CEACAM5 (TPP-1438) | Cynomolgus CEACAM6 (APP-319) |
| 9A6-hIgG1 | TPP-1745 | 0.09 | – | – | – |
| Neo201-hIgG1 | TPP-1173 | 0.11 | – | 0.09 | 1.35 |

denotes $EC_{50}$ > 10 nM

High affinity binding of 9A6 to human CEACAM6 was confirmed. Consistent with SPR experiments using rhesus monkey CEACAM6, 9A6 also fails to bind to cynomolgus monkey CEACAM6. It is, however, selective for CEACAM6 since no binding to human CEACAM3 or CEACAM5 was observed.

In contrast, Neo201-hIgG1 displays similar high affinity binding to human CEACAM6 and is even cross-reactive to cynomolgus CEACAM6. This comes at a reduced selectivity, since it displays also high affinity binding to human CEACAM5.

Example 3: Protein Sequence Alignment of CEACAMs

The mature extracellular form of human CEACAM6 (amino acids 35-320 of UniProtKB/Swiss-Prot: P40199.3) consists of different domains: N-terminal domain 1 (according to amino acids 35-142 of UniProtKB/Swiss-Prot: P40199.3), domain 2 (according to amino acids 145-232 of UniProtKB/Swiss-Prot: P40199.3), and domain 3 (according to amino acids 237-314 of UniProtKB/Swiss-Prot: P40199.3). Since the goal was to identify a selective, high affinity antibody to N-terminal domain 1 of CEACAM6, yet being cross-reactive to cynomolgus monkey CEACAM6, the probability of combining the desired properties in one molecule was assessed.

To this end, the protein sequence of N-terminal domain 1 of human CEACAM6 was compared to other proteins using Blastp algorithm (NCBI) using standard settings to identify most relevant CEACAM6 homologs. (Partial) mature extracellular domains of human CEACAM6 (amino acids 35-320 of UniProtKB/Swiss-Prot: P40199.3), human CEACAM1 (amino acids 35-428 of UniProtKB/Swiss-Prot: P13688.2), human CEACAM3 (amino acids 35-155 of UniProtKB/Swiss-Prot: P40198.2), human CEACAM5 (amino acids 35-417 of UniProtKB/Swiss-Prot: P06731.3) and cynomolgus (*Macaca fascicularis*) CEACAM6 (amino acids 35-320 of TPP-4189) were aligned using "Global Alignment—Wilbur and Lipman (fast)" in Phylosopher software (Genedata). The alignment is shown in FIG. 1. The percentage sequence identities of N-terminal domain1 of human CEACAM6 to other N-terminal domains (according to alignment) were determined using Vector NTI Software (Life Technologies). Those results are shown in Table 7.

TABLE 7

| Percentage of protein sequence identities of N-terminal domains of different CEACAMs to N-terminal domain 1 of human CEACAM6. | |
|---|---|
| | Sequence identity of N-terminal domains to N-terminal domain 1 of human CEACAM6 |
| Human CEACAM6 | (100%) |
| Human CEACAM3 | 90% |
| Human CEACAM1 | 90% |
| Human CEACAM5 | 89% |
| Cynomolgus CEACAM6 | 81% |

The sequence alignment in FIG. 1 shows a very high degree of similarity of protein sequences of human CEACM6 and human CEACAM3, human CEACAM5 and human CEACAM1 throughout the entire extracellular region. The target region (domain 1 of human CEACAM6) is especially similar to other CEACAMs, which is also reflected in Table 7. The paralogs of human CEACAM6 are much more similar to human CEACAM6 than the cynomolgus ortholog. In fact, there are only 2 positions in N-terminal region in the primary sequence that are identical in human and cynomolgus CEACAM6 but different from amino acids in this position in the other human paralogs (marked in FIG. 1 with asterisks).

To conclude: it is highly challenging to identify a high affinity antibody to the N-terminal domain 1 of human CEACAM6 that is selective but still cross-reactive to monkey CEACAM6.

Example 4: Antibody Generation by Phage Display

To identify human anti-CEACAM6 antibodies, various selections with the human Fab-phage library FAB-300 from DYAX were performed, essentially as described earlier (Hoet et al., 2005; Huang et al., 2006). As summarized in Table 8, different strategies with up to 4 rounds of phage selection were employed using biotinylated Fc-tagged recombinant CEACAM6 from human and cynomolgus monkey (TPP-1436 & TPP-2443), coated on strepavidin-beads, and the human tumor cell line KPL-4 (Kurebayashi et al., Br J Cancer. 1999 February; 79 (5-6):707-17), which is expressing high amounts of endogenous target protein on the cell surface. In addition, depletion for binder against CEACAM5 (TPP-1438; hC5) and CEACAM1 (TPP-1437; hC1) (off-targets) or recombinant human IgG1-Fc (Fc) was included as indicated prior to each selection on protein targets. For example, in strategy A after depletion on human CEACAM1-coated beads (hC1), the first round of panning was done on human CEACAM6 (hC6). The resulting output was divided and one part was used for a second and a third round of selection on human CEACAM6. The other part was used for second round of panning on KPL-4 cells, a third round on human CEACAM6 and a final fourth panning round on KLP-4 cells. In strategy C, a specific elution step was performed, using the mouse mAb 9A6-mIgG1 (TPP-1744).

TABLE 8

Phage selection strategies:
human hC6 = TPP-1790; cynomolgus cynoC6 = TPP-2443,
hC1 = TPP-1438, hC5 = TPP-1437,
Fc = Recombinant Human IgG1 Fc (R & D Systems # 110-HG-100)

| Strategy: | A | | B | | C | | D |
|---|---|---|---|---|---|---|---|
| Round 1 | hC6 | | hC6 | | hC6 | | cynoC6 |
| Round 2 | hC6 | KPL-4 | hC6 | KPL-4 | hC6 | KPL-4 | hC6 |
| Round 3 | hC6 | hC6 | hC6 | hC6 | hC6 | hC6 | cynoC6 |
| Round 4 | — | KPL-4 | — | KPL-4 | — | KPL-4 | hC6 |
| Depletion | hC1 | | hC1 and hC5 | | hC1 | | Fc |
| Specific elution | — | | — | | 9A6 | | — |

Phage pools enriched from different rounds of selections were screened for binders to target and off-target by Fab-phage ELISA as described (Hoet et al., Nat Biotechnol. 2005 March; 23(3):344-8) or by FACS-analysis on CEACAM6-expressing cells. Phage pools with a favorable profile were selected for geneIII-removal and subsequent ELISA-screening of soluble Fabs in an ELISA. DNA of resulting sFab-hits was sequenced and unique representatives characterized for cell-binding by FACS-analysis on KPL-4 cells (Table 9). In some strategies phage binder according to the invention were directly re-cloned into IgG.

TABLE 9

FACS-titration of unique sFab-hits:

| Protein-ID (as hIgG1) | FACS-titration as sFab on KPL-4 cells |
|---|---|
| TPP-1667 | ++ |
| TPP-1668 | + |
| TPP-1669 | + |
| TPP-1670 | + |
| TPP-1672 | + |
| TPP-1673 | + |
| TPP-1674 | + |
| TPP-1676 | + |
| TPP-1677 | 0 |
| TPP-1678 | 0 |
| TPP-1679 | +++ |
| TPP-1680 | + |
| TPP-1684 | 0 |
| TPP-1686 | + |

+++: >1000 events @ ~2.2 μg/ml sFab
++: >100 events @ ~2.2 μg/ml sFab
+: >100 events @ ~6.7 μg/ml sFab
0: below threshold Binding of phage display selected, purified Fab fragments (see list in Table 9) to biotinylated variants of human CEACAM1 (TPP-1437), human CEACAM5 (TPP-1438) and human CEACAM6 (TPP-1436) was analyzed by bio-layer interferometry using an Octet RED384 instrument (Pall ForteBio Corp.). Biotinylated antigens were loaded onto Streptavidin (SA) Biosensors (ForteBio Part number 18-5019) and after a baseline equilibrium step in assay buffer (PBS supplemented with 0.1% (w/v) BSA, 0.02% (v/v) Tween20 and 0.05% (v/v) sodium azide; ForteBio Part number 18-5032), binding of Fabs diluted in assay buffer to a final concentration of 200 nM was monitored for 300 seconds followed by a dissociation phase of 300 seconds.

The corresponding purified Fab fragments from Table 9 also displayed binding to human CEACAM6 but not to human CEACAM5 or human CEACAM1.

In order to analyze whether the Fabs compete with 9A6 for binding to human CEACAM6, a competition experiment was carried out. Here, biotinylated human CEACAM6 (TPP-1436) was loaded onto SA Biosensors and binding responses of Fabs were compared to binding responses of Fabs obtained with loaded CEACAM6 saturated with 9A6-mIgG1 (TPP-1744) (as outlined in Example 1). If the binding response in presence of 9A6 is significantly reduced or abolished this is a strong indication that a tested Fab binds to an epitope similar to that of 9A6.

Surprisingly, all Fabs tested were able to compete with 9A6 for binding to human CEACAM6.

The Fab sequences were reformatted into human IgG1 format for further characterization.

Affinities (monovalent $K_D$) of reformatted antibodies towards recombinant human CEACAM6 (TPP-1436) were determined by SPR analogously to experimental procedures described in Example 2. Sensorgrams were either evaluated by globally fitting sensorgrams with a first order 1:1 Langmuir binding model or with a steady-state affinity analysis implemented in the Biacore Evaluation Software (Biacore T200/4000 Evaluation Software) Package. Results are shown in Table 10:

TABLE 10

| SPR analysis: monovalent $K_D$ (in nM) | |
|---|---|
| Protein-ID | $K_D$ (in nM) |
| TPP-1667 | (750) |
| TPP-1668 | (550) |
| TPP-1669 | (185) |
| TPP-1670 | (340) |
| TPP-1672 | (580) |
| TPP-1673 | (515) |
| TPP-1674 | (600) |
| TPP-1676 | (1980) |
| TPP-1677 | (580) |
| TPP-1678 | (300) |
| TPP-1679 | 76 |
| TPP-1680 | (870) |
| TPP-1684 | (480) |
| TPP-1686 | (310) |
| TPP-2968 | weak |

values in brackets: not accurately determined under present experimental conditions but are sufficient for comparison among each other As evident from Table 10, the antibodies displayed rather low monovalent affinities, the lowest value (highest affinity) being 76 nM for TPP-1679. Three IgGs displaying the highest monovalent affinities were analyzed with regards to their selectivity and cross-reactivity to cynomolgus CEACAM6 in an ELISA binding experiment (carried out in analogy to the protocol given in Example 2)

TABLE 11

| Selectivity/cross-reactivity analysis by binding ELISA: $EC_{50}$ values in nM | | | | |
|---|---|---|---|---|
| TPP- | Human CEACAM6 (TPP-1436) | Human CEACAM3 (TPP-2755) | Human CEACAM5 (TPP-1438) | Cynomolgus CEACAM6 (APP-319) |
| TPP-1679 | 0.16 | 2.24 | 0.86 | – |
| TPP-1669 | 0.22 | – | 1.01 | – |
| TPP-1678 | 0.19 | – | – | 42.74 |

"–" denotes $EC_{50}$ > 10 nM (in the case of cynomolgus CEACAM6 > 100 nM)

To summarize, antibodies with rather poor monovalent affinities have been obtained. This might be a trade-off due to avoiding binding to other paralogs. Still, selectivity profile is often insufficient (see TPP-1679 & TPP-1669 in Table 11). From all antibodies tested, TPP-1678 is the only one with a very marginal cross-reactivity to recombinant cynomolgus CEACAM6 (see Table 11).

In conclusion, no therapeutically useful anti-CEACAM6 antibodies have been obtained using phage display without further maturation.

Example 5: Antibody Maturation of Phage Display-Derived Antibodies

To obtain antibodies with desirable affinity, selectivity and cross-reactivity profiles, some phage display-derived antibodies were affinity-matured.

Therefore, all CDR amino acid positions of TPP-1669, TPP-1678 and TPP-1679 were randomized individually. The resulting variants were expressed and assessed for binding to multiple CEACAM family members (human CEACAM6, cynomolgus CEACAM6, human CEACAM3 and human CEACAM5) by binding ELISA in cell supernatants.

For TPP-1669, individual mutations enhancing binding to cynomolgus CEACAM6 without at the same time enhancing binding to other human CEACAM family members as well could not be identified.

For TPP-1679, several individual mutations were identified, which enhanced binding to human CEACAM6 without concomitant enhanced binding to other human CEACAM family members, and a recombination library containing all possible permutations was generated. The corresponding variants were expressed as human IgG2 isotypes, purified and assessed for binding to multiple CEACAM family members by SPR analogously to experimental procedures described in Example 2. Table 12 summarizes the properties of selected antibodies obtained by this process.

TABLE 12

| SPR analysis: monovalent $K_D$ (in nM) | | | | | |
|---|---|---|---|---|---|
| | Human CEACAM6 (R&D Systems; TPP-1436) | Cynomolgus CEACAM6 (APP-319; (TPP-2443 cleaved) | Human CEACAM5 (R&D Systems; TPP-1438) | Human CEACAM3 (Sino Biological; TPP-2755) | Human CEACAM1 (R&D Systems; TPP-1437) |
| TPP-3399 | 9 | – | weak | weak | – |
| TPP-3400 | 6 | weak | weak | – | – |
| TPP-3401 | 16 | – | (94) | – | – |
| TPP-3402 | 18 | – | (172) | – | – |
| TPP-3403 | 13 | weak | (144) | – | – |
| TPP-3404 | 11 | (363) | (138) | – | – |
| TPP-3405 | 14 | (522) | (126) | weak | – |
| TPP-3406 | (15) | – | – | – | – |

TABLE 12-continued

| SPR analysis: monovalent $K_D$ (in nM) | | | | | |
|---|---|---|---|---|---|
| | Human CEACAM6 (R&D Systems; TPP-1436) | Cynomolgus CEACAM6 (APP-319; (TPP-2443 cleaved) | Human CEACAM5 (R&D Systems; TPP-1438) | Human CEACAM3 (Sino Biological; TPP-2755) | Human CEACAM1 (R&D Systems; TPP-1437) |
| TPP-3407 | (12) | – | – | weak | – |
| TPP-3408 | (27) | – | – | – | – |

values in brackets: not accurately determined under present experimental conditions "–": no binding detected under current experimental conditions "weak": if at most the two highest analyte concentrations analyzed (i.e. 100 and 200 nM) resulted in a binding signal that is between three times the signal to noise ratio and 20 percent of the theoretical maximum binding response ($Rmax_{theoretical}$)

The results obtained in Table 12 indicate that affinity and selectivity enhancement is very well possible. However, it also underscores the challenge to obtain cynomolgus CEACAM6 cross-reactive binders, which are at least within one order of magnitude close to the monovalent affinity towards human CEACAM6.

For TPP-1678, several individual mutations were identified, which enhanced binding to human CEACAM6 and cynomolgus CEACAM6 without greater concomitant enhanced binding to other human CEACAM family members, and a recombination library containing several permutations was generated. The corresponding variants were expressed as human IgG2 isotypes, purified and assessed for binding to multiple CEACAM family members by SPR analogously to experimental procedures described in Example 2 (summarized in Table 13).

The binding characteristics of these antibodies were also determined by a binding ELISA (monovalent binding, biotinylated CEACAM proteins): A 1:440 dilution of an anti-human IgG (Sigma, 12136) in Coating buffer (Candor) was used to coat black 384-well Maxisorp plates (Nunc) for 1 hour at 37° C. After one wash with PBS/0.05% Tween-20 the plates were blocked with 100% SmartBlock (Candor) for 1 hour at 37° C. After three washes, 2 µg/ml of the relevant antibodies were added to the plate in PBS/0.05% Tween-20/10% SmartBlock. The plates were incubated for 1 hour at room temperature. After three washes dilution series of the relevant biotinylated CEACAM proteins in PBS/0.05% Tween-20/10% SmartBlock were added and the plates were incubated for one hour at room temperature. After three washes 1 µg/ml of Streptavidin-Peroxidase (Sigma, S5512) in PBS/0.05% Tween-20/10% SmartBlock was added and the plates were incubated for 30 minutes at room temperature. After three washes, the plates were developed with Amplex Red (Life Technologies) and fluorescence was read at an emission wavelength of 590 nm. GraphPad Prism 6.0 software was used to calculate $EC_{50}$ values using four-parameter non-linear curve fit.

Variants with a substantially improved affinity, selectivity and cross-reactivity profile were identified as summarized in Table 13 and Table 14 for selected antibodies obtained by this process.

TABLE 13

| SPR analysis: monovalent $K_D$ (in nM) | | | | | |
|---|---|---|---|---|---|
| | Human CEACAM6 (R&D Systems; TPP-1436) | Cynomolgus CEACAM6 (APP-319; (TPP-2443 cleaved) | Human CEACAM5 (R&D Systems; TPP-1438) | Human CEACAM3 (Sino Biological; TPP-2755) | Human CEACAM1 (R&D Systems; TPP-1437) |
| TPP-3705 | 28 | 32 | – | – | – |
| TPP-3707 | 28 | 32 | – | – | – |
| TPP-3708 | 3 | 5 | – | weak | (158) |
| TPP-3709 | 8 | 20 | – | – | (408) |

values in brackets: not accurately determined under present experimental conditions "–": no binding detected under current experimental conditions "weak": if at most the two highest analyte concentrations analyzed (i.e. 100 and 200 nM) resulted in a binding signal that is between three times the signal to noise ratio and 20 percent of the theoretical maximum binding response ($Rmax_{theoretical}$)

TABLE 14

| Selectivity/cross-reactivity analysis by binding ELISA: $EC_{50}$ values in nM | | | | | |
|---|---|---|---|---|---|
| TPP- | Human CEACAM6 (R&D Systems TPP-1436 biotinylated) | Cynomolgus CEACAM6 (APP-319-biotinylated) | Human CEACAM1 (R&D Systems TPP-1437 biotinylated) | Human CEACAM3 (Sino Biological Inc. TPP-2755 biotinylated) | Human CEACAM5 (R&D Systems TPP-1438 biotinylated) |
| TPP-3705 | 0.18 | 0.12 | ~$3.82 \times 10^6$ (ambiguous fit) | 113.04 | – |
| TPP-3707 | 0.19 | 0.11 | ~$8.94 \times 10^5$ (ambiguous fit) | 139.18 | – |

TABLE 14-continued

Selectivity/cross-reactivity analysis by binding ELISA: $EC_{50}$ values in nM

| TPP- | Human CEACAM6 (R&D Systems TPP-1436 biotinylated) | Cynomolgus CEACAM6 (APP-319-biotinylated) | Human CEACAM1 (R&D Systems TPP-1437 biotinylated) | Human CEACAM3 (Sino Biological Inc. TPP-2755 biotinylated) | Human CEACAM5 (R&D Systems TPP-1438 biotinylated) |
|---|---|---|---|---|---|
| TPP-3708 | 0.02 | 0.03 | 9.64 | 1.04 | – |
| TPP-3709 | 0.04 | 0.07 | 36.53 | 4.68 | – |
| TPP-3470 (9A6-hIgG2) | 0.08 | – | – | – | – |

"–" denotes no binding detectable up to highest concentrations tested (150 ng/ml for human and cynomolgus CEACAM6; 2000 ng/ml for human CEACAM1, human CEACAM3, human CEACAM5)

In conclusion, using the TPP-1678 precursor, it was possible to obtain few high affinity human antibodies to human CECACAM6 that are truly cross-reactive to cynomolgus CEACAM6 and that are selective to CEACAM6: binding of TPP-3707 to human CEACAM6 is about 730-fold better than to human CEACAM3 (620-fold for TPP-3705) as judged by comparing their corresponding $EC_{50}$ values.

Example 6: Antibody Generation by Mouse Immunization

To generate mouse monoclonal antibodies against CEACAM6, two different immunization strategies were performed based on the sequence of immunogens applied to the Balb/c mice (strategy A and B in Table 15). Within each strategy, mice were immunized either via footpad or intra-peritoneal application of antigens over 5 rounds of injection, as depicted in Table 15. Strategy A was focusing on the immunization with cynomolgus CEACAM6-Domain1, whereas Strategy B was based on the combination of full-length extracellular CEACAM6 from human and cynomolgus monkey as immunogens.

Immunisations by footpad were based on 5 injections of 1 μg antigen once weekly. Immunizations by intra-peritoneal route were based on 4 IP injections biweekly (10 μg of antigen) followed by one boost by intravenous injection.

TABLE 15

Immunization schedule

| | Strategy A | | Stategy B | |
|---|---|---|---|---|
| | Footpad immu-nization | Intra-peritoneal immu-nization | Footpad immu-nization | Intra-peritoneal immu-nization |
| 1st injection | cynoC6-D1 (APP-325) | cynoC6-D1 (APP-325) | hC6 (APP-320) | hC6 (APP-320) |
| 2nd injection | cynoC6-D1 (APP-325) | cynoC6-D1 (APP-325) | CynoC6 (APP-319) | CynoC6 (APP-319) |
| 3rd injection | cynoC6-D1 (APP-325) | cynoC6-D1 (APP-325) | hC6 (APP-320) | hC6 (APP-320) |
| 4th injection | cynoC6-D1 (APP-325) | cynoC6-D1 (APP-325) | CynoC6 (APP-319) | CynoC6 (APP-319) |
| 5th injection | cynoC6-D1 (APP-325) | cynoC6-D1* (APP-325) | hC6 (APP-320) + CynoC6 (APP-319) | hC6 (APP-320) + CynoC6 (APP-319)* |

*i.v. boost

Four days after the last injection, lymph nodes or spleen cells of mice were fused according to standard methods (e.g. Köhler and Milstein Nature. 1975 Aug. 7; 256(5517):495-7). Screening of resulting hybridoma-clones was done in an ELISA using biotinylated antigens and off-target proteins (as listed in Table 16). In more detail, microtiter-plates were coated with goat anti-mouse antibodies overnight at 4° C. The following day plates were washed and blocked with 5% BSA for 2 h at room temperature, followed by another washing step. 20 μl of hybridoma supernatants were incubated with biotinylated antigens for 1 h at room temperature and the mixtures transferred to the coated wells followed by an incubation step (1 h at room temperature). After washing the plates, anti-streptavidin-HRP conjugates were added for 30 min at room temperature. Finally, wells were washed, and the color reaction was developed by addition of 50 μl TMB and recorded in a plate reader.

TABLE 16

List of proteins used in ELISA-screening of hybridomas (target and off-targets)

| Target (all biotinylated) | Off-target (all biotinylated) |
|---|---|
| Human CEACAM-6 (TPP-1436) | hCEACAM1 (TPP-1437) |
| Cynomolgus CEACAM6-Fc (TPP-2443) | hCEACAM5 (TPP-1438) |
| Cynomolgus CEACAM6 (APP-319) Fc cleaved | |

Surprisingly, only Strategy A resulted in clones showing a favorable profile with regards to human & cynomolgus CEACAM6 cross-reactivity as well as selectivity. In addition, some species specific clones were obtained from both strategies.

Candidates selected positively by ELISA were subcloned over at least 3 cloning rounds and produced at larger amounts from ascites fluid by protein A chromatography.

Antibodies from mouse immunizations were also characterized for binding to CEACAM6 in a cellular context. HeLa-cells overexpressing human or cynomolgus CEACAM6 were employed in FACS experiments with either supernatants from hybridoma or purified mIgs (see Example 1). Non-transfected HeLa-cells served as negative control. Table 17 summarizes the profile of identified candidates from ELISA and FACS-analysis:

TABLE 17

Summary of qualitative results for binding of murine hybridoma-derived antibodies to human and cynomolgus CEACAM6 from ELISA (using biotinylated TPP-1436, TPP-2443 and APP-319) and FACS-analysis (using transfected HeLa cells see Example 1: TPP-4639 and TPP-4189)

| Protein-ID | Human CEACAM6 | Cynomolgus CEACAM6 |
|---|---|---|
| TPP-2969 | no binding detectable | binding |
| TPP-2970 | no binding detectable | binding |

TABLE 17-continued

Summary of qualitative results for binding of murine hybridoma-derived antibodies to human and cynomolgus CEACAM6 from ELISA (using biotinylated TPP-1436, TPP-2443 and APP-319) and FACS-analysis (using transfected HeLa cells see Example 1: TPP-4639 and TPP-4189)

| Protein-ID | Human CEACAM6 | Cynomolgus CEACAM6 |
|---|---|---|
| TPP-2971 | binding | binding |
| TPP-3100 | binding | binding |
| TPP-3187 | binding | binding |
| TPP-3101 | binding | binding |
| TPP-3186 | binding | binding |

The murine antibodies obtained were characterized more closely with regards to their monovalent affinities ($K_D$), their selectivity towards other human paralogs and their degree of cross-reactivity to cynomolgus CEACAM6 by SPR analysis as purified mIgGs.

SPR was conducted analogously to experimental procedures described in Example 2.

Results are summarized in Table 18:

TABLE 18

SPR analysis: monovalent $K_D$ (in nM)

| | Human CEACA M6 (R & D Systems; TPP-1436) | Cynomolgus CEACAM6 Domain 1 (APP-319; (TPP-2443 cleaved) | Cynomolgus CEACAM6 (APP-325; TPP-2452 cleaved) | Human CEACAM5 (R & D Systems; TPP-1438) | Human CEACAM3 (Sino Biological; TPP-2755) | Human CEACAM1 (R & D Systems; TPP-1437) |
|---|---|---|---|---|---|---|
| TPP-2969 | 72 | (109) | 51 | — | — | — |
| TPP-2970 | 72 | 56 | 47 | — | — | — |
| TPP-2971 | 61 | 25 | 30 | — | — | — |
| TPP-3100 | 79 | n.t. | 52 | — | — | n.t. |
| TPP-3101 | 69 | n.t. | 13 | (300) | weak | n.t. |
| TPP-3186 | 74 | n.t. | 53 | — | — | n.t. |
| TPP-3187 | 68 | n.t. | 42 | — | — | n.t. |

values in brackets: not accurately determined under present experimental conditions "—"no binding detected under current experimental conditions "weak": if at most the two highest analyte concentrations analyzed (i.e. 100 and 200 nM) resulted in a binding signal that is between three times the signal to noise ratio and 20 percent of the theoretical maximum binding response ($Rmax_{theoretical}$)

n.t. not tested

There were unresolved discrepancies for TPP-2969 & TPP-2970 observed: in initial ELISA and FACS analysis they appeared cynomolgus CEACAM6 specific, whereas in later SPR experiment they exhibited also binding to recombinant human CEACAM6.

To summarize: immunization of mice with cynomolgus CEACAM6 N-terminal domain 1 (APP-325) suprisingly yielded some antibodies (e.g. TPP-3186, TPP-2971, TPP-3187) that are truly human—cynomolgus CEACAM6 cross-reactive and at the same time selective with regards to other human paralogs. The affinities are in an acceptable range for therapeutic puposes, yet their murine origine and associated immunogenicities preclude therapeutic applications in humans.

Example 7: Antibody Humanization

To generate antibodies suitable for therapeutic applications in humans, selected murine antibodies were humanized.

Selected sequences of the murine hybridoma-derived antibodies were determined by sequencing the antibody cDNAs of the respective hybridoma cell lines (see Table 17). According to the sequencing results, TPP-3100 and TPP-3186 are identical. TPP-3101 yielded a single heavy chain but two light chain sequences. TPP-2971 and TPP-3187 were highly similar. They differed in four amino acids (see FIG. 2).

The deciphered murine VH and VL sequences of the antibody TPP-2971 and TPP-3187 were humanized by grafting the CDRs according to the Kabat definition into human germline frameworks. As an exception, HCDR2 was partially grafted. Since this CDR is very long (16 amino acids) according to the Kabat definition, only the first 9 amino acids were grafted. These amino acids represent the part of HCDR2 which is identical to HCDR2 according to the Chothia definition (for CDR definitions according to Kabat and Chothia see: Andre C. R. Martin, "Protein sequence and structure analysis of antibody variable domains" in Antibody Engineering (Springer Lab Manuals), Eds.: Duebel, S. and Kontermann, R., Springer-Verlag, Heidelberg).

The human germline frameworks were chosen based on similarity searches of the murine framework pieces FW1, FW2, FW3, and FW4 with the set of human VH and VL as well as J element germline sequences. The murine CDRs were grafted into the best matching germline sequences (excluding the CDRs), which were IGKV1-9*01 and IGKJ2*01 for VL (Identities 69.6%, FW1; 86.7%, FW2; 71.9%, FW3; 80.0%, FW4) and IGHV2-70*01 and IGHJ6*01 for VH ((Identities: 73.3% (TPP-2971) and 70.0% (TPP-3187), FW1; 85.7%, FW2; 71.9%, FW3; 90.9%, FW4)). Germline sequences applied in similarity searches were derived from the VBASE2 data set (Retter I, Althaus H H, Münch R, Müller W: VBASE2, an integrative V gene database. Nucleic Acids Res. 2005 Jan. 1; 33(Database issue):D671-4). The names assigned to the most similar germline sequences were taken from the IMGT system (Lefranc, M.-P., Giudicelli, V., Ginestoux, C., Jabado-Michaloud, J., Folch, G., Bellahcene, F., Wu, Y., Gemrot, E., Brochet, X., Lane, J., Regnier, L., Ehrenmann, F., Lefranc, G. and Duroux, P. IMGT®, the international ImMunoGeneTics Information System®. Nucl. Acids Res, 37, D1006-D1012 (2009); doi:10.1093/nar/gkn838)).

Two variants of humanized sequences derived from TPP-2971 have been generated: TPP-3310 and TPP-3714. In VH of TPP-3310 the J element was kept unchanged compared to the murine originator, whereas in VH of TPP-3714 the J element was made completely human germline-like (see FIG. 3). No glycosylation sites or unpaired cysteines were found in the humanized sequences.

In addition, two variants of humanized sequences derived from TPP-3187 were generated: TPP-3820 and TPP-3821 (see FIG. 4). In comparison to TPP-3714, VH of TPP-3820 contained threonine instead of serine at the position 30 in HFW1, and glycine instead of alanine at position 46 in HFW2, while VL contained two asparagine residues instead of two serine residues at positions 92 and 93 in LCDR3. These four amino acid exchanges reflect the differences between the murine originator sequences of TPP-3187 and TPP-2971.

The variable domain VH of TPP-3821 is identical to TPP-3714, while VL contained two asparagine residues instead of two serine residues at positions 92 and 93 in LCDR3 in comparison TPP-3714. These two amino acid exchanges reflect the differences in the CDRs between the murine originator sequences of TPP-3187 and TPP-2971. No glycosylation sites or unpaired cysteine residues were found in the sequences of TPP-3820 and TPP-3821.

Affinity determination and sandwich competition experiments of chimerized and humanized antibodies were performed by SPR analogously to experimental procedures described in Example 2 and the results are summarized in Table 19 and Table 20:

TABLE 19

Sandwich competition experiments by SPR on recombinant human CEACAM6 (R&D Systems, TPP-1436)

| | TPP-3308 (hIgG2 chimera of TPP-2971) | TPP-3322 (hIgG2 chimera of TPP-3186) | TPP-3323 (hIgG2 chimera of TPP-3187) | TPP-3470 (hIgG2 chimera of 9A6) |
|---|---|---|---|---|
| TPP-3308 (hIgG2 chimera of TPP-2971) | – | – | – | – |
| TPP-3322 (hIgG2 chimera of TPP-3186) | – | – | – | – |
| TPP-3323 (hIgG2 chimera of TPP-3187) | – | – | – | – |
| TPP-3470 (hIgG2 chimera of 9A6 | – | – | – | – |

If the second antibody binds to the antigen bound by the first antibody (+), both antibodies do not show competition and vice versa, if no binding is observed by injection of the second antibody (–), both antibodies compete for a similar epitope

TABLE 20

SPR analysis: monovalent $K_D$ (in nM)

| | Human CEACAM6 (R&D Systems; TPP-1436) | Cynomolgus CEACAM6 (APP-319; (TPP-2443 cleaved) | Human CEACAM5 (R&D Systems; TPP-1438) | Human CEACAM3 (Sino Biological; TPP-2755) | Human CEACAM1 (R&D Systems; TPP-1437) |
|---|---|---|---|---|---|
| TPP-3310 | 13 | 31 | – | – | – |
| TPP-3714 | 13 | 27 | – | – | – |
| TPP-3820 | 27 | 54 | – | – | – |
| TPP-3821 | 24 | 49 | – | – | – |

"–" denotes no binding detected under current experimental conditions

Selectivity and cross-reactivity analysis was carried out by binding ELISA (monovalent, biotinylated CEACAM proteins) in analogy to the protocol provided in Example 5. Results obtained are summarized in Table 21.

TABLE 21

Selectivity/cross-reactivity analysis by binding ELISA: $EC_{50}$ values in nM

| TPP- | Human CEACAM6 (R&D Systems TPP-1436 biotinylated) | Cynomolgus CEACAM6 (APP-319-biotinylated) | Human CEACAM1 (R&D Systems TPP-1437 biotinylated) | Human CEACAM3 (Sino Biological Inc. TPP-2755 biotinylated) | Human CEACAM5 (R&D Systems TPP-1438 biotinylated) |
|---|---|---|---|---|---|
| TPP-3310 | 0.09 | 0.07 | – | – | – |
| TPP-3714 | 0.09 | 0.07 | – | – | – |
| TPP-3470 (hIgG2 | 0.08 | – | – | – | – |

TABLE 21-continued

| Selectivity/cross-reactivity analysis by binding ELISA: $EC_{50}$ values in nM | | | | | |
|---|---|---|---|---|---|
| TPP- | Human CEACAM6 (R&D Systems TPP-1436 biotinylated) | Cynomolgus CEACAM6 (APP-319-biotinylated) | Human CEACAM1 (R&D Systems TPP-1437 biotinylated) | Human CEACAM3 (Sino Biological Inc. TPP-2755 biotinylated) | Human CEACAM5 (R&D Systems TPP-1438 biotinylated) |
| chimera of 9A6 | | | | | |

"–" denotes no binding detectable up to highest concentrations tested (150 ng/ml for human and cynomolgus CEACAM6; 2000 ng/ml for human CEACAM1, human CEACAM3, human CEACAM5)

The results in Table 19 indicate TPP-2971, TPP-3186 & TPP-3187 compete for the same or a similar epitope on human CEACAM6 as 9A6-hIgG2. The results in Table 20 and Table 21 underscore a high affinity binding to human & cynomolgus CEACAM6 with true crossreactivity while being selective to CEACAM6 and not binding to CEACAM6 paralogs.

In conclusion, humanization was fully successful, with antibodies exhibiting even higher affinities than their murine precursors, enabling a therapeutic application in humans.

Example 8: Selective CEACAM6 Binding on Cells

To demonstrate binding and selectivity of the anti-CEACAM6 antibodies to authentic antigens, the antibodies were tested for binding to native CEACAM6 on the cell surface of different cell lines by FACS experiments.

CEACAM6 selectivity was tested on a panel of HeLa-cells which have been transfected with different CEACAM-receptors (human CEACAM1, human CEACAM3, human CEACAM5, human CEACAM6, human CEACAM8, human CEACAM19 and cynomolgus CEACAM6—see Example 1) in comparison to binding of HeLa wild type cells which were shown to be CEACAM6 negative. $EC_{50}$ values were determined for the binding to human and cynomolgus monkey CEACAM6 transfected HeLa cells. Results are shown in Table 22.

For FACS experiments HeLa wild type cells were cultured in RPMI-1640, 10% FCS, while CEACAM-receptor transfected HeLa cells received in addition 0.5% Gentamycin (stock 10 mg/ml, Fa. PAA) and 200 Pg/ml Hygromycin B (stock 50 mg/ml, Invitrogen). Cells were washed 3 times with PBS w/o $Ca^{2+}/Mg^{2+}$ and were detached from the culture plate non-enzymatically with EDTA dissociation buffer (Gibco). Cells were washed in cold FACS buffer (PBS w/o $Ca^{2+}/Mg^{2+}$ and heat-inactivated 3% FCS) and were counted using a countess machine (Invitrogen). $10^5$ cells per well were plated and incubated with the respective primary antibody (5 Pg/ml) for 1 h at 4° C. on a plate shaker. Then cells were washed (400 g, 5') with FACS buffer 2 times, were resuspended in 100 µl containing the secondary antibody (PE-anti-mouse or anti-human IgG, 1:150 dilution, Dianova #115-115-164, #109-115-098) and were incubated for another 1 h at 4° C. on a plate shaker. After 2 times washing the cells were resuspended in 100 Pll FACS buffer and were analysed on a FACS Canto II machine (Beckton Dickinson) or a FACS Array (Beckton Dickinson).

For $EC_{50}$ analysis, the primary antibodies were used at increasing concentrations in a range from 0.1 nM to 100 nM. Half maximal binding values ($EC_{50}$) were determined by plotting the median fluorescence intensity signal against the concentration (logarithmic scale). Curve fitting of data was performed using the Graph Pad prism analysis software.

TABLE 22

Specific binding to CEACAM-receptor transfected HeLa cell line panel.

| Test antibody | Species, isotype | HeLa wild type | HeLa human CEA CAM1 TPP-4185 | HeLa human CEA CAM3 TPP-4187 | HeLa human CEA CAM5 TPP-4188 | HeLa human CEA CAM6 TPP-4639 $EC_{50}$ [nM] | HeLa human CEA CAM8 TPP-4190 | HeLa human CEA CAM 19 TPP-4186 | HeLa Cyno-molgus CEA CAM6 TPP-4189 $EC_{50}$ [nM] |
|---|---|---|---|---|---|---|---|---|---|
| TPP-2971 | mIgG1 | | – | – | – | +0.5 | – | | ++0.5 |
| TPP-3100 | mIgG1 | | – | – | – | ++0.35 | – | | ++3 |
| TPP-3186 | mIgG1 | | – | – | – | ++0.5 | – | | ++0.5 |
| TPP-3187 | mIgG1 | | – | – | – | ++0.35 | – | | ++4 |
| TPP-3322 | Hu/mIgG1 | – | – | – | – | +0.6 | – | | ++0.8 |
| TPP-3323 | Hu/mIgG1 | – | – | – | – | +0.6 | – | | ++0.8 |
| TPP-3308 | Hu/mIgG1 | – | – | – | – | +0.45 | – | | ++0.6 |
| TPP-3820 | hIgG2 | – | – | – | – | +++ (+) 1 | – | – | 1 |
| TPP-3821 | hIgG2 | – | – | – | – | +++ (+) 1 | – | – | 1 |
| TPP-3310 | hIgG2 | – | – | – | – | +++ (+) 0.6 | – | – | 1.5 |
| TPP-3714 | hIgG2 | – | – | – | – | +++ (+) 1 | – | – | 1 |
| TPP-3707 | hIgG2 | – | + | + | – | +++19 | – | – | 4 |
| TPP-3470 (9A6-hIgG2) | hIgG2 | | | | | 1 | | | >100 |
| Anti-CEACAM 6 clone 9A6 | mIgG1 | – | – | – | – | +++ | – | – | |

TABLE 22-continued

Specific binding to CEACAM-receptor transfected HeLa cell line panel.

| Test antibody | Species, isotype | HeLa wild type | HeLa human CEA CAM1 TPP-4185 | HeLa human CEA CAM3 TPP-4187 | HeLa human CEA CAM5 TPP-4188 | HeLa human CEA CAM6 TPP-4639 $EC_{50}$ [nM] | HeLa human CEA CAM8 TPP-4190 | HeLa human CEA CAM 19 TPP-4186 | HeLa Cyno-molgus CEA CAM6 TPP-4189 $EC_{50}$ [nM] |
|---|---|---|---|---|---|---|---|---|---|
| (Genovac #GM0509) | | | | | | | | | |

Definition of –, +, ++, +++ as determined from FACS median fluorescence log shift:
– = no shift;
+ = log shift as compared to control antibody, median 10-100;
++ = 2 log shift, median 100-1,000;
+++ = 3 log shift, median 1,000-10,000

Anti-CEACAM6 antibodies were also tested for their binding to different cancer cell lines that endogenously express CEACAM6 by FACS analysis. Cell lines were cultured according to the protocols provided by the American tissue culture collection (ATCC). The observed binding signal was specific as the non-binding isotype control did not result into a shift of the fluorescence signal. Half maximal binding (EC50) values are in the low nanomolar range (Table 23).

TABLE 23

Binding of anti-CEACAM6 antibodies to endogenously CEACAM6 positive tumor cell lines ($EC_{50}$ values)

| Cell line* | TPP-3310 EC50 [nM] | TPP-3470 (9A6-hIgG2) EC50 [nM] |
|---|---|---|
| PaTu-8902 | 0.15 | 0.2 |
| SNU-C1 | 0.5 | 0.8 |
| KS | 0.8 | 1.0 |
| NCI-H1993 | 0.8-1.6 | 1.6 |
| T84 | 0.3 | 0.35 |

*All cell lines from public tissue bank such as the American tissue culture collection etc, except KS breast cancer cell line kindly provided by Dr. Brigitte Gückel (University of T übingen).

In conclusion, for the murine TPP-2971, TPP-3100, TPP-3186 & TPP-3187 antibodies as well as the human TPP-3820, TPP-3821, TPP-3310, TPP-3714 & TPP-3707 antibodies, selective binding to human authentic cell-surface CEACAM6 was demonstrated (no binding to other human paralogs). The binding of these antibodies to human CEACAM6 is comparable to 9A6 on human CEACAM6 expressing cell lines. For TPP-3310, a similar binding as 9A6-hIgG2 to endogenously expressed CEACAM6 on human tumor cell lines was demonstrated.

Antibodies of the invention also bind to cynomolgus CEACAM6 with a comparable avidity as to the human receptor in the single-digit to subnanomolar binding $EC_{50}$ range while no binding of 9A6 to the cynomolgus CEACAM6 on the cell surface was detected up to 100 nM. This result indicates a true crossreactivity to human and cynomolgus CEACAM6 for the antibodies of the invention while 9A6 clearly binds preferentially to human CEACAM6.

Example 9: Thermal Stability Analysis

Thermal stability of IgGs was investigated using Differential Scanning Calorimetry (DSC) using a VP-Capillary DSC system (MicoCal Inc.) with a cell volume of 0.137 mL. All samples were diluted in DPBS pH.7.4 to a final concentration of 0.5 mg/mL and a buffer control without protein was used as a reference. The samples were scanned from 20° C. to 120° C. at a scan rate of 120° C./h. Resulting thermograms were corrected by subtraction of buffer control scans and normalized for protein concentration using Origin 7.0 Data analysis (OriginLab Corp.). Melting temperatures were obtained by fitting the DSC data to a nonlinear regression routine ("Non-2-state: Cursor init") provided with Origin.

TABLE 24

Thermal Stability of Fab domain

| | Thermal Stability of Fab domain |
|---|---|
| TPP-3310 | 88.2° C. |
| TPP-3714 | 88.5° C. */95.1° C. * |
| TPP-3400 | 74.7° C. |
| TPP-3707 | 80.6° C. |
| TPP-3470 (9A6-hIgG2) | 80.2° C. |

* Fab unfolds non-cooperatively

All of the IgGs measured display a high thermal stability within the Fab domain. The thermal stability of TPP-3310 and TPP-3714 is remarkably high and exceeding by far the thermal stability of TPP-3470 (9A6-hIgG2). This is surprising since high stability has been associated with antibodies possessing VH3 framework (Honegger et al., 2009, Protein Eng Des Sel. 22(3):121-134).

High thermal stability is indicative of a better pharmaceutical suitability of TPP-3310 and TPP-3174 as compared to TPP-3470 (9A6-hIgG2) (better stability, less propensity to aggregation, less risk of immunogenicity).

Example 10: Interference with Interaction Between CEACAM6 and CEACAM1

It has been hypothesized that CEACAM1 might be the binding partner for CEACAM6 in trans on activated T cells (Witzens-Harig et al., Blood 2013 May 30; 121(22):4493-503): trans and cis homophilic and heterophilic interactions amongst CEACAMs have been described, for example between CEACAM1 and CEACAM5 or CEACAM6 and CEACAM8. CEACAM1 is displayed on activated T cells, CEACAM1 ligation and phosphorylation recruits SH2-domain-containing protein tyrosine phosphatase 1 (SHP1).

SHP1 dephosphorylates ZAP70, which results in the inhibition of TCR signaling. Thereby, CEACAM1 ligation leads to an early inhibition of T-cell activation within 10 minutes after activation.

Moreover, a role for CEACAM5 in the inhibition of natural killer (NK) cell responses against colorectal cancer cells was reported (Zheng et al., PLoS One. 2011; 6(6): e21146), which might be based on its heterophilic binding to inhibitory CEACAM1 expressed on the NK cells.

Therefore, a direct CEACAM6-CEACAM1 interaction was tested using recombinant proteins in a binding ELISA. After establishing in preliminary experiments that a moderate but specific interaction between CEACAM1 and CEACAM6 could be detected, the following protocol was used: Black 384-well Maxisorb plates (Nunc) were coated with 1 μg/ml CEACAM1 (R&D Systems, TPP-1437) in Coating Buffer (Candor) for 1 h at 37° C. or were left uncoated as a control. After one wash with PBS/0.05% Tween-20 the wells were blocked with 100% Smart Block (Candor) for 1 h at 37° C. In separate plates, dilution series of antibodies of interest in PBS/0.05% Tween-20, 10% SmartBlock were incubated with 2 μg/ml CEACAM6-Fc (TPP-1790) for 1 h at RT. The blocked plates were washed three times and the preformed antibody-CEACAM6-complexes were added. The plates were incubated for 1 h at RT. After three washes an anti-human IgG HRP (Sigma A1070) was added at 1:10.000 and the plates were incubated for 1 h at RT. After three washes the plates were developed with Amplex Red (Life Technologies) and fluorescence was read at an emission wavelength of 590 nm.

TABLE 25

Competition ELISA for antibodies competing with binding of human CEACAM6-Fc (TPP-1790) to passively coated human CEACAM1 (TPP-1437).

| | Competition with binding of human CEACAM6-Fc to human CEACAM1 |
|---|---|
| TPP-3400 | + |
| TPP-3310 | + |
| TPP-3714 | + |
| TPP-3323 | + |
| TPP-3705 | + |
| TPP-3707 | + |
| TPP-3470 (9A6-hIgG2) | + |
| TPP-3688 (Neo201-hIgG2) | − |

"+" denotes competition
"−" denotes no competition

As shown in Table 25, it was possible to compete the interaction of CEACAM6 with CEACAM1 with all antibodies tested except for TPP-3688 (Neo201-hIgG2).

In conclusion, this observation is consistent with the hypothesis of a) CEACAM1 on activated T cells being a possible interaction partner for CEACAM6 leading to inhibition of T cells, b) the N-terminal D1 domain of CEACAM6 being implicated in the interaction between CEACAM1 and CEACAM6, and c) antibodies of the invention being capable to interfere with CEACAM6-CEACAM1 interaction.

Example 11: Inhibition of Immunosuppressive Activity of CEACAM6 In Vitro

The immunosuppressive function of CEACAM6 on tumor cells was studied recently in vitro (Witzens-Harig et al., Blood 2013 May 30; 121(22):4493-503) and in vivo (Khandelwal et al., Poster Abstract 61, Meeting Abstract from 22nd Annual International Cancer Immunotherapy Symposium Oct. 6-8, 2014, New York City, USA). Commercially available 9A6 antibody (Genovac/Aldevron) was shown to be able to inhibit immunosuppressive activity of CEACAM6, leading to enhanced cytokine secretion by T cells in vitro and anti-tumor efficacy in vivo.

To study the effect of the antibodies of the invention on the immunosuppressive activity of CEACAM6, co-culture experiments of a model tumor cell line with a model tumor antigen-specific T cell clone were conducted:

Tumor-antigen specific T cells were generated by a procedure described in Brackertz et al (Brackertz et al., Blood Cancer J. 2011 March; 1(3):e11). Briefly, survivin specific $CD8^+$ T cells were isolated from peripheral mononuclear cells via CD8-specific magnetic-activated cell sorting. The isolated HLA-A2-$CD8^+$ T cells were repetitively stimulated with allogenic HLA-$A2^+$ dendritic cells loaded with 10 μg of the HLA-restricted peptide epitope $Survivin_{95-104}$ (ELTLGEFLKL). After stimulation, the proliferating T cells were stained with HLA-A2/$Survivin_{95-104}$ multimers (A*02: 01 391 LMLGEFLKL Survivin 96-104 labeled with APC, ProImmune Limited, #F391-4A-E), FACS sorted and cloned by limiting dilution in 96-well plates.

The T cell clone expansion was performed by culturing $2\times10^5$ T cell clones and feeder cells composed of $5\times10^7$ irradiated PBMCs (30 Gy) and $1\times10^7$ irradiated LCL (these B lymphoblastoid cell lines that were generated by EBV transduction of peripheral blood B cells from healthy donors with a EBV-infected monkey cell line (B95/8, ATTC), as described in Brackertz et al., Blood Cancer J. 2011 March; 1(3):e11 and Dissertation Andreas Moosmann, Ludwig-Maximilians-University Munich, Germany, 2002) from different donors (100-150 Gy) in 40 ml of RPMI-1640 medium with glutamine (Sigma-Aldrich), 10% human serum (Human AB serum, Valley Biomedical, Inc, #HP1022), 1% Penicillin/Streptomycin (Life Technologies) at 37° C. and 5% $CO_2$. The expansion occurred in the presence of 50 U/ml IL-2 (Proleukin, Novartis, #1003780), 2.5 ng/ml IL-15 (rhIL-15-CF R&D #247_IL-025/CF) and 30 ng/ml anti-human CD3 antibody (OKT3 eBiosciences 16-0037-85) for 14 days. The KS human breast cancer cell line (obtained from Dr. Brigitte Gückel (University of Tübingen, Germany)) was cultured in DMEM (Sigma-Aldrich) with 10% FCS (FBS Superior, Biochrom) and 1% Penicillin/Streptomycin at 37° C. and 5% $CO_2$.

To analyze the modulatory activity of the anti-CEACAM6 antibodies on the immunosuppressive function of CEACAM6 in vitro, the survivin-peptide specific $CD8^+$ T cell clone was co-cultivated together with the $CEACAM6^+$, HLA-$A2^+$ and $survivin^+$ human breast cancer cell line KS and IFN-gamma secretion as readout for T cell activity was measured either by IFN-gamma ELISpot or IFN-gamma ELISA.

For the co-culture, KS tumor cells were detached non-enzymatically using PBS-EDTA for 5 min, centrifuged, washed and counted. Cell concentration was adjusted to $1\times10^5$ cells/ml in X-Vivo-20 (Lonza) and cells were pretreated with anti-CEACAM6 antibodies or isotype-matched control antibodies for 10 min on ice. After the incubation step, 10,000 KS target cells were seeded directly in triplicates to IFN-gamma-ELISpot or U-96-Well ELISA plates, respectively. In the meantime, survivin-peptide specific T cells were harvested, washed with X-Vivo-20 and seeded in the cell numbers indicated on the KS target cells. The co-culture of tumor cells, anti-CEACAM6 antibodies and T cells was incubated for 20-40 h at 37° C. IFN-gamma ELISpot plates (MABTECH: ELISpot Assay for human Interferon gamma #3420-3PT, Antibodies mAB 1-D1K anti-IFNg, mAB 7-B6-1-Biotin, Steptavivin-ALP, BCIP/NBT plus substrate for ELISpot #3650-10) and IFN-gamma-ELISA (BD human IFN-gamma ELISA Set #555142) were developed according to the manufacturer's instructions. ELISpot plates were counted with a C.T.L. ELISpot plate reader and optical density for ELISA plates was measured with a Tecan Infinite M200 plate reader. An experiment was considered as valid if the positive control TPP-3470 (9A6-hIgG2) was statistically significant compared to the isotype-matched antibody control.

Co-culture of KS tumor cells with survivin-peptide specific $CD8^+$ T cells in the presence of anti-CEACAM6 antibodies resulted in a statistically significant increase of IFN-gamma production by the T cells (FIG. 5) compared to the samples not treated with anti-CEACAM6 antibody or treated with isotype-matched control antibody.

In conclusion, cynomolgus cross-reactive antibodies TPP-3310, TPP-3707, and TPP-3323 were able to relieve CEACAM6 mediated immunosuppression of tumor antigen specific T cells to the same extent as TPP-3470 (9A6-hIgG2) as measured by either IFN-gamma secretion of survivin-peptide specific $CD8^+$ T cells or number of IFN-gamma secreting activated T cells.

Example 12: Analysis of Cytokine/Chemokine Profile Secreted by T Cells Treated with Anti-CEACAM6 Antibodies In order to study the effects of anti-CEACAM6 antibodies on the human T cell cytokine/chemokine profile towards an improved cytotoxicity and an effective anti-tumor immune response, Luminex-based multiplex cytokine analysis of co-culture experiments of a model tumor cell line and a model tumor antigen specific T cell clone were performed.

A survivin-peptide specific $CD8^+$ T cell clone was generated and expanded in vitro as described in Example 11. Tumor cell culture and ELISA co-culture were performed as described in Example 11.

After 20 h of co-culture plates were centrifuged for 10 min at 1400 rpm and supernatant was collected. Multiplex analysis was performed using the MILLIPLEX Human Cytokine/Chemokine Magnetic Bead Panel—Premixed 38 Plex analytes (Merck Millipore #HCYTMAG-60K-PX38) on a BioPlex100 System (Bio-Rad) according to manufacturer's instructions. Standard curves and concentrations were calculated with Bio-Plex Manager 6.0. An experiment was considered as valid if the positive control TPP-3470 (9A6-hIgG2) was >1.5× increased compared to the isotype-matched antibody control.

Blockade of CEACAM6 by antibodies of the invention in the co-culture of survivin-peptide specific T cells with KS tumor cells yields a >1.5 times increase in IFN-gamma, IL-2 and TNF-alpha secretion compared to the control samples that were treated with the isotype-matched control (FIG. 6).

In conclusion, the cynomolgus cross-reactive antibodies TPP-3310 and TPP-3707 are able to change the cytokine profile of survivin-peptide specific $CD8^+$ T cells towards a more cytotoxic and activated phenotype characterized by increased IFN-gamma, IL-2 and TNF-alpha secretion as measured by Luminex-based multiplex analysis to the same extent as TPP-3470 (9A6-hIgG2).

Example 13: Anti-Tumor Efficacy in Adoptive T Cell Transfer KS Model

The anti-tumor efficacy of an anti-CEACAM6 antibody (9A6; Genovac/Aldevron) has been studied in vivo in adoptive human T cell transfer systems in which tumor-antigen specific human T cells are expanded in vitro and co-injected with an anti-CEACAM6 antibody into nude mice bearing human xenograft tumors (Khandelwal et al., Poster Abstract 61, Meeting Abstract from 22nd Annual International Cancer Immunotherapy Symposium Oct. 6-8, 2014, New York City, USA).

To study the effect of antibodies of the invention on anti-tumor efficacy, the following adoptive T cell transfer experiment was conducted:

A survivin-peptide specific $CD8^+$ T cell clone was generated and expanded in vitro as described in Example 11.

Six to eight weeks old female NOD-Scid mice (NOD.CB17-$Prkdc^{scid}$/J; Charles River, France) were injected subcutaneously with $2\times10^6$ KS tumor cells (see Example 11). Randomization of mice was performed on day 16 and mice with a tumor surface lower than 40 $mm^2$ were excluded (=no tumor take). Mice (n=8-10 mice per group) were treated on day 23 and 27 with i.v. adoptive transfer of $5\times10^6$ survivin-peptide specific T cell clone. 200 μg of the anti-CEACAM6 antibodies TPP-3740, TPP-3707, TPP-3310 or the respective isotype-matched control antibody were administered i.p. on days 22, 24, 26 and 28. The control group was injected with PBS instead of T cells and antibodies. Subcutaneously grown tumors were measured with a caliper and the surface was then calculated by using the formula "length×width". Only experiments were considered as valid, in which the vehicle-treated control group of mice exhibited a steady and significant increase of tumor surface and tumor volume throughout the entire duration of the study. The outcome of the experiment might be influenced by parameters that are difficult to control: not only the in vivo growth of KS cell lines proved to be variable but also survival of human T cells in mice as well T cell infiltration into tumors exhibited considerable variation.

Figure 7:
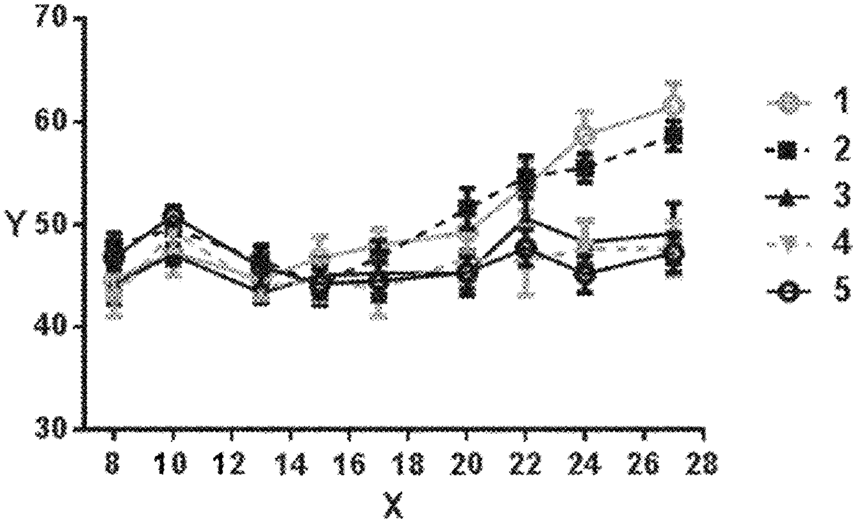
FIG. 7: Effect of anti-CEACAM6 antibodies on tumor growth in vivo. $2\times10^6$ KS breast cancer cells were inoculated s.c. On day 23 and 27 tumor-antigen specific T cells (survivin-peptide specific) were injected i.v. 200 μg of anti-CEACAM6 antibodies or the matched isotype control were administered i.p. on day 22, 24, 26 and 28. Tumor growth was assessed every 2-3 days. Error bars represent SEM. Y-axis=tumor surface ($mm^2$); X-axis=days; TC=survivin-peptide specific T cells. 1=PBS-treated; 2=treatment with T cells and isotype matched antibody control; 3=treatment with T cells and TPP-3470 (9A6-hIgG2); 4=treatment with T cells and TPP-3310; 5=treatment with T cells and TPP-3707.

Adoptive transfer of survivin-peptide specific T cells in combination with the anti-CEACAM6 antibodies tested resulted in a reduced tumor burden compared to T cells injected with the matched isotype control or the PBS control group (FIG. 7). Similar efficacy was observed using TPP-3740 (9A6-hIgG2).

In conclusion, cynomolgus cross-reactive antibodies TPP-3310 and TPP-3707 exhibited anti-tumor efficacy to the same extent as TPP-3470 (9A6-hIgG2) in an adoptive T cell transfer model using survivin-peptide specific $CD8^+$ T cells and KS tumors.

Example 14: Tumor Cell Lines and Tumor Tissues that are CEACAM6 Positive

CEACAM6 is expressed in various cancers which are potential target indications for treatment with CEACAM6 immunomodulating antibodies. Therefore cancer cell lines of different origin and which represent different cancers were tested for CEACAM6 expression by FACS analysis. The results are shown in Table 26.

Cancer cell lines which were acquired from public tissue banks such as the American tissue culture collection (ATCC) etc. were cultured according to the provider's instructions.

Cells were washed 3 times with PBS w/o $Ca^{2+}/Mg^{2+}$ and were detached from the culture plate non-enzymatically with EDTA dissociation buffer (Gibco). Cells were washed in cold FACS buffer (PBS w/o $Ca^{2+}/Mg^{2+}$ and heat-inactivated 3% FCS) and were counted using the cell counter countess machine (Invitrogen). $10^5$ cells per well were plated and incubated with the mouse monoclonal antibody 9A6 (TPP-1744; 5 μg/ml) or the purified NA/LE Mouse IgG1 Isotype control antibody (BD Pharmingen #553447) for 1 h at 4° C.

on a plate shaker. Then cells were washed (400 g, 5') with FACS buffer 2 times, were resuspended in 100 μl containing the PE-labeled anti-mouse secondary antibody (1:150 dilution, Dianova #115-115-164) and were incubated for another 1 h at 4° C. on a plate shaker. After 2 times washing the cells were resuspended in 100 μl FACS buffer and were analyzed on a FACS Canto II machine (Beckton Dickinson) or a FACS Array (Beckton Dickinson). The observed binding signal was specific as the non-binding isotype control did not result into a shift of the fluorescence signal (Table 26).

TABLE 26

Result of human cancer cell line screening by FACS for binding of CEACAM6 specific antibody 9A6 mIgG1 (TPP-1744) and thus CEACAM6 expression

| Cell line* | Cancer Origin | Type | CEACAM6 surface expression |
|---|---|---|---|
| MCF7 | breast | adenocarcinoma | + |
| MCF7/AdrVp (MDR breast CA) | breast | adenocarcinoma | + |
| KS | breast | malignant effusion, breast cancer patient | +++ |
| BT-20 | breast | adenocarcinoma, ER negative | – |
| BT-474 | breast | ductal carcinoma; | +++ |
| HCC38 | breast | primary ductal carcinoma | – |
| MDA-MB-361 | breast | adenocarcinoma, derived from metastatic site: brain | +++ |
| MDA-MB-453 | breast | metastatic carcinoma, derived from metastatic site: pericardial effusion | – |
| MFM-223 | breast | epithelial-like, ductal carcinoma | +/– |
| MX-1 | breast | infiltrating ductal carcinoma, ER-negative | – |
| SUM 149 | breast | invasive ductal carcinoma, ER-PR- inflammatory breast cancer | – |
| SUM 159 | breast | Er-, PR- anaplastic carcinoma of the breast | – |
| T-47D | breast | ductal carcinoma, from metastatic site: pleural effusion | + |
| ZR-75-1 | breast | ductal carcinoma, from metastatic site: ascites | ++ |
| HPAC | pancreas | adenocarcinoma | ++++ |
| SW1990 | pancreas | adenocarcinoma, from metastatic site: spleen | – |
| PaTu 8902 | pancreas | adenocarcinoma | +–++ |
| AsPC-1 | pancreas | adenocarcinoma, from metastatic site: ascites | +++ |
| DAN-G | pancreas | adenocarcinoma | + |
| MIA PaCa-2 | pancreas | | – |
| Panc1 | pancreas | ductal, epithelioid pancreatic carcinoma | – – |
| BxPc3 | pancreas | adenocarcinoma | +++ |
| Capan-2 | pancreas | adenocarcinoma | – |
| PC3.gd.neo (PaCa) | prostate | adenocarcinoma, from metastatic site: bone | – |
| HPAFII (PaCa) | pancreas | adenocarcinoma | +++ |
| SW 1463 | rectum | epithelials, Dukes' type C, colorectal adenocarcinoma | +/– |
| SNU-C1 | colon | adencarcinoma, from metastatic site: peritoneum | ++ |
| HT55 | colon | epithelial | +++ |
| Colo 201 | colon | Dukes type D, adenocarcinoma, from metastatic site: ascites | – |
| Colo320DM | colon | Dukes type D, colorectal adenocarcinoma | – |
| CaCo-2 | colon | adenocarcinoma | +–++ |
| SW403 | colon | Dukes type C adenocarcinoma | – |
| HCC2998 | colon | adenocarcinoma | ++ |
| RKO | colon | | – |
| KM-12 | colon | adenocarcinoma | ++ |
| CL-34 | large intestine | adenocarcinoma | + |
| COLO 205 | colon | Dukes type D, adenocarcinoma | '+/– |
| HCT 116 | colon | | – |
| SW480 | colon | Duke type B, colorectal adenocarcinoma | – – |
| WiDr | colon | adenocarcinoma | ++ |
| DLD-1 | colon | Dukes Type C, adenocarcinoma | – |
| SW 620 | colon | Dukes Type C, adenocarcinoma, from metastatic site: lymph node | – |
| SW1116 | colon | adenocarcinoma | +++ |
| T-84 | colon | colon metatases from the lung | + – ++ |

TABLE 26-continued

Result of human cancer cell line screening by FACS for binding of CEACAM6 specific antibody 9A6 mIgG1 (TPP-1744) and thus CEACAM6 expression

| Cell line* | Cancer Origin | Type | CEACAM6 surface expression |
|---|---|---|---|
| LoVo | colon | adenocarcinoma | ++ |
| HCT15 | colon | Dukes type C, adenocarcinoma | − |
| HT29 | colon | adenocarcinoma | ++ |
| LS174T | colon | Dukes type B, adenocarcinoma | +/− |
| EKVX | lung | adenocarcinoma | − |
| A549 | lung | | +++ |
| NCI-H1688 | lung | SCLC | + |
| Calu-1 | lung | epidermoid carcinoma, K-ras positive | − |
| Calu-3 | lung | adenocarcinoma | + |
| HCC827 | lung | adenocarcinoma | ++ |
| LXF-289 | lung | adenocarcinoma | − |
| NCI-H1299 | lung | from metastatic site: lymph node | − |
| NCI-H1437 | lung | adenocarcinoma, from metastic site. pleural effusion | +++ |
| NCI-H146 (SCLC) | lung | derived from metastatic site (bone marrow) | +/− |
| NCI-H1581 | lung | Large cell NSCLC | − |
| NCI-H1975 | lung | adenocarcinoma | − |
| NCI-H1993 | lung | adenocarcinoma, from metastatic site: lymph node | +++ |
| NCI-H2228 | lung | adenocarcinoma | ++ |
| NCI-H226 | lung | squamous cell carcinoma, mesothelioma, from metastatic site: pleural effusion | − |
| NCI-H23 | lung | adenocarcinoma | − |
| NCI-H292 | lung | mucoepidermoid pulmonary carcinoma | − |
| NCI-H322 | lung | bronchioalveolar carcinoma | − |
| NCI-H358 | lung | bronchioalveolar carcinoma, from metastatic site alveolus | − |
| NCI-H441 | lung | papillary adenocarcinoma | ++ |
| NCI-H460 | lung | Large cell lung carcinoma, from metastatic site: pleural effusion | − |
| NCI-H520 | lung | squamous cell carcinoma | − |
| NCI-H522 | lung | adenocarcinoma K-ras, mutated p53 | − |
| NCI-H661 | lung | large cell lung carcinoma, from metastatic site: lymph node | − |
| NCI-H69 (SCLC) | lung | | − |
| NCI-H82 (SCLC) | lung | from metastic sit:e pleural effusion | − |
| SW 900 | lung | squamous cell carcinoma | − |
| HCC-2935 | lung | adenocarcinoma | ++++ |
| HCC-1395 | lung | primary ductal carcinoma | − |
| RPMI-8226 | myeloma | plasmacytoma; multiple myeloma (IgG lambda-type) B lymphocyte; lymphoblast | + |
| SKMM2 | myeloma | | − |
| L-363 | myeloma | plasma cell leukemia | − |
| JJN-3 | myeloma | plasma cell leukemia | − |
| KMS-12-BM | myeloma | | − |
| KMS-12-PE | myeloma | | − |
| LP-1 | myeloma | | − |
| MOLP-2 | myeloma | | |
| MOLP-8 | myeloma | | − |
| SNU-1 | gastric | from metastatic site: ascites | +++ |
| Hela | cervix | adenocarcinoma | − |
| DMS-153 (SCLC) | lung | from metastatic site: liver | − |
| MeWo | skin | fibroblast, malignant melanoma, from metastic site: lymph node | − |

Definition of −, +, ++, +++ as determined from FACS median fluorescence log shift:

− = no shift;

+ = log shift as compared to control antibody, median 10-100;

++ = 2 log shift, median 100-1,000;

+++ = 3 log shift, median 1,000-10,000;

++++ = 4 log shif; median >10000

*All cell lines from public tissue bank such as the American tissue culture collection etc, except KS breast cancer cell line which was kindly provided by Dr. Gückel (Tübingen); B. Gueckel, Cancer Cell International 2004, 4(Suppl 1): S38).

In conclusion, CEACAM6 is expressed in cell lines which represent various cancers (e.g. colorectal cancer, non-small-cell lung cancer (NSCLC), small cell lung cancer (SCLC), pancreatic cancer, gastric cancer, breast cancer and multiple myeloma) which constitute potential target indications for treatment with CEACAM6 immunomodulating antibodies and other response modifiers (e.g. peptides, small molecules, artificial scaffold binders etc).

Example 15: Binding to Single Domain 1 of Human and Cynomolgus CEACAM6

To test whether antibodies of the invention can bind to the isolated single domain 1 of human and cynomolgus CEACAM6, SPR experiments were conducted as in Example 1.

The single N-terminal domain 1 of cynomolgus CEACAM6 (TPP-2453) was produced as described in Example 1 in analogy to TPP-1794:

| Name | Protein-ID | Description | SEQ-ID |
|---|---|---|---|
| Macaca fascicularis CEACAM6-Domain 1-His | TPP-2453 | Domain 1, fusion to His (expressed in *E. coli*) | SEQ-ID NO: 180 |

(TPP-2453)

SEQ-ID NO: 180

MQLTIESRPENVAEGKEVLLLAHNLPQNTLGFNWYKGERVDAKRLIVAY

VIGTQQTTPGPAHSGREMIYSNASLLIQNVTQNDTGSYTLQAIKEDLVT

EEATGRFWVYPELGSGSHHHHHHHH

Affinities (monovalent $K_D$) of antibodies of the invention towards recombinant single domain 1 of human and cynomolgus CEACAM6 were determined by SPR analogously to experimental procedures described in Example 1, and are shown in Table 27.

TABLE 27

SPR analysis: monovalent $K_D$ (in nM)

| Test Antibody | Isotype | Recombinant single domain 1 of human CEACAM6 (TPP-1794) $K_D$ [nM] | Recombinant single domain 1 of *Macaca fascicularis* CEACAM6 (TPP-2453) $K_D$ [nM] |
|---|---|---|---|
| TPP-2971 | Mouse IgG1 | 11 | 5.3 |
| TPP-3186 | Mouse IgG1 | 15 | 8.7 |
| TPP-3187 | Mouse IgG1 | 12 | 6.9 |
| TPP-3308 | Human IgG2 chimera | 9.5 | 5.4 |
| TPP-3310 | Human IgG2 | 3.7 | 3.4 |
| TPP-3322 | Human IgG2 chimera | 12 | 8.8 |
| TPP-3323 | Human IgG2 chimera | 9 | 6.9 |
| TPP-3705 | Human IgG2 | 6.7 | 2.7 |
| TPP-3707 | Human IgG2 | 6.4 | 2.4 |
| TPP-3714 | Human IgG2 | 3.7 | 3.2 |
| TPP-3820 | Human IgG2 | 5.1 | 5.2 |
| TPP-3821 | Human IgG2 | 4.5 | 4.7 |
| TPP-1745 | Human IgG1 | 3.3 | – |

"–": no binding detected

In conclusion, antibodies of the invention bind to both human and cynomolgus N-terminal domain 1 of CEACAM6 with comparable affinities.

Example 16: X-Ray Crystal Structure of the Human CEACAM6 Single N-Terminal Domain1 in Complex with Fab Fragment APP-1574

The crystal structure of single N-terminal domain 1 of human CEACAM6 (TPP-1794; SEQ ID NO 169) bound to a Fab fragment related to TPP-3310 (called APP-1574) was determined.

To facilitate production of the Fab fragment TPP-3310 was produced as human IgG1 variant (called TPP-5468, see Table 28). Papain cleavage of TPP-5468 and subsequent purification results in APP-1574. This Fab fragment comprises the variable domains (VH and VL) of TPP-3310 (see Table 28).

TABLE 28

Amino acid sequences of IgG and Fab used for crystal structure determination

| Protein | Heavy Chain | Light Chain |
|---|---|---|
| TPP-5468 | SEQ ID NO: 181 | SEQ ID NO: 182 |
| APP-1574 | SEQ ID NO: 183 | SEQ ID NO: 184 |

As detailed in Example 1, CEACAM6 domain 1 has been expressed and refolded from *E. coli*. The Fab-fragment has been generated by digestion of the antibody with Papain, followed by complex formation. Protein crystallography was then employed to generate atomic resolution for single N-terminal domain 1 of human CEACAM6 bound to APP-1574 Fab to define the epitope.

Protein Production

The single N-terminal domain 1 of human CEACAM6 (TPP-1794; SEQ-ID 169) was produced as 6× His fused protein construct as described in Example 1. The protein was concentrated to 6.7 mg/ml prior to complex formation.

The corresponding Fab-fragment of TPP-5468 (human IgG1) has been obtained by cleavage with the protease Papain. 1 mg of the antibody was mixed with 50 al immobilized papain (ThermoFisher #20341) in digestion buffer (20 mM Na-Phosphate pH 7.0, 10 mM EDTA, 20 mM Cystein-HCl) and incubated for 4 h at 37° C. with continuous stirring. Immobilized papain was removed by centrifugation and resulting Fc-fragments and non-cleaved IgG were removed by passing over MabSelectSURE (GE Healthcare, #11-0034-89 AC). The Fab-fragment in the flow-through was further purified via size exclusion chromatography in 30 mM Tris buffer pH 8.5, 150 mM NaCl on Superdex 75 and concentrated to 7.2 mg/ml.

For complex formation, purified Fab-fragment and human CEACAM6 N-terminal domain 1 were mixed in ratio 1 Fab to 1.4 human CEACAM6 N-terminal domain 1 for 1 human CEACAM6 N-terminal domain 1 h at 4 C. The resulting protein complex was isolated by size exclusion chromatography in 30 mM Tris buffer pH 8.5, 150 mM NaCl on Superdex 75 and further concentrated to 21.2 mg/ml prior to crystallization.

Crystallization and Structure Determination

The complex of single N-terminal domain1 of human CEACAM6 and the Fab fragment APP-1574 was concentrated to 21.2 mg/ml, centrifuged at 20,000 g for 10 minutes and screened for crystallization. Crystals for data collection were grown by hanging drop vapor diffusion at 20° C. In detail, 0.2 µl of the complex was mixed with 0.2 µl of reservoir solution containing 100 mM tri-sodium citrate pH 4.9, 19% (w/v) PEG 4000 and 10% (v/v) isopropanol. The drop was then equilibrated against 80 11 of the same reservoir solution. Before data collection, the crystals were flash cooled in liquid nitrogen.

Diffraction data were collected at beamline 14-1 at the BESSY II Synchrotron Source (Helmholtz Zentrum Berlin) and processed using XDS (Kabsch, W. XDS. Acta Cryst. D66, 125-132 (2010). The data of human CEACAM6 single N-terminal domain1-Fab fragment APP-1574 complex were processed to 2.7 Å in the space group P1 with cell dimensions a=64.7 Å, b=65.2 Å, c=78.6 Å, alpha=66.1°, beta=87.2° and gamma=88.5°. The structure of the complex was solved by molecular replacement using PHASER (McCoy A J et al, J Appl Cryst (2007). 40, 658-674). with in-house structures of the human CEACAM6 single N-terminal domain1 and a Fab as search models. The final model was built in COOT (Emsley, P. et al, Acta Cryst D66, 486-501 (2010)) and refined using CCP4 (Winn, M. D. et al. Acta. Cryst. D67, 235-242 (2011)).

The epitope was defined as residues of human CEACAM6 single N-terminal domain1 that contain atoms within 5 Å to any atom in Fab fragment APP-1574, identified by NCONT in the CCP4 program suite (Winn, M. D. et al. Acta. Cryst. D67, 235-242 (2011)) and listed in Table 29). There are two copies of human CEACAM6 single N-terminal domain1-Fab fragment APP-1574 complex in the asymmetric unit (the smallest unique unit in the crystal). Only those antibody-contacting residues that are common in both copies are listed as epitope residues.

Epitope

The crystal structure of the human CEACAM6 single N-terminal domain1-Fab fragment APP-1574 complex was used to identify the epitope of Fab fragment APP-1574 on CEACAM6. The interaction surface on human CEACAM6 single N-terminal domain1 by Fab fragment APP-1574 is formed by several continuous and discontinuous (i.e. non-contiguous) sequences; namely residues Pro59, Gln60, Asn61, Arg62, Ile63, Gly64, Val83, Ile84, Gly85, Thr86, Gln88, Thr90, Pro91, Ile125, Ser127, Asp128 and Leu129 (numbering according to SEQ-ID:179; TPP-4639) as detailed in Table 29.

In a very close direct contact are residues having at least one atom that is 3.6 Å or less away from the antibody. These residues are: Gln60, Asn61, Arg62, Ile63, Val83, Ile84, Gly85, Thr90, Ser127, Asp128 and Leu129 (numbering according to SEQ-ID:179; TPP-4639).

Figure 9:
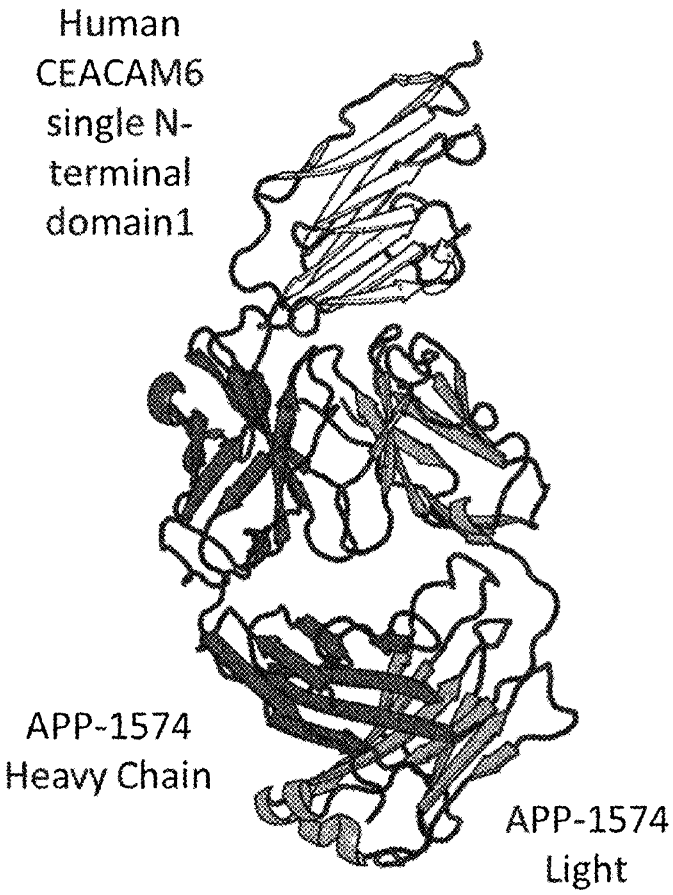
FIG. 9: Cartoon representation of the single N-terminal domain 1 of human CEACAM6 (TPP-1794, white) bound to the Fab fragment APP-1574 (heavy and light chains are colored dark and light gray, respectively).
Figure 10:
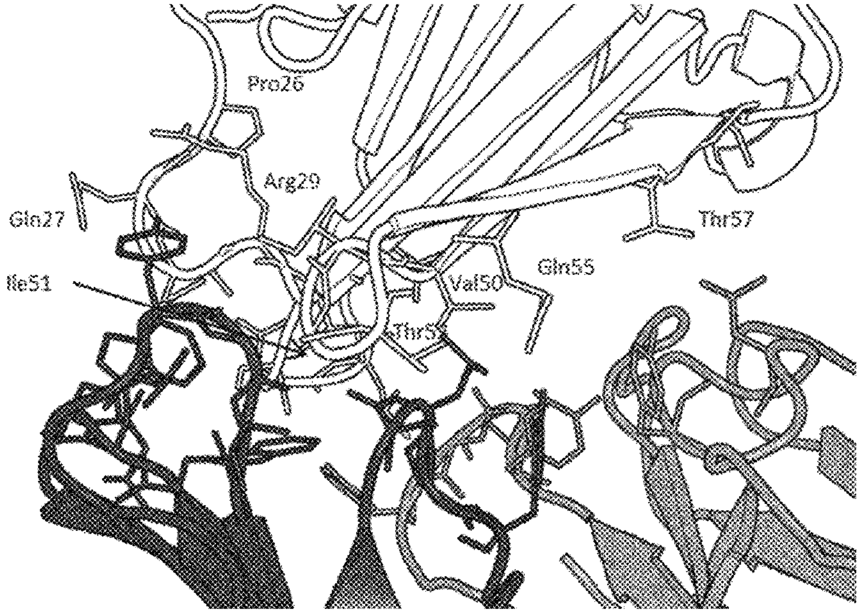
FIG. 10: Details of the protein interface shown in FIG. 9. Selected residues are depicted in stick representation and colored as in FIG. 9. The numbering corresponds to TPP-1794 (SEQ-ID NO: 169)

These residues form the exemplary three-dimensional conformational epitope that is recognized by the Fab fragment APP-1574 (FIGS. 9 and 10).

TABLE 29

Interactions between single N-terminal domain 1 of human CEACAM6 and Fab APP-1574

| N-terminal domain 1 of human CEACAM6 (TPP-1794; SEQ-ID 169) | | Fab APP-1574 | | |
|---|---|---|---|---|
| Amino Acid | Number as in SEQ-ID 169 (number as in SEQ-ID NO: 179 in brackets) | Amino Acid | Number | Chain |
| Pro | 26 (59) | Tyr | 32 | H |
| Gln | 27 (60) | Tyr | 32 | H |

TABLE 29-continued

Interactions between single N-terminal domain 1 of human CEACAM6 and Fab APP-1574

| N-terminal domain 1 of human CEACAM6 (TPP-1794; SEQ-ID 169) | | Fab APP-1574 | | |
|---|---|---|---|---|
| Amino Acid | Number as in SEQ-ID 169 (number as in SEQ-ID NO: 179 in brackets) | Amino Acid | Number | Chain |
| Asn | 28 (61) | Trp | 55 | H |
| | | Asn | 56 | H |
| | | Tyr | 32 | H |
| | | Asn | 58 | H |
| Arg | 29 (62) | Trp | 55 | H |
| | | Tyr | 32 | H |
| | | Gly | 33 | H |
| Ile | 30 (63) | Ser | 101 | H |
| | | Gly | 33 | H |
| | | Trp | 54 | H |
| | | Leu | 102 | H |
| | | Ser | 101 | H |
| | | Pro | 103 | H |
| | | Trp | 55 | H |
| Gly | 31 (64) | Leu | 102 | H |
| Val | 50 (83) | Ser | 101 | H |
| | | Leu | 102 | H |
| | | Tyr | 104 | H |
| Ile | 51 (84) | Gly | 33 | H |
| | | Tyr | 32 | H |
| Gly | 52 (85) | Ile | 34 | H |
| | | Gly | 33 | H |
| | | Ser | 101 | H |
| | | Tyr | 32 | H |
| | | Thr | 31 | H |
| Thr | 53 (86) | Ser | 101 | H |
| | | Ile | 34 | H |
| | | Arg | 99 | H |
| Gln | 55 (88) | Tyr | 49 | L |
| Thr | 57 (90) | Tyr | 49 | L |
| | | Asn | 53 | L |
| Pro | 58 (91) | Asn | 53 | L |
| Ile | 92 (125) | Leu | 102 | H |
| Ser | 94 (127) | Tyr | 94 | L |
| | | Trp | 54 | H |
| | | Tyr | 60 | H |
| | | Trp | 55 | H |
| | | Asn | 56 | H |
| | | Asn | 58 | H |
| Asp | 95 (128) | Tyr | 94 | L |
| | | Tyr | 60 | H |
| Leu | 96 (129) | Tyr | 94 | L |
| | | Ser | 92 | L |
| | | Ser | 93 | L |
| | | Tyr | 91 | L |
| | | Pro | 103 | H |

CEACAM6 N-terminal domain1 residues numbered as in SEQ ID NO 169. The antibody residues are numbered based upon their linear amino acid sequence (SEQ ID NO: 183 and SEQ ID NO: 184) and corresponding chains are labeled ("H" for heavy chain, "L" for light chain). Human CEACAM6 single N-terminal domain1 residues shown here to have at least one atom with 5 Å to any atom in Fab fragment APP-1574, to account for potential water mediated interactions.

When carefully analyzing the epitope, it becomes apparent that Isoleucine-63 (according to SEQ-ID NO: 179) of human CEACAM6 is a central part of the epitope. The Isoleucine side-chain has good shape complementary with APP-1574. Modelling indicates that a Leucine at this position in cynomolgus CEACAM6 can be sterically accommodated and will not disrupt the interaction. This explains a retained binding activity to cynomolgus CEACAM6 activity and is the basis for human-cynomolgus cross-reactivity. In contrast, a Phenylalanine at this position (as in human CEACAM1, human CEACAM3 and human CEACAM5) cannot be sterically accommodated and will lead to loss in binding activity. This is the basis for CEACAM6 selectivity.

Thereby, recognition of Isoleucine-63 (according to SEQ-ID NO: 179) represents the most significant "selectivity tuner" between target CEACAMs. The APP-1574 recognition mode of human CEACAM6 optimally exploits key residue difference between targets and off-targets. Previous analysis of a structure of the Fab fragment of TPP-1679 (which selectivity profile is insufficient, see Example 4) in complex with N-terminal domain 1 also identified Isoleucine-63 (according to SEQ-ID NO: 179) as potential selectivity switch (data not shown). However, since the molecular recognition mechanism by TPP-1679 is different, whereby Ileucine-63 (according to SEQ-ID NO: 179) is located at the binding site periphery, it was difficult to exploit.

In summary, binders that in addition to other residues forming the epitope (Table 29) also optimally exploit binding to the selectivity & cross-reactivity determining residue Isoleucine-63 (according to SEQ-ID O: 179) of CEACAM6 and still allowing the accommodation of a Leucine at that position, but not Phenylalanine, will be CEACAM6 selective, but at the same time human-cynomolgus CEACAM6 cross-reactive.

Mutagenesis

To substantiate the findings and predictions of structural analysis in binding studies, the following mutants of N-terminal domain 1 of human CEACAM6 were generated:

TABLE 30

Amino acid sequences of proteins used in mutational binding studies

| Protein | Protein-ID | Amino Acid Sequence |
|---|---|---|
| Human CEACAM6-Domain 1-His | TPP-1794; SEQ-ID NO: 169 | MKLTIESTPF NVAEGKEVLL LAHNLPQNRI GYSWYKGERV DGNSLIVGYV IGTQQATPGP AYSGRETIYP NASLLIQNVT QNDTGFYTLQ VIKSDLVNEE ATGQFHVYPG SGSHHHHHHH H |
| Human CEACAM6-Domain 1-His-130L (I63L according to SEQ-ID NO: 179) | TPP-8697 SEQ-ID NO: 185 | MKLTIESTPF NVAEGKEVLL LAHNLPQNRL GYSWYKGERV DGNSLIVGYV IGTQQATPGP AYSGRETIYP NASLLIQNVT QNDTGFYTLQ VIKSDLVNEE ATGQFHVYPG SGSHHHHHHH H |
| Human CEACAM6-Domain 1-His-130F (I63F accordingto SEQ-ID NO: 179) | TPP-8698 SEQ-ID NO: 186 | MKLTIESTPF NVAEGKEVLL LAHNLPQNRF GYSWYKGERV DGNSLIVGYV IGTQQATPGP AYSGRETIYP NASLLIQNVT QNDTGFYTLQ VIKSDLVNEE ATGQFHVYPG SGSHHHHHHH H |

The proteins were expressed in *E. coli*, refolded and purified as described in Example 1. Comparative binding activity to domain 1 wild-type protein and the two single mutations was determined by ELISA method. 1.5 ug/ml protein solutions in PBS were coated overnight to 384 Nunc MaxiSorp plates (Sigma, P6491). Plates were washed with PBS/T and blocked with Smart block (CANDOR Bioscience GmbH, 113125). Subsequently, dilution series of TPP-3310, TPP-1679 and an isotype control antibody were applied to the wells. After washing with PBS/T, bound antibodies were detected with Anti Human IgG Fc POD (Sigma, A0170) and 10 μM Amplex Red solution (Thermo, A12222). Positive binding signals were detected via Fluorescence (Ex. 535 nm/Em. 590 nm). Table 32 shows binding activity for TPP-3310 to the domain 1 wild-type protein and the mutation of Isoleucine 63 (as in SEQ-ID NO: 179) to Leucine (as in cynomolgus). The mutation of amino acid position 63 (as in SEQ-ID NO: 179) to Phenylalanine (as in human CEACAM1, human CEACAM3 and human CEACAM5) results in complete loss of binding ability. As a control for demonstration of efficient refolding of CEACAM6 N-terminal domain 1 proteins, TPP-1679 was employed (see Example 4), for which binding to a similar extent to all antigens tested in Table 31 was observed.

TABLE 31

Binding activity on CEACAM6 N-terminal domain 1 mutants.

| Antibody | Human CEACAM6-Domain 1-His Wild-type TPP-1794; SEQ-ID NO: 169 | Human CEACAM6-Domain 1-His I30L (I63L according to SEQ-ID NO: 179) TPP-8697; SEQ-ID NO: 185 | Human CEACAM6-Domain 1-His I30F (I63F according to SEQ-ID NO: 179) TPP-8698; SEQ-ID NO: 186 |
|---|---|---|---|
| TPP-3310 | + | + | − |
| TPP-1679 | + | + | + |
| Isotype control | − | − | − |

"+" denotes binding detected;
"−" denotes no binding detected

In conclusion, the truly human—cynomolgus CEACAM6 cross-reactive antibody TPP-3310, which is at the same time selective with regards to other human paralogs, was able to tolerate an 163L substitution (according to SEQ-ID: 179) (corresponding to cynomolgus CEACAM6 residue) but not an 163F substitution (according to SEQ-ID: 179) (corresponding residue in human paralogs CEACAM1, CEACAM3, and CEACAM5) in the context of human CEACAM6 N-terminal domain 1 consistent with results obtained from X-ray crystallography and substantiating our prediction.

Example 17: Analysis of T Cell Mediated Cytotoxicity in the Presence of CEACAM6 Antibodies The effect of the anti-CEACAM6 antibodies on T cell mediated cytotoxicity was studied in cytotoxicity experiments with co-cultures of CEACAM6 positive tumor cells and T cells derived of different sources. These T cells were either $CD8^+$ survivin T cells or patient-derived T cells from a pancreatic cancer. For these tumor cell killing experiments an impedance based cytotoxicity assay (xCELLigence) system was used.

The survivin-peptide specific $CD8^+$ T cell clone was generated and expanded in vitro as described in Example 11. Pancreatic cancer tumor infiltrating lymphocyte cell lines (TILs) were isolated from fresh primary culture of tumor tissue from surgery. In brief, fresh primary tissue material was cut into small pieces and cultured in small dishes in X-Vivo-15 medium (Lonza) containing 2% human serum albumin, 2.5 μg/ml Fungizone, 20 μg/ml Gentamycin, 1% Penicillin/Streptomycin with 6000 IU/IL-2 for 10-18 days. Afterwards cells from the supernatant were harvested and either frozen or used directly for a "rapid expansion protocol" (REP). For rapid expansion of TILs, frozen TILs were gently thawed and cultured with $0.6*10^6$ cells/ml for 1 day in Complete Lymphocyte Medium CLM RPMI-1640 (Life Technologies #21875034), 10% human AB Serum (MILAN Analytica #000083), 1% Penicillin/Streptomycin (Life Technologies #15140122), 1% ml HEPES (Life Technologies #15630056), 0.01% 1-mercaptoethanol [stock 50 mM] (Life Technologies #31350010)) with 6000 IU/ml IL-2. TILs were harvested and expanded at a 1:100 ratio with 60 Gy irradiated feeder PBMCs from 3 different donors in 400 ml REP medium (50% CLM mixed with 50% AIM-V serum free medium (Gibco #12055091) containing 3000 IU/ml IL-2 and 30 ng/ml OKT-3 antibody (eBioscience #16-0037-85)) in G-REX-100 Flasks (Wilson Wolf #80500S). Cells were cultured and splitted as described in Jin et al., J Immunother. 2012 April; 35(3):283-92. After 14 days cells were harvested and frozen in aliquots. Prior to co-culture cytotoxicity assays, individual aliquots of TILs were gently thawed and cultured with $0.6*10^6$ cells/ml for 2 days in CLM containing 6000 IU/ml IL-2 and 1 day in CLM without IL-2.

Tumor Cells were Cultivated According to Standard Protocols and Provider's Instructions T cell mediated cytotoxity was analyzed in an impedance based cytotoxicity assay (xCELLigence) system. In this label free assay system cytotoxicity is measured directly and continuously over a long time period of around 100-150 h (real time). Adherent tumor cells are attached to microelectrodes at the bottom of a 96-Well E-plate (E-Plate VIEW 96 PET; ACEA Biosciences #ID:H000568) which changes the electrical impedance of these electrodes. This is monitored as an increase of the dimensionless "cell index". After adherence of the tumor cells (~24 h) antibodies and T cells are added to the wells which, if T cells exert cytotoxic activity, results in lysis of the tumor cells and detachment from the electrodes. This detachment changes the impedance of the wells and is measured as a decrease of the "cell index" or "normalized cell index" which is the "cell index" normalized to the time point of T cell addition. The T cells alone do not affect the electrical impedance of the electrodes and thus only the cytolysis of the tumor cells is measured. (Peper et al, J Immunol Methods. 2014 March; 405:192-8)

In first experiments we established that tumor cell killing observed in this assay system is T cell dose dependent and works for different tumor cell:T cell ratios and different T cell sources (Survivin-peptide specific $CD8^+$ T cells, TILs from pancreatic cancer patients).

Figure 11A:
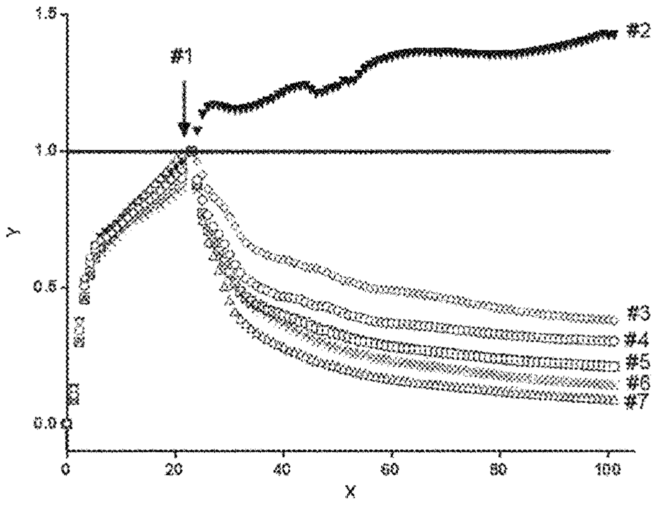
FIGS. 11A-B: xCELLigence cytotoxicity assay using survivin-peptide specific $CD8^+$ T cells.
Figure 11B:
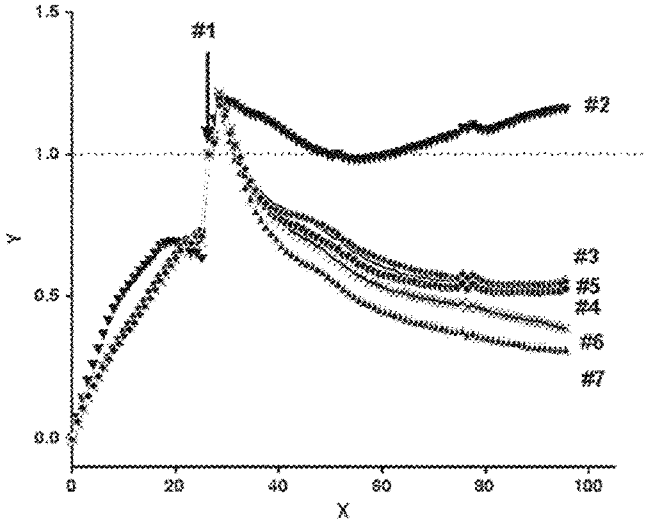

We then studied the effect of anti-CEACAM6 antibodies on the cytolytic efficacy of survivin T cells. Therefore, the CEACAM6 positive breast cancer KS or the CEACAM6 transfected colon cancer HCT-116 (HCT116-hC6) was added to 96-well plates for 24 h before survivin-peptide specific T cells were added at different cell ratios together with the anti-CEACAM6 mAbs. The coculture was followed for a time period ~100 h. In these experiments we observed an improved T cell dependent cytotoxicity in the presence of the anti-CEACAM6 antibodies TPP-3310 and TPP-3470 of ~21% on both cell lines. The results are displayed in FIGS. 11 A and B) exemplarily for one cell ratio. Notably, the survivin-peptide specific $CD8^+$ T cells alone show already a high cytotoxic impact of 45-62%, which is most likely due to the preactivation of the cultured T cells and is thus considered as background cytolysis. In summary, the increase of IFN-gamma secretion observed in the previous ELISA assays translates into a cytotoxic effect within approximately 24 h of co-culture. We conclude that treatment of CEACAM6 positive tumor cells with anti-CEACAM6 antibodies leads to improved survivin-peptide specific $CD8^+$ T cell mediated killing of both tumor cell lines.

Figure 12A:
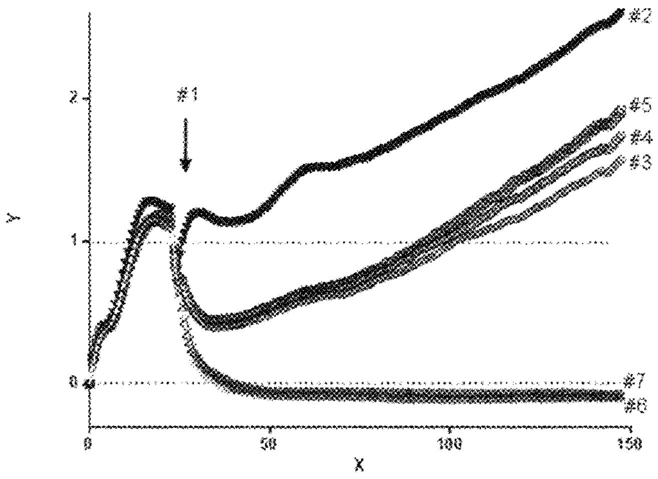
FIGS. 12A-B: xCELLigence cytotoxicity assay using patient-derived T cells of a pancreatic cancer (TIL-12).
Figure 12B:
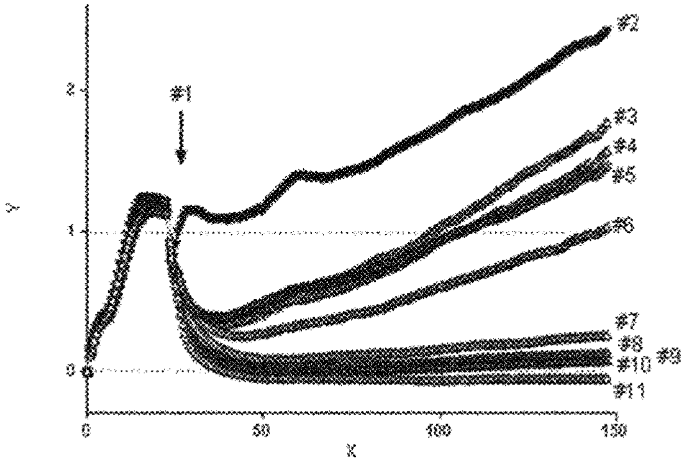

In subsequent experiments we tested the effect of the CEACAM6 antibodies on the cytolytic activity of patient-derived TILs cells of a pancreatic cancer. Therefore, the CEACAM6 positive lung cancer cell line HCC2935 was added to 96-well plates and cultivated for 24 h. Then, TILs were added at different ratios in the presence of the CEACAM6 antibody (30 μg/ml) and of a bispecific antibody anti-CD3× anti-EPCAM IgG (0.25 ng/ml) (Marme et al., Int J Cancer. 2002 Sep. 10; 101(2):183-9; Salnikov et al., J Cell Mol Med. 2009 September; 13(9B):4023-33) to allow for HLA-independent T cell mediated tumor cell killing. In the presence of the anti-CEACAM6 antibodies TPP-3310 and TPP-3470 we observed a complete drop of impedance which was not observed in the presence of the isotype matched control antibody. The drop in impedance is interpreted as complete cytolytic kill of the target cell line HCC2935. In an additional experiment it could be demonstrated that the effect of the CEACAM6 antibody TPP-3310 is dose dependent and an $IC_{50}$ value of 0.62-0.21 μg/ml was determined. FIG. 12 shows exemplarily the results for TIL-12.

In summary these experiments show that the CEACAM6 antibodies of the invention have the potential to effectively block the immunosuppressive receptor CEACAM6 and improve the cytotoxic efficacy not only of model T cells but also of patient-derived Tumor infiltrating lymphocytes against CEACAM6 positive tumor cells.

Table of Sequences

TABLE 32

Correlation of SEQ ID NO to TPP-ID and associated sequence features (heavy and light chain of antibody, variable regions, complementarity determining regions (CDR)) for proteins (PRT) and nucleic acids (DNA)

| "TPP ID" | "Sequence Name" | "Sequence Region" | "Sequence Type" | "SEQ ID" |
|---|---|---|---|---|
| TPP-1173 | h16C3-hIgG1 | Heavy Chain | PRT | SEQ ID NO: 1 |
| TPP-1173 | h16C3-hIgG1 | Light Chain | PRT | SEQ ID NO: 2 |
| TPP-2971 | 792.15H12C9 | VH | PRT | SEQ ID NO: 3 |
| TPP-2971 | 792.15H12C9 | HCDR1 | PRT | SEQ ID NO: 4 |
| TPP-2971 | 792.15H12C9 | HCDR2 | PRT | SEQ ID NO: 5 |
| TPP-2971 | 792.15H12C9 | HCDR3 | PRT | SEQ ID NO: 6 |
| TPP-2971 | 792.15H12C9 | VL | PRT | SEQ ID NO: 7 |
| TPP-2971 | 792.15H12C9 | LCDR1 | PRT | SEQ ID NO: 8 |
| TPP-2971 | 792.15H12C9 | LCDR2 | PRT | SEQ ID NO: 9 |
| TPP-2971 | 792.15H12C9 | LCDR3 | PRT | SEQ ID NO: 10 |
| TPP-3186 | 792.11G2D10 | VH | PRT | SEQ ID NO: 13 |
| TPP-3186 | 792.11G2D10 | HCDR1 | PRT | SEQ ID NO: 14 |
| TPP-3186 | 792.11G2D10 | HCDR2 | PRT | SEQ ID NO: 15 |
| TPP-3186 | 792.11G2D10 | HCDR3 | PRT | SEQ ID NO: 16 |
| TPP-3186 | 792.11G2D10 | VL | PRT | SEQ ID NO: 17 |
| TPP-3186 | 792.11G2D10 | LCDR1 | PRT | SEQ ID NO: 18 |
| TPP-3186 | 792.11G2D10 | LCDR2 | PRT | SEQ ID NO: 19 |
| TPP-3186 | 792.11G2D10 | LCDR3 | PRT | SEQ ID NO: 20 |
| TPP-3187 | 792.15C4F4 | VH | PRT | SEQ ID NO: 23 |
| TPP-3187 | 792.15C4F4 | HCDR1 | PRT | SEQ ID NO: 24 |
| TPP-3187 | 792.15C4F4 | HCDR2 | PRT | SEQ ID NO: 25 |
| TPP-3187 | 792.15C4F4 | HCDR3 | PRT | SEQ ID NO: 26 |
| TPP-3187 | 792.15C4F4 | VL | PRT | SEQ ID NO: 27 |
| TPP-3187 | 792.15C4F4 | LCDR1 | PRT | SEQ ID NO: 28 |
| TPP-3187 | 792.15C4F4 | LCDR2 | PRT | SEQ ID NO: 29 |
| TPP-3187 | 792.15C4F4 | LCDR3 | PRT | SEQ ID NO: 30 |
| TPP-3308 | TPP-2971X1-hIgG2Kappa | VH | PRT | SEQ ID NO: 33 |
| TPP-3308 | TPP-2971X1-hIgG2Kappa | HCDR1 | PRT | SEQ ID NO: 34 |
| TPP-3308 | TPP-2971X1-hIgG2Kappa | HCDR2 | PRT | SEQ ID NO: 35 |
| TPP-3308 | TPP-2971X1-hIgG2Kappa | HCDR3 | PRT | SEQ ID NO: 36 |
| TPP-3308 | TPP-2971X1-hIgG2Kappa | VL | PRT | SEQ ID NO: 37 |
| TPP-3308 | TPP-2971X1-hIgG2Kappa | LCDR1 | PRT | SEQ ID NO: 38 |
| TPP-3308 | TPP-2971X1-hIgG2Kappa | LCDR2 | PRT | SEQ ID NO: 39 |
| TPP-3308 | TPP-2971X1-hIgG2Kappa | LCDR3 | PRT | SEQ ID NO: 40 |
| TPP-3308 | TPP-2971X1-hIgG2Kappa | VH | DNA | SEQ ID NO: 41 |
| TPP-3308 | TPP-2971X1-hIgG2Kappa | VL | DNA | SEQ ID NO: 42 |
| TPP-3308 | TPP-2971X1-hIgG2Kappa | Heavy Chain | PRT | SEQ ID NO: 43 |
| TPP-3308 | TPP-2971X1-hIgG2Kappa | Light Chain | PRT | SEQ ID NO: 44 |
| TPP-3308 | TPP-2971X1-hIgG2Kappa | Heavy Chain | DNA | SEQ ID NO: 45 |
| TPP-3308 | TPP-2971X1-hIgG2Kappa | Light Chain | DNA | SEQ ID NO: 46 |
| TPP-3310 | TPP-2971HU1-hIgG2Kappa | VH | PRT | SEQ ID NO: 47 |
| TPP-3310 | TPP-2971HU1-hIgG2Kappa | HCDR1 | PRT | SEQ ID NO: 48 |
| TPP-3310 | TPP-2971HU1-hIgG2Kappa | HCDR2 | PRT | SEQ ID NO: 49 |
| TPP-3310 | TPP-2971HU1-hIgG2Kappa | HCDR3 | PRT | SEQ ID NO: 50 |
| TPP-3310 | TPP-2971HU1-hIgG2Kappa | VL | PRT | SEQ ID NO: 51 |
| TPP-3310 | TPP-2971HU1-hIgG2Kappa | LCDR1 | PRT | SEQ ID NO: 52 |
| TPP-3310 | TPP-2971HU1-hIgG2Kappa | LCDR2 | PRT | SEQ ID NO: 53 |
| TPP-3310 | TPP-2971HU1-hIgG2Kappa | LCDR3 | PRT | SEQ ID NO: 54 |

TABLE 32-continued

Correlation of SEQ ID NO to TPP-ID and associated sequence features (heavy and light chain of antibody, variable regions, complementarity determining regions (CDR)) for proteins (PRT) and nucleic acids (DNA)

| "TPP ID" | "Sequence Name" | "Sequence Region" | "Sequence Type" | "SEQ ID" |
|---|---|---|---|---|
| TPP-3310 | TPP-2971HU1-hIgG2Kappa | VH | DNA | SEQ ID NO: 55 |
| TPP-3310 | TPP-2971HU1-hIgG2Kappa | VL | DNA | SEQ ID NO: 56 |
| TPP-3310 | TPP-2971HU1-hIgG2Kappa | Heavy Chain | PRT | SEQ ID NO: 57 |
| TPP-3310 | TPP-2971HU1-hIgG2Kappa | Light Chain | PRT | SEQ ID NO: 58 |
| TPP-3310 | TPP-2971HU1-hIgG2Kappa | Heavy Chain | DNA | SEQ ID NO: 59 |
| TPP-3310 | TPP-2971HU1-hIgG2Kappa | Light Chain | DNA | SEQ ID NO: 60 |
| TPP-3322 | TPP-3186X1-hIgG2 | VH | PRT | SEQ ID NO: 61 |
| TPP-3322 | TPP-3186X1-hIgG2 | HCDR1 | PRT | SEQ ID NO: 62 |
| TPP-3322 | TPP-3186X1-hIgG2 | HCDR2 | PRT | SEQ ID NO: 63 |
| TPP-3322 | TPP-3186X1-hIgG2 | HCDR3 | PRT | SEQ ID NO: 64 |
| TPP-3322 | TPP-3186X1-hIgG2 | VL | PRT | SEQ ID NO: 65 |
| TPP-3322 | TPP-3186X1-hIgG2 | LCDR1 | PRT | SEQ ID NO: 66 |
| TPP-3322 | TPP-3186X1-hIgG2 | LCDR2 | PRT | SEQ ID NO: 67 |
| TPP-3322 | TPP-3186X1-hIgG2 | LCDR3 | PRT | SEQ ID NO: 68 |
| TPP-3322 | TPP-3186X1-hIgG2 | VH | DNA | SEQ ID NO: 69 |
| TPP-3322 | TPP-3186X1-hIgG2 | VL | DNA | SEQ ID NO: 70 |
| TPP-3322 | TPP-3186X1-hIgG2 | Heavy Chain | PRT | SEQ ID NO: 71 |
| TPP-3322 | TPP-3186X1-hIgG2 | Light Chain | PRT | SEQ ID NO: 72 |
| TPP-3322 | TPP-3186X1-hIgG2 | Heavy Chain | DNA | SEQ ID NO: 73 |
| TPP-3322 | TPP-3186X1-hIgG2 | Light Chain | DNA | SEQ ID NO: 74 |
| TPP-3323 | TPP-3187X1-hIgG2 | VH | PRT | SEQ ID NO: 75 |
| TPP-3323 | TPP-3187X1-hIgG2 | HCDR1 | PRT | SEQ ID NO: 76 |
| TPP-3323 | TPP-3187X1-hIgG2 | HCDR2 | PRT | SEQ ID NO: 77 |
| TPP-3323 | TPP-3187X1-hIgG2 | HCDR3 | PRT | SEQ ID NO: 78 |
| TPP-3323 | TPP-3187X1-hIgG2 | VL | PRT | SEQ ID NO: 79 |
| TPP-3323 | TPP-3187X1-hIgG2 | LCDR1 | PRT | SEQ ID NO: 80 |
| TPP-3323 | TPP-3187X1-hIgG2 | LCDR2 | PRT | SEQ ID NO: 81 |
| TPP-3323 | TPP-3187X1-hIgG2 | LCDR3 | PRT | SEQ ID NO: 82 |
| TPP-3323 | TPP-3187X1-hIgG2 | VH | DNA | SEQ ID NO: 83 |
| TPP-3323 | TPP-3187X1-hIgG2 | VL | DNA | SEQ ID NO: 84 |
| TPP-3323 | TPP-3187X1-hIgG2 | Heavy Chain | PRT | SEQ ID NO: 85 |
| TPP-3323 | TPP-3187X1-hIgG2 | Light Chain | PRT | SEQ ID NO: 86 |
| TPP-3323 | TPP-3187X1-hIgG2 | Heavy Chain | DNA | SEQ ID NO: 87 |
| TPP-3323 | TPP-3187X1-hIgG2 | Light Chain | DNA | SEQ ID NO: 88 |
| TPP-3688 | h16C3-hIgG2Kappa | Heavy Chain | PRT | SEQ ID NO: 89 |
| TPP-3688 | h16C3-hIgG2Kappa | Light Chain | PRT | SEQ ID NO: 90 |
| TPP-3705 | 090E-M007-A09-Mat1-hIgG2-hIgG2Kappa | VH | PRT | SEQ ID NO: 91 |
| TPP-3705 | 090E-M007-A09-Mat1-hIgG2-hIgG2Kappa | HCDR1 | PRT | SEQ ID NO: 92 |
| TPP-3705 | 090E-M007-A09-Mat1-hIgG2-hIgG2Kappa | HCDR2 | PRT | SEQ ID NO: 93 |
| TPP-3705 | 090E-M007-A09-Mat1-hIgG2-hIgG2Kappa | HCDR3 | PRT | SEQ ID NO: 94 |
| TPP-3705 | 090E-M007-A09-Mat1-hIgG2-hIgG2Kappa | VL | PRT | SEQ ID NO: 95 |
| TPP-3705 | 090E-M007-A09-Mat1-hIgG2-hIgG2Kappa | LCDR1 | PRT | SEQ ID NO: 96 |
| TPP-3705 | 090E-M007-A09-Mat1-hIgG2-hIgG2Kappa | LCDR2 | PRT | SEQ ID NO: 97 |
| TPP-3705 | 090E-M007-A09-Mat1-hIgG2-hIgG2Kappa | LCDR3 | PRT | SEQ ID NO: 98 |
| TPP-3705 | 090E-M007-A09-Mat1-hIgG2-hIgG2Kappa | VH | DNA | SEQ ID NO: 99 |
| TPP-3705 | 090E-M007-A09-Mat1-hIgG2-hIgG2Kappa | VL | DNA | SEQ ID NO: 100 |

TABLE 32-continued

Correlation of SEQ ID NO to TPP-ID and associated sequence features (heavy and light chain of antibody, variable regions, complementarity determining regions (CDR)) for proteins (PRT) and nucleic acids (DNA)

| "TPP ID" | "Sequence Name" | "Sequence Region" | "Sequence Type" | "SEQ ID" |
|---|---|---|---|---|
| TPP-3705 | 090E-M007-A09-Mat1-hIgG2-hIgG2Kappa | Heavy Chain | PRT | SEQ ID NO: 101 |
| TPP-3705 | 090E-M007-A09-Mat1-hIgG2-hIgG2Kappa | Light Chain | PRT | SEQ ID NO: 102 |
| TPP-3705 | 090E-M007-A09-Mat1-hIgG2-hIgG2Kappa | Heavy Chain | DNA | SEQ ID NO: 103 |
| TPP-3705 | 090E-M007-A09-Mat1-hIgG2-hIgG2Kappa | Light Chain | DNA | SEQ ID NO: 104 |
| TPP-3707 | 090E-M007-A09-Mat2-hIgG2-hIgG2Kappa | VH | PRT | SEQ ID NO: 105 |
| TPP-3707 | 090E-M007-A09-Mat2-hIgG2-hIgG2Kappa | HCDR1 | PRT | SEQ ID NO: 106 |
| TPP-3707 | 090E-M007-A09-Mat2-hIgG2-hIgG2Kappa | HCDR2 | PRT | SEQ ID NO: 107 |
| TPP-3707 | 090E-M007-A09-Mat2-hIgG2-hIgG2Kappa | HCDR3 | PRT | SEQ ID NO: 108 |
| TPP-3707 | 090E-M007-A09-Mat2-hIgG2-hIgG2Kappa | VL | PRT | SEQ ID NO: 109 |
| TPP-3707 | 090E-M007-A09-Mat2-hIgG2-hIgG2Kappa | LCDR1 | PRT | SEQ ID NO: 110 |
| TPP-3707 | 090E-M007-A09-Mat2-hIgG2-hIgG2Kappa | LCDR2 | PRT | SEQ ID NO: 111 |
| TPP-3707 | 090E-M007-A09-Mat2-hIgG2-hIgG2Kappa | LCDR3 | PRT | SEQ ID NO: 112 |
| TPP-3707 | 090E-M007-A09-Mat2-hIgG2-hIgG2Kappa | VH | DNA | SEQ ID NO: 113 |
| TPP-3707 | 090E-M007-A09-Mat2-hIgG2-hIgG2Kappa | VL | DNA | SEQ ID NO: 114 |
| TPP-3707 | 090E-M007-A09-Mat2-hIgG2-hIgG2Kappa | Heavy Chain | PRT | SEQ ID NO: 115 |
| TPP-3707 | 090E-M007-A09-Mat2-hIgG2-hIgG2Kappa | Light Chain | PRT | SEQ ID NO: 116 |
| TPP-3707 | 090E-M007-A09-Mat2-hIgG2-hIgG2Kappa | Heavy Chain | DNA | SEQ ID NO: 117 |
| TPP-3707 | 090E-M007-A09-Mat2-hIgG2-hIgG2Kappa | Light Chain | DNA | SEQ ID NO: 118 |
| TPP-3714 | TPP-2971HU2-hIgG2Kappa | VH | PRT | SEQ ID NO: 119 |
| TPP-3714 | TPP-2971HU2-hIgG2Kappa | HCDR1 | PRT | SEQ ID NO: 120 |
| TPP-3714 | TPP-2971HU2-hIgG2Kappa | HCDR2 | PRT | SEQ ID NO: 121 |
| TPP-3714 | TPP-2971HU2-hIgG2Kappa | HCDR3 | PRT | SEQ ID NO: 122 |
| TPP-3714 | TPP-2971HU2-hIgG2Kappa | VL | PRT | SEQ ID NO: 123 |
| TPP-3714 | TPP-2971HU2-hIgG2Kappa | LCDR1 | PRT | SEQ ID NO: 124 |
| TPP-3714 | TPP-2971HU2-hIgG2Kappa | LCDR2 | PRT | SEQ ID NO: 125 |
| TPP-3714 | TPP-2971HU2-hIgG2Kappa | LCDR3 | PRT | SEQ ID NO: 126 |
| TPP-3714 | TPP-2971HU2-hIgG2Kappa | VH | DNA | SEQ ID NO: 127 |

TABLE 32-continued

Correlation of SEQ ID NO to TPP-ID and associated sequence features (heavy and light chain of antibody, variable regions, complementarity determining regions (CDR)) for proteins (PRT) and nucleic acids (DNA)

| "TPP ID" | "Sequence Name" | "Sequence Region" | "Sequence Type" | "SEQ ID" |
|---|---|---|---|---|
| TPP-3714 | TPP-2971HU2-hIgG2Kappa | VL | DNA | SEQ ID NO: 128 |
| TPP-3714 | TPP-2971HU2-hIgG2Kappa | Heavy Chain | PRT | SEQ ID NO: 129 |
| TPP-3714 | TPP-2971HU2-hIgG2Kappa | Light Chain | PRT | SEQ ID NO: 130 |
| TPP-3714 | TPP-2971HU2-hIgG2Kappa | Heavy Chain | DNA | SEQ ID NO: 131 |
| TPP-3714 | TPP-2971HU2-hIgG2Kappa | Light Chain | DNA | SEQ ID NO: 132 |
| TPP-3820 | 3187HU1-hIgG2Kappa | VH | PRT | SEQ ID NO: 133 |
| TPP-3820 | 3187HU1-hIgG2Kappa | HCDR1 | PRT | SEQ ID NO: 134 |
| TPP-3820 | 3187HU1-hIgG2Kappa | HCDR2 | PRT | SEQ ID NO: 135 |
| TPP-3820 | 3187HU1-hIgG2Kappa | HCDR3 | PRT | SEQ ID NO: 136 |
| TPP-3820 | 3187HU1-hIgG2Kappa | VL | PRT | SEQ ID NO: 137 |
| TPP-3820 | 3187HU1-hIgG2Kappa | LCDR1 | PRT | SEQ ID NO: 138 |
| TPP-3820 | 3187HU1-hIgG2Kappa | LCDR2 | PRT | SEQ ID NO: 139 |
| TPP-3820 | 3187HU1-hIgG2Kappa | LCDR3 | PRT | SEQ ID NO: 140 |
| TPP-3820 | 3187HU1-hIgG2Kappa | VH | DNA | SEQ ID NO: 141 |
| TPP-3820 | 3187HU1-hIgG2Kappa | VL | DNA | SEQ ID NO: 142 |
| TPP-3820 | 3187HU1-hIgG2Kappa | Heavy Chain | PRT | SEQ ID NO: 143 |
| TPP-3820 | 3187HU1-hIgG2Kappa | Light Chain | PRT | SEQ ID NO: 144 |
| TPP-3820 | 3187HU1-hIgG2Kappa | Heavy Chain | DNA | SEQ ID NO: 145 |
| TPP-3820 | 3187HU1-hIgG2Kappa | Light Chain | DNA | SEQ ID NO: 146 |
| TPP-3821 | 3187HU2-hIgG2Kappa | VH | PRT | SEQ ID NO: 147 |
| TPP-3821 | 3187HU2-hIgG2Kappa | HCDR1 | PRT | SEQ ID NO: 148 |
| TPP-3821 | 3187HU2-hIgG2Kappa | HCDR2 | PRT | SEQ ID NO: 149 |
| TPP-3821 | 3187HU2-hIgG2Kappa | HCDR3 | PRT | SEQ ID NO: 150 |
| TPP-3821 | 3187HU2-hIgG2Kappa | VL | PRT | SEQ ID NO: 151 |
| TPP-3821 | 3187HU2-hIgG2Kappa | LCDR1 | PRT | SEQ ID NO: 152 |
| TPP-3821 | 3187HU2-hIgG2Kappa | LCDR2 | PRT | SEQ ID NO: 153 |
| TPP-3821 | 3187HU2-hIgG2Kappa | LCDR3 | PRT | SEQ ID NO: 154 |
| TPP-3821 | 3187HU2-hIgG2Kappa | VH | DNA | SEQ ID NO: 155 |
| TPP-3821 | 3187HU2-hIgG2Kappa | VL | DNA | SEQ ID NO: 156 |
| TPP-3821 | 3187HU2-hIgG2Kappa | Heavy Chain | PRT | SEQ ID NO: 157 |
| TPP-3821 | 3187HU2-hIgG2Kappa | Light Chain | PRT | SEQ ID NO: 158 |
| TPP-3821 | 3187HU2-hIgG2Kappa | Heavy Chain | DNA | SEQ ID NO: 159 |
| TPP-3821 | 3187HU2-hIgG2Kappa | Light Chain | DNA | SEQ ID NO: 160 |
| TPP-1306 | *macaca mulatta* CEACAM6-Xa-Fc-His | Chain 1 | PRT | SEQ ID NO: 161 |
| TPP-1436 | Ceacam6 | Chain 1 | PRT | SEQ ID NO: 162 |
| TPP-1437 | Ceacam1 | Chain 1 | PRT | SEQ ID NO: 163 |
| TPP-1438 | Ceacam5 | Chain 1 | PRT | SEQ ID NO: 164 |
| TPP-1790 | hCeacam6-WT-Fc-6xHis | Chain 1 | PRT | SEQ ID NO: 165 |

TABLE 32-continued

Correlation of SEQ ID NO to TPP-ID and associated sequence features (heavy and light chain of antibody, variable regions, complementarity determining regions (CDR)) for proteins (PRT) and nucleic acids (DNA)

| "TPP ID" | "Sequence Name" | "Sequence Region" | "Sequence Type" | "SEQ ID" |
|---|---|---|---|---|
| TPP-1791 | hCeacam6-Dom1-MacMul-Xa-Fc-His | Chain 1 | PRT | SEQ ID NO: 166 |
| TPP-1792 | hCeacam6-Dom2-MacMul-Xa-Fc-His | Chain 1 | PRT | SEQ ID NO: 167 |
| TPP-1793 | hCeacam6-Dom3-MacMul-Xa-Fc-His | Chain 1 | PRT | SEQ ID NO: 168 |
| TPP-1794 | hCeacam6-Dom1-8xHis (*E. coli*) | Chain 1 | PRT | SEQ ID NO: 169 |
| TPP-2443 | cyno CEACAM-6-Xa-Fc-His | Chain 1 | PRT | SEQ ID NO: 170 |
| TPP-2452 | cynomolgus Ceacam6-Dom1-Xa-Fc-His | Chain 1 | PRT | SEQ ID NO: 171 |
| TPP-2755 | human CEACAM3 | Chain 1 | PRT | SEQ ID NO: 172 |
| TPP-4185 | CEACAM1 | Chain 1 | PRT | SEQ ID NO: 173 |
| TPP-4186 | CEACAM19 | Chain 1 | PRT | SEQ ID NO: 174 |
| TPP-4187 | CEACAM3 | Chain 1 | PRT | SEQ ID NO: 175 |
| TPP-4188 | CEACAM5 | Chain 1 | PRT | SEQ ID NO: 176 |
| TPP-4189 | CEACAM6_macfa | Chain 1 | PRT | SEQ ID NO: 177 |
| TPP-4190 | CEACAM8 | Chain 1 | PRT | SEQ ID NO: 178 |
| TPP-4639 | CEACAM6 | Chain 1 | PRT | SEQ ID NO: 179 |
| TPP-2453 | *Macaca fascicularis* CEACAM6-Domain 1-His | Chain 1 | PRT | SEQ-ID NO: 180 |
| TPP-5468 | TPP-2971HU1-hIgG1Kappa | Heavy Chain | PRT | SEQ-ID NO: 181 |
| TPP-5468 | TPP-2971HU1-hIgG1Kappa | Light Chain | PRT | SEQ-ID NO: 182 |
| APP-1574 | Papain-cleaved Fab fragment of TPP-5468 | Heavy Chain | PRT | SEQ-ID NO: 183 |
| APP-1574 | Papain-cleaved Fab fragment of TPP-5468 | Light Chain | PRT | SEQ-ID NO: 184 |
| TPP-8697 | Human CEACAM6-Domain 1-His - I30F | Chain 1 | PRT | SEQ-ID NO: 185 |
| TPP-8698 | Human CEACAM6-Domain 1-His - I30F | Chain 1 | PRT | SEQ-ID NO: 186 |

Additional Aspects of the Disclosure Include, without Limitation:

Aspect A: An isolated antibody or antigen-binding fragment thereof specifically binding to human CEACAM6 and *Macaca fascicularis* CEACAM6.

Aspect B: The antibody or antigen-binding fragment thereof according to Aspect A binding to CEACAM6 domain 1 represented by amino acids 35-142 of SEQ-ID NO:179 and amino acids 35-142 of SEQ-ID NO:177.

Aspect C: The antibody or antigen-binding fragment thereof according to Aspect A or B which does not significantly cross-react with human CEACAM1, human CEACAM3, and human CEACAM5.

Aspect D: The antibody or antigen-binding fragment thereof according to any one of Aspect A to C which interferes with the CEACAM6 and CEACAM1 interaction.

Aspect E: The antibody or antigen-binding fragment thereof according to any one of Aspect A to D which is able to change the cytokine profile of tumor antigen specific T cells towards a more activated phenotype characterized by an IFN-gamma secretion increase, preferably by a 21.5 times increase compared to control samples.

Aspect F: The antibody or antigen-binding fragment thereof according to any one of the preceding Aspects which binds to an epitope of human CEACAM6, wherein said epitope comprises one or more amino acid residues selected from the group consisting of Gln60, Asn61, Arg62, Ile63, Va183, Ile84, Gly85, Thr90, Ser127, Asp128 and Leu129 of SEQ ID NO: 17

Aspect G: The antibody or antigen-binding fragment thereof according Aspect F which binds to an epitope of human CEACAM6, wherein said epitope comprises the amino acid residues Gln60, Asn61, Arg62, Ile63, Va183, Ile84, Gly85, Thr90, Ser127, Asp128 and Leu129 of SEQ ID NO: 179.

Aspect H: The antibody or antigen-binding fragment thereof according to Aspect F or G which binds to a human CEACAM6 protein comprising an Ile63Leu mutation and which does not bind to a human CEACAM6 protein comprising an Ile63Phe mutation according to SEQ ID NO: 179.

Aspect I: The antibody or antigen-binding fragment thereof according to any one of Aspect A to E comprising i. a heavy chain antigen-binding region that comprises an H-CDR1 comprising SEQ ID NO:48, an H-CDR2 comprising SEQ ID NO:49, and an H-CDR3 comprising SEQ ID NO:50 and a light chain antigen-binding region that comprises a L-CDR1 comprising SEQ ID NO:52, a L-CDR2 comprising SEQ ID NO:53, and a L-CDR3 comprising SEQ ID NO:54, or ii. a heavy chain antigen-binding region that comprises an H-CDR1 comprising SEQ ID NO:106, an H-CDR2 comprising SEQ ID NO:107, and an H-CDR3 comprising SEQ ID NO:108 and a light chain antigen-binding region that comprises a L-CDR1 comprising SEQ ID NO:110, a L-CDR2 comprising SEQ ID NO:111, and a L-CDR3 comprising SEQ ID NO:112, or iii. a heavy chain antigen-binding region that comprises an H-CDR1 comprising SEQ ID NO:4, an H-CDR2 comprising SEQ ID NO:5, and an H-CDR3 comprising SEQ ID NO:6 and a light chain antigen-binding region that comprises a L-CDR1 comprising SEQ ID NO:8, a L-CDR2 comprising SEQ ID NO:9, and a L-CDR3 comprising SEQ ID NO:10, or iv. a heavy chain antigen-binding region that comprises an H-CDR1 comprising SEQ ID NO:34, an H-CDR2 comprising SEQ ID NO:35, and an H-CDR3 comprising SEQ ID NO:36 and a light chain antigen-binding region that comprises a L-CDR1 comprising SEQ ID NO:38, a L-CDR2 comprising SEQ ID NO:39, and a L-CDR3 comprising SEQ ID NO:40, or v. a heavy chain antigen-binding region that comprises an H-CDR1 comprising SEQ ID NO:120, an H-CDR2 comprising SEQ ID NO:121, and an H-CDR3 comprising SEQ ID NO:122 and a light chain antigen-binding region that comprises a L-CDR1 comprising SEQ ID NO:124, a L-CDR2 comprising SEQ ID NO:125, and a L-CDR3 comprising SEQ ID NO:126, or vi. a heavy chain antigen-binding region that comprises an H-CDR1 comprising SEQ ID NO:24, an H-CDR2 comprising SEQ ID NO:25, and an H-CDR3 comprising SEQ ID NO:26 and a light chain antigen-binding region that comprises a L-CDR1 comprising SEQ ID NO:28, a L-CDR2 comprising SEQ ID NO:29, and a L-CDR3 comprising SEQ ID NO:30, or vii. a heavy chain antigen-binding region that comprises an H-CDR1 comprising SEQ ID NO:76, an H-CDR2 comprising SEQ ID NO:77, and an H-CDR3 comprising SEQ ID NO:78 and a light chain antigen-binding region that comprises a L-CDR1 comprising SEQ ID NO:80, a L-CDR2 comprising SEQ ID NO:81, and a L-CDR3 comprising SEQ ID NO:82, or viii. a heavy chain antigen-binding region that comprises an H-CDR1 comprising SEQ ID NO:134, an H-CDR2 comprising SEQ ID NO:135, and an H-CDR3 comprising SEQ ID NO:136 and a light chain antigen-binding region that comprises a L-CDR1 comprising SEQ ID NO:138, a L-CDR2 comprising SEQ ID NO:139, and a L-CDR3 comprising SEQ ID NO:140, or ix. a heavy chain antigen-binding region that comprises an H-CDR1 comprising SEQ ID NO:148, an H-CDR2 comprising SEQ ID NO:149, and an H-CDR3 comprising SEQ ID NO:150 and a light chain antigen-binding region that comprises a L-CDR1 comprising SEQ ID NO:152, a L-CDR2 comprising SEQ ID NO:153, and a L-CDR3 comprising SEQ ID NO:154, or x. a heavy chain antigen-binding region that comprises an H-CDR1 comprising SEQ ID NO:14, an H-CDR2 comprising SEQ ID NO:15, and an H-CDR3 comprising SEQ ID NO:16 and a light chain antigen-binding region that comprises a L-CDR1 comprising SEQ ID NO:18, a L-CDR2 comprising SEQ ID NO:19, and a L-CDR3 comprising SEQ ID NO:20, or xi. a heavy chain antigen-binding region that comprises an H-CDR1 comprising SEQ ID NO:62, an H-CDR2 comprising SEQ ID NO:63, and an H-CDR3 comprising SEQ ID NO:64 and a light chain antigen-binding region that comprises a L-CDR1 comprising SEQ ID NO:66, a L-CDR2 comprising SEQ ID NO:67, and a L-CDR3 comprising SEQ ID NO:68, or xii. a heavy chain antigen-binding region that comprises an H-CDR1 comprising SEQ ID NO:92, an H-CDR2 comprising SEQ ID NO:93, and an H-CDR3 comprising SEQ ID NO:94 and a light chain antigen-binding region that comprises a L-CDR1 comprising SEQ ID NO:96, a L-CDR2 comprising SEQ ID NO:97, and a L-CDR3 comprising SEQ ID NO:98..

Aspect J: The antibody or antigen-binding fragment thereof according to any one of Aspects A to E and Aspect I comprising i. a variable heavy chain sequence as presented by SEQ ID NO: 47 and a variable light chain sequence as presented by SEQ ID NO: 51, or ii. a variable heavy chain sequence as presented by SEQ ID NO: 105 and a variable light chain sequence as presented by SEQ ID NO: 109, or iii. a variable heavy chain sequence as presented by SEQ ID NO: 3 and a variable light chain sequence as presented by SEQ ID NO: 7, or iv. a variable heavy chain sequence as presented by SEQ ID NO: 33 and a variable light chain sequence as presented by SEQ ID NO: 37, or v. a variable heavy chain sequence as presented by SEQ ID NO: 119 and a variable light chain sequence as presented by SEQ ID NO: 123, or vi. a variable heavy chain sequence as presented by SEQ ID NO: 23 and a variable light chain sequence as presented by SEQ ID NO: 27, or vii. a variable heavy chain sequence as presented by SEQ ID NO: 75 and a variable light chain sequence as presented by SEQ ID NO: 79, or viii. a variable heavy chain sequence as presented by SEQ ID NO: 133 and a variable light chain sequence as presented by SEQ ID NO: 137, or ix. a variable heavy chain sequence as presented by SEQ ID NO: 147 and a variable light chain sequence as presented by SEQ ID NO: 151, or x. a variable heavy chain sequence as presented by SEQ ID NO: 13 and a variable light chain sequence as presented by SEQ ID NO: 17, or xi. a variable heavy chain sequence as presented by SEQ ID NO: 61 and a variable light chain sequence as presented by SEQ ID NO: 65, or xii. a variable heavy chain sequence as presented by SEQ ID NO: 91 and a variable light chain sequence as presented by SEQ ID NO: 95.

Aspect K: The antibody according to any one of the preceding Aspects, which is an IgG antibody.

Aspect L: The antibody according to any one of Aspects A to E and Aspects I and J comprising:
- i. a heavy chain region corresponding to SEQ ID NO: 57 and a light chain region corresponding to SEQ ID NO: 58, or
- ii. a heavy chain region corresponding to SEQ ID NO: 115 and a light chain region corresponding to SEQ ID NO: 116, or
- iii. a heavy chain region corresponding to SEQ ID NO: 43 and a light chain region corresponding to SEQ ID NO: 44, or
- iv. a heavy chain region corresponding to SEQ ID NO: 129 and a light chain region corresponding to SEQ ID NO: 130, or
- v. a heavy chain region corresponding to SEQ ID NO: 85 and a light chain region corresponding to SEQ ID NO: 86, or
- vi. a heavy chain region corresponding to SEQ ID NO: 143 and a light chain region corresponding to SEQ ID NO: 144, or
- vii. a heavy chain region corresponding to SEQ ID NO: 157 and a light chain region corresponding to SEQ ID NO: 158, or
- viii. a heavy chain region corresponding to SEQ ID NO: 71 and a light chain region corresponding to SEQ ID NO: 72, or
- ix. a heavy chain region corresponding to SEQ ID NO: 101 and a light chain region corresponding to SEQ ID NO: 102.

Aspect M: The antigen-binding fragment according to Aspects A to J, which is an scFv, Fab, Fab' fragment or a F(ab')2 fragment.

Aspect N: The antibody or antigen-binding fragment according to any one of the preceding Aspects, which is a monoclonal antibody or antigen-binding fragment.

Aspect O: The antibody or antigen-binding fragment according to any one of the preceding Aspects, which is human, humanized or chimeric antibody or antigen-binding fragment.

Aspect P: An antibody-drug conjugate, comprising an antibody or antigen binding fragment thereof according to any one of the Aspects A to O.

Aspect Q: An isolated nucleic acid sequence that encodes the antibody or antigen-binding fragment according to any one of the Aspects A to O.

Aspect R: A vector comprising a nucleic acid sequence according to Aspect Q.

Aspect S: An isolated cell expressing an antibody or antigen-binding fragment according to any one of the Aspects A to O and/or comprising a nucleic acid according to Aspect Q or a vector according to Aspect R.

Aspect T: An isolated cell according to Aspect S, wherein said cell is a prokaryotic or a eukaryotic cell.

Aspect U: A method of producing an antibody or antigen-binding fragment according to any one of the Aspects A to O comprising culturing of a cell according to Aspect T and purification of the antibody or antigen-binding fragment.

Aspect V: An antibody or antigen-binding fragment according to any one of the Aspects A to O or an antibody-drug conjugate according to Aspect P for use as a medicament.

Aspect W: An antibody or antigen-binding fragment according to any one of the Aspects A to O or an antibody-drug conjugate according to Aspect P for use as a diagnostic agent.

Aspect X: An antibody or antigen-binding fragment according to any one of the Aspects A to O or an antibody-drug conjugate according to Aspect P for use as a medicament for the treatment of cancer.

Aspect Y: A pharmaceutical composition comprising an antibody or antigen-binding fragment according to any one of the Aspects A to M or an antibody-drug conjugate according to Aspect P.

Aspect Z: A combination of a pharmaceutical composition according to Aspect Y and one or more therapeutically active compounds.

Aspect AA: A method for treating a disorder or condition associated with the undesired presence of CEACAM6, comprising administering to a subject in need thereof an effective amount of the pharmaceutical composition according to Aspect Y or a combination according to Aspect Z.

Aspect BB: A process for the preparation of anti-CEACAM6 antibodies specifically binding to human CEACAM6 and *Macaca fascicularis* CEACAM6, which process comprises immunization of an animal, preferentially a mouse, with a protein comprising cynomolgus CECAM6 domain 1 represented by amino acids 35-142 of SEQ-ID NO:177, determining the amino acid sequence of antibodies specifically binding to human CEACAM6 and to cynomolgus CEACAM6, followed optionally by humanization or generation of a chimeric antibody, and recombinant expression of said antibodies.

The invention claimed is:

1. An isolated antibody or antigen-binding fragment thereof specifically binding to human CEACAM6, wherein said antibody or antigen-binding fragment:

i. binds to an epitope of human CEACAM6, wherein said epitope comprises the amino acid residues GIn60, Asn61, Arg62, Ile63, Va183, Ile84, Gly85, Thr90, Ser127, Asp128 and Leu129 of SEQ ID NO: 179, and ii. binds to a human CEACAM6 protein comprising an Ile63Leu mutation and does not bind to a human CEACAM6 protein comprising an 11 e63Phe mutation according to SEQ ID NO: 179, and wherein the antibody or antigen-binding fragment includes a) a heavy chain antigen-binding region that comprises an H-CDR1 comprising SEQ ID NO:48, an H-CDR2 comprising SEQ ID NO:49, and an H-CDR3 comprising SEQ ID NO:50 and a light chain antigen-binding region that comprises a L-CDR1 comprising SEQ ID NO:52, a L-CDR2 comprising SEQ ID NO:53, and a L-CDR3 comprising SEQ ID NO:54; or b) a heavy chain antigen-binding region that comprises an H-CDR1 comprising SEQ ID NO:106, an H-CDR2 comprising SEQ ID NO:107, and an H-CDR3 comprising SEQ ID NO:108 and a light chain antigen-binding region that comprises a L-CDR1 comprising SEQ ID NO:110, a L-CDR2 comprising SEQ ID NO:111, and a L-CDR3 comprising SEQ ID NO:112; or c) a heavy chain antigen-binding region that comprises an H-CDR1 comprising SEQ ID NO:4, an H-CDR2 comprising SEQ ID NO:5, and an H-CDR3 comprising SEQ ID NO:6 and a light chain antigen-binding region that comprises a L-CDR1 comprising SEQ ID NO:8, a L-CDR2 comprising SEQ ID NO:9, and a L-CDR3 comprising SEQ ID NO:10; or d) a heavy chain antigen-binding region that comprises an H-CDR1 comprising SEQ ID NO:34, an H-CDR2 comprising SEQ ID NO:35, and an H-CDR3 comprising SEQ ID NO:36 and a light chain antigen-binding region that comprises a L-CDR1 comprising SEQ ID NO:38, a L-CDR2 comprising SEQ ID NO:39, and a L-CDR3 comprising SEQ ID NO:40; or e) a heavy chain antigen-binding region that comprises an H-CDR1 comprising SEQ ID NO:120, an H-CDR2 comprising SEQ ID NO:121, and an H-CDR3 comprising SEQ ID NO:122 and a light chain antigen-binding region that comprises a L-CDR1 comprising SEQ ID NO:124, a L-CDR2 comprising SEQ ID NO:125, and a L-CDR3 comprising SEQ ID NO:126; or f) a heavy chain antigen-binding region that comprises an H-CDR1 comprising SEQ ID NO:24, an H-CDR2 comprising SEQ ID NO:25, and an H-CDR3 comprising SEQ ID NO:26 and a light chain antigen-binding region that comprises a L-CDR1 comprising SEQ ID NO:28, a L-CDR2 comprising SEQ ID NO:29, and a L-CDR3 comprising SEQ ID NO:30; or g) a heavy chain antigen-binding region that comprises an H-CDR1 comprising SEQ ID NO:76, an H-CDR2 comprising SEQ ID NO:77, and an H-CDR3 comprising SEQ ID NO:78 and a light chain antigen-binding region that comprises a L-CDR1 comprising SEQ ID NO:80, a L-CDR2 comprising SEQ ID NO:81, and a L-CDR3 comprising SEQ ID NO:82; or h) a heavy chain antigen-binding region that comprises an H-CDR1 comprising SEQ ID NO:134, an H-CDR2 comprising SEQ ID NO:135, and an H-CDR3 comprising SEQ ID NO:136 and a light chain antigen-binding region that comprises a L-CDR1 comprising SEQ ID NO:138, a L-CDR2 comprising SEQ ID NO:139, and a L-CDR3 comprising SEQ ID NO:140; or i) a heavy chain antigen-binding region that comprises an H-CDR1 comprising SEQ ID NO:148, an H-CDR2 comprising SEQ ID NO:149, and an H-CDR3 comprising SEQ ID NO:150 and a light chain antigen-binding region that comprises a L-CDR1 comprising SEQ ID NO:152, a L-CDR2 comprising SEQ ID NO:153, and a L-CDR3 comprising SEQ ID NO:154; or j) a heavy chain antigen-binding region that comprises an H-CDR1 comprising SEQ ID NO:14, an H-CDR2 comprising SEQ ID NO:15, and an H-CDR3 comprising SEQ ID NO:16 and a light chain antigen-binding region that comprises a L-CDR1 comprising SEQ ID NO:18, a L-CDR2 comprising SEQ ID NO:19, and a L-CDR3 comprising SEQ ID NO:20; or k) a heavy chain antigen-binding region that comprises an H-CDR1 comprising SEQ ID NO:62, an H-CDR2 comprising SEQ ID NO:63, and an H-CDR3 comprising SEQ ID NO:64 and a light chain antigen-binding region that comprises a L-CDR1 comprising SEQ ID NO:66, a L-CDR2 comprising SEQ ID NO:67, and a L-CDR3 comprising SEQ ID NO:68; or l) a heavy chain antigen-binding region that comprises an H-CDR1 comprising SEQ ID NO:92, an H-CDR2 comprising SEQ ID NO:93, and an H-CDR3 comprising SEQ ID NO:94 and a light chain antigen-binding region that comprises a L-CDR1 comprising SEQ ID NO:96, a L-CDR2 comprising SEQ ID NO:97, and a L-CDR3 comprising SEQ ID NO:98.

2. The antibody or antigen-binding fragment according to claim 1, which is an IgG antibody.

3. The antibody or antigen-binding fragment according to claim 1, which is a scFv, Fab, Fab', or F(ab')2 fragment.

4. The antibody or antigen-binding fragment according to claim 1, which is a monoclonal antibody or antigen-binding fragment.

5. The antibody or antigen-binding fragment according to claim 1, which is a human, humanized or chimeric antibody or antigen-binding fragment.

6. An antibody-drug conjugate, comprising an antibody or antigen binding fragment according to claim 1.

7. An isolated nucleic acid that encodes the antibody or antigen-binding fragment according to claim 1.

8. A vector comprising a nucleic acid according to claim 7.

9. An isolated cell expressing an antibody or antigen-binding fragment according to claim 1.

10. An isolated cell according to claim 9, wherein said cell is a prokaryotic or a eukaryotic cell.

11. A method of producing an antibody or antigen-binding fragment thereof specifically binding to human CEACAM6 comprising culturing of a cell according to claim 9 and purifying the antibody or antigen-binding fragment thereof.

12. A pharmaceutical composition comprising an antibody or antigen-binding fragment according to claim 1.

13. A combination of a pharmaceutical composition according to claim 12 and one or more therapeutically active compounds.

14. A method for treating cancer expressing CEACAM6, comprising administering to a subject in need thereof an effective amount of the antibody or antigen-binding fragment according to claim 1.

15. A method for treating cancer expressing CEACAM6, comprising administering to a subject in need thereof an effective amount of the pharmaceutical composition according to claim 12.

16. A method for treating cancer expressing CEACAM6, comprising administering to a subject in need thereof an effective amount of the combination according to claim 13.

17. A pharmaceutical composition comprising an antibody-drug conjugate according to claim 6.

18. A combination of a pharmaceutical composition according to claim 17 and one or more therapeutically active compounds.

19. A method for treating cancer, comprising administering to a subject in need thereof an effective amount of the pharmaceutical composition according to claim 17.

20. A method for treating cancer, comprising administering to a subject in need thereof an effective amount of the combination according to claim 18.

* * * * *

SEQUENCE LISTING

```
<160> NUMBER OF SEQ ID NOS: 186

<210> SEQ ID NO 1
<211> LENGTH: 450
<212> TYPE: PRT
<213> ORGANISM: Artificial Sequence
<220> FEATURE:
<223> OTHER INFORMATION: TPP-1173, h16C3-hIgG1, Heavy Chain

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

-continued

```
Ala Met His Trp Val Arg Gln Ala Pro Gly Gln Arg Leu Glu Trp Met
        35                  40                  45

Gly Leu Ile Ser Thr Tyr Ser Gly Asp Thr Lys Tyr Asn Gln Asn Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
```

450

<210> SEQ ID NO 2
<211> LENGTH: 214
<212> TYPE: PRT
<213> ORGANISM: Artificial Sequence
<220> FEATURE:
<223> OTHER INFORMATION: TPP-1173, h16C3-hIgG1, Light Chain

<400> SEQUENCE: 2

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asn Ile Tyr Gly Ala
20 25 30

Leu Asn Trp Tyr Gln Arg Lys Pro Gly Lys Ser Pro Lys Leu Leu Ile
35 40 45

Tyr Gly Ala Ser Asn Leu Ala Thr Gly Met Pro Ser Arg Phe Ser Gly
50 55 60

Ser Gly Ser Gly Thr Asp Tyr Thr Phe Thr Ile Ser Ser Leu Gln Pro
65 70 75 80

Glu Asp Ile Ala Thr Tyr Tyr Cys Gln Gln Val Leu Ser Ser Pro Tyr
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 3
<211> LENGTH: 118
<212> TYPE: PRT
<213> ORGANISM: Artificial Sequence
<220> FEATURE:
<223> OTHER INFORMATION: TPP-2971, 792.15H12C9, VH

<400> SEQUENCE: 3

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

Gly Ile Gly Val Gly Trp Ile Arg Gln Pro Ser Gly Lys Asp Leu Glu
35 40 45

Trp Leu Ala His Ile Trp Trp Asn Asp Asn Lys Tyr Tyr Asn Thr Ala
50 55 60

Leu Lys Ser Arg Leu Thr Ile Ser Lys Asp Thr Ser Asn Asn Gln Val
65 70 75 80

```
Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115


<210> SEQ ID NO 4
<211> LENGTH: 7
<212> TYPE: PRT
<213> ORGANISM: Artificial Sequence
<220> FEATURE:
<223> OTHER INFORMATION: TPP-2971, 792.15H12C9, HCDR1

<400> SEQUENCE: 4

Thr Tyr Gly Ile Gly Val Gly
1               5


<210> SEQ ID NO 5
<211> LENGTH: 16
<212> TYPE: PRT
<213> ORGANISM: Artificial Sequence
<220> FEATURE:
<223> OTHER INFORMATION: TPP-2971, 792.15H12C9, HCDR2

<400> SEQUENCE: 5

His Ile Trp Trp Asn Asp Asn Lys Tyr Tyr Asn Thr Ala Leu Lys Ser
1               5                   10                  15


<210> SEQ ID NO 6
<211> LENGTH: 8
<212> TYPE: PRT
<213> ORGANISM: Artificial Sequence
<220> FEATURE:
<223> OTHER INFORMATION: TPP-2971, 792.15H12C9, HCDR3

<400> SEQUENCE: 6

Ile Ser Leu Pro Tyr Phe Asp Tyr
1               5


<210> SEQ ID NO 7
<211> LENGTH: 107
<212> TYPE: PRT
<213> ORGANISM: Artificial Sequence
<220> FEATURE:
<223> OTHER INFORMATION: TPP-2971, 792.15H12C9, VL

<400> SEQUENCE: 7

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105
```

<210> SEQ ID NO 8
<211> LENGTH: 11
<212> TYPE: PRT
<213> ORGANISM: Artificial Sequence
<220> FEATURE:
<223> OTHER INFORMATION: TPP-2971, 792.15H12C9, LCDR1

<400> SEQUENCE: 8

Lys Ala Ser Gln Asn Val Gly Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: TPP-2971, 792.15H12C9, LCDR2

<400> SEQUENCE: 9

Ser Ala Ser Asn Arg Tyr Thr
1               5

<210> SEQ ID NO 10
<211> LENGTH: 9
<212> TYPE: PRT
<213> ORGANISM: Artificial Sequence
<220> FEATURE:
<223> OTHER INFORMATION: TPP-2971, 792.15H12C9, LCDR3

<400> SEQUENCE: 10

Gln Gln Tyr Ser Ser Tyr Pro Leu Thr
1               5

<210> SEQ ID NO 11
<211> LENGTH: 129
<212> TYPE: PRT
<213> ORGANISM: Artificial Sequence
<220> FEATURE:
<223> OTHER INFORMATION: TPP-2971, 792.15H12C9, Heavy Chain

<400> SEQUENCE: 11

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Trp Ile Arg Gln Pro Ser Gly Lys Asp Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser Ala Lys Thr Thr Pro Pro Ser Val Tyr Pro
        115                 120                 125

Leu

<210> SEQ ID NO 12
<211> LENGTH: 122
<212> TYPE: PRT

```
<213> ORGANISM: Artificial Sequence
<220> FEATURE:
<223> OTHER INFORMATION: TPP-2971, 792.15H12C9, Light Chain

<400> SEQUENCE: 12

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser
        115                 120


<210> SEQ ID NO 13
<211> LENGTH: 118
<212> TYPE: PRT
<213> ORGANISM: Artificial Sequence
<220> FEATURE:
<223> OTHER INFORMATION: TPP-3186, 792.11G2D10, VH

<400> SEQUENCE: 13

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Cys Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115


<210> SEQ ID NO 14
<211> LENGTH: 7
<212> TYPE: PRT
<213> ORGANISM: Artificial Sequence
<220> FEATURE:
<223> OTHER INFORMATION: TPP-3186, 792.11G2D10, HCDR1

<400> SEQUENCE: 14

Thr Tyr Gly Ile Gly Val Gly
1               5


<210> SEQ ID NO 15
```

<211> LENGTH: 16
<212> TYPE: PRT
<213> ORGANISM: Artificial Sequence
<220> FEATURE:
<223> OTHER INFORMATION: TPP-3186, 792.11G2D10, HCDR2

<400> SEQUENCE: 15

His Ile Trp Trp Asn Asp Asn Lys Tyr Tyr Asn Thr Ala Leu Lys Ser
1 5 10 15

<210> SEQ ID NO 16
<211> LENGTH: 8
<212> TYPE: PRT
<213> ORGANISM: Artificial Sequence
<220> FEATURE:
<223> OTHER INFORMATION: TPP-3186, 792.11G2D10, HCDR3

<400> SEQUENCE: 16

Ile Ser Leu Pro Tyr Phe Asp Tyr
1 5

<210> SEQ ID NO 17
<211> LENGTH: 107
<212> TYPE: PRT
<213> ORGANISM: Artificial Sequence
<220> FEATURE:
<223> OTHER INFORMATION: TPP-3186, 792.11G2D10, VL

<400> SEQUENCE: 17

Asp Ile Val Met Thr Gln Ser Gln Lys Phe Met Ser Thr Ser Val Gly
1 5 10 15

Asp Arg Val Ser Ile Thr Cys Lys Ala Ser Gln Asn Val Gly Thr Ala
20 25 30

Val Ala Trp Tyr Gln Gln Lys Pro Gly Gln Ser Pro Lys Leu Leu Ile
35 40 45

Tyr Ser Ala Ser Asn Arg Tyr Thr Gly Val Pro Asp Arg Phe Thr Gly
50 55 60

Ser Gly Ser Gly Thr Asp Phe Thr Phe Thr Ile Ser Asn Met Gln Ser
65 70 75 80

Glu Asp Leu Ala Asp Tyr Phe Cys Gln Gln Tyr Ser Ser Tyr Pro Leu
85 90 95

Thr Phe Gly Ala Gly Thr Lys Leu Glu Leu Lys
100 105

<210> SEQ ID NO 18
<211> LENGTH: 11
<212> TYPE: PRT
<213> ORGANISM: Artificial Sequence
<220> FEATURE:
<223> OTHER INFORMATION: TPP-3186, 792.11G2D10, LCDR1

<400> SEQUENCE: 18

Lys Ala Ser Gln Asn Val Gly Thr Ala Val Ala
1 5 10

<210> SEQ ID NO 19
<211> LENGTH: 7
<212> TYPE: PRT
<213> ORGANISM: Artificial Sequence
<220> FEATURE:
<223> OTHER INFORMATION: TPP-3186, 792.11G2D10, LCDR2

<400> SEQUENCE: 19

Ser Ala Ser Asn Arg Tyr Thr 1 5

<210> SEQ ID NO 20
<211> LENGTH: 9
<212> TYPE: PRT
<213> ORGANISM: Artificial Sequence
<220> FEATURE:
<223> OTHER INFORMATION: TPP-3186, 792.11G2D10, LCDR3

<400> SEQUENCE: 20

Gln Gln Tyr Ser Ser Tyr Pro Leu Thr
1 5

<210> SEQ ID NO 21
<211> LENGTH: 129
<212> TYPE: PRT
<213> ORGANISM: Artificial Sequence
<220> FEATURE:
<223> OTHER INFORMATION: TPP-3186, 792.11G2D10, Heavy Chain

<400> SEQUENCE: 21

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

Gly Ile Gly Val Gly Cys Ile Arg Gln Pro Ser Gly Lys Gly Leu Glu
35 40 45

Trp Leu Ala His Ile Trp Trp Asn Asp Asn Lys Tyr Tyr Asn Thr Ala
50 55 60

Leu Lys Ser Arg Leu Thr Ile Ser Lys Asp Thr Ser Asn Asn Gln Val
65 70 75 80

Phe Leu Lys Ile Ala Ser Val Asp Thr Ala Asp Thr Ala Thr Tyr Tyr
85 90 95

Cys Ala Arg Ile Ser Leu Pro Tyr Phe Asp Tyr Trp Gly Gln Gly Thr
100 105 110

Thr Leu Thr Val Ser Ser Ala Lys Thr Thr Pro Pro Ser Val Tyr Pro
115 120 125

Leu

<210> SEQ ID NO 22
<211> LENGTH: 122
<212> TYPE: PRT
<213> ORGANISM: Artificial Sequence
<220> FEATURE:
<223> OTHER INFORMATION: TPP-3186, 792.11G2D10, Light Chain

<400> SEQUENCE: 22

Asp Ile Val Met Thr Gln Ser Gln Lys Phe Met Ser Thr Ser Val Gly
1 5 10 15

Asp Arg Val Ser Ile Thr Cys Lys Ala Ser Gln Asn Val Gly Thr Ala
20 25 30

Val Ala Trp Tyr Gln Gln Lys Pro Gly Gln Ser Pro Lys Leu Leu Ile
35 40 45

Tyr Ser Ala Ser Asn Arg Tyr Thr Gly Val Pro Asp Arg Phe Thr Gly
50 55 60

Ser Gly Ser Gly Thr Asp Phe Thr Phe Thr Ile Ser Asn Met Gln Ser
65 70 75 80

Glu Asp Leu Ala Asp Tyr Phe Cys Gln Gln Tyr Ser Ser Tyr Pro Leu
85 90 95

```
Thr Phe Gly Ala Gly Thr Lys Leu Glu Leu Lys Arg Ala Asp Ala Ala
            100                 105                 110

Pro Thr Val Ser Ile Phe Pro Pro Ser Ser
        115                 120


<210> SEQ ID NO 23
<211> LENGTH: 118
<212> TYPE: PRT
<213> ORGANISM: Artificial Sequence
<220> FEATURE:
<223> OTHER INFORMATION: TPP-3187, 792.15C4F4, VH

<400> SEQUENCE: 23

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115


<210> SEQ ID NO 24
<211> LENGTH: 7
<212> TYPE: PRT
<213> ORGANISM: Artificial Sequence
<220> FEATURE:
<223> OTHER INFORMATION: TPP-3187, 792.15C4F4, HCDR1

<400> SEQUENCE: 24

Thr Tyr Gly Ile Gly Val Gly
1               5


<210> SEQ ID NO 25
<211> LENGTH: 16
<212> TYPE: PRT
<213> ORGANISM: Artificial Sequence
<220> FEATURE:
<223> OTHER INFORMATION: TPP-3187, 792.15C4F4, HCDR2

<400> SEQUENCE: 25

His Ile Trp Trp Asn Asp Asn Lys Tyr Tyr Asn Thr Ala Leu Lys Ser
1               5                   10                  15


<210> SEQ ID NO 26
<211> LENGTH: 8
<212> TYPE: PRT
<213> ORGANISM: Artificial Sequence
<220> FEATURE:
<223> OTHER INFORMATION: TPP-3187, 792.15C4F4, HCDR3

<400> SEQUENCE: 26

Ile Ser Leu Pro Tyr Phe Asp Tyr
1               5
```

<210> SEQ ID NO 27
<211> LENGTH: 107
<212> TYPE: PRT
<213> ORGANISM: Artificial Sequence
<220> FEATURE:
<223> OTHER INFORMATION: TPP-3187, 792.15C4F4, VL

<400> SEQUENCE: 27

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys
            100                 105
```

<210> SEQ ID NO 28
<211> LENGTH: 11
<212> TYPE: PRT
<213> ORGANISM: Artificial Sequence
<220> FEATURE:
<223> OTHER INFORMATION: TPP-3187, 792.15C4F4, LCDR1

<400> SEQUENCE: 28

```
Lys Ala Ser Gln Asn Val Gly Thr Ala Val Ala
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: TPP-3187, 792.15C4F4, LCDR2

<400> SEQUENCE: 29

```
Ser Ala Ser Asn Arg Tyr Thr
1               5
```

<210> SEQ ID NO 30
<211> LENGTH: 9
<212> TYPE: PRT
<213> ORGANISM: Artificial Sequence
<220> FEATURE:
<223> OTHER INFORMATION: TPP-3187, 792.15C4F4, LCDR3

<400> SEQUENCE: 30

```
Gln Gln Tyr Asn Asn Tyr Pro Leu Thr
1               5
```

<210> SEQ ID NO 31
<211> LENGTH: 129
<212> TYPE: PRT
<213> ORGANISM: Artificial Sequence
<220> FEATURE:
<223> OTHER INFORMATION: TPP-3187, 792.15C4F4, Heavy Chain

<400> SEQUENCE: 31

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Thr Thr Tyr
20 25 30

Gly Ile Gly Val Gly Trp Ile Arg Gln Pro Ser Gly Lys Gly Leu Glu
35 40 45

Trp Leu Ala His Ile Trp Trp Asn Asp Asn Lys Tyr Tyr Asn Thr Ala
50 55 60

Leu Lys Ser Arg Leu Thr Ile Ser Lys Asp Thr Ser Asn Asn Gln Val
65 70 75 80

Phe Leu Lys Ile Ala Ser Val Asp Thr Ala Asp Thr Ala Thr Tyr Tyr
85 90 95

Cys Ala Arg Ile Ser Leu Pro Tyr Phe Asp Tyr Trp Gly Gln Gly Thr
100 105 110

Thr Leu Thr Val Ser Ser Ala Lys Thr Thr Pro Pro Ser Val Tyr Pro
115 120 125

Leu

<210> SEQ ID NO 32
<211> LENGTH: 122
<212> TYPE: PRT
<213> ORGANISM: Artificial Sequence
<220> FEATURE:
<223> OTHER INFORMATION: TPP-3187, 792.15C4F4, Light Chain

<400> SEQUENCE: 32

Asp Ile Val Met Thr Gln Ser Gln Lys Phe Met Ser Thr Ser Val Gly
1 5 10 15

Asp Arg Val Ser Ile Thr Cys Lys Ala Ser Gln Asn Val Gly Thr Ala
20 25 30

Val Ala Trp Tyr Gln Gln Lys Pro Gly Gln Ser Pro Lys Leu Leu Ile
35 40 45

Tyr Ser Ala Ser Asn Arg Tyr Thr Gly Val Pro Asp Arg Phe Thr Gly
50 55 60

Ser Gly Ser Gly Thr Asp Phe Thr Leu Thr Ile Ser Asn Met Gln Ser
65 70 75 80

Glu Asp Leu Ala Asp Tyr Phe Cys Gln Gln Tyr Asn Asn Tyr Pro Leu
85 90 95

Thr Phe Gly Ala Gly Thr Lys Leu Glu Leu Lys Arg Ala Asp Ala Ala
100 105 110

Pro Thr Val Ser Ile Phe Pro Pro Ser Ser
115 120

<210> SEQ ID NO 33
<211> LENGTH: 118
<212> TYPE: PRT
<213> ORGANISM: Artificial Sequence
<220> FEATURE:
<223> OTHER INFORMATION: TPP-3308, TPP-2971X1-hIgG2Kappa, VH

<400> SEQUENCE: 33

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

Gly Ile Gly Val Gly Trp Ile Arg Gln Pro Ser Gly Lys Asp Leu Glu
35 40 45

```
Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115


<210> SEQ ID NO 34
<211> LENGTH: 7
<212> TYPE: PRT
<213> ORGANISM: Artificial Sequence
<220> FEATURE:
<223> OTHER INFORMATION: TPP-3308, TPP-2971X1-hIgG2Kappa, HCDR1

<400> SEQUENCE: 34

Thr Tyr Gly Ile Gly Val Gly
1               5


<210> SEQ ID NO 35
<211> LENGTH: 16
<212> TYPE: PRT
<213> ORGANISM: Artificial Sequence
<220> FEATURE:
<223> OTHER INFORMATION: TPP-3308, TPP-2971X1-hIgG2Kappa, HCDR2

<400> SEQUENCE: 35

His Ile Trp Trp Asn Asp Asn Lys Tyr Tyr Asn Thr Ala Leu Lys Ser
1               5                   10                  15


<210> SEQ ID NO 36
<211> LENGTH: 8
<212> TYPE: PRT
<213> ORGANISM: Artificial Sequence
<220> FEATURE:
<223> OTHER INFORMATION: TPP-3308, TPP-2971X1-hIgG2Kappa, HCDR3

<400> SEQUENCE: 36

Ile Ser Leu Pro Tyr Phe Asp Tyr
1               5


<210> SEQ ID NO 37
<211> LENGTH: 107
<212> TYPE: PRT
<213> ORGANISM: Artificial Sequence
<220> FEATURE:
<223> OTHER INFORMATION: TPP-3308, TPP-2971X1-hIgG2Kappa, VL

<400> SEQUENCE: 37

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80
```

```
Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105


<210> SEQ ID NO 38
<211> LENGTH: 11
<212> TYPE: PRT
<213> ORGANISM: Artificial Sequence
<220> FEATURE:
<223> OTHER INFORMATION: TPP-3308, TPP-2971X1-hIgG2Kappa, LCDR1

<400> SEQUENCE: 38

Lys Ala Ser Gln Asn Val Gly Thr Ala Val Ala
1               5                   10


<210> SEQ ID NO 39
<211> LENGTH: 7
<212> TYPE: PRT
<213> ORGANISM: Artificial Sequence
<220> FEATURE:
<223> OTHER INFORMATION: TPP-3308, TPP-2971X1-hIgG2Kappa, LCDR2

<400> SEQUENCE: 39

Ser Ala Ser Asn Arg Tyr Thr
1               5


<210> SEQ ID NO 40
<211> LENGTH: 9
<212> TYPE: PRT
<213> ORGANISM: Artificial Sequence
<220> FEATURE:
<223> OTHER INFORMATION: TPP-3308, TPP-2971X1-hIgG2Kappa, LCDR3

<400> SEQUENCE: 40

Gln Gln Tyr Ser Ser Tyr Pro Leu Thr
1               5


<210> SEQ ID NO 41
<211> LENGTH: 354
<212> TYPE: DNA
<213> ORGANISM: Artificial Sequence
<220> FEATURE:
<223> OTHER INFORMATION: TPP-3308, TPP-2971X1-hIgG2Kappa, VH

<400> SEQUENCE: 41

caggtcacac tgaaagagag cggccctggc atcctgcagc ccagccagac cctgagcctg     60

acctgcagct tcagcggctt cagcctgagc acctacggca tcggcgtggg ctggatcaga    120

cagcccagcg gcaaggacct ggaatggctg gcccacatct ggtggaacga caacaagtac    180

tacaacaccg ccctgaagtc ccggctgacc atcagcaagg acaccagcaa caaccaggtg    240

ttcctgaaga tcgccagcgt ggacaccgcc gataccgcca cctactactg cgcccggatc    300

agcctgccct acttcgacta ctggggccag ggcaccaccc tgaccgtgtc ctca          354


<210> SEQ ID NO 42
<211> LENGTH: 321
<212> TYPE: DNA
<213> ORGANISM: Artificial Sequence
<220> FEATURE:
<223> OTHER INFORMATION: TPP-3308, TPP-2971X1-hIgG2Kappa, VL

<400> SEQUENCE: 42

gacatcgtga tgacccagag ccagaaattc atgagcacca gcgtgggcga ccgggtgtcc     60
```

```
atcacatgca aggccagcca gaacgtgggc accgccgtgg cctggtatca gcagaagccc    120

ggccagagcc ccaagctgct gatctacagc gccagcaacc ggtacaccgg cgtgcccgac    180

agattcacag gcagcggcag cggcaccgac ttcaccctga ccatcagcaa catgcagagc    240

gaggacctgg ccgactactt ctgccagcag tacagcagct accccctgac cttcggagcc    300

ggcaccaagc tggaactgaa a                                               321


<210> SEQ ID NO 43
<211> LENGTH: 443
<212> TYPE: PRT
<213> ORGANISM: Artificial Sequence
<220> FEATURE:
<223> OTHER INFORMATION: TPP-3308, TPP-2971X1-hIgG2Kappa, Heavy Chain

<400> SEQUENCE: 43

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Trp Ile Arg Gln Pro Ser Gly Lys Asp Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
```

```
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 44
<211> LENGTH: 214
<212> TYPE: PRT
<213> ORGANISM: Artificial Sequence
<220> FEATURE:
<223> OTHER INFORMATION: TPP-3308, TPP-2971X1-hIgG2Kappa, Light Chain

<400> SEQUENCE: 44

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 45
<211> LENGTH: 1329
<212> TYPE: DNA
<213> ORGANISM: Artificial Sequence
<220> FEATURE:
<223> OTHER INFORMATION: TPP-3308, TPP-2971X1-hIgG2Kappa, Heavy Chain

<400> SEQUENCE: 45
caggtcacac tgaaagagag cggccctggc atcctgcagc ccagccagac cctgagcctg 60
acctgcagct tcagcggctt cagcctgagc acctacggca tcggcgtggg ctggatcaga 120
cagcccagcg gcaaggacct ggaatggctg gcccacatct ggtggaacga caacaagtac 180
tacaacaccg ccctgaagtc ccggctgacc atcagcaagg acaccagcaa caaccaggtg 240
ttcctgaaga tcgccagcgt ggacaccgcc gataccgcca cctactactg cgcccggatc 300
agcctgccct acttcgacta ctggggccag ggcaccaccc tgaccgtgtc ctcagccagc 360
accaagggcc ccagcgtgtt ccctctggcc ccttgtagca gaagcaccag cgagtctaca 420
gccgccctgg gctgcctcgt gaaggactac tttcccgagc ccgtgaccgt gtcctggaac 480
tctggcgctc tgacaagcgg cgtgcacacc tttccagccg tgctgcagag cagcggcctg 540
tactctctga gcagcgtcgt gacagtgccc agcagcaact tcggcaccca gacctacacc 600
tgtaacgtgg accacaagcc cagcaacacc aaggtggaca agaccgtgga acggaagtgc 660
tgcgtggaat gccccccttg tcctgcccct ccagtggctg gcccttccgt gttcctgttc 720
cccccaaagc ccaaggacac cctgatgatc agccggaccc ccgaagtgac ctgcgtggtg 780
gtggatgtgt cccacgagga ccccgaggtg cagttcaatt ggtacgtgga cggcgtggaa 840
gtgcacaacg ccaagaccaa gcccagagag gaacagttca acagcacctt ccgggtggtg 900
tccgtgctga ccgtggtgca tcaggactgg ctgaacggca aagagtacaa gtgcaaggtg 960
tccaacaagg gcctgcctgc ccccatcgag aaaaccatca gcaagaccaa aggccagccc 1020
cgcgagcccc aggtgtacac actgcctcca agccgggaag agatgaccaa gaaccaggtg 1080
tccctgacct gtctcgtgaa aggcttctac ccctccgata tcgccgtgga atgggagagc 1140
aacggccagc ccgagaacaa ctacaagacc acccccccca tgctggacag cgacggctca 1200
ttcttcctgt acagcaagct gacagtggac aagtcccggt ggcagcaggg caacgtgttc 1260
agctgcagcg tgatgcacga ggccctgcac aaccactaca cccagaagtc cctgagcctg 1320
agccctggc 1329

<210> SEQ ID NO 46
<211> LENGTH: 642
<212> TYPE: DNA
<213> ORGANISM: Artificial Sequence
<220> FEATURE:
<223> OTHER INFORMATION: TPP-3308, TPP-2971X1-hIgG2Kappa, Light Chain

<400> SEQUENCE: 46
gacatcgtga tgacccagag ccagaaattc atgagcacca gcgtgggcga ccgggtgtcc 60
atcacatgca aggccagcca gaacgtgggc accgccgtgg cctggtatca gcagaagccc 120
ggccagagcc ccaagctgct gatctacagc gccagcaacc ggtacaccgg cgtgcccgac 180
agattcacag gcagcggcag cggcaccgac ttcaccctga ccatcagcaa catgcagagc 240
gaggacctgg ccgactactt ctgccagcag tacagcagct accccctgac cttcggagcc 300
ggcaccaagc tggaactgaa acgaaccgtg gccgctccca gcgtgttcat cttcccacct 360
agcgacgagc agctgaagtc cggcacagcc tctgtcgtgt gcctgctgaa caacttctac 420

```
ccccgcgagg ccaaggtgca gtggaaggtg gacaatgccc tgcagagcgg caacagccag    480

gaaagcgtga ccgagcagga cagcaaggac tccacctaca gcctgagcag caccctgacc    540

ctgagcaagg ccgactacga gaagcacaag gtgtacgcct gcgaagtgac ccaccagggc    600

ctgtctagcc ccgtgaccaa gagcttcaac cggggcgagt gt                        642


<210> SEQ ID NO 47
<211> LENGTH: 118
<212> TYPE: PRT
<213> ORGANISM: Artificial Sequence
<220> FEATURE:
<223> OTHER INFORMATION: TPP-3310, TPP-2971HU1-hIgG2Kappa, VH

<400> SEQUENCE: 47

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Ile Gly Val Gly Trp Ile Arg Gln Pro Pro Gly Lys Ala Leu Glu
        35                  40                  45

Trp Leu Ala His Ile Trp Trp Asn Asp Asn Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115


<210> SEQ ID NO 48
<211> LENGTH: 7
<212> TYPE: PRT
<213> ORGANISM: Artificial Sequence
<220> FEATURE:
<223> OTHER INFORMATION: TPP-3310, TPP-2971HU1-hIgG2Kappa, HCDR1

<400> SEQUENCE: 48

Thr Tyr Gly Ile Gly Val Gly
1               5


<210> SEQ ID NO 49
<211> LENGTH: 16
<212> TYPE: PRT
<213> ORGANISM: Artificial Sequence
<220> FEATURE:
<223> OTHER INFORMATION: TPP-3310, TPP-2971HU1-hIgG2Kappa, HCDR2

<400> SEQUENCE: 49

His Ile Trp Trp Asn Asp Asn Lys Tyr Tyr Ser Thr Ser Leu Lys Thr
1               5                   10                  15


<210> SEQ ID NO 50
<211> LENGTH: 8
<212> TYPE: PRT
<213> ORGANISM: Artificial Sequence
<220> FEATURE:
<223> OTHER INFORMATION: TPP-3310, TPP-2971HU1-hIgG2Kappa, HCDR3

<400> SEQUENCE: 50

Ile Ser Leu Pro Tyr Phe Asp Tyr
```

1 5

<210> SEQ ID NO 51
<211> LENGTH: 107
<212> TYPE: PRT
<213> ORGANISM: Artificial Sequence
<220> FEATURE:
<223> OTHER INFORMATION: TPP-3310, TPP-2971HU1-hIgG2Kappa, VL

<400> SEQUENCE: 51

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Gly Thr Ala
20 25 30

Val Ala Trp Tyr Gln Gln Lys Pro Gly Lys Ala Pro Lys Leu Leu Ile
35 40 45

Tyr Ser Ala Ser Asn Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Ser Ser Tyr Pro Leu
85 90 95

Thr Phe Gly Gly Gly Thr Lys Val Glu Ile Lys
100 105

<210> SEQ ID NO 52
<211> LENGTH: 11
<212> TYPE: PRT
<213> ORGANISM: Artificial Sequence
<220> FEATURE:
<223> OTHER INFORMATION: TPP-3310, TPP-2971HU1-hIgG2Kappa, LCDR1

<400> SEQUENCE: 52

Lys Ala Ser Gln Asn Val Gly Thr Ala Val Ala
1 5 10

<210> SEQ ID NO 53
<211> LENGTH: 7
<212> TYPE: PRT
<213> ORGANISM: Artificial Sequence
<220> FEATURE:
<223> OTHER INFORMATION: TPP-3310, TPP-2971HU1-hIgG2Kappa, LCDR2

<400> SEQUENCE: 53

Ser Ala Ser Asn Arg Tyr Thr
1 5

<210> SEQ ID NO 54
<211> LENGTH: 9
<212> TYPE: PRT
<213> ORGANISM: Artificial Sequence
<220> FEATURE:
<223> OTHER INFORMATION: TPP-3310, TPP-2971HU1-hIgG2Kappa, LCDR3

<400> SEQUENCE: 54

Gln Gln Tyr Ser Ser Tyr Pro Leu Thr
1 5

<210> SEQ ID NO 55
<211> LENGTH: 354
<212> TYPE: DNA
<213> ORGANISM: Artificial Sequence
<220> FEATURE:
<223> OTHER INFORMATION: TPP-3310, TPP-2971HU1-hIgG2Kappa, VH

<400> SEQUENCE: 55
caagtgaccc tgagagagtc cggccctgcc ctcgtgaagc ctacccagac cctgacactg 60
acctgcacct tctccggctt ctccctgtcc acctacggca tcggcgtggg ctggatcaga 120
cagcctcctg gcaaggccct ggaatggctg gctcacatct ggtggaacga caacaagtac 180
tactccacct ccctgaaaac ccggctgacc atctccaagg acacctccaa gaaccaggtg 240
gtgctgacca tgaccaacat ggaccccgtg gacaccgcca cctactactg cgccagaatc 300
tccctgccct acttcgacta ctggggccag ggcaccacac tgaccgtcag ctca 354

<210> SEQ ID NO 56
<211> LENGTH: 321
<212> TYPE: DNA
<213> ORGANISM: Artificial Sequence
<220> FEATURE:
<223> OTHER INFORMATION: TPP-3310, TPP-2971HU1-hIgG2Kappa, VL

<400> SEQUENCE: 56
gatatccagc tgacccagtc ccccagcttc ctgtctgcct ctgtgggcga cagagtgacc 60
atcacatgca aggcctccca gaacgtgggc accgccgtgg cttggtatca gcagaagcct 120
ggcaaggccc ccaagctgct gatctactcc gcctccaacc ggtacaccgg cgtgccctct 180
agattctccg gctctggctc tggcaccgag tttaccctga ccatctccag cctgcagccc 240
gaggacttcg ccacctacta ctgccagcag tactcctcct accccctgac ctttggcgga 300
ggcaccaagg tggaaatcaa g 321

<210> SEQ ID NO 57
<211> LENGTH: 443
<212> TYPE: PRT
<213> ORGANISM: Artificial Sequence
<220> FEATURE:
<223> OTHER INFORMATION: TPP-3310, TPP-2971HU1-hIgG2Kappa, Heavy Chain

<400> SEQUENCE: 57

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Tyr
20 25 30

Gly Ile Gly Val Gly Trp Ile Arg Gln Pro Pro Gly Lys Ala Leu Glu
35 40 45

Trp Leu Ala His Ile Trp Trp Asn Asp Asn Lys Tyr Tyr Ser Thr Ser
50 55 60

Leu Lys Thr Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Ile Ser Leu Pro Tyr Phe Asp Tyr Trp Gly Gln Gly Thr
100 105 110

Thr Leu Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

```
Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 58
<211> LENGTH: 214
<212> TYPE: PRT
<213> ORGANISM: Artificial Sequence
<220> FEATURE:
<223> OTHER INFORMATION: TPP-3310, TPP-2971HU1-hIgG2Kappa, Light Chain

<400> SEQUENCE: 58

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 59
<211> LENGTH: 1329
<212> TYPE: DNA
<213> ORGANISM: Artificial Sequence
<220> FEATURE:
<223> OTHER INFORMATION: TPP-3310, TPP-2971HU1-hIgG2Kappa, Heavy Chain

<400> SEQUENCE: 59

caagtgaccc tgagagagtc cggccctgcc ctcgtgaagc ctacccagac cctgacactg     60

acctgcacct tctccggctt ctccctgtcc acctacggca tcggcgtggg ctggatcaga    120

cagcctcctg gcaaggccct ggaatggctg gctcacatct ggtggaacga caacaagtac    180

tactccacct ccctgaaaac ccggctgacc atctccaagg acacctccaa gaaccaggtg    240

gtgctgacca tgaccaacat ggaccccgtg gacaccgcca cctactactg cgccagaatc    300

tccctgccct acttcgacta ctggggccag ggcaccacac tgaccgtcag ctcagcttcc    360

accaagggcc cctccgtgtt ccctctggcc ccttgctccc ggtccacctc tgagtctacc    420

gccgctctgg gctgcctggt gaaagactac ttccccgagc ccgtgaccgt gtcctggaac    480

tctggcgccc tgacctccgg cgtgcacacc tttccagccg tgctgcagtc ctccggcctg    540

tactccctgt cctccgtggt gacagtgccc tcctccaact tcggcaccca gacctacacc    600

tgtaacgtgg accacaagcc ctccaacacc aaggtggaca agaccgtgga acggaagtgc    660

tgcgtggaat gcccaccctg tcctgctcca cctgtggctg gccccagcgt gttcctgttc    720

cccccaaagc ccaaggacac cctgatgatc tcccggaccc ccgaagtgac ctgcgtggtg    780

gtggacgtgt cccacgagga ccccgaggtg cagttcaatt ggtacgtgga cggcgtggaa    840

gtgcacaacg ccaagaccaa gcccagagag gaacagttca actccacctt ccgggtggtg    900

tccgtgctga ccgtggtgca tcaggactgg ctgaacggca aagagtacaa gtgcaaggtc    960

tccaacaagg gcctgcctgc ccccatcgaa aagaccatca gcaagaccaa gggccagccc   1020

cgcgagcccc aggtgtacac actgcccccc agccgggaag agatgaccaa gaaccaggtg   1080

tccctgacct gtctggtgaa aggcttctac ccctccgaca ttgccgtgga atgggagtcc   1140

aacggacagc ctgagaacaa ctacaagacc accccccccca tgctggactc cgacggctca   1200

ttcttcctgt actccaagct gacagtggac aagtcccggt ggcagcaggg caacgtgttc   1260

tcctgctccg tgatgcacga ggccctgcac aaccactaca cccagaagtc cctgtccctg   1320
```

```
agccccggc                                                          1329


<210> SEQ ID NO 60
<211> LENGTH: 642
<212> TYPE: DNA
<213> ORGANISM: Artificial Sequence
<220> FEATURE:
<223> OTHER INFORMATION: TPP-3310, TPP-2971HU1-hIgG2Kappa, Light Chain

<400> SEQUENCE: 60

gatatccagc tgacccagtc ccccagcttc ctgtctgcct ctgtgggcga cagagtgacc     60

atcacatgca aggcctccca gaacgtgggc accgccgtgg cttggtatca gcagaagcct    120

ggcaaggccc ccaagctgct gatctactcc gcctccaacc ggtacaccgg cgtgccctct    180

agattctccg gctctggctc tggcaccgag tttaccctga ccatctccag cctgcagccc    240

gaggacttcg ccacctacta ctgccagcag tactcctcct accccctgac ctttggcgga    300

ggcaccaagg tggaaatcaa gcggaccgtg gccgctccct ccgtgtttat cttcccaccc    360

tccgacgagc agctgaagtc cggcacagct tccgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642


<210> SEQ ID NO 61
<211> LENGTH: 118
<212> TYPE: PRT
<213> ORGANISM: Artificial Sequence
<220> FEATURE:
<223> OTHER INFORMATION: TPP-3322, TPP-3186X1-hIgG2, VH

<400> SEQUENCE: 61

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Cys Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115


<210> SEQ ID NO 62
<211> LENGTH: 7
<212> TYPE: PRT
<213> ORGANISM: Artificial Sequence
<220> FEATURE:
<223> OTHER INFORMATION: TPP-3322, TPP-3186X1-hIgG2, HCDR1

<400> SEQUENCE: 62

Thr Tyr Gly Ile Gly Val Gly
```

1 5

<210> SEQ ID NO 63
<211> LENGTH: 16
<212> TYPE: PRT
<213> ORGANISM: Artificial Sequence
<220> FEATURE:
<223> OTHER INFORMATION: TPP-3322, TPP-3186X1-hIgG2, HCDR2

<400> SEQUENCE: 63

His Ile Trp Trp Asn Asp Asn Lys Tyr Tyr Asn Thr Ala Leu Lys Ser
1 5 10 15

<210> SEQ ID NO 64
<211> LENGTH: 8
<212> TYPE: PRT
<213> ORGANISM: Artificial Sequence
<220> FEATURE:
<223> OTHER INFORMATION: TPP-3322, TPP-3186X1-hIgG2, HCDR3

<400> SEQUENCE: 64

Ile Ser Leu Pro Tyr Phe Asp Tyr
1 5

<210> SEQ ID NO 65
<211> LENGTH: 107
<212> TYPE: PRT
<213> ORGANISM: Artificial Sequence
<220> FEATURE:
<223> OTHER INFORMATION: TPP-3322, TPP-3186X1-hIgG2, VL

<400> SEQUENCE: 65

Asp Ile Val Met Thr Gln Ser Gln Lys Phe Met Ser Thr Ser Val Gly
1 5 10 15

Asp Arg Val Ser Ile Thr Cys Lys Ala Ser Gln Asn Val Gly Thr Ala
20 25 30

Val Ala Trp Tyr Gln Gln Lys Pro Gly Gln Ser Pro Lys Leu Leu Ile
35 40 45

Tyr Ser Ala Ser Asn Arg Tyr Thr Gly Val Pro Asp Arg Phe Thr Gly
50 55 60

Ser Gly Ser Gly Thr Asp Phe Thr Phe Thr Ile Ser Asn Met Gln Ser
65 70 75 80

Glu Asp Leu Ala Asp Tyr Phe Cys Gln Gln Tyr Ser Ser Tyr Pro Leu
85 90 95

Thr Phe Gly Ala Gly Thr Lys Leu Glu Leu Lys
100 105

<210> SEQ ID NO 66
<211> LENGTH: 11
<212> TYPE: PRT
<213> ORGANISM: Artificial Sequence
<220> FEATURE:
<223> OTHER INFORMATION: TPP-3322, TPP-3186X1-hIgG2, LCDR1

<400> SEQUENCE: 66

Lys Ala Ser Gln Asn Val Gly Thr Ala Val Ala
1 5 10

<210> SEQ ID NO 67
<211> LENGTH: 7
<212> TYPE: PRT
<213> ORGANISM: Artificial Sequence
<220> FEATURE:
<223> OTHER INFORMATION: TPP-3322, TPP-3186X1-hIgG2, LCDR2

<400> SEQUENCE: 67

Ser Ala Ser Asn Arg Tyr Thr
1 5

<210> SEQ ID NO 68
<211> LENGTH: 9
<212> TYPE: PRT
<213> ORGANISM: Artificial Sequence
<220> FEATURE:
<223> OTHER INFORMATION: TPP-3322, TPP-3186X1-hIgG2, LCDR3

<400> SEQUENCE: 68

Gln Gln Tyr Ser Ser Tyr Pro Leu Thr
1 5

<210> SEQ ID NO 69
<211> LENGTH: 354
<212> TYPE: DNA
<213> ORGANISM: Artificial Sequence
<220> FEATURE:
<223> OTHER INFORMATION: TPP-3322, TPP-3186X1-hIgG2, VH

<400> SEQUENCE: 69
caggtcacac tgaaagagag cggccctggc atcctgcagc ccagccagac cctgagcctg 60
acctgcagct tcagcggctt cagcctgagc acctacggca tcggcgtggg ctgcatcaga 120
cagcccagcg gcaagggcct ggaatggctg gcccacatct ggtggaacga caacaagtac 180
tacaacaccg ccctgaagtc ccggctgacc atcagcaagg acaccagcaa caaccaggtg 240
ttcctgaaga tcgccagcgt ggacaccgcc gataccgcca cctactactg cgcccggatc 300
agcctgccct acttcgacta ctggggccag ggcaccaccc tgaccgtgtc ctca 354

<210> SEQ ID NO 70
<211> LENGTH: 321
<212> TYPE: DNA
<213> ORGANISM: Artificial Sequence
<220> FEATURE:
<223> OTHER INFORMATION: TPP-3322, TPP-3186X1-hIgG2, VL

<400> SEQUENCE: 70
gacatcgtga tgacccagag ccagaaattc atgagcacca gcgtgggcga ccgggtgtcc 60
atcacatgca aggccagcca gaacgtgggc accgccgtgg cctggtatca gcagaagccc 120
ggccagagcc ccaagctgct gatctacagc gccagcaacc ggtacaccgg cgtgcccgac 180
agattcacag gcagcggcag cggcaccgac ttcaccttca ccatcagcaa catgcagagc 240
gaggacctgg ccgactactt ctgccagcag tacagcagct accccctgac cttcggagcc 300
ggcaccaagc tggaactgaa a 321

<210> SEQ ID NO 71
<211> LENGTH: 443
<212> TYPE: PRT
<213> ORGANISM: Artificial Sequence
<220> FEATURE:
<223> OTHER INFORMATION: TPP-3322, TPP-3186X1-hIgG2, Heavy Chain

<400> SEQUENCE: 71

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

-continued

```
Gly Ile Gly Val Gly Cys Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440
```

<210> SEQ ID NO 72
<211> LENGTH: 214
<212> TYPE: PRT
<213> ORGANISM: Artificial Sequence
<220> FEATURE:
<223> OTHER INFORMATION: TPP-3322, TPP-3186X1-hIgG2, Light Chain

<400> SEQUENCE: 72

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Phe Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 73
<211> LENGTH: 1329
<212> TYPE: DNA
<213> ORGANISM: Artificial Sequence
<220> FEATURE:
<223> OTHER INFORMATION: TPP-3322, TPP-3186X1-hIgG2, Heavy Chain

<400> SEQUENCE: 73

```
caggtcacac tgaaagagag cggccctggc atcctgcagc ccagccagac cctgagcctg      60

acctgcagct tcagcggctt cagcctgagc acctacggca tcggcgtggg ctgcatcaga     120

cagcccagcg gcaagggcct ggaatggctg gcccacatct ggtggaacga caacaagtac     180

tacaacaccg ccctgaagtc ccggctgacc atcagcaagg acaccagcaa caaccaggtg     240

ttcctgaaga tcgccagcgt ggacaccgcc gataccgcca cctactactg cgcccggatc     300

agcctgccct acttcgacta ctggggccag ggcaccaccc tgaccgtgtc ctcagccagc     360

accaagggcc ccagcgtgtt ccctctggcc ccttgtagca gaagcaccag cgagtctaca     420

gccgccctgg gctgcctcgt gaaggactac tttcccgagc ccgtgaccgt gtcctggaac     480

tctggcgctc tgacaagcgg cgtgcacacc tttccagccg tgctgcagag cagcggcctg     540
```

-continued

```
tactctctga gcagcgtcgt gacagtgccc agcagcaact tcggcaccca gacctacacc    600

tgtaacgtgg accacaagcc cagcaacacc aaggtggaca agaccgtgga acggaagtgc    660

tgcgtggaat gccccccttg tcctgcccct ccagtggctg gcccttccgt gttcctgttc    720

cccccaaagc ccaaggacac cctgatgatc agccggaccc ccgaagtgac ctgcgtggtg    780

gtggatgtgt cccacgagga ccccgaggtg cagttcaatt ggtacgtgga cggcgtggaa    840

gtgcacaacg ccaagaccaa gcccagagag gaacagttca acagcacctt ccgggtggtg    900

tccgtgctga ccgtggtgca tcaggactgg ctgaacggca aagagtacaa gtgcaaggtg    960

tccaacaagg gcctgcctgc ccccatcgag aaaaccatca gcaagaccaa aggccagccc   1020

cgcgagcccc aggtgtacac actgcctcca agccgggaag agatgaccaa gaaccaggtg   1080

tccctgacct gtctcgtgaa aggcttctac cctccgata tcgccgtgga atgggagagc   1140

aacggccagc ccgagaacaa ctacaagacc acccccccca tgctggacag cgacggctca   1200

ttcttcctgt acagcaagct gacagtggac aagtcccggt ggcagcaggg caacgtgttc   1260

agctgcagcg tgatgcacga ggccctgcac aaccactaca cccagaagtc cctgagcctg   1320

agccctggc                                                           1329
```

<210> SEQ ID NO 74
<211> LENGTH: 642
<212> TYPE: DNA
<213> ORGANISM: Artificial Sequence
<220> FEATURE:
<223> OTHER INFORMATION: TPP-3322, TPP-3186X1-hIgG2, Light Chain

<400> SEQUENCE: 74

```
gacatcgtga tgacccagag ccagaaattc atgagcacca gcgtgggcga ccgggtgtcc     60

atcacatgca aggccagcca gaacgtgggc accgccgtgg cctggtatca gcagaagccc    120

ggccagagcc ccaagctgct gatctacagc gccagcaacc ggtacaccgg cgtgcccgac    180

agattcacag gcagcggcag cggcaccgac ttcaccttca ccatcagcaa catgcagagc    240

gaggacctgg ccgactactt ctgccagcag tacagcagct accccctgac cttcggagcc    300

ggcaccaagc tggaactgaa acgaaccgtg gccgctccca gcgtgttcat cttcccacct    360

agcgacgagc agctgaagtc cggcacagcc tctgtcgtgt gcctgctgaa caacttctac    420

ccccgcgagg ccaaggtgca gtggaaggtg gacaatgccc tgcagagcgg caacagccag    480

gaaagcgtga ccgagcagga cagcaaggac tccacctaca gcctgagcag caccctgacc    540

ctgagcaagg ccgactacga gaagcacaag gtgtacgcct gcgaagtgac ccaccagggc    600

ctgtctagcc ccgtgaccaa gagcttcaac cggggcgagt gt                       642
```

<210> SEQ ID NO 75
<211> LENGTH: 118
<212> TYPE: PRT
<213> ORGANISM: Artificial Sequence
<220> FEATURE:
<223> OTHER INFORMATION: TPP-3323, TPP-3187X1-hIgG2, VH

<400> SEQUENCE: 75

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Ile Gly Val Gly Trp Ile Arg Gln Pro Ser Gly Lys Gly Leu Glu
        35                  40                  45
```

-continued

```
Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser
        115


<210> SEQ ID NO 76
<211> LENGTH: 7
<212> TYPE: PRT
<213> ORGANISM: Artificial Sequence
<220> FEATURE:
<223> OTHER INFORMATION: TPP-3323, TPP-3187X1-hIgG2, HCDR1

<400> SEQUENCE: 76

Thr Tyr Gly Ile Gly Val Gly
1               5


<210> SEQ ID NO 77
<211> LENGTH: 16
<212> TYPE: PRT
<213> ORGANISM: Artificial Sequence
<220> FEATURE:
<223> OTHER INFORMATION: TPP-3323, TPP-3187X1-hIgG2, HCDR2

<400> SEQUENCE: 77

His Ile Trp Trp Asn Asp Asn Lys Tyr Tyr Asn Thr Ala Leu Lys Ser
1               5                   10                  15


<210> SEQ ID NO 78
<211> LENGTH: 8
<212> TYPE: PRT
<213> ORGANISM: Artificial Sequence
<220> FEATURE:
<223> OTHER INFORMATION: TPP-3323, TPP-3187X1-hIgG2, HCDR3

<400> SEQUENCE: 78

Ile Ser Leu Pro Tyr Phe Asp Tyr
1               5


<210> SEQ ID NO 79
<211> LENGTH: 107
<212> TYPE: PRT
<213> ORGANISM: Artificial Sequence
<220> FEATURE:
<223> OTHER INFORMATION: TPP-3323, TPP-3187X1-hIgG2, VL

<400> SEQUENCE: 79

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80
```

Glu Asp Leu Ala Asp Tyr Phe Cys Gln Gln Tyr Asn Asn Tyr Pro Leu
85 90 95

Thr Phe Gly Ala Gly Thr Lys Leu Glu Leu Lys
100 105

<210> SEQ ID NO 80
<211> LENGTH: 11
<212> TYPE: PRT
<213> ORGANISM: Artificial Sequence
<220> FEATURE:
<223> OTHER INFORMATION: TPP-3323, TPP-3187X1-hIgG2, LCDR1

<400> SEQUENCE: 80

Lys Ala Ser Gln Asn Val Gly Thr Ala Val Ala
1 5 10

<210> SEQ ID NO 81
<211> LENGTH: 7
<212> TYPE: PRT
<213> ORGANISM: Artificial Sequence
<220> FEATURE:
<223> OTHER INFORMATION: TPP-3323, TPP-3187X1-hIgG2, LCDR2

<400> SEQUENCE: 81

Ser Ala Ser Asn Arg Tyr Thr
1 5

<210> SEQ ID NO 82
<211> LENGTH: 9
<212> TYPE: PRT
<213> ORGANISM: Artificial Sequence
<220> FEATURE:
<223> OTHER INFORMATION: TPP-3323, TPP-3187X1-hIgG2, LCDR3

<400> SEQUENCE: 82

Gln Gln Tyr Asn Asn Tyr Pro Leu Thr
1 5

<210> SEQ ID NO 83
<211> LENGTH: 354
<212> TYPE: DNA
<213> ORGANISM: Artificial Sequence
<220> FEATURE:
<223> OTHER INFORMATION: TPP-3323, TPP-3187X1-hIgG2, VH

<400> SEQUENCE: 83
caagtgaccc tgaaagagtc cggccctggc atcctgcagc cttcccagac cctgtccctg 60
acctgctcct tctccggctt ctccctgacc acctacggca tcggcgtggg ctggatcaga 120
cagccttctg gcaagggcct ggaatggctg gcccacatct ggtggaacga caacaagtac 180
tacaacaccg ccctgaagtc ccggctgacc atctccaagg acacctccaa caaccaggtg 240
ttcctgaaga tcgcctccgt ggacaccgcc gataccgcca cctactactg cgcccggatc 300
tccctgccct acttcgacta ttggggccag ggcaccaccc tgaccgtcag ctca 354

<210> SEQ ID NO 84
<211> LENGTH: 321
<212> TYPE: DNA
<213> ORGANISM: Artificial Sequence
<220> FEATURE:
<223> OTHER INFORMATION: TPP-3323, TPP-3187X1-hIgG2, VL

<400> SEQUENCE: 84
gacatcgtga tgacccagtc ccagaaattc atgtccacct ccgtgggcga ccgggtgtcc 60

-continued

```
atcacatgca aggcctctca gaacgtgggc accgccgtgg cctggtatca gcagaagcct    120

ggccagtccc ccaagctgct gatctactcc gcctccaacc ggtacaccgg cgtgcccgat    180

agattcaccg gctctggctc tggcaccgac ttcaccctga ccatctccaa catgcagtcc    240

gaggacctgg ccgactactt ctgccagcag tacaacaact accccctgac cttcggcgct    300

ggcaccaagc tggaactgaa g                                              321
```

```
<210> SEQ ID NO 85
<211> LENGTH: 443
<212> TYPE: PRT
<213> ORGANISM: Artificial Sequence
<220> FEATURE:
<223> OTHER INFORMATION: TPP-3323, TPP-3187X1-hIgG2, Heavy Chain

<400> SEQUENCE: 85

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320
```

```
Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 86
<211> LENGTH: 214
<212> TYPE: PRT
<213> ORGANISM: Artificial Sequence
<220> FEATURE:
<223> OTHER INFORMATION: TPP-3323, TPP-3187X1-hIgG2, Light Chain

<400> SEQUENCE: 86

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 87
```

<211> LENGTH: 1329
<212> TYPE: DNA
<213> ORGANISM: Artificial Sequence
<220> FEATURE:
<223> OTHER INFORMATION: TPP-3323, TPP-3187X1-hIgG2, Heavy Chain

<400> SEQUENCE: 87
caagtgaccc tgaaagagtc cggccctggc atcctgcagc cttcccagac cctgtccctg 60
acctgctcct tctccggctt ctccctgacc acctacggca tcggcgtggg ctggatcaga 120
cagccttctg gcaagggcct ggaatggctg gcccacatct ggtggaacga caacaagtac 180
tacaacaccg ccctgaagtc ccggctgacc atctccaagg acacctccaa caaccaggtg 240
ttcctgaaga tcgcctccgt ggacaccgcc gataccgcca cctactactg cgcccggatc 300
tccctgccct acttcgacta ttggggccag ggcaccaccc tgaccgtcag ctcagcttcc 360
accaagggcc cctccgtgtt ccctctggcc ccttgctccc ggtccacctc tgagtctacc 420
gccgctctgg gctgcctggt gaaagactac ttccccgagc ccgtgaccgt gtcctggaac 480
tctggcgccc tgacctccgg cgtgcacacc tttccagccg tgctgcagtc ctccggcctg 540
tactccctgt cctccgtggt gacagtgccc tcctccaact tcggcaccca gacctacacc 600
tgtaacgtgg accacaagcc ctccaacacc aaggtggaca agaccgtgga acggaagtgc 660
tgcgtggaat gcccaccctg tcctgctcca cctgtggctg gccccagcgt gttcctgttc 720
cccccaaagc ccaaggacac cctgatgatc tcccggaccc ccgaagtgac ctgcgtggtg 780
gtggacgtgt cccacgagga ccccgaggtg cagttcaatt ggtacgtgga cggcgtggaa 840
gtgcacaacg ccaagaccaa gcccagagag gaacagttca actccacctt ccgggtggtg 900
tccgtgctga ccgtggtgca tcaggactgg ctgaacggca aagagtacaa gtgcaaggtc 960
tccaacaagg gcctgcctgc ccccatcgaa aagaccatca gcaagaccaa gggccagccc 1020
cgcgagcccc aggtgtacac actgcccccc agccgggaag agatgaccaa gaaccaggtg 1080
tccctgacct gtctggtgaa aggcttctac ccctccgaca ttgccgtgga atgggagtcc 1140
aacggacagc ctgagaacaa ctacaagacc acccccccca tgctggactc cgacggctca 1200
ttcttcctgt actccaagct gacagtggac aagtcccggt ggcagcaggg caacgtgttc 1260
tcctgctccg tgatgcacga ggccctgcac aaccactaca cccagaagtc cctgtccctg 1320
agccccggc 1329

<210> SEQ ID NO 88
<211> LENGTH: 642
<212> TYPE: DNA
<213> ORGANISM: Artificial Sequence
<220> FEATURE:
<223> OTHER INFORMATION: TPP-3323, TPP-3187X1-hIgG2, Light Chain

<400> SEQUENCE: 88
gacatcgtga tgacccagtc ccagaaattc atgtccacct ccgtgggcga ccgggtgtcc 60
atcacatgca aggcctctca gaacgtgggc accgccgtgg cctggtatca gcagaagcct 120
ggccagtccc ccaagctgct gatctactcc gcctccaacc ggtacaccgg cgtgcccgat 180
agattcaccg gctctggctc tggcaccgac ttcaccctga ccatctccaa catgcagtcc 240
gaggacctgg ccgactactt ctgccagcag tacaacaact accccctgac cttcggcgct 300
ggcaccaagc tggaactgaa gagaaccgtg gccgctccct ccgtgtttat cttcccaccc 360
tccgacgagc agctgaagtc cggcacagct tccgtcgtgt gcctgctgaa caacttctac 420
ccccgcgagg ccaaggtgca gtggaaggtg gacaacgccc tgcagtccgg caactcccag 480

```
gaatccgtga ccgagcagga ctccaaggac agcacctact ccctgtcctc taccctgacc    540

ctgtccaagg ccgattacga gaagcacaag gtgtacgcct gcgaagtgac ccaccagggc    600

ctgtctagcc ccgtgaccaa gtctttcaac cggggcgagt gt                       642


<210> SEQ ID NO 89
<211> LENGTH: 446
<212> TYPE: PRT
<213> ORGANISM: Artificial Sequence
<220> FEATURE:
<223> OTHER INFORMATION: TPP-3688, h16C3-hIgG2Kappa, Heavy Chain

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Met
        35                  40                  45

Gly Leu Ile Ser Thr Tyr Ser Gly Asp Thr Lys Tyr Asn Gln Asn Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335
```

```
Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 90
<211> LENGTH: 214
<212> TYPE: PRT
<213> ORGANISM: Artificial Sequence
<220> FEATURE:
<223> OTHER INFORMATION: TPP-3688, h16C3-hIgG2Kappa, Light Chain

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Val Leu Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 91
<211> LENGTH: 121
<212> TYPE: PRT
<213> ORGANISM: Artificial Sequence
```

<220> FEATURE:
<223> OTHER INFORMATION: TPP-3705, 090E-M007-A09-Mat1-hIgG2-hIgG2Kappa, VH

<400> SEQUENCE: 91

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Leu Tyr
20 25 30

Gln Met His Trp Val Arg Gln Ala Pro Gly Lys Gly Leu Glu Trp Val
35 40 45

Ser Trp Ile Ser Phe Ser Gly Gly Asn Thr Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ala Thr Gly Tyr Ser Ser Pro Trp Tyr Leu Asp Pro Trp Gly
100 105 110

Gln Gly Thr Leu Val Thr Val Ser Ser
115 120

<210> SEQ ID NO 92
<211> LENGTH: 5
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, HCDR1

<400> SEQUENCE: 92

Leu Tyr Gln Met His
1 5

<210> SEQ ID NO 93
<211> LENGTH: 17
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, HCDR2

<400> SEQUENCE: 93

Trp Ile Ser Phe Ser Gly Gly Asn Thr Gly Tyr Ala Asp Ser Val Lys
1 5 10 15

Gly

<210> SEQ ID NO 94
<211> LENGTH: 12
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, HCDR3

<400> SEQUENCE: 94

Ala Thr Gly Tyr Ser Ser Pro Trp Tyr Leu Asp Pro
1 5 10

<210> SEQ ID NO 95
<211> LENGTH: 107
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, VL

<400> SEQUENCE: 95

```
Asp Ile Gln Met Thr Gln Ser Pro Ser Ser Leu Ser Ala Ser Val Gly
1               5                   10                  15

Asp Arg Val Thr Ile Thr Cys Gln Ala Ser His Glu Ile Asp Asn Tyr
            20                  25                  30

Leu Asn Trp Tyr Gln Gln Lys Pro Gly Lys Ala Pro Lys Leu Leu Ile
        35                  40                  45

Tyr Asp Ala Tyr Trp Leu Lys Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gly Tyr Asp Asp Leu Ser Val
                85                  90                  95

Thr Phe Gly Gly Gly Thr Lys Val Asp Ile Lys
            100                 105
```

<210> SEQ ID NO 96
<211> LENGTH: 11
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, LCDR1

<400> SEQUENCE: 96

```
Gln Ala Ser His Glu Ile Asp Asn Tyr Leu Asn
1               5                   10
```

<210> SEQ ID NO 97
<211> LENGTH: 7
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, LCDR2

<400> SEQUENCE: 97

```
Asp Ala Tyr Trp Leu Lys Thr
1               5
```

<210> SEQ ID NO 98
<211> LENGTH: 9
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, LCDR3

<400> SEQUENCE: 98

```
Gln Gly Tyr Asp Asp Leu Ser Val Thr
1               5
```

<210> SEQ ID NO 99
<211> LENGTH: 363
<212> TYPE: DNA
<213> ORGANISM: Artificial Sequence
<220> FEATURE:
<223> OTHER INFORMATION: TPP-3705, 090E-M007-A09-Mat1-hIgG2-hIgG2Kappa, VH

<400> SEQUENCE: 99

```
gaagtgcagc tggtggaatc cggcggaggc ctggtgcagc ctggcggatc tctgagactg     60

tcttgtgccg cctccggctt caccttcagc ctgtaccaga tgcactgggt gcgacaggcc    120

cctggcaagg gactggaatg ggtgtcctgg atctccttct ccggcggcaa taccggctac    180

gccgactccg tgaagggccg gttcaccatc tcccgggaca actccaagaa caccctgtac    240

ctgcagatga actccctgcg ggccgaggac accgccgtgt actactgtgc tagagccacc    300

ggctactcct ccccctggta tctggatcct tggggccagg gcacactcgt gaccgtcagc    360

tca                                                                  363
```

<210> SEQ ID NO 100
<211> LENGTH: 321
<212> TYPE: DNA
<213> ORGANISM: Artificial Sequence
<220> FEATURE:
<223> OTHER INFORMATION: TPP-3705, 090E-M007-A09-Mat1-hIgG2-hIgG2Kappa, VL

<400> SEQUENCE: 100

```
gacatccaga tgacccagag cccttccagc ctgtccgcct ctgtgggcga cagagtgacc     60

atcacctgtc aggcctccca cgagatcgac aactacctga actggtatca gcagaagccc    120

ggcaaggccc ccaagctgct gatctacgat gcctactggc tgaaaaccgg cgtgccctcc    180

agattctccg gctctggctc tggcaccgac tttaccctga ccatctccag cctgcagccc    240

gaggatatcg ccacctacta ttgtcagggc tacgacgacc tgtccgtgac ctttggcgga    300

ggcaccaagg tggacatcaa g                                              321
```

<210> SEQ ID NO 101
<211> LENGTH: 446
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa, Heavy Chain

<400> SEQUENCE: 101

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Gln Met His Trp Val Arg Gln Ala Pro Gly Lys Gly Leu Glu Trp Val
        35                  40                  45

Ser Trp Ile Ser Phe Ser Gly Gly Asn Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Gly Tyr Ser Ser Pro Trp Tyr Leu Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 102
<211> LENGTH: 214
<212> TYPE: PRT
<213> ORGANISM: Artificial Sequence
<220> FEATURE:
<223> OTHER INFORMATION: TPP-3705, 090E-M007-A09-Mat1-hIgG2-hIgG2Kappa,
      Light Chain

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Gln Ala Ser His Glu Ile Asp Asn Tyr
            20                  25                  30

Leu Asn Trp Tyr Gln Gln Lys Pro Gly Lys Ala Pro Lys Leu Leu Ile
        35                  40                  45

Tyr Asp Ala Tyr Trp Leu Lys Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Ile Ala Thr Tyr Tyr Cys Gln Gly Tyr Asp Asp Leu Ser Val
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 103
<211> LENGTH: 1338
<212> TYPE: DNA
<213> ORGANISM: Artificial Sequence
<220> FEATURE:
<223> OTHER INFORMATION: TPP-3705, 090E-M007-A09-Mat1-hIgG2-hIgG2Kappa,
      Heavy Chain

<400> SEQUENCE: 103

gaagtgcagc tggtggaatc cggcggaggc ctggtgcagc ctggcggatc tctgagactg     60

tcttgtgccg cctccggctt caccttcagc ctgtaccaga tgcactgggt gcgacaggcc    120

cctggcaagg gactggaatg ggtgtcctgg atctccttct ccggcggcaa taccggctac    180

gccgactccg tgaagggccg gttcaccatc tcccgggaca actccaagaa caccctgtac    240

ctgcagatga actccctgcg ggccgaggac accgccgtgt actactgtgc tagagccacc    300

ggctactcct ccccctggta tctggatcct tggggccagg gcacactcgt gaccgtcagc    360

tcagcttcca ccaagggccc ctccgtgttc cctctggccc cttgctcccg gtccacctct    420

gagtctaccg ccgctctggg ctgcctggtg aaagactact tccccgagcc cgtgaccgtg    480

tcctggaact ctggcgccct gacctccggc gtgcacacct ttccagccgt gctgcagtcc    540

tccggcctgt actccctgtc ctccgtggtg acagtgccct cctccaactt cggcacccag    600

acctacacct gtaacgtgga ccacaagccc tccaacacca aggtggacaa gaccgtggaa    660

cggaagtgct gcgtggaatg cccaccctgt cctgctccac ctgtggctgg ccccagcgtg    720

ttcctgttcc ccccaaagcc caaggacacc ctgatgatct cccggacccc cgaagtgacc    780

tgcgtggtgg tggacgtgtc ccacgaggac cccgaggtgc agttcaattg gtacgtggac    840

ggcgtggaag tgcacaacgc caagaccaag cccagagagg aacagttcaa ctccaccttc    900

cgggtggtgt ccgtgctgac cgtggtgcat caggactggc tgaacggcaa agagtacaag    960

tgcaaggtct ccaacaaggg cctgcctgcc cccatcgaaa agaccatcag caagaccaag   1020

ggccagcccc gcgagcccca ggtgtacaca ctgcccccca gccgggaaga gatgaccaag   1080

aaccaggtgt ccctgacctg tctggtgaaa ggcttctacc cctccgacat tgccgtggaa   1140

tgggagtcca acggacagcc tgagaacaac tacaagacca cccccccat gctggactcc   1200
```

```
gacggctcat tcttcctgta ctccaagctg acagtggaca agtcccggtg gcagcagggc   1260

aacgtgttct cctgctccgt gatgcacgag gccctgcaca accactacac ccagaagtcc   1320

ctgtccctga gccccggc                                                 1338


<210> SEQ ID NO 104
<211> LENGTH: 642
<212> TYPE: DNA
<213> ORGANISM: Artificial Sequence
<220> FEATURE:
<223> OTHER INFORMATION: TPP-3705, 090E-M007-A09-Mat1-hIgG2-hIgG2Kappa,
      Light Chain

<400> SEQUENCE: 104

gacatccaga tgacccagag cccttccagc ctgtccgcct ctgtgggcga cagagtgacc     60

atcacctgtc aggcctccca cgagatcgac aactacctga actggtatca gcagaagccc    120

ggcaaggccc ccaagctgct gatctacgat gcctactggc tgaaaaccgg cgtgccctcc    180

agattctccg gctctggctc tggcaccgac tttaccctga ccatctccag cctgcagccc    240

gaggatatcg ccacctacta ttgtcagggc tacgacgacc tgtccgtgac ctttggcgga    300

ggcaccaagg tggacatcaa gcggacagtg gccgctccct ccgtgtttat cttcccaccc    360

tccgacgagc agctgaagtc cggcacagct tccgtcgtgt gcctgctgaa caacttctac    420

ccccgcgagg ccaaggtgca gtggaaagtg gataacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642


<210> SEQ ID NO 105
<211> LENGTH: 121
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa,
      VH

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Gln Met His Trp Val Arg Gln Ala Pro Gly Lys Gly Leu Glu Trp Val
        35                  40                  45

Ser Trp Ile Ser Phe Ser Gly Gly Asn Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Gly Tyr Ser Ser Pro Trp Tyr Leu Asp Pro Trp Gly
            100                 105                 110

Gln Gly Thr Leu Val Thr Val Ser Ser
        115                 120


<210> SEQ ID NO 106
<211> LENGTH: 5
<212> TYPE: PRT
<213> ORGANISM: Artificial Sequence
```

```
<220> FEATURE:
<223> OTHER INFORMATION: TPP-3707, 090E-M007-A09-Mat2-hIgG2-hIgG2Kappa,
      HCDR1

<400> SEQUENCE: 106

Leu Tyr Gln Met His
1               5


<210> SEQ ID NO 107
<211> LENGTH: 17
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa,
      HCDR2

<400> SEQUENCE: 107

Trp Ile Ser Phe Ser Gly Gly Asn Thr Gly Tyr Ala Asp Ser Val Lys
1               5                   10                  15

Gly


<210> SEQ ID NO 108
<211> LENGTH: 12
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa,
      HCDR3

<400> SEQUENCE: 108

Ala Thr Gly Tyr Ser Ser Pro Trp Tyr Leu Asp Pro
1               5                   10


<210> SEQ ID NO 109
<211> LENGTH: 107
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa,
      VL

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Gln Ala Ser His Glu Ile Asp Asn Tyr
            20                  25                  30

Leu Asn Trp Tyr Gln Gln Lys Pro Gly Lys Ala Pro Lys Leu Leu Ile
        35                  40                  45

Tyr Asp Ala Tyr Trp Ser Lys Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gly Tyr Asp Asp Leu Ser Val
                85                  90                  95

Thr Phe Gly Gly Gly Thr Lys Val Asp Ile Lys
            100                 105


<210> SEQ ID NO 110
<211> LENGTH: 11
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa,
      LCDR1
```

<400> SEQUENCE: 110

Gln Ala Ser His Glu Ile Asp Asn Tyr Leu Asn
1 5 10

<210> SEQ ID NO 111
<211> LENGTH: 7
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa, LCDR2

<400> SEQUENCE: 111

Asp Ala Tyr Trp Ser Lys Thr
1 5

<210> SEQ ID NO 112
<211> LENGTH: 9
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa, LCDR3

<400> SEQUENCE: 112

Gln Gly Tyr Asp Asp Leu Ser Val Thr
1 5

<210> SEQ ID NO 113
<211> LENGTH: 363
<212> TYPE: DNA
<213> ORGANISM: Artificial Sequence
<220> FEATURE:
<223> OTHER INFORMATION: TPP-3707, 090E-M007-A09-Mat2-hIgG2-hIgG2Kappa, VH

<400> SEQUENCE: 113
gaagtgcagc tggtggaatc cggcggaggc ctggtgcagc ctggcggatc tctgagactg 60
tcttgtgccg cctccggctt caccttcagc ctgtaccaga tgcactgggt gcgacaggcc 120
cctggcaagg gactggaatg ggtgtcctgg atctccttct ccggcggcaa taccggctac 180
gccgactccg tgaagggccg gttcaccatc tcccgggaca actccaagaa caccctgtac 240
ctgcagatga actccctgcg ggccgaggac accgccgtgt actactgtgc tagagccacc 300
ggctactcct ccccctggta tctggatcct tggggccagg gcacactcgt gaccgtcagc 360
tca 363

<210> SEQ ID NO 114
<211> LENGTH: 321
<212> TYPE: DNA
<213> ORGANISM: Artificial Sequence
<220> FEATURE:
<223> OTHER INFORMATION: TPP-3707, 090E-M007-A09-Mat2-hIgG2-hIgG2Kappa, VL

<400> SEQUENCE: 114
gacatccaga tgacccagag cccttccagc ctgtccgcct ctgtgggcga cagagtgacc 60
atcacctgtc aggcctccca cgagatcgac aactacctga actggtatca gcagaagccc 120
ggcaaggccc ccaagctgct gatctacgac gcctactggt ccaagaccgg cgtgccctcc 180
agattctccg gctctggctc tggcaccgac tttaccctga ccatctccag cctgcagccc 240
gaggatatcg ccacctacta ttgtcagggc tacgacgacc tgtccgtgac ctttggcgga 300
ggcaccaagg tggacatcaa g 321

<210> SEQ ID NO 115
<211> LENGTH: 446
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa,
Heavy Chain

<400> SEQUENCE: 115

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Leu Tyr
20 25 30

Gln Met His Trp Val Arg Gln Ala Pro Gly Lys Gly Leu Glu Trp Val
35 40 45

Ser Trp Ile Ser Phe Ser Gly Gly Asn Thr Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ala Thr Gly Tyr Ser Ser Pro Trp Tyr Leu Asp Pro Trp Gly
100 105 110

Gln Gly Thr Leu Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Cys Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 116
<211> LENGTH: 214
<212> TYPE: PRT
<213> ORGANISM: Artificial Sequence
<220> FEATURE:
<223> OTHER INFORMATION: TPP-3707, 090E-M007-A09-Mat2-hIgG2-hIgG2Kappa, Light Chain

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Gln Ala Ser His Glu Ile Asp Asn Tyr
            20                  25                  30

Leu Asn Trp Tyr Gln Gln Lys Pro Gly Lys Ala Pro Lys Leu Leu Ile
        35                  40                  45

Tyr Asp Ala Tyr Trp Ser Lys Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gly Tyr Asp Asp Leu Ser Val
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 117
<211> LENGTH: 1338
<212> TYPE: DNA
<213> ORGANISM: Artificial Sequence
<220> FEATURE:
<223> OTHER INFORMATION: TPP-3707, 090E-M007-A09-Mat2-hIgG2-hIgG2Kappa, Heavy Chain

<400> SEQUENCE: 117

```
gaagtgcagc tggtggaatc cggcggaggc ctggtgcagc ctggcggatc tctgagactg     60
tcttgtgccg cctccggctt caccttcagc ctgtaccaga tgcactgggt gcgacaggcc    120
cctggcaagg gactggaatg ggtgtcctgg atctccttct ccggcggcaa taccggctac    180
gccgactccg tgaagggccg gttcaccatc tcccgggaca actccaagaa caccctgtac    240
ctgcagatga actccctgcg ggccgaggac accgccgtgt actactgtgc tagagccacc    300
ggctactcct ccccctggta tctggatcct tggggccagg gcacactcgt gaccgtcagc    360
tcagcttcca ccaagggccc ctccgtgttc cctctggccc cttgctcccg gtccacctct    420
gagtctaccg ccgctctggg ctgcctggtg aaagactact tccccgagcc cgtgaccgtg    480
tcctggaact ctggcgccct gacctccggc gtgcacacct ttccagccgt gctgcagtcc    540
tccggcctgt actccctgtc ctccgtggtg acagtgccct cctccaactt cggcacccag    600
acctacacct gtaacgtgga ccacaagccc tccaacacca aggtggacaa gaccgtggaa    660
cggaagtgct gcgtggaatg cccaccctgt cctgctccac ctgtggctgg ccccagcgtg    720
ttcctgttcc ccccaaagcc caaggacacc ctgatgatct cccggacccc cgaagtgacc    780
tgcgtggtgg tggacgtgtc ccacgaggac cccgaggtgc agttcaattg gtacgtggac    840
ggcgtggaag tgcacaacgc caagaccaag cccagagagg aacagttcaa ctccaccttc    900
cgggtggtgt ccgtgctgac cgtggtgcat caggactggc tgaacggcaa agagtacaag    960
tgcaaggtct ccaacaaggg cctgcctgcc cccatcgaaa agaccatcag caagaccaag   1020
ggccagcccc gcgagcccca ggtgtacaca ctgcccccca gccgggaaga gatgaccaag   1080
aaccaggtgt ccctgacctg tctggtgaaa ggcttctacc cctccgacat tgccgtggaa   1140
tgggagtcca acggacagcc tgagaacaac tacaagacca ccccccccat gctggactcc   1200
gacggctcat tcttcctgta ctccaagctg acagtggaca agtcccggtg gcagcagggc   1260
aacgtgttct cctgctccgt gatgcacgag gccctgcaca accactacac ccagaagtcc   1320
ctgtccctga gccccggc                                                 1338
```

<210> SEQ ID NO 118
<211> LENGTH: 642
<212> TYPE: DNA
<213> ORGANISM: Artificial Sequence
<220> FEATURE:
<223> OTHER INFORMATION: TPP-3707, 090E-M007-A09-Mat2-hIgG2-hIgG2Kappa, Light Chain

<400> SEQUENCE: 118

```
gacatccaga tgacccagag cccttccagc ctgtccgcct ctgtgggcga cagagtgacc     60
atcacctgtc aggcctccca cgagatcgac aactacctga actggtatca gcagaagccc    120
ggcaaggccc ccaagctgct gatctacgac gcctactggt ccaagaccgg cgtgccctcc    180
agattctccg gctctggctc tggcaccgac tttaccctga ccatctccag cctgcagccc    240
gaggatatcg ccacctacta ttgtcagggc tacgacgacc tgtccgtgac ctttggcgga    300
ggcaccaagg tggacatcaa gcggacagtg gccgctccct ccgtgtttat cttcccaccc    360
tccgacgagc agctgaagtc cggcacagct tccgtcgtgt gcctgctgaa caacttctac    420
cccgcgagg ccaaggtgca gtggaaagtg gataacgccc tgcagtccgg caactcccag    480
gaatccgtga ccgagcagga ctccaaggac agcacctact ccctgtcctc caccctgacc    540
```

ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 119
<211> LENGTH: 118
<212> TYPE: PRT
<213> ORGANISM: Artificial Sequence
<220> FEATURE:
<223> OTHER INFORMATION: TPP-3714, TPP-2971HU2-hIgG2Kappa, VH

<400> SEQUENCE: 119

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Tyr
20 25 30

Gly Ile Gly Val Gly Trp Ile Arg Gln Pro Pro Gly Lys Ala Leu Glu
35 40 45

Trp Leu Ala His Ile Trp Trp Asn Asp Asn Lys Tyr Tyr Ser Thr Ser
50 55 60

Leu Lys Thr Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Ile Ser Leu Pro Tyr Phe Asp Tyr Trp Gly Gln Gly Thr
100 105 110

Leu Val Thr Val Ser Ser
115

<210> SEQ ID NO 120
<211> LENGTH: 7
<212> TYPE: PRT
<213> ORGANISM: Artificial Sequence
<220> FEATURE:
<223> OTHER INFORMATION: TPP-3714, TPP-2971HU2-hIgG2Kappa, HCDR1

<400> SEQUENCE: 120

Thr Tyr Gly Ile Gly Val Gly
1 5

<210> SEQ ID NO 121
<211> LENGTH: 16
<212> TYPE: PRT
<213> ORGANISM: Artificial Sequence
<220> FEATURE:
<223> OTHER INFORMATION: TPP-3714, TPP-2971HU2-hIgG2Kappa, HCDR2

<400> SEQUENCE: 121

His Ile Trp Trp Asn Asp Asn Lys Tyr Tyr Ser Thr Ser Leu Lys Thr
1 5 10 15

<210> SEQ ID NO 122
<211> LENGTH: 8
<212> TYPE: PRT
<213> ORGANISM: Artificial Sequence
<220> FEATURE:
<223> OTHER INFORMATION: TPP-3714, TPP-2971HU2-hIgG2Kappa, HCDR3

<400> SEQUENCE: 122

Ile Ser Leu Pro Tyr Phe Asp Tyr
1 5

<210> SEQ ID NO 123

<211> LENGTH: 107
<212> TYPE: PRT
<213> ORGANISM: Artificial Sequence
<220> FEATURE:
<223> OTHER INFORMATION: TPP-3714, TPP-2971HU2-hIgG2Kappa, VL

<400> SEQUENCE: 123

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Gly Thr Ala
20 25 30

Val Ala Trp Tyr Gln Gln Lys Pro Gly Lys Ala Pro Lys Leu Leu Ile
35 40 45

Tyr Ser Ala Ser Asn Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Ser Ser Tyr Pro Leu
85 90 95

Thr Phe Gly Gly Gly Thr Lys Val Glu Ile Lys
100 105

<210> SEQ ID NO 124
<211> LENGTH: 11
<212> TYPE: PRT
<213> ORGANISM: Artificial Sequence
<220> FEATURE:
<223> OTHER INFORMATION: TPP-3714, TPP-2971HU2-hIgG2Kappa, LCDR1

<400> SEQUENCE: 124

Lys Ala Ser Gln Asn Val Gly Thr Ala Val Ala
1 5 10

<210> SEQ ID NO 125
<211> LENGTH: 7
<212> TYPE: PRT
<213> ORGANISM: Artificial Sequence
<220> FEATURE:
<223> OTHER INFORMATION: TPP-3714, TPP-2971HU2-hIgG2Kappa, LCDR2

<400> SEQUENCE: 125

Ser Ala Ser Asn Arg Tyr Thr
1 5

<210> SEQ ID NO 126
<211> LENGTH: 9
<212> TYPE: PRT
<213> ORGANISM: Artificial Sequence
<220> FEATURE:
<223> OTHER INFORMATION: TPP-3714, TPP-2971HU2-hIgG2Kappa, LCDR3

<400> SEQUENCE: 126

Gln Gln Tyr Ser Ser Tyr Pro Leu Thr
1 5

<210> SEQ ID NO 127
<211> LENGTH: 354
<212> TYPE: DNA
<213> ORGANISM: Artificial Sequence
<220> FEATURE:
<223> OTHER INFORMATION: TPP-3714, TPP-2971HU2-hIgG2Kappa, VH

<400> SEQUENCE: 127
caagtgaccc tgagagagtc cggccctgcc ctcgtgaagc ctacccagac cctgacactg 60

```
acctgcacct tctccggctt ctccctgtcc acctacggca tcggcgtggg ctggatcaga    120

cagcctcctg gcaaggccct ggaatggctg gctcacatct ggtggaacga caacaagtac    180

tactccacct ccctgaaaac ccggctgacc atctccaagg acacctccaa gaaccaggtg    240

gtgctgacca tgaccaacat ggaccccgtg gacaccgcca cctactactg cgccagaatc    300

tccctgccct acttcgacta ctggggccag ggcacactcg tgaccgtcag ctca          354


<210> SEQ ID NO 128
<211> LENGTH: 321
<212> TYPE: DNA
<213> ORGANISM: Artificial Sequence
<220> FEATURE:
<223> OTHER INFORMATION: TPP-3714, TPP-2971HU2-hIgG2Kappa, VL

<400> SEQUENCE: 128

gatatccagc tgacccagtc ccccagcttc ctgtctgcct ctgtgggcga cagagtgacc     60

atcacatgca aggcctccca gaacgtgggc accgccgtgg cttggtatca gcagaagcct    120

ggcaaggccc ccaagctgct gatctactcc gcctccaacc ggtacaccgg cgtgccctct    180

agattctccg gctctggctc tggcaccgag tttaccctga ccatctccag cctgcagccc    240

gaggacttcg ccacctacta ctgccagcag tactcctcct accccctgac ctttggcgga    300

ggcaccaagg tggaaatcaa g                                              321


<210> SEQ ID NO 129
<211> LENGTH: 443
<212> TYPE: PRT
<213> ORGANISM: Artificial Sequence
<220> FEATURE:
<223> OTHER INFORMATION: TPP-3714, TPP-2971HU2-hIgG2Kappa, Heavy Chain

<400> SEQUENCE: 129

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Ile Gly Val Gly Trp Ile Arg Gln Pro Pro Gly Lys Ala Leu Glu
        35                  40                  45

Trp Leu Ala His Ile Trp Trp Asn Asp Asn Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

-continued

```
Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 130
<211> LENGTH: 214
<212> TYPE: PRT
<213> ORGANISM: Artificial Sequence
<220> FEATURE:
<223> OTHER INFORMATION: TPP-3714, TPP-2971HU2-hIgG2Kappa, Light Chain

<400> SEQUENCE: 130

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 131
<211> LENGTH: 1329
<212> TYPE: DNA
<213> ORGANISM: Artificial Sequence
<220> FEATURE:
<223> OTHER INFORMATION: TPP-3714, TPP-2971HU2-hIgG2Kappa, Heavy Chain

<400> SEQUENCE: 131

caagtgaccc tgagagagtc cggccctgcc ctcgtgaagc ctacccagac cctgacactg      60

acctgcacct tctccggctt ctccctgtcc acctacggca tcggcgtggg ctggatcaga     120

cagcctcctg gcaaggccct ggaatggctg gctcacatct ggtggaacga caacaagtac     180

tactccacct ccctgaaaac ccggctgacc atctccaagg acacctccaa gaaccaggtg     240

gtgctgacca tgaccaacat ggaccccgtg gacaccgcca cctactactg cgccagaatc     300

tccctgccct acttcgacta ctggggccag ggcacactcg tgaccgtcag ctcagcttcc     360

accaagggcc cctccgtgtt ccctctggcc ccttgctccc ggtccacctc tgagtctacc     420

gccgctctgg gctgcctggt gaaagactac ttccccgagc ccgtgaccgt gtcctggaac     480

tctggcgccc tgacctccgg cgtgcacacc tttccagccg tgctgcagtc ctccggcctg     540

tactccctgt cctccgtggt gacagtgccc tcctccaact tcggcaccca gacctacacc     600

tgtaacgtgg accacaagcc ctccaacacc aaggtggaca agaccgtgga acggaagtgc     660

tgcgtggaat gcccaccctg tcctgctcca cctgtggctg gccccagcgt gttcctgttc     720

cccccaaagc ccaaggacac cctgatgatc tcccggaccc ccgaagtgac ctgcgtggtg     780

gtggacgtgt cccacgagga ccccgaggtg cagttcaatt ggtacgtgga cggcgtggaa     840

gtgcacaacg ccaagaccaa gcccagagag gaacagttca actccacctt ccgggtggtg     900

tccgtgctga ccgtggtgca tcaggactgg ctgaacggca aagagtacaa gtgcaaggtc     960

tccaacaagg gcctgcctgc ccccatcgaa aagaccatca gcaagaccaa gggccagccc    1020

cgcgagcccc aggtgtacac actgcccccc agccgggaag agatgaccaa gaaccaggtg    1080

tccctgacct gtctggtgaa aggcttctac ccctccgaca ttgccgtgga atgggagtcc    1140

aacggacagc ctgagaacaa ctacaagacc acccccccca tgctggactc cgacggctca    1200

ttcttcctgt actccaagct gacagtggac aagtcccggt ggcagcaggg caacgtgttc    1260

tcctgctccg tgatgcacga ggccctgcac aaccactaca cccagaagtc cctgtccctg    1320

agccccggc                                                             1329

<210> SEQ ID NO 132
```

<211> LENGTH: 642
<212> TYPE: DNA
<213> ORGANISM: Artificial Sequence
<220> FEATURE:
<223> OTHER INFORMATION: TPP-3714, TPP-2971HU2-hIgG2Kappa, Light Chain

<400> SEQUENCE: 132
gatatccagc tgacccagtc ccccagcttc ctgtctgcct ctgtgggcga cagagtgacc 60
atcacatgca aggcctccca gaacgtgggc accgccgtgg cttggtatca gcagaagcct 120
ggcaaggccc ccaagctgct gatctactcc gcctccaacc ggtacaccgg cgtgccctct 180
agattctccg gctctggctc tggcaccgag tttaccctga ccatctccag cctgcagccc 240
gaggacttcg ccacctacta ctgccagcag tactcctcct accccctgac ctttggcgga 300
ggcaccaagg tggaaatcaa gcggaccgtg gccgctccct ccgtgtttat cttcccaccc 360
tccgacgagc agctgaagtc cggcacagct tccgtcgtgt gcctgctgaa caacttctac 420
ccccgcgagg ccaaggtgca gtggaaggtg gacaacgccc tgcagtccgg caactcccag 480
gaatccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 133
<211> LENGTH: 118
<212> TYPE: PRT
<213> ORGANISM: Artificial Sequence
<220> FEATURE:
<223> OTHER INFORMATION: TPP-3820, 3187HU1-hIgG2Kappa, VH

<400> SEQUENCE: 133

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Thr Thr Tyr
20 25 30

Gly Ile Gly Val Gly Trp Ile Arg Gln Pro Pro Gly Lys Gly Leu Glu
35 40 45

Trp Leu Ala His Ile Trp Trp Asn Asp Asn Lys Tyr Tyr Ser Thr Ser
50 55 60

Leu Lys Thr Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Ile Ser Leu Pro Tyr Phe Asp Tyr Trp Gly Gln Gly Thr
100 105 110

Leu Val Thr Val Ser Ser
115

<210> SEQ ID NO 134
<211> LENGTH: 7
<212> TYPE: PRT
<213> ORGANISM: Artificial Sequence
<220> FEATURE:
<223> OTHER INFORMATION: TPP-3820, 3187HU1-hIgG2Kappa, HCDR1

<400> SEQUENCE: 134

Thr Tyr Gly Ile Gly Val Gly
1 5

<210> SEQ ID NO 135

<211> LENGTH: 16
<212> TYPE: PRT
<213> ORGANISM: Artificial Sequence
<220> FEATURE:
<223> OTHER INFORMATION: TPP-3820, 3187HU1-hIgG2Kappa, HCDR2

<400> SEQUENCE: 135

His Ile Trp Trp Asn Asp Asn Lys Tyr Tyr Ser Thr Ser Leu Lys Thr
1 5 10 15

<210> SEQ ID NO 136
<211> LENGTH: 8
<212> TYPE: PRT
<213> ORGANISM: Artificial Sequence
<220> FEATURE:
<223> OTHER INFORMATION: TPP-3820, 3187HU1-hIgG2Kappa, HCDR3

<400> SEQUENCE: 136

Ile Ser Leu Pro Tyr Phe Asp Tyr
1 5

<210> SEQ ID NO 137
<211> LENGTH: 107
<212> TYPE: PRT
<213> ORGANISM: Artificial Sequence
<220> FEATURE:
<223> OTHER INFORMATION: TPP-3820, 3187HU1-hIgG2Kappa, VL

<400> SEQUENCE: 137

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Gly Thr Ala
20 25 30

Val Ala Trp Tyr Gln Gln Lys Pro Gly Lys Ala Pro Lys Leu Leu Ile
35 40 45

Tyr Ser Ala Ser Asn Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Asn Asn Tyr Pro Leu
85 90 95

Thr Phe Gly Gly Gly Thr Lys Val Glu Ile Lys
100 105

<210> SEQ ID NO 138
<211> LENGTH: 11
<212> TYPE: PRT
<213> ORGANISM: Artificial Sequence
<220> FEATURE:
<223> OTHER INFORMATION: TPP-3820, 3187HU1-hIgG2Kappa, LCDR1

<400> SEQUENCE: 138

Lys Ala Ser Gln Asn Val Gly Thr Ala Val Ala
1 5 10

<210> SEQ ID NO 139
<211> LENGTH: 7
<212> TYPE: PRT
<213> ORGANISM: Artificial Sequence
<220> FEATURE:
<223> OTHER INFORMATION: TPP-3820, 3187HU1-hIgG2Kappa, LCDR2

<400> SEQUENCE: 139

Ser Ala Ser Asn Arg Tyr Thr 1 5

<210> SEQ ID NO 140
<211> LENGTH: 9
<212> TYPE: PRT
<213> ORGANISM: Artificial Sequence
<220> FEATURE:
<223> OTHER INFORMATION: TPP-3820, 3187HU1-hIgG2Kappa, LCDR3

<400> SEQUENCE: 140

Gln Gln Tyr Asn Asn Tyr Pro Leu Thr
1 5

<210> SEQ ID NO 141
<211> LENGTH: 354
<212> TYPE: DNA
<213> ORGANISM: Artificial Sequence
<220> FEATURE:
<223> OTHER INFORMATION: TPP-3820, 3187HU1-hIgG2Kappa, VH

<400> SEQUENCE: 141
caagtgaccc tgagagagtc cggccctgcc ctcgtgaagc ctacccagac cctgacactg 60
acctgcacct tcagcggctt cagcctgacc acctacggca tcggcgtggg ctggatcaga 120
cagcctcctg gcaagggcct ggaatggctg gcccacatct ggtggaacga caacaagtac 180
tacagcacca gcctgaaaac ccggctgacc atcagcaagg acaccagcaa gaaccaggtg 240
gtgctgacca tgaccaacat ggaccccgtg gacaccgcca cctactactg cgccagaatc 300
agcctgccct acttcgacta ctggggccag ggcaccctcg tgacagtgtc atca 354

<210> SEQ ID NO 142
<211> LENGTH: 321
<212> TYPE: DNA
<213> ORGANISM: Artificial Sequence
<220> FEATURE:
<223> OTHER INFORMATION: TPP-3820, 3187HU1-hIgG2Kappa, VL

<400> SEQUENCE: 142
gatatccagc tgacccagag ccccagcttt ctgagcgcca gcgtgggcga cagagtgacc 60
atcacatgca aggccagcca gaacgtgggc acagccgtgg cctggtatca gcagaagcct 120
ggcaaggccc ccaagctgct gatctacagc gccagcaacc ggtacaccgg cgtgcccagc 180
agattttctg gcagcggctc cggcaccgag ttcaccctga caatcagcag cctgcagccc 240
gaggacttcg ccacctacta ctgccagcag tacaacaact accccctgac cttcggcgga 300
ggcaccaagg tggaaattaa a 321

<210> SEQ ID NO 143
<211> LENGTH: 443
<212> TYPE: PRT
<213> ORGANISM: Artificial Sequence
<220> FEATURE:
<223> OTHER INFORMATION: TPP-3820, 3187HU1-hIgG2Kappa, Heavy Chain

<400> SEQUENCE: 143

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Thr Thr Tyr
20 25 30

Gly Ile Gly Val Gly Trp Ile Arg Gln Pro Pro Gly Lys Gly Leu Glu
35 40 45

Trp Leu Ala His Ile Trp Trp Asn Asp Asn Lys Tyr Tyr Ser Thr Ser

```
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440
```

<210> SEQ ID NO 144
<211> LENGTH: 214
<212> TYPE: PRT
<213> ORGANISM: Artificial Sequence
<220> FEATURE:
<223> OTHER INFORMATION: TPP-3820, 3187HU1-hIgG2Kappa, Light Chain

<400> SEQUENCE: 144

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 145
<211> LENGTH: 1329
<212> TYPE: DNA
<213> ORGANISM: Artificial Sequence
<220> FEATURE:
<223> OTHER INFORMATION: TPP-3820, 3187HU1-hIgG2Kappa, Heavy Chain

<400> SEQUENCE: 145

```
caagtgaccc tgagagagtc cggccctgcc ctcgtgaagc ctacccagac cctgacactg      60

acctgcacct tcagcggctt cagcctgacc acctacggca tcggcgtggg ctggatcaga     120

cagcctcctg gcaagggcct ggaatggctg gcccacatct ggtggaacga caacaagtac     180

tacagcacca gcctgaaaac ccggctgacc atcagcaagg acaccagcaa gaaccaggtg     240

gtgctgacca tgaccaacat ggaccccgtg gacaccgcca cctactactg cgccagaatc     300

agcctgccct acttcgacta ctggggccag ggcaccctcg tgacagtgtc atcagccagc     360

accaagggcc ccagcgtgtt ccctctggcc ccttgtagca gaagcaccag cgagtctaca     420

gccgccctgg gctgcctcgt gaaggactac tttcccgagc ccgtgaccgt gtcctggaac     480

tctggcgctc tgacaagcgg cgtgcacacc tttccagccg tgctgcagag cagcggcctg     540

tactctctga gcagcgtcgt gacagtgccc agcagcaact tcggcaccca gacctacacc     600

tgtaacgtgg accacaagcc cagcaacacc aaggtggaca agaccgtgga acggaagtgc     660
```

tgcgtggaat gcccccttg tcctgcccct ccagtggctg gcccttccgt gttcctgttc 720
cccccaaagc ccaaggacac cctgatgatc agccggaccc ccgaagtgac ctgcgtggtg 780
gtggatgtgt cccacgagga ccccgaggtg cagttcaatt ggtacgtgga cggcgtggaa 840
gtgcacaacg ccaagaccaa gcccagagag gaacagttca acagcacctt ccgggtggtg 900
tccgtgctga ccgtggtgca tcaggactgg ctgaacggca aagagtacaa gtgcaaggtg 960
tccaacaagg gcctgcctgc ccccatcgag aaaaccatca gcaagaccaa aggccagccc 1020
cgcgagcccc aggtgtacac actgcctcca agccgggaag agatgaccaa gaaccaggtg 1080
tccctgacct gtctcgtgaa aggcttctac ccctccgata tcgccgtgga atgggagagc 1140
aacggccagc ccgagaacaa ctacaagacc acccccccca tgctggacag cgacggctca 1200
ttcttcctgt acagcaagct gacagtggac aagtcccggt ggcagcaggg caacgtgttc 1260
agctgcagcg tgatgcacga ggccctgcac aaccactaca cccagaagtc cctgagcctg 1320
agccctggc 1329

<210> SEQ ID NO 146
<211> LENGTH: 642
<212> TYPE: DNA
<213> ORGANISM: Artificial Sequence
<220> FEATURE:
<223> OTHER INFORMATION: TPP-3820, 3187HU1-hIgG2Kappa, Light Chain

<400> SEQUENCE: 146
gatatccagc tgacccagag ccccagcttt ctgagcgcca gcgtgggcga cagagtgacc 60
atcacatgca aggccagcca gaacgtgggc acagccgtgg cctggtatca gcagaagcct 120
ggcaaggccc ccaagctgct gatctacagc gccagcaacc ggtacaccgg cgtgcccagc 180
agattttctg gcagcggctc cggcaccgag ttcaccctga caatcagcag cctgcagccc 240
gaggacttcg ccacctacta ctgccagcag tacaacaact accccctgac cttcggcgga 300
ggcaccaagg tggaaattaa acgaaccgtg gccgctccca gcgtgttcat cttcccacct 360
agcgacgagc agctgaagtc cggcacagcc tctgtcgtgt gcctgctgaa caacttctac 420
ccccgcgagg ccaaggtgca gtggaaggtg gacaatgccc tgcagagcgg caacagccag 480
gaaagcgtga ccgagcagga cagcaaggac tccacctaca gcctgagcag caccctgacc 540
ctgagcaagg ccgactacga gaagcacaag gtgtacgcct gcgaagtgac ccaccagggc 600
ctgtctagcc ccgtgaccaa gagcttcaac cggggcgagt gt 642

<210> SEQ ID NO 147
<211> LENGTH: 118
<212> TYPE: PRT
<213> ORGANISM: Artificial Sequence
<220> FEATURE:
<223> OTHER INFORMATION: TPP-3821, 3187HU2-hIgG2Kappa, VH

<400> SEQUENCE: 147

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Ile Gly Val Gly Trp Ile Arg Gln Pro Pro Gly Lys Ala Leu Glu
        35                  40                  45

Trp Leu Ala His Ile Trp Trp Asn Asp Asn Lys Tyr Tyr Ser Thr Ser
    50                  55                  60

Leu Lys Thr Arg Leu Thr Ile Ser Lys Asp Thr Ser Lys Asn Gln Val 65 70 75 80

Val Leu Thr Met Thr Asn Met Asp Pro Val Asp Thr Ala Thr Tyr Tyr
85 90 95

Cys Ala Arg Ile Ser Leu Pro Tyr Phe Asp Tyr Trp Gly Gln Gly Thr
100 105 110

Leu Val Thr Val Ser Ser
115

<210> SEQ ID NO 148
<211> LENGTH: 7
<212> TYPE: PRT
<213> ORGANISM: Artificial Sequence
<220> FEATURE:
<223> OTHER INFORMATION: TPP-3821, 3187HU2-hIgG2Kappa, HCDR1

<400> SEQUENCE: 148

Thr Tyr Gly Ile Gly Val Gly
1 5

<210> SEQ ID NO 149
<211> LENGTH: 16
<212> TYPE: PRT
<213> ORGANISM: Artificial Sequence
<220> FEATURE:
<223> OTHER INFORMATION: TPP-3821, 3187HU2-hIgG2Kappa, HCDR2

<400> SEQUENCE: 149

His Ile Trp Trp Asn Asp Asn Lys Tyr Tyr Ser Thr Ser Leu Lys Thr
1 5 10 15

<210> SEQ ID NO 150
<211> LENGTH: 8
<212> TYPE: PRT
<213> ORGANISM: Artificial Sequence
<220> FEATURE:
<223> OTHER INFORMATION: TPP-3821, 3187HU2-hIgG2Kappa, HCDR3

<400> SEQUENCE: 150

Ile Ser Leu Pro Tyr Phe Asp Tyr
1 5

<210> SEQ ID NO 151
<211> LENGTH: 107
<212> TYPE: PRT
<213> ORGANISM: Artificial Sequence
<220> FEATURE:
<223> OTHER INFORMATION: TPP-3821, 3187HU2-hIgG2Kappa, VL

<400> SEQUENCE: 151

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Gly Thr Ala
20 25 30

Val Ala Trp Tyr Gln Gln Lys Pro Gly Lys Ala Pro Lys Leu Leu Ile
35 40 45

Tyr Ser Ala Ser Asn Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Asn Asn Tyr Pro Leu
85 90 95

Thr Phe Gly Gly Gly Thr Lys Val Glu Ile Lys 100 105

<210> SEQ ID NO 152
<211> LENGTH: 11
<212> TYPE: PRT
<213> ORGANISM: Artificial Sequence
<220> FEATURE:
<223> OTHER INFORMATION: TPP-3821, 3187HU2-hIgG2Kappa, LCDR1

<400> SEQUENCE: 152

Lys Ala Ser Gln Asn Val Gly Thr Ala Val Ala
1 5 10

<210> SEQ ID NO 153
<211> LENGTH: 7
<212> TYPE: PRT
<213> ORGANISM: Artificial Sequence
<220> FEATURE:
<223> OTHER INFORMATION: TPP-3821, 3187HU2-hIgG2Kappa, LCDR2

<400> SEQUENCE: 153

Ser Ala Ser Asn Arg Tyr Thr
1 5

<210> SEQ ID NO 154
<211> LENGTH: 9
<212> TYPE: PRT
<213> ORGANISM: Artificial Sequence
<220> FEATURE:
<223> OTHER INFORMATION: TPP-3821, 3187HU2-hIgG2Kappa, LCDR3

<400> SEQUENCE: 154

Gln Gln Tyr Asn Asn Tyr Pro Leu Thr
1 5

<210> SEQ ID NO 155
<211> LENGTH: 354
<212> TYPE: DNA
<213> ORGANISM: Artificial Sequence
<220> FEATURE:
<223> OTHER INFORMATION: TPP-3821, 3187HU2-hIgG2Kappa, VH

<400> SEQUENCE: 155
caggtcacac tgagagagtc cggccctgcc ctggtgaaac ccacccagac cctgaccctg 60
acatgcacct tcagcggctt cagcctgagc acctacggca tcggcgtggg ctggatcaga 120
cagccccctg gcaaggccct ggaatggctg gcccacatct ggtggaacga caacaagtac 180
tacagcacca gcctgaaaac ccggctgacc atcagcaagg acaccagcaa gaaccaggtg 240
gtgctgacca tgaccaacat ggaccccgtg gacaccgcca cctactactg cgcccggatc 300
agcctgccct acttcgacta ctggggccag ggcaccctgg tgaccgtgtc ctca 354

<210> SEQ ID NO 156
<211> LENGTH: 321
<212> TYPE: DNA
<213> ORGANISM: Artificial Sequence
<220> FEATURE:
<223> OTHER INFORMATION: TPP-3821, 3187HU2-hIgG2Kappa, VL

<400> SEQUENCE: 156
gatatccagc tgacccagag ccccagcttt ctgagcgcca gcgtgggcga cagagtgacc 60
atcacatgca aggccagcca gaacgtgggc acagccgtgg cctggtatca gcagaagcct 120
ggcaaggccc ccaagctgct gatctacagc gccagcaacc ggtacaccgg cgtgcccagc 180

```
agattttctg gcagcggctc cggcaccgag ttcaccctga caatcagcag cctgcagccc    240

gaggacttcg ccacctacta ctgccagcag tacaacaact accccctgac cttcggcgga    300

ggcaccaagg tggaaattaa a                                              321

<210> SEQ ID NO 157
<211> LENGTH: 443
<212> TYPE: PRT
<213> ORGANISM: Artificial Sequence
<220> FEATURE:
<223> OTHER INFORMATION: TPP-3821, 3187HU2-hIgG2Kappa, Heavy Chain

<400> SEQUENCE: 157

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Ile Gly Val Gly Trp Ile Arg Gln Pro Pro Gly Lys Ala Leu Glu
        35                  40                  45

Trp Leu Ala His Ile Trp Trp Asn Asp Asn Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335
```

```
Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 158
<211> LENGTH: 214
<212> TYPE: PRT
<213> ORGANISM: Artificial Sequence
<220> FEATURE:
<223> OTHER INFORMATION: TPP-3821, 3187HU2-hIgG2Kappa, Light Chain

<400> SEQUENCE: 158

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 159
<211> LENGTH: 1329
<212> TYPE: DNA
<213> ORGANISM: Artificial Sequence
<220> FEATURE:
```

<223> OTHER INFORMATION: TPP-3821, 3187HU2-hIgG2Kappa, Heavy Chain

<400> SEQUENCE: 159

```
caggtcacac tgagagagtc cggccctgcc ctggtgaaac ccacccagac cctgaccctg      60

acatgcacct tcagcggctt cagcctgagc acctacggca tcggcgtggg ctggatcaga     120

cagccccctg gcaaggccct ggaatggctg gcccacatct ggtggaacga caacaagtac     180

tacagcacca gcctgaaaac ccggctgacc atcagcaagg acaccagcaa gaaccaggtg     240

gtgctgacca tgaccaacat ggaccccgtg gacaccgcca cctactactg cgcccggatc     300

agcctgccct acttcgacta ctggggccag ggcaccctgg tgaccgtgtc ctcagccagc     360

accaagggcc ccagcgtgtt ccctctggcc ccttgtagca gaagcaccag cgagtctaca     420

gccgccctgg gctgcctcgt gaaggactac tttcccgagc ccgtgaccgt gtcctggaac     480

tctggcgctc tgacaagcgg cgtgcacacc tttccagccg tgctgcagag cagcggcctg     540

tactctctga gcagcgtcgt gacagtgccc agcagcaact tcggcaccca gacctacacc     600

tgtaacgtgg accacaagcc cagcaacacc aaggtggaca agaccgtgga acggaagtgc     660

tgcgtggaat gccccccttg tcctgcccct ccagtggctg gcccttccgt gttcctgttc     720

cccccaaagc ccaaggacac cctgatgatc agccggaccc ccgaagtgac ctgcgtggtg     780

gtggatgtgt cccacgagga ccccgaggtg cagttcaatt ggtacgtgga cggcgtggaa     840

gtgcacaacg ccaagaccaa gcccagagag gaacagttca acagcacctt ccgggtggtg     900

tccgtgctga ccgtggtgca tcaggactgg ctgaacggca aagagtacaa gtgcaaggtg     960

tccaacaagg gcctgcctgc ccccatcgag aaaaccatca gcaagaccaa aggccagccc    1020

cgcgagcccc aggtgtacac actgcctcca agccgggaag agatgaccaa gaaccaggtg    1080

tccctgacct gtctcgtgaa aggcttctac ccctccgata tcgccgtgga atgggagagc    1140

aacggccagc ccgagaacaa ctacaagacc acccccccca tgctggacag cgacggctca    1200

ttcttcctgt acagcaagct gacagtggac aagtcccggt ggcagcaggg caacgtgttc    1260

agctgcagcg tgatgcacga ggccctgcac aaccactaca cccagaagtc cctgagcctg    1320

agccctggc                                                           1329
```

<210> SEQ ID NO 160
<211> LENGTH: 642
<212> TYPE: DNA
<213> ORGANISM: Artificial Sequence
<220> FEATURE:
<223> OTHER INFORMATION: TPP-3821, 3187HU2-hIgG2Kappa, Light Chain

<400> SEQUENCE: 160

```
gatatccagc tgacccagag ccccagcttt ctgagcgcca gcgtgggcga cagagtgacc      60

atcacatgca aggccagcca gaacgtgggc acagccgtgg cctggtatca gcagaagcct     120

ggcaaggccc ccaagctgct gatctacagc gccagcaacc ggtacaccgg cgtgcccagc     180

agattttctg gcagcggctc cggcaccgag ttcaccctga caatcagcag cctgcagccc     240

gaggacttcg ccacctacta ctgccagcag tacaacaact acccccctgac cttcggcgga     300

ggcaccaagg tggaaattaa acgaaccgtg gccgctccca gcgtgttcat cttcccacct     360

agcgacgagc agctgaagtc cggcacagcc tctgtcgtgt gcctgctgaa caacttctac     420

ccccgcgagg ccaaggtgca gtggaaggtg gacaatgccc tgcagagcgg caacagccag     480

gaaagcgtga ccgagcagga cagcaaggac tccacctaca gcctgagcag caccctgacc     540

ctgagcaagg ccgactacga gaagcacaag gtgtacgcct gcgaagtgac ccaccagggc     600
```

ctgtctagcc ccgtgaccaa gagcttcaac cggggcgagt gt 642

<210> SEQ ID NO 161
<211> LENGTH: 532
<212> TYPE: PRT
<213> ORGANISM: Macaca mulatta

<400> SEQUENCE: 161

Gln Leu Thr Ile Glu Ser Arg Pro Phe Asn Val Ala Glu Gly Lys Glu
1 5 10 15

Val Leu Leu Leu Ala His Asn Leu Pro Gln Asn Leu Ile Gly Phe Asn
20 25 30

Trp Tyr Lys Gly Glu Arg Val Asp Ala Lys Arg Leu Ile Val Ala Tyr
35 40 45

Val Ile Glu Thr Gln Gln Thr Thr Pro Gly Pro Ala His Ser Gly Arg
50 55 60

Glu Thr Val Tyr Ser Asn Ala Ser Leu Leu Ile Gln Asn Val Thr Gln
65 70 75 80

Asn Asp Thr Gly Ser Tyr Thr Leu Gln Val Ile Lys Gly Asp Leu Val
85 90 95

Asn Glu Glu Ala Thr Gly Arg Phe Trp Val Tyr Pro Glu Leu Pro Lys
100 105 110

Pro Tyr Ile Thr Ser Asn Asn Ser Asn Pro Val Glu Asp Lys Asp Ala
115 120 125

Val Asp Phe Thr Cys Glu Pro Asp Ile His Ser Thr Thr Tyr Leu Trp
130 135 140

Trp Val Asn Asp Gln Ser Leu Pro Val Ser Pro Arg Leu Gln Leu Ser
145 150 155 160

Asn Gly Asn Arg Thr Leu Thr Leu Leu Ser Val Lys Arg Asn Asp Ala
165 170 175

Gly Ala Tyr Glu Cys Glu Ile Gln Asn Pro Val Ser Ala Asn Leu Ser
180 185 190

Asp Pro Val Ile Leu Asn Val Leu Tyr Gly Pro Asp Val Pro Thr Ile
195 200 205

Ser Pro Ser Asn Ser Asn Tyr Arg Pro Gly Glu Asn Leu Asn Leu Ser
210 215 220

Cys His Ala Ala Ser Asn Pro Thr Ala Gln Tyr Ser Trp Phe Val Asn
225 230 235 240

Gly Thr Phe Gln Gln Ser Thr Gln Glu Leu Phe Ile Pro Asn Ile Thr
245 250 255

Val Asn Asn Ser Gly Ser Tyr Met Cys Gln Ala Tyr Asn Ser Ala Thr
260 265 270

Gly Leu Asn Arg Thr Thr Val Met Met Ile Thr Val Ser Gly Ile Glu
275 280 285

Gly Arg Asp Met Asp Thr Gly Pro Lys Ser Cys Asp Lys Thr His Thr
290 295 300

Cys Pro Pro Cys Pro Ala Pro Glu Leu Leu Gly Gly Pro Ser Val Phe
305 310 315 320

Leu Phe Pro Pro Lys Pro Lys Asp Thr Leu Met Ile Ser Arg Thr Pro
325 330 335

Glu Val Thr Cys Val Val Val Asp Val Ser His Glu Asp Pro Glu Val
340 345 350

Lys Phe Asn Trp Tyr Val Asp Gly Val Glu Val His Asn Ala Lys Thr
355 360 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys His His
        515                 520                 525

His His His His
    530

<210> SEQ ID NO 162
<211> LENGTH: 292
<212> TYPE: PRT
<213> ORGANISM: Homo sapiens

<400> SEQUENCE: 162

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Met Thr Leu Thr Leu Leu Ser Val Lys Arg Asn Asp Ala
                165                 170                 175

Gly Ser Tyr Glu Cys Glu Ile Gln Asn Pro Ala Ser Ala Asn Arg Ser
            180                 185                 190

Asp Pro Val Thr Leu Asn Val Leu Tyr Gly Pro Asp Gly Pro Thr Ile

```
        195                 200                 205

Ser Pro Ser Lys Ala Asn Tyr Arg Pro Gly Glu Asn Leu Asn Leu Ser
    210                 215                 220

Cys His Ala Ala Ser Asn Pro Pro Ala Gln Tyr Ser Trp Phe Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Met Ile Thr Val Ser Gly His His
        275                 280                 285

His His His His
    290


<210> SEQ ID NO 163
<211> LENGTH: 404
<212> TYPE: PRT
<213> ORGANISM: Homo sapiens

<400> SEQUENCE: 163

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
    210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270
```

Gly Cys Asn Arg Thr Thr Val Lys Thr Ile Ile Val Thr Glu Leu Ser
275 280 285

Pro Val Val Ala Lys Pro Gln Ile Lys Ala Ser Lys Thr Thr Val Thr
290 295 300

Gly Asp Lys Asp Ser Val Asn Leu Thr Cys Ser Thr Asn Asp Thr Gly
305 310 315 320

Ile Ser Ile Arg Trp Phe Phe Lys Asn Gln Ser Leu Pro Ser Ser Glu
325 330 335

Arg Met Lys Leu Ser Gln Gly Asn Thr Thr Leu Ser Ile Asn Pro Val
340 345 350

Lys Arg Glu Asp Ala Gly Thr Tyr Trp Cys Glu Val Phe Asn Pro Ile
355 360 365

Ser Lys Asn Gln Ser Asp Pro Ile Met Leu Asn Val Asn Tyr Asn Ala
370 375 380

Leu Pro Gln Glu Asn Gly Leu Ser Pro Gly His His His His His His
385 390 395 400

His His His His

<210> SEQ ID NO 164
<211> LENGTH: 657
<212> TYPE: PRT
<213> ORGANISM: Homo sapiens

<400> SEQUENCE: 164

Lys Leu Thr Ile Glu Ser Thr Pro Phe Asn Val Ala Glu Gly Lys Glu
1 5 10 15

Val Leu Leu Leu Val His Asn Leu Pro Gln His Leu Phe Gly Tyr Ser
20 25 30

Trp Tyr Lys Gly Glu Arg Val Asp Gly Asn Arg Gln Ile Ile Gly Tyr
35 40 45

Val Ile Gly Thr Gln Gln Ala Thr Pro Gly Pro Ala Tyr Ser Gly Arg
50 55 60

Glu Ile Ile Tyr Pro Asn Ala Ser Leu Leu Ile Gln Asn Ile Ile Gln
65 70 75 80

Asn Asp Thr Gly Phe Tyr Thr Leu His Val Ile Lys Ser Asp Leu Val
85 90 95

Asn Glu Glu Ala Thr Gly Gln Phe Arg Val Tyr Pro Glu Leu Pro Lys
100 105 110

Pro Ser Ile Ser Ser Asn Asn Ser Lys Pro Val Glu Asp Lys Asp Ala
115 120 125

Val Ala Phe Thr Cys Glu Pro Glu Thr Gln Asp Ala Thr Tyr Leu Trp
130 135 140

Trp Val Asn Asn Gln Ser Leu Pro Val Ser Pro Arg Leu Gln Leu Ser
145 150 155 160

Asn Gly Asn Arg Thr Leu Thr Leu Phe Asn Val Thr Arg Asn Asp Ser
165 170 175

Ala Ser Tyr Lys Cys Glu Thr Gln Asn Pro Val Ser Ala Arg Arg Ser
180 185 190

Asp Ser Val Ile Leu Asn Val Leu Tyr Gly Pro Asp Ala Pro Thr Ile
195 200 205

Ser Pro Leu Asn Thr Ser Tyr Arg Ser Gly Glu Asn Leu Asn Leu Ser
210 215 220

Cys His Ala Ala Ser Asn Pro Pro Ala Gln Tyr Ser Trp Phe Val Asn
225 230 235 240

```
Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Glu Leu Ser Val Asp
        355                 360                 365

His Ser Asp Pro Val Ile Leu Asn Val Leu Tyr Gly Pro Asp Asp Pro
    370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
        435                 440                 445

Ala Ser Gly His Ser Arg Thr Thr Val Lys Thr Ile Thr Val Ser Ala
    450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
        515                 520                 525

Arg Asn Asp Ala Arg Ala Tyr Val Cys Gly Ile Gln Asn Ser Val Ser
    530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
        595                 600                 605

Ala Lys Ile Thr Pro Asn Asn Asn Gly Thr Tyr Ala Cys Phe Val Ser
    610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala His His His His His
                645                 650                 655

His
```

<210> SEQ ID NO 165
<211> LENGTH: 532
<212> TYPE: PRT
<213> ORGANISM: Artificial Sequence
<220> FEATURE:
<223> OTHER INFORMATION: TPP-1790, hCeacam6-WT-Fc-6xHis

<400> SEQUENCE: 165

```
Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Met Thr Leu Thr Leu Leu Ser Val Lys Arg Asn Asp Ala
                165                 170                 175

Gly Ser Tyr Glu Cys Glu Ile Gln Asn Pro Ala Ser Ala Asn Arg Ser
            180                 185                 190

Asp Pro Val Thr Leu Asn Val Leu Tyr Gly Pro Asp Gly Pro Thr Ile
        195                 200                 205

Ser Pro Ser Lys Ala Asn Tyr Arg Pro Gly Glu Asn Leu Asn Leu Ser
    210                 215                 220

Cys His Ala Ala Ser Asn Pro Pro Ala Gln Tyr Ser Trp Phe Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Met Ile Thr Val Ser Gly Ile Glu
        275                 280                 285

Gly Arg Asp Met Asp Thr Gly Pro Lys Ser Cys Asp Lys Thr His Thr
    290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365
```

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys His His
        515                 520                 525

His His His His
    530

<210> SEQ ID NO 166
<211> LENGTH: 532
<212> TYPE: PRT
<213> ORGANISM: Artificial Sequence
<220> FEATURE:
<223> OTHER INFORMATION: TPP-1791, hCeacam6-Dom1-MacMul-Xa-Fc-His

<400> SEQUENCE: 166

Gln Leu Thr Ile Glu Ser Arg Pro Phe Asn Val Ala Glu Gly Lys Glu
1               5                   10                  15

Val Leu Leu Leu Ala His Asn Leu Pro Gln Asn Leu Ile Gly Phe Asn
            20                  25                  30

Trp Tyr Lys Gly Glu Arg Val Asp Ala Lys Arg Leu Ile Val Ala Tyr
        35                  40                  45

Val Ile Glu Thr Gln Gln Thr Thr Pro Gly Pro Ala His Ser Gly Arg
    50                  55                  60

Glu Thr Val Tyr Ser Asn Ala Ser Leu Leu Ile Gln Asn Val Thr Gln
65                  70                  75                  80

Asn Asp Thr Gly Ser Tyr Thr Leu Gln Val Ile Lys Gly Asp Leu Val
                85                  90                  95

Asn Glu Glu Ala Thr Gly Arg Phe Trp Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Met Thr Leu Thr Leu Leu Ser Val Lys Arg Asn Asp Ala
                165                 170                 175

Gly Ser Tyr Glu Cys Glu Ile Gln Asn Pro Ala Ser Ala Asn Arg Ser
            180                 185                 190

Asp Pro Val Thr Leu Asn Val Leu Tyr Gly Pro Asp Gly Pro Thr Ile
195 200 205

Ser Pro Ser Lys Ala Asn Tyr Arg Pro Gly Glu Asn Leu Asn Leu Ser
210 215 220

Cys His Ala Ala Ser Asn Pro Pro Ala Gln Tyr Ser Trp Phe Ile Asn
225 230 235 240

Gly Thr Phe Gln Gln Ser Thr Gln Glu Leu Phe Ile Pro Asn Ile Thr
245 250 255

Val Asn Asn Ser Gly Ser Tyr Met Cys Gln Ala His Asn Ser Ala Thr
260 265 270

Gly Leu Asn Arg Thr Thr Val Thr Met Ile Thr Val Ser Gly Ile Glu
275 280 285

Gly Arg Asp Met Asp Thr Gly Pro Lys Ser Cys Asp Lys Thr His Thr
290 295 300

Cys Pro Pro Cys Pro Ala Pro Glu Leu Leu Gly Gly Pro Ser Val Phe
305 310 315 320

Leu Phe Pro Pro Lys Pro Lys Asp Thr Leu Met Ile Ser Arg Thr Pro
325 330 335

Glu Val Thr Cys Val Val Val Asp Val Ser His Glu Asp Pro Glu Val
340 345 350

Lys Phe Asn Trp Tyr Val Asp Gly Val Glu Val His Asn Ala Lys Thr
355 360 365

Lys Pro Arg Glu Glu Gln Tyr Asn Ser Thr Tyr Arg Val Val Ser Val
370 375 380

Leu Thr Val Leu His Gln Asp Trp Leu Asn Gly Lys Glu Tyr Lys Cys
385 390 395 400

Lys Val Ser Asn Lys Ala Leu Pro Ala Pro Ile Glu Lys Thr Ile Ser
405 410 415

Lys Ala Lys Gly Gln Pro Arg Glu Pro Gln Val Tyr Thr Leu Pro Pro
420 425 430

Ser Arg Asp Glu Leu Thr Lys Asn Gln Val Ser Leu Thr Cys Leu Val
435 440 445

Lys Gly Phe Tyr Pro Ser Asp Ile Ala Val Glu Trp Glu Ser Asn Gly
450 455 460

Gln Pro Glu Asn Asn Tyr Lys Thr Thr Pro Pro Val Leu Asp Ser Asp
465 470 475 480

Gly Ser Phe Phe Leu Tyr Ser Lys Leu Thr Val Asp Lys Ser Arg Trp
485 490 495

Gln Gln Gly Asn Val Phe Ser Cys Ser Val Met His Glu Ala Leu His
500 505 510

Asn His Tyr Thr Gln Lys Ser Leu Ser Leu Ser Pro Gly Lys His His
515 520 525

His His His His
530

<210> SEQ ID NO 167
<211> LENGTH: 532
<212> TYPE: PRT
<213> ORGANISM: Artificial Sequence
<220> FEATURE:
<223> OTHER INFORMATION: TPP-1792, hCeacam6-Dom2-MacMul-Xa-Fc-His

<400> SEQUENCE: 167

Lys Leu Thr Ile Glu Ser Thr Pro Phe Asn Val Ala Glu Gly Lys Glu
1 5 10 15

-continued

```
Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Tyr Ile Thr Ser Asn Asn Ser Asn Pro Val Glu Asp Lys Asp Ala
        115                 120                 125

Val Asp Phe Thr Cys Glu Pro Asp Ile His Ser Thr Thr Tyr Leu Trp
    130                 135                 140

Trp Val Asn Asp Gln Ser Leu Pro Val Ser Pro Arg Leu Gln Leu Ser
145                 150                 155                 160

Asn Gly Asn Arg Thr Leu Thr Leu Leu Ser Val Lys Arg Asn Asp Ala
                165                 170                 175

Gly Ala Tyr Glu Cys Glu Ile Gln Asn Pro Val Ser Ala Asn Leu Ser
            180                 185                 190

Asp Pro Val Ile Leu Asn Val Leu Tyr Gly Pro Asp Gly Pro Thr Ile
        195                 200                 205

Ser Pro Ser Lys Ala Asn Tyr Arg Pro Gly Glu Asn Leu Asn Leu Ser
    210                 215                 220

Cys His Ala Ala Ser Asn Pro Pro Ala Gln Tyr Ser Trp Phe Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Met Ile Thr Val Ser Gly Ile Glu
        275                 280                 285

Gly Arg Asp Met Asp Thr Gly Pro Lys Ser Cys Asp Lys Thr His Thr
    290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430
```

```
Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys His His
        515                 520                 525

His His His His
    530


<210> SEQ ID NO 168
<211> LENGTH: 532
<212> TYPE: PRT
<213> ORGANISM: Artificial Sequence
<220> FEATURE:
<223> OTHER INFORMATION: TPP-1793, hCeacam6-Dom3-MacMul-Xa-Fc-His

<400> SEQUENCE: 168

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Met Thr Leu Thr Leu Leu Ser Val Lys Arg Asn Asp Ala
                165                 170                 175

Gly Ser Tyr Glu Cys Glu Ile Gln Asn Pro Ala Ser Ala Asn Arg Ser
            180                 185                 190

Asp Pro Val Thr Leu Asn Val Leu Tyr Gly Pro Asp Val Pro Thr Ile
        195                 200                 205

Ser Pro Ser Asn Ser Asn Tyr Arg Pro Gly Glu Asn Leu Asn Leu Ser
    210                 215                 220

Cys His Ala Ala Ser Asn Pro Thr Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255
```

```
Val Asn Asn Ser Gly Ser Tyr Met Cys Gln Ala Tyr Asn Ser Ala Thr
            260                 265                 270

Gly Leu Asn Arg Thr Thr Val Met Met Ile Thr Val Ser Gly Ile Glu
        275                 280                 285

Gly Arg Asp Met Asp Thr Gly Pro Lys Ser Cys Asp Lys Thr His Thr
    290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys His His
        515                 520                 525

His His His His
    530
```

<210> SEQ ID NO 169
<211> LENGTH: 121
<212> TYPE: PRT
<213> ORGANISM: Artificial Sequence
<220> FEATURE:
<223> OTHER INFORMATION: TPP-1794, hCeacam6-Dom1-8xHis (E.coli)

<400> SEQUENCE: 169

```
Met Lys Leu Thr Ile Glu Ser Thr Pro Phe Asn Val Ala Glu Gly Lys
1               5                   10                  15

Glu Val Leu Leu Leu Ala His Asn Leu Pro Gln Asn Arg Ile Gly Tyr
            20                  25                  30

Ser Trp Tyr Lys Gly Glu Arg Val Asp Gly Asn Ser Leu Ile Val Gly
        35                  40                  45

Tyr Val Ile Gly Thr Gln Gln Ala Thr Pro Gly Pro Ala Tyr Ser Gly
    50                  55                  60

Arg Glu Thr Ile Tyr Pro Asn Ala Ser Leu Leu Ile Gln Asn Val Thr
65                  70                  75                  80
```

```
Gln Asn Asp Thr Gly Phe Tyr Thr Leu Gln Val Ile Lys Ser Asp Leu
                85                  90                  95

Val Asn Glu Glu Ala Thr Gly Gln Phe His Val Tyr Pro Gly Ser Gly
            100                 105                 110

Ser His His His His His His His His
        115                 120


<210> SEQ ID NO 170
<211> LENGTH: 533
<212> TYPE: PRT
<213> ORGANISM: Artificial Sequence
<220> FEATURE:
<223> OTHER INFORMATION: TPP-2443, cyno CEACAM-6-Xa-Fc-His

<400> SEQUENCE: 170

Gln Leu Thr Ile Glu Ser Arg Pro Phe Asn Val Ala Glu Gly Lys Glu
1               5                   10                  15

Val Leu Leu Leu Ala His Asn Leu Pro Gln Asn Thr Leu Gly Phe Asn
            20                  25                  30

Trp Tyr Lys Gly Glu Arg Val Asp Ala Lys Arg Leu Ile Val Ala Tyr
        35                  40                  45

Val Ile Gly Thr Gln Gln Thr Thr Pro Gly Pro Ala His Ser Gly Arg
    50                  55                  60

Glu Met Ile Tyr Ser Asn Ala Ser Leu Leu Ile Gln Asn Val Thr Gln
65                  70                  75                  80

Asn Asp Thr Gly Ser Tyr Thr Leu Gln Ala Ile Lys Glu Asp Leu Val
                85                  90                  95

Thr Glu Glu Ala Thr Gly Arg Phe Trp Val Tyr Pro Glu Leu Pro Lys
            100                 105                 110

Pro Tyr Ile Thr Ser Asn Asn Ser Asn Pro Val Glu Asp Lys Asp Ala
        115                 120                 125

Val Asp Phe Thr Cys Glu Pro Asp Ile His Ser Thr Thr Tyr Leu Trp
    130                 135                 140

Trp Val Asn Asp Gln Ser Leu Pro Val Ser Pro Arg Leu Gln Leu Ser
145                 150                 155                 160

Asn Gly Asn Arg Thr Leu Thr Leu Leu Ser Val Lys Arg Asn Asp Ala
                165                 170                 175

Gly Ala Tyr Glu Cys Glu Ile Gln Asn Pro Val Ser Ala Asn Leu Ser
            180                 185                 190

Asp Pro Val Ile Leu Asn Val Leu Tyr Gly Pro Asp Val Pro Thr Ile
        195                 200                 205

Ser Pro Ser Asn Ser Asn Tyr Arg Pro Gly Glu Asn Leu Asn Leu Ser
    210                 215                 220

Cys His Ala Ala Ser Asn Pro Thr Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala Tyr Asn Ser Ala Thr
            260                 265                 270

Gly Leu Asn Arg Thr Thr Val Met Met Ile Thr Val Ser Gly Ser Ile
        275                 280                 285

Glu Gly Arg Asp Met Asp Thr Gly Pro Lys Ser Cys Asp Lys Thr His
    290                 295                 300

Thr Cys Pro Pro Cys Pro Ala Pro Glu Leu Leu Gly Gly Pro Ser Val
305                 310                 315                 320
```

-continued

```
Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
                405                 410                 415

Ser Lys Ala Lys Gly Gln Pro Arg Glu Pro Gln Val Tyr Thr Leu Pro
            420                 425                 430

Pro Ser Arg Asp Glu Leu Thr Lys Asn Gln Val Ser Leu Thr Cys Leu
        435                 440                 445

Val Lys Gly Phe Tyr Pro Ser Asp Ile Ala Val Glu Trp Glu Ser Asn
    450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
                485                 490                 495

Trp Gln Gln Gly Asn Val Phe Ser Cys Ser Val Met His Glu Ala Leu
            500                 505                 510

His Asn His Tyr Thr Gln Lys Ser Leu Ser Leu Ser Pro Gly Lys His
        515                 520                 525

His His His His His
    530
```

<210> SEQ ID NO 171
<211> LENGTH: 356
<212> TYPE: PRT
<213> ORGANISM: Artificial Sequence
<220> FEATURE:
<223> OTHER INFORMATION: TPP-2452, cynomolgus Ceacam6-Dom1-Xa-Fc-His

<400> SEQUENCE: 171

```
Gln Leu Thr Ile Glu Ser Arg Pro Phe Asn Val Ala Glu Gly Lys Glu
1               5                   10                  15

Val Leu Leu Leu Ala His Asn Leu Pro Gln Asn Thr Leu Gly Phe Asn
            20                  25                  30

Trp Tyr Lys Gly Glu Arg Val Asp Ala Lys Arg Leu Ile Val Ala Tyr
        35                  40                  45

Val Ile Gly Thr Gln Gln Thr Thr Pro Gly Pro Ala His Ser Gly Arg
    50                  55                  60

Glu Met Ile Tyr Ser Asn Ala Ser Leu Leu Ile Gln Asn Val Thr Gln
65                  70                  75                  80

Asn Asp Thr Gly Ser Tyr Thr Leu Gln Ala Ile Lys Glu Asp Leu Val
                85                  90                  95

Thr Glu Glu Ala Thr Gly Arg Phe Trp Val Tyr Pro Glu Leu Ile Glu
            100                 105                 110

Gly Arg Asp Met Asp Thr Gly Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140
```

```
Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys His His
            340                 345                 350

His His His His
        355
```

<210> SEQ ID NO 172
<211> LENGTH: 127
<212> TYPE: PRT
<213> ORGANISM: Homo sapiens

<400> SEQUENCE: 172

```
Lys Leu Thr Ile Glu Ser Met Pro Leu Ser Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Ala Ala Tyr Ser Gly Arg
    50                  55                  60

Glu Thr Ile Tyr Thr Asn Ala Ser Leu Leu Ile Gln Asn Val Thr Gln
65                  70                  75                  80

Asn Asp Ile Gly Phe Tyr Thr Leu Gln Val Ile Lys Ser Asp Leu Val
                85                  90                  95

Asn Glu Glu Ala Thr Gly Gln Phe His Val Tyr Gln Glu Asn Ala Pro
            100                 105                 110

Gly Leu Pro Val Gly Ala Val Ala Gly His His His His His His
        115                 120                 125
```

<210> SEQ ID NO 173
<211> LENGTH: 526
<212> TYPE: PRT
<213> ORGANISM: Homo sapiens

<400> SEQUENCE: 173

```
Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
```

```
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510

Leu Thr Ala Thr Glu Ile Ile Tyr Ser Glu Val Lys Lys Gln
        515                 520                 525


<210> SEQ ID NO 174
<211> LENGTH: 300
<212> TYPE: PRT
<213> ORGANISM: Homo sapiens

<400> SEQUENCE: 174

Met Glu Ile Pro Met Gly Thr Gln Gly Cys Phe Ser Lys Ser Leu Leu
1               5                   10                  15

Leu Ser Ala Ser Ile Leu Val Leu Trp Met Leu Gln Gly Ser Gln Ala
            20                  25                  30

Ala Leu Tyr Ile Gln Lys Ile Pro Glu Gln Pro Gln Lys Asn Gln Asp
        35                  40                  45

Leu Leu Leu Ser Val Gln Gly Val Pro Asp Thr Phe Gln Asp Phe Asn
    50                  55                  60

Trp Tyr Leu Gly Glu Glu Thr Tyr Gly Gly Thr Arg Leu Phe Thr Tyr
65                  70                  75                  80

Ile Pro Gly Ile Gln Arg Pro Gln Arg Asp Gly Ser Ala Met Gly Gln
                85                  90                  95

Arg Asp Ile Val Gly Phe Pro Asn Gly Ser Met Leu Leu Arg Arg Ala
            100                 105                 110

Gln Pro Thr Asp Ser Gly Thr Tyr Gln Val Ala Ile Thr Ile Asn Ser
        115                 120                 125

Glu Trp Thr Met Lys Ala Lys Thr Glu Val Gln Val Ala Glu Lys Asn
    130                 135                 140

Lys Glu Leu Pro Ser Thr His Leu Pro Thr Asn Ala Gly Ile Leu Ala
145                 150                 155                 160

Ala Thr Ile Ile Gly Ser Leu Ala Ala Gly Ala Leu Leu Ile Ser Cys
                165                 170                 175

Ile Ala Tyr Leu Leu Val Thr Arg Asn Trp Arg Gly Gln Ser His Arg
            180                 185                 190

Leu Pro Ala Pro Arg Gly Gln Gly Ser Leu Ser Ile Leu Cys Ser Ala
        195                 200                 205

Val Ser Pro Val Pro Ser Val Thr Pro Ser Thr Trp Met Ala Thr Thr
    210                 215                 220

Glu Lys Pro Glu Leu Gly Pro Ala His Asp Ala Gly Asp Asn Asn Ile
225                 230                 235                 240

Tyr Glu Val Met Pro Ser Pro Val Leu Leu Val Ser Pro Ile Ser Asp
                245                 250                 255
```

-continued

```
Thr Arg Ser Ile Asn Pro Ala Arg Pro Leu Pro Thr Pro Pro His Leu
            260                 265                 270

Gln Ala Glu Pro Glu Asn His Gln Tyr Gln Gln Asp Leu Leu Asn Pro
        275                 280                 285

Asp Pro Ala Pro Tyr Cys Gln Leu Val Pro Thr Ser
    290                 295                 300


<210> SEQ ID NO 175
<211> LENGTH: 252
<212> TYPE: PRT
<213> ORGANISM: Homo sapiens

<400> SEQUENCE: 175

Met Gly Pro Pro Ser Ala Ser Pro His Arg Glu Cys Ile Pro Trp Gln
1               5                   10                  15

Gly Leu Leu Leu Thr Ala Ser Leu Leu Asn Phe Trp Asn Pro Pro Thr
            20                  25                  30

Thr Ala Lys Leu Thr Ile Glu Ser Met Pro Leu Ser Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Ala Ala Tyr Ser
                85                  90                  95

Gly Arg Glu Thr Ile Tyr Thr Asn Ala Ser Leu Leu Ile Gln Asn Val
            100                 105                 110

Thr Gln Asn Asp Ile Gly Phe Tyr Thr Leu Gln Val Ile Lys Ser Asp
        115                 120                 125

Leu Val Asn Glu Glu Ala Thr Gly Gln Phe His Val Tyr Gln Glu Asn
    130                 135                 140

Ala Pro Gly Leu Pro Val Gly Ala Val Ala Gly Ile Val Thr Gly Val
145                 150                 155                 160

Leu Val Gly Val Ala Leu Val Ala Ala Leu Val Cys Phe Leu Leu Leu
                165                 170                 175

Ala Lys Thr Gly Arg Thr Ser Ile Gln Arg Asp Leu Lys Glu Gln Gln
            180                 185                 190

Pro Gln Ala Leu Ala Pro Gly Arg Gly Pro Ser His Ser Ser Ala Phe
        195                 200                 205

Ser Met Ser Pro Leu Ser Thr Ala Gln Ala Pro Leu Pro Asn Pro Arg
    210                 215                 220

Thr Ala Ala Ser Ile Tyr Glu Glu Leu Leu Lys His Asp Thr Asn Ile
225                 230                 235                 240

Tyr Cys Arg Met Asp His Lys Ala Glu Val Ala Ser
                245                 250


<210> SEQ ID NO 176
<211> LENGTH: 702
<212> TYPE: PRT
<213> ORGANISM: Homo sapiens

<400> SEQUENCE: 176

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30
```

-continued

```
Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
```

```
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700


<210> SEQ ID NO 177
<211> LENGTH: 344
<212> TYPE: PRT
<213> ORGANISM: Macaca fascicularis

<400> SEQUENCE: 177

Met Gly Pro Pro Ser Ala Pro Pro Cys Arg Ile Cys Val Pro Trp Lys
1               5                   10                  15

Glu Val Leu Leu Thr Ala Ser Leu Leu Thr Phe Trp Ser Pro Pro Thr
            20                  25                  30

Thr Ala Gln Leu Thr Ile Glu Ser Arg Pro Phe Asn Val Ala Glu Gly
        35                  40                  45

Lys Glu Val Leu Leu Leu Ala His Asn Leu Pro Gln Asn Thr Leu Gly
    50                  55                  60

Phe Asn Trp Tyr Lys Gly Glu Arg Val Asp Ala Lys Arg Leu Ile Val
65                  70                  75                  80

Ala Tyr Val Ile Gly Thr Gln Gln Thr Thr Pro Gly Pro Ala His Ser
                85                  90                  95

Gly Arg Glu Met Ile Tyr Ser Asn Ala Ser Leu Leu Ile Gln Asn Val
            100                 105                 110

Thr Gln Asn Asp Thr Gly Ser Tyr Thr Leu Gln Ala Ile Lys Glu Asp
        115                 120                 125
```

```
Leu Val Thr Glu Glu Ala Thr Gly Arg Phe Trp Val Tyr Pro Glu Leu
    130                 135                 140

Pro Lys Pro Tyr Ile Thr Ser Asn Asn Ser Asn Pro Val Glu Asp Lys
145                 150                 155                 160

Asp Ala Val Asp Phe Thr Cys Glu Pro Asp Ile His Ser Thr Thr Tyr
                165                 170                 175

Leu Trp Trp Val Asn Asp Gln Ser Leu Pro Val Ser Pro Arg Leu Gln
            180                 185                 190

Leu Ser Asn Gly Asn Arg Thr Leu Thr Leu Leu Ser Val Lys Arg Asn
        195                 200                 205

Asp Ala Gly Ala Tyr Glu Cys Glu Ile Gln Asn Pro Val Ser Ala Asn
    210                 215                 220

Leu Ser Asp Pro Val Ile Leu Asn Val Leu Tyr Gly Pro Asp Val Pro
225                 230                 235                 240

Thr Ile Ser Pro Ser Asn Ser Asn Tyr Arg Pro Gly Glu Asn Leu Asn
                245                 250                 255

Leu Ser Cys His Ala Ala Ser Asn Pro Thr Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala Tyr Asn Ser
    290                 295                 300

Ala Thr Gly Leu Asn Arg Thr Thr Val Met Met Ile Thr Val Ser Gly
305                 310                 315                 320

Ser Ala Pro Gly Leu Ser Ala Val Ala Thr Val Gly Ile Met Ile Gly
                325                 330                 335

Val Leu Ala Arg Val Ala Leu Ile
            340
```

<210> SEQ ID NO 178
<211> LENGTH: 349
<212> TYPE: PRT
<213> ORGANISM: Homo sapiens

<400> SEQUENCE: 178

```
Met Gly Pro Ile Ser Ala Pro Ser Cys Arg Trp Arg Ile Pro Trp Gln
1               5                   10                  15

Gly Leu Leu Leu Thr Ala Ser Leu Phe Thr Phe Trp Asn Pro Pro Thr
            20                  25                  30

Thr Ala Gln Leu Thr Ile Glu Ala Val Pro Ser Asn Ala Ala Glu Gly
        35                  40                  45

Lys Glu Val Leu Leu Leu Val His Asn Leu Pro Gln Asp Pro Arg Gly
    50                  55                  60

Tyr Asn Trp Tyr Lys Gly Glu Thr Val Asp Ala Asn Arg Arg Ile Ile
65                  70                  75                  80

Gly Tyr Val Ile Ser Asn Gln Gln Ile Thr Pro Gly Pro Ala Tyr Ser
                85                  90                  95

Asn Arg Glu Thr Ile Tyr Pro Asn Ala Ser Leu Leu Met Arg Asn Val
            100                 105                 110

Thr Arg Asn Asp Thr Gly Ser Tyr Thr Leu Gln Val Ile Lys Leu Asn
        115                 120                 125

Leu Met Ser Glu Glu Val Thr Gly Gln Phe Ser Val His Pro Glu Thr
    130                 135                 140

Pro Lys Pro Ser Ile Ser Ser Asn Asn Ser Asn Pro Val Glu Asp Lys
145                 150                 155                 160
```

```
Asp Ala Val Ala Phe Thr Cys Glu Pro Glu Thr Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Val Gly Pro Tyr Glu Cys Glu Ile Gln Asn Pro Ala Ser Ala Asn
    210                 215                 220

Phe Ser Asp Pro Val Thr Leu Asn Val Leu Tyr Gly Pro Asp Ala Pro
225                 230                 235                 240

Thr Ile Ser Pro Ser Asp Thr Tyr Tyr His Ala Gly Val Asn Leu Asn
                245                 250                 255

Leu Ser Cys His Ala Ala Ser Asn Pro Pro Ser Gln Tyr Ser Trp Ser
            260                 265                 270

Val Asn Gly Thr Phe Gln Gln Tyr Thr Gln Lys Leu Phe Ile Pro Asn
        275                 280                 285

Ile Thr Thr Lys Asn Ser Gly Ser Tyr Ala Cys His Thr Thr Asn Ser
    290                 295                 300

Ala Thr Gly Arg Asn Arg Thr Thr Val Arg Met Ile Thr Val Ser Asp
305                 310                 315                 320

Ala Leu Val Gln Gly Ser Ser Pro Gly Leu Ser Ala Arg Ala Thr Val
                325                 330                 335

Ser Ile Met Ile Gly Val Leu Ala Arg Val Ala Leu Ile
            340                 345


<210> SEQ ID NO 179
<211> LENGTH: 344
<212> TYPE: PRT
<213> ORGANISM: Homo sapiens

<400> SEQUENCE: 179

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
```

```
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340


<210> SEQ ID NO 180
<211> LENGTH: 123
<212> TYPE: PRT
<213> ORGANISM: Artificial Sequence
<220> FEATURE:
<223> OTHER INFORMATION: Macaca fascicularis CEACAM6-Domain 1-His

<400> SEQUENCE: 180

Met Gln Leu Thr Ile Glu Ser Arg Pro Phe Asn Val Ala Glu Gly Lys
1               5                   10                  15

Glu Val Leu Leu Leu Ala His Asn Leu Pro Gln Asn Thr Leu Gly Phe
            20                  25                  30

Asn Trp Tyr Lys Gly Glu Arg Val Asp Ala Lys Arg Leu Ile Val Ala
        35                  40                  45

Tyr Val Ile Gly Thr Gln Gln Thr Thr Pro Gly Pro Ala His Ser Gly
    50                  55                  60

Arg Glu Met Ile Tyr Ser Asn Ala Ser Leu Leu Ile Gln Asn Val Thr
65                  70                  75                  80

Gln Asn Asp Thr Gly Ser Tyr Thr Leu Gln Ala Ile Lys Glu Asp Leu
                85                  90                  95

Val Thr Glu Glu Ala Thr Gly Arg Phe Trp Val Tyr Pro Glu Leu Gly
            100                 105                 110

Ser Gly Ser His His His His His His His His
        115                 120


<210> SEQ ID NO 181
<211> LENGTH: 447
<212> TYPE: PRT
<213> ORGANISM: Artificial Sequence
<220> FEATURE:
<223> OTHER INFORMATION: TPP-5468 - Heavy Chain

<400> SEQUENCE: 181

Gln Val Thr Leu Arg Glu Ser Gly Pro Ala Leu Val Lys Pro Thr Gln
1               5                   10                  15
```

-continued

```
Thr Leu Thr Leu Thr Cys Thr Phe Ser Gly Phe Ser Leu Ser Thr Tyr
            20                  25                  30

Gly Ile Gly Val Gly Trp Ile Arg Gln Pro Pro Gly Lys Ala Leu Glu
        35                  40                  45

Trp Leu Ala His Ile Trp Trp Asn Asp Asn Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
```

435 440 445

<210> SEQ ID NO 182
<211> LENGTH: 214
<212> TYPE: PRT
<213> ORGANISM: Artificial Sequence
<220> FEATURE:
<223> OTHER INFORMATION: TPP-5468 - Light Chain

<400> SEQUENCE: 182

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Gly Thr Ala
20 25 30

Val Ala Trp Tyr Gln Gln Lys Pro Gly Lys Ala Pro Lys Leu Leu Ile
35 40 45

Tyr Ser Ala Ser Asn Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Ser Ser Tyr Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 183
<211> LENGTH: 225
<212> TYPE: PRT
<213> ORGANISM: Artificial Sequence
<220> FEATURE:
<223> OTHER INFORMATION: APP-1574 - Heavy Chain (Fab)

<400> SEQUENCE: 183

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Tyr
20 25 30

Gly Ile Gly Val Gly Trp Ile Arg Gln Pro Pro Gly Lys Ala Leu Glu
35 40 45

Trp Leu Ala His Ile Trp Trp Asn Asp Asn Lys Tyr Tyr Ser Thr Ser
50 55 60

Leu Lys Thr Arg Leu Thr Ile Ser Lys Asp Thr Ser Lys Asn Gln Val
65 70 75 80

```
Val Leu Thr Met Thr Asn Met Asp Pro Val Asp Thr Ala Thr Tyr Tyr
                85                  90                  95

Cys Ala Arg Ile Ser Leu Pro Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His
225


<210> SEQ ID NO 184
<211> LENGTH: 214
<212> TYPE: PRT
<213> ORGANISM: Artificial Sequence
<220> FEATURE:
<223> OTHER INFORMATION: APP-1574 - Light Chain (Fab)

<400> SEQUENCE: 184

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

-continued

```
Phe Asn Arg Gly Glu Cys
    210


<210> SEQ ID NO 185
<211> LENGTH: 121
<212> TYPE: PRT
<213> ORGANISM: Artificial Sequence
<220> FEATURE:
<223> OTHER INFORMATION: TPP-8697, hCEACAM6-Domain 1-His - I30L

<400> SEQUENCE: 185

Met Lys Leu Thr Ile Glu Ser Thr Pro Phe Asn Val Ala Glu Gly Lys
1               5                   10                  15

Glu Val Leu Leu Leu Ala His Asn Leu Pro Gln Asn Arg Leu Gly Tyr
            20                  25                  30

Ser Trp Tyr Lys Gly Glu Arg Val Asp Gly Asn Ser Leu Ile Val Gly
        35                  40                  45

Tyr Val Ile Gly Thr Gln Gln Ala Thr Pro Gly Pro Ala Tyr Ser Gly
    50                  55                  60

Arg Glu Thr Ile Tyr Pro Asn Ala Ser Leu Leu Ile Gln Asn Val Thr
65                  70                  75                  80

Gln Asn Asp Thr Gly Phe Tyr Thr Leu Gln Val Ile Lys Ser Asp Leu
                85                  90                  95

Val Asn Glu Glu Ala Thr Gly Gln Phe His Val Tyr Pro Gly Ser Gly
            100                 105                 110

Ser His His His His His His His His
        115                 120


<210> SEQ ID NO 186
<211> LENGTH: 121
<212> TYPE: PRT
<213> ORGANISM: Artificial Sequence
<220> FEATURE:
<223> OTHER INFORMATION: TPP-8698, hCEACAM6-Domain 1-His - I30F

<400> SEQUENCE: 186

Met Lys Leu Thr Ile Glu Ser Thr Pro Phe Asn Val Ala Glu Gly Lys
1               5                   10                  15

Glu Val Leu Leu Leu Ala His Asn Leu Pro Gln Asn Arg Phe Gly Tyr
            20                  25                  30

Ser Trp Tyr Lys Gly Glu Arg Val Asp Gly Asn Ser Leu Ile Val Gly
        35                  40                  45

Tyr Val Ile Gly Thr Gln Gln Ala Thr Pro Gly Pro Ala Tyr Ser Gly
    50                  55                  60

Arg Glu Thr Ile Tyr Pro Asn Ala Ser Leu Leu Ile Gln Asn Val Thr
65                  70                  75                  80

Gln Asn Asp Thr Gly Phe Tyr Thr Leu Gln Val Ile Lys Ser Asp Leu
                85                  90                  95

Val Asn Glu Glu Ala Thr Gly Gln Phe His Val Tyr Pro Gly Ser Gly
            100                 105                 110

Ser His His His His His His His His
        115                 120
```